(12) United States Patent
Hansen et al.

(10) Patent No.: US 9,006,150 B2
(45) Date of Patent: Apr. 14, 2015

(54) STRUCTURAL NUCLEIC ACID GUIDED CHEMICAL SYNTHESIS

(75) Inventors: Nils Jokob Vest Hansen, Copenhagen V (DK); Peter Blakskjaer, Copenhagen (DK); Margit Haahr Hansen, Copenhagen O (DK); Lars Kolster Petersen, Skaevinge (DK); Tara Renee Heitner, Copenhagen V (DK)

(73) Assignee: Vipergen ApS, Copenhagen O (DK)

( * ) Notice: Subject to any disclaimer, the term of this patent is extended or adjusted under 35 U.S.C. 154(b) by 92 days.

(21) Appl. No.: 13/474,475

(22) Filed: May 17, 2012

(65) Prior Publication Data

US 2013/0005581 A1    Jan. 3, 2013

Related U.S. Application Data

(62) Division of application No. 11/577,649, filed as application No. PCT/DK2005/000714 on Nov. 8, 2005, now Pat. No. 8,202,823.

(60) Provisional application No. 60/687,849, filed on Jun. 7, 2005, provisional application No. 60/725,347, filed on Oct. 11, 2005.

(30) Foreign Application Priority Data

Nov. 8, 2004    (EP) .................................... 04105597

(51) Int. Cl.
| | | |
|---|---|---|
| C40B 50/00 | (2006.01) | |
| C40B 30/00 | (2006.01) | |
| C40B 50/10 | (2006.01) | |
| C40B 50/16 | (2006.01) | |
| C12N 15/10 | (2006.01) | |
| C40B 40/00 | (2006.01) | |

(52) U.S. Cl.
CPC ........ *C12N 15/1075* (2013.01); *C12N 15/1068* (2013.01)

(58) Field of Classification Search
None
See application file for complete search history.

(56) References Cited

U.S. PATENT DOCUMENTS

2002/0110535 A1    8/2002   Jones
2008/0193983 A1*   8/2008   Gouliaev et al. ............. 435/91.2

FOREIGN PATENT DOCUMENTS

WO    85/00813 A1    2/1985
WO    92/12164 A1    7/1992

(Continued)

OTHER PUBLICATIONS

Nadrian C. Seeman, "DNA in a material world", Nature, 2003, 421: 427-431.

*Primary Examiner* — Samuel Woolwine
(74) *Attorney, Agent, or Firm* — Sughrue Mion, PLLC

(57) ABSTRACT

Disclosed is a composition comprising the nucleic acid and a chemical compound, said composition forming a star structure defining 3 or more stems extending from a reaction center. The stems are formed by a nucleic acid duplex and the chemical compound has been formed in the reaction center as the reaction product of 3 or more chemical groups. The advantage of the composition is that a close proximity is provided between the chemical groups in the reaction center, thereby promoting a reaction. The invention also relates to a method for preparation of the composition. The advantage of the method is that it does not require the pre-synthesis of a large number of templates and that it is not dependent upon codon/anti-codon recognition for an encoded molecule to be formed.

17 Claims, 75 Drawing Sheets

(56) References Cited

FOREIGN PATENT DOCUMENTS

| WO | 93/12244 | A3 | 6/1993 |
| WO | 97/41142 | A1 | 11/1997 |
| WO | 00/61775 | A1 | 10/2000 |
| WO | 2004/024929 | A2 | 3/2004 |
| WO | 2004/039825 | A2 | 5/2004 |
| WO | 2004/056994 | A2 | 7/2004 |

* cited by examiner

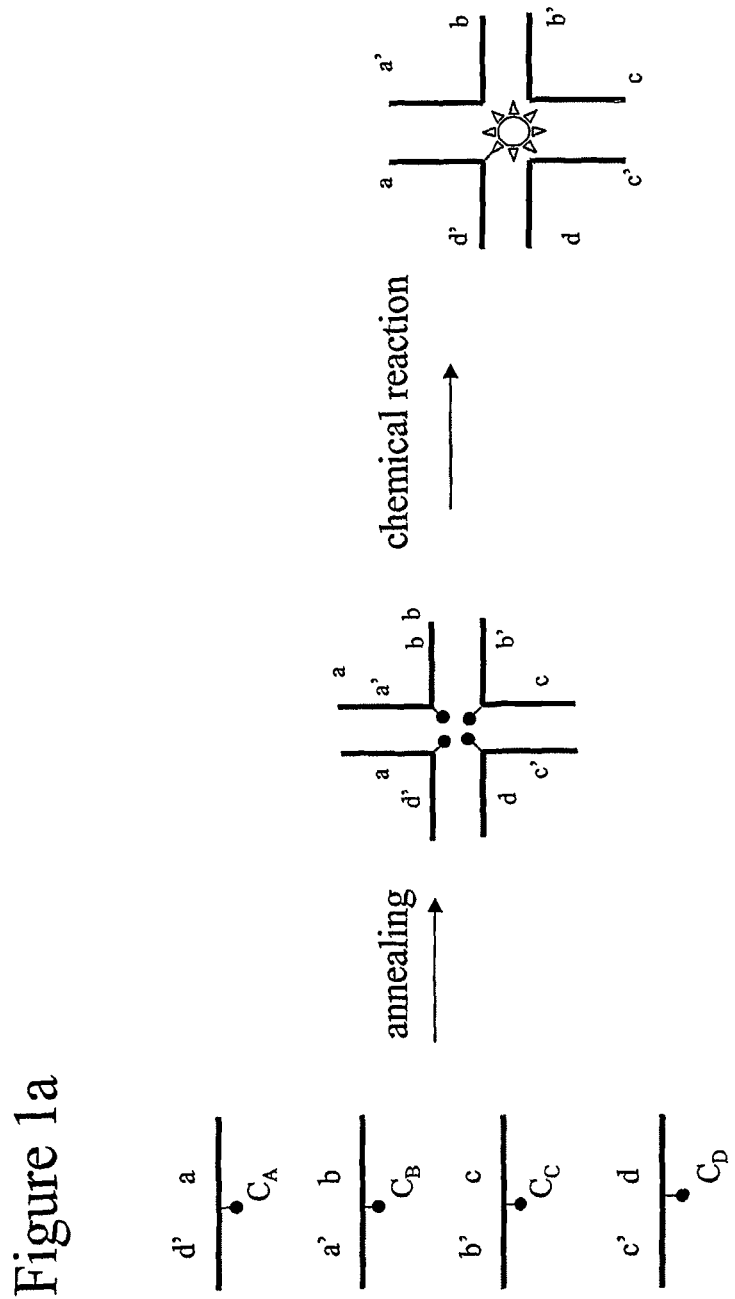

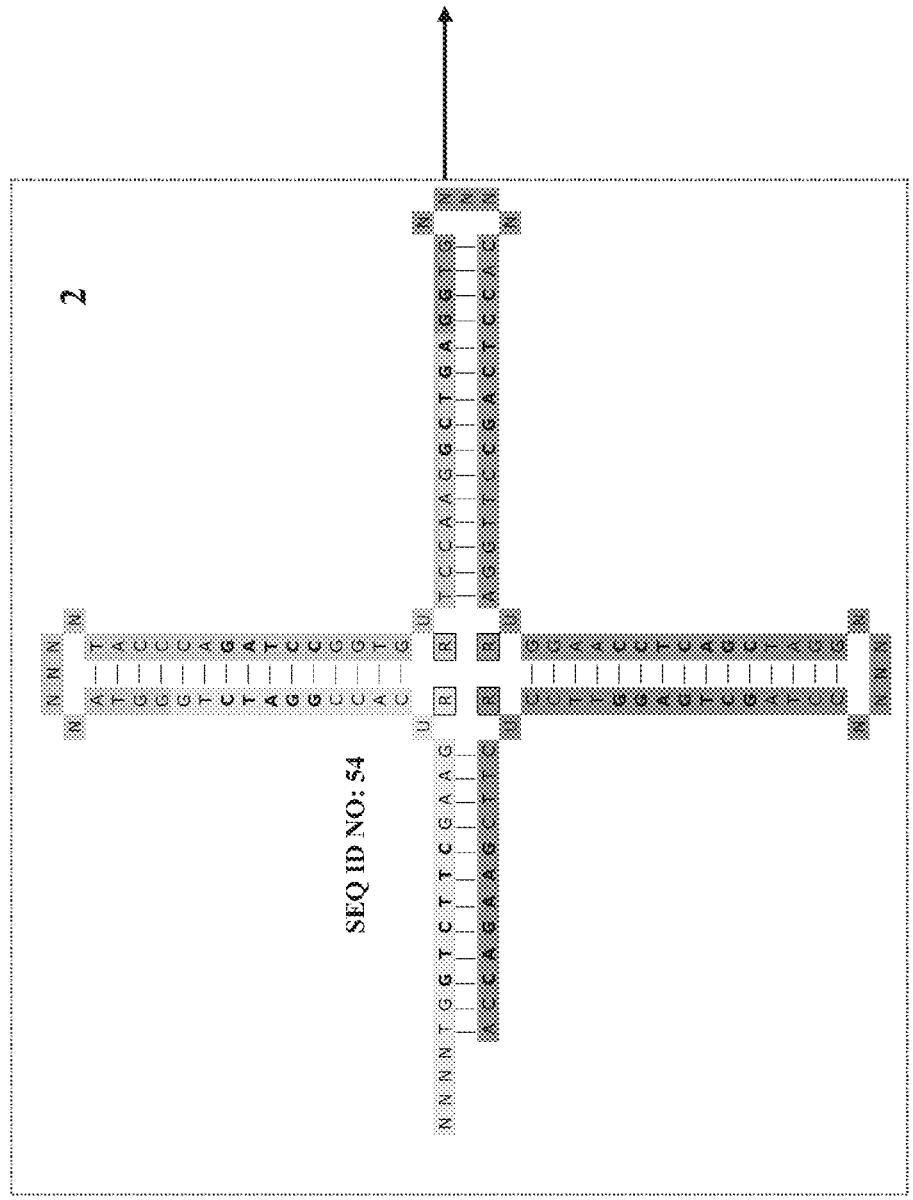
Figure 1d, continued

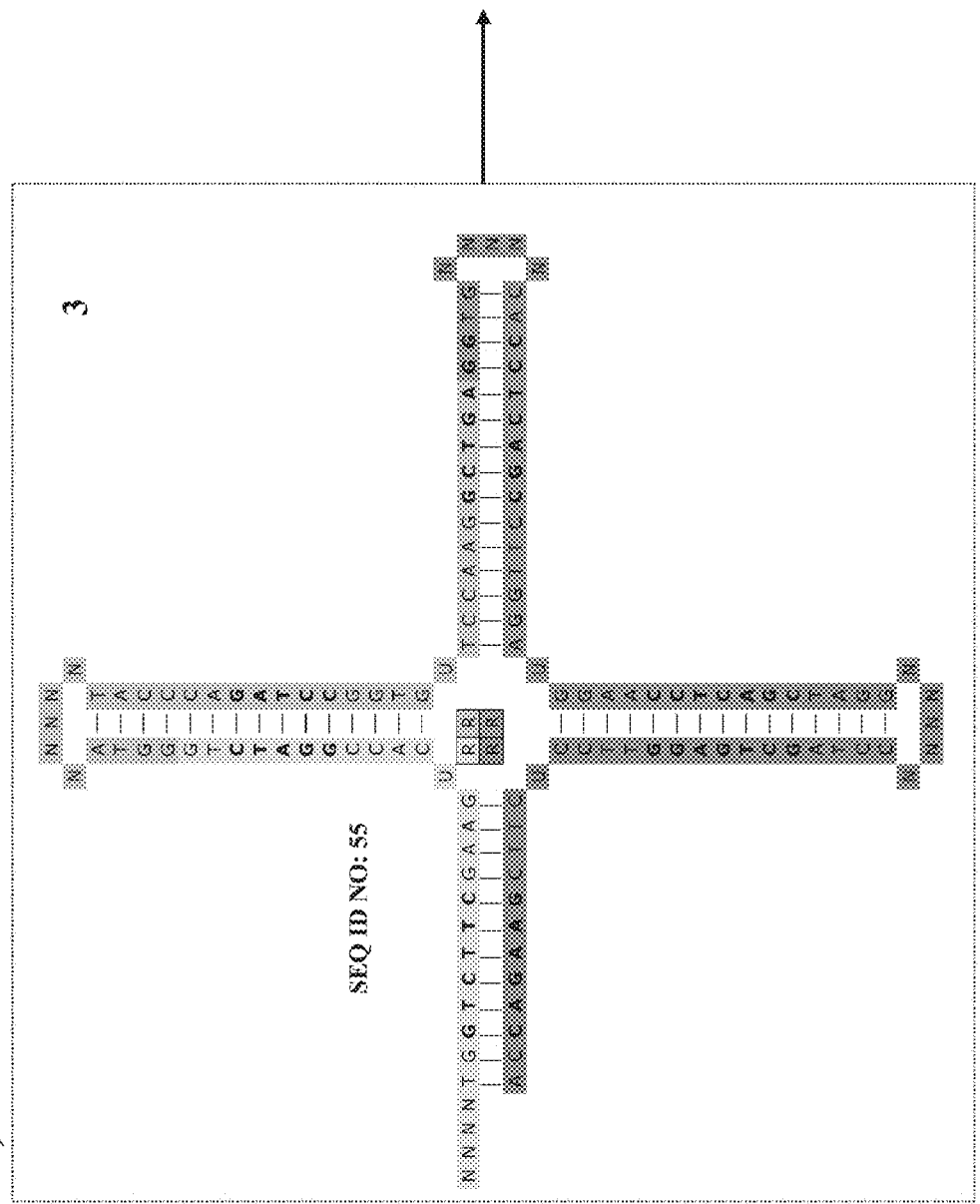
Figure 1d, continued

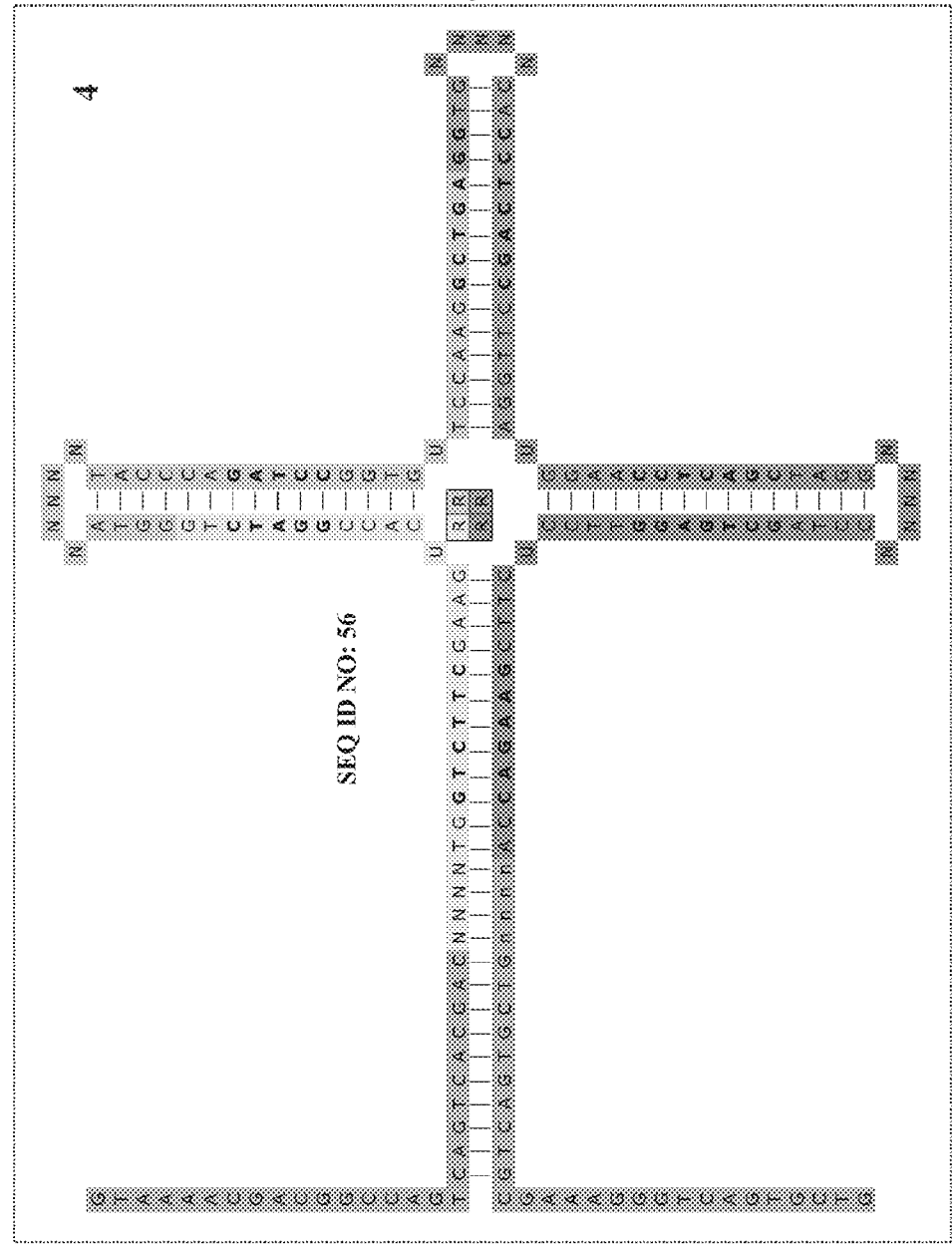
Figure 1d, continued

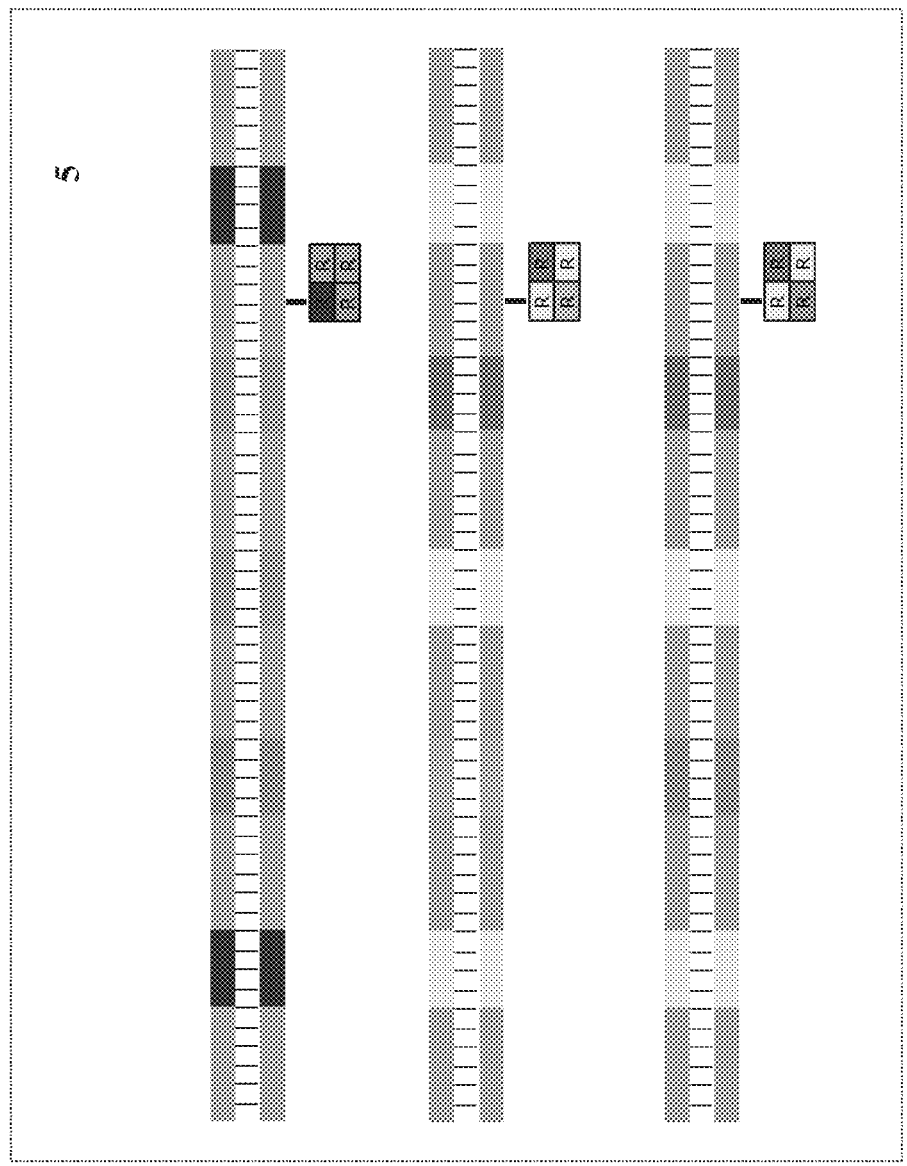
Figure 1d, continued

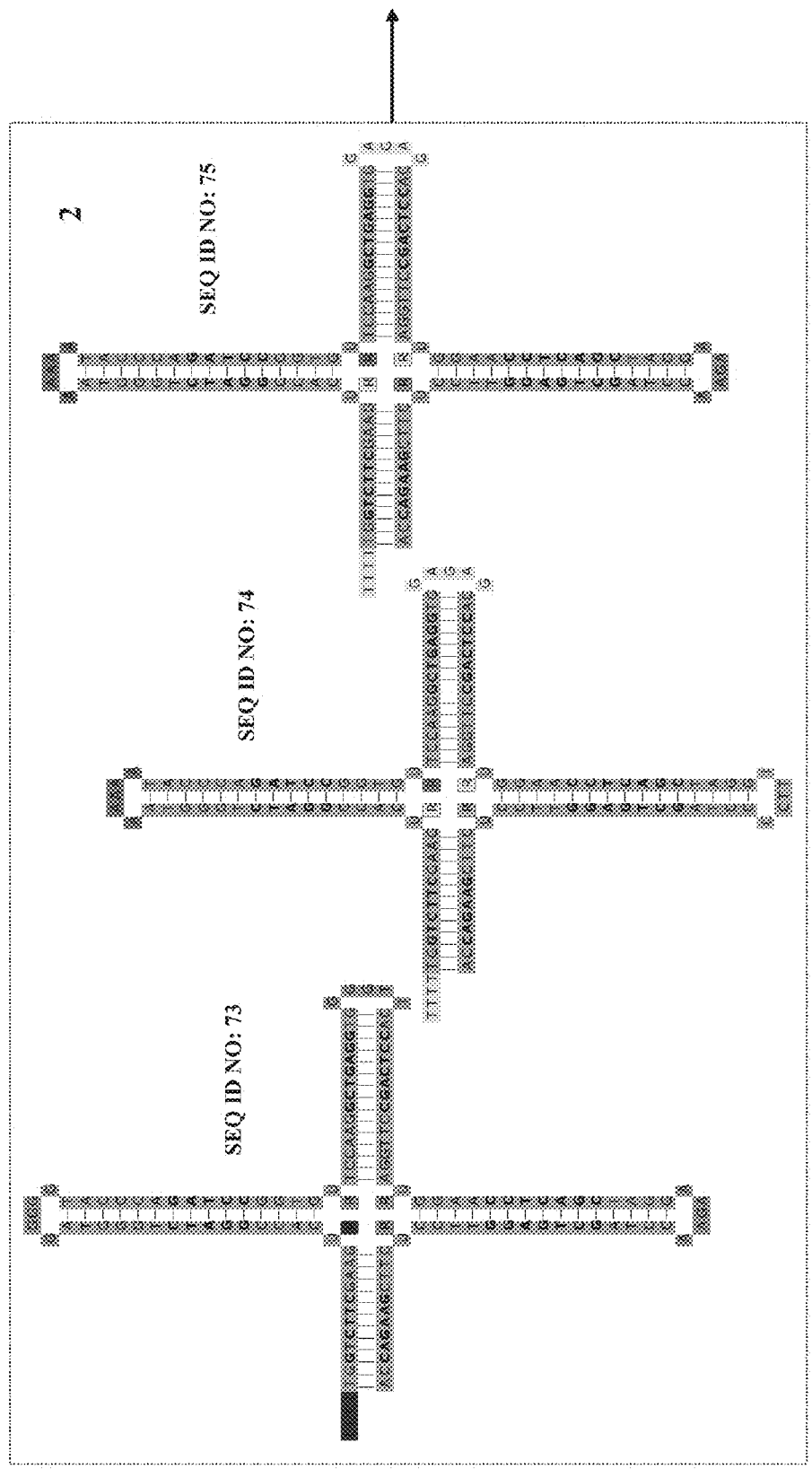
Figure 2a, continued

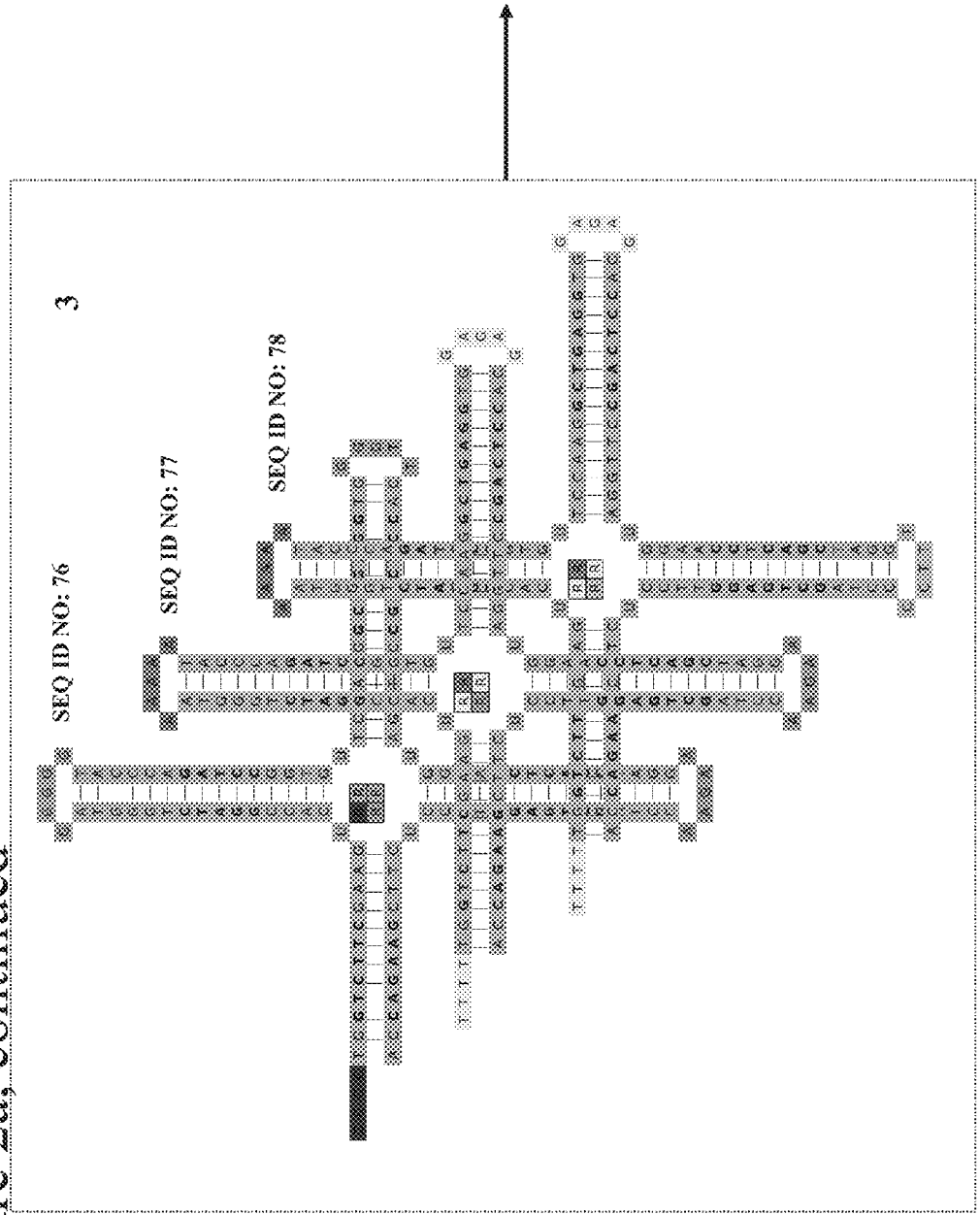
Figure 2a, continued

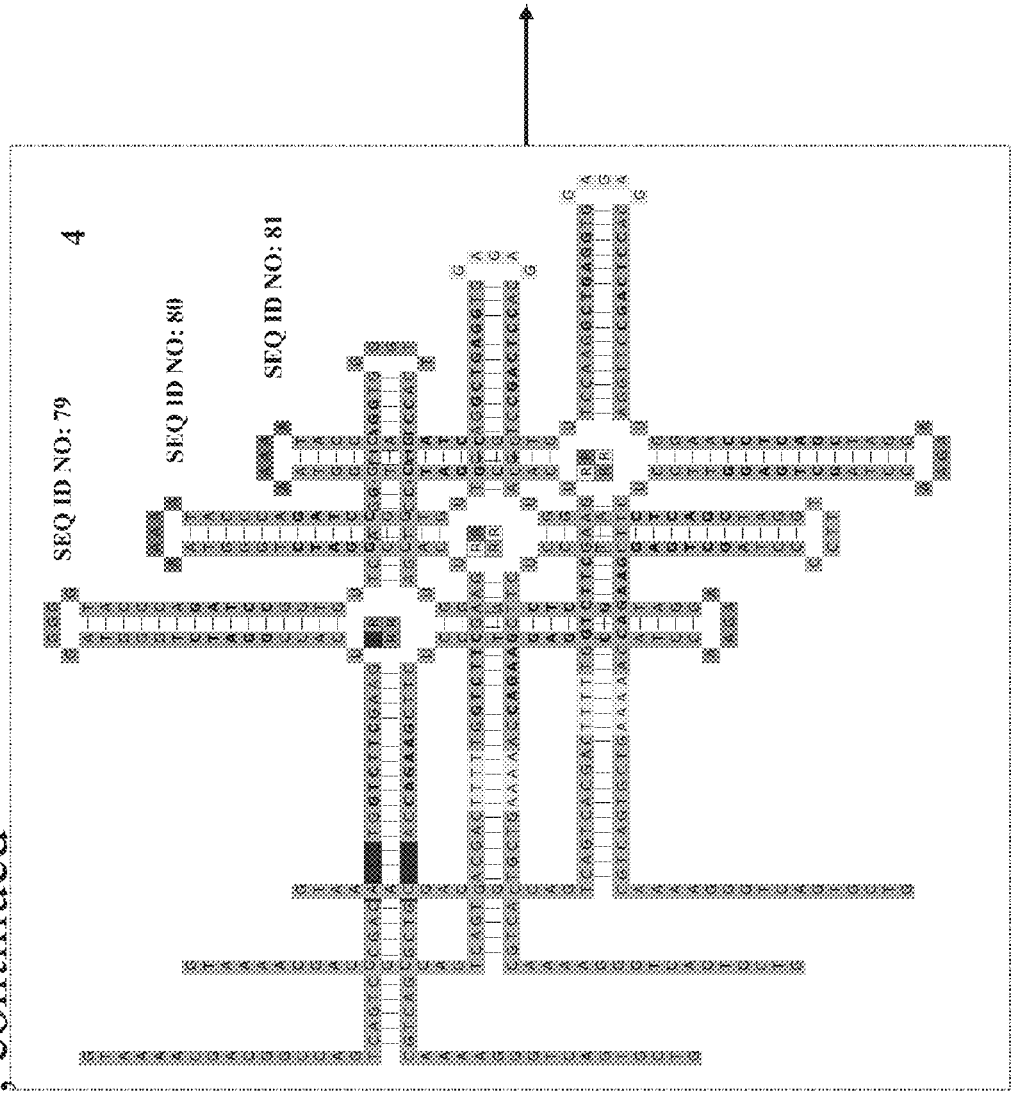
Figure 2a, continued

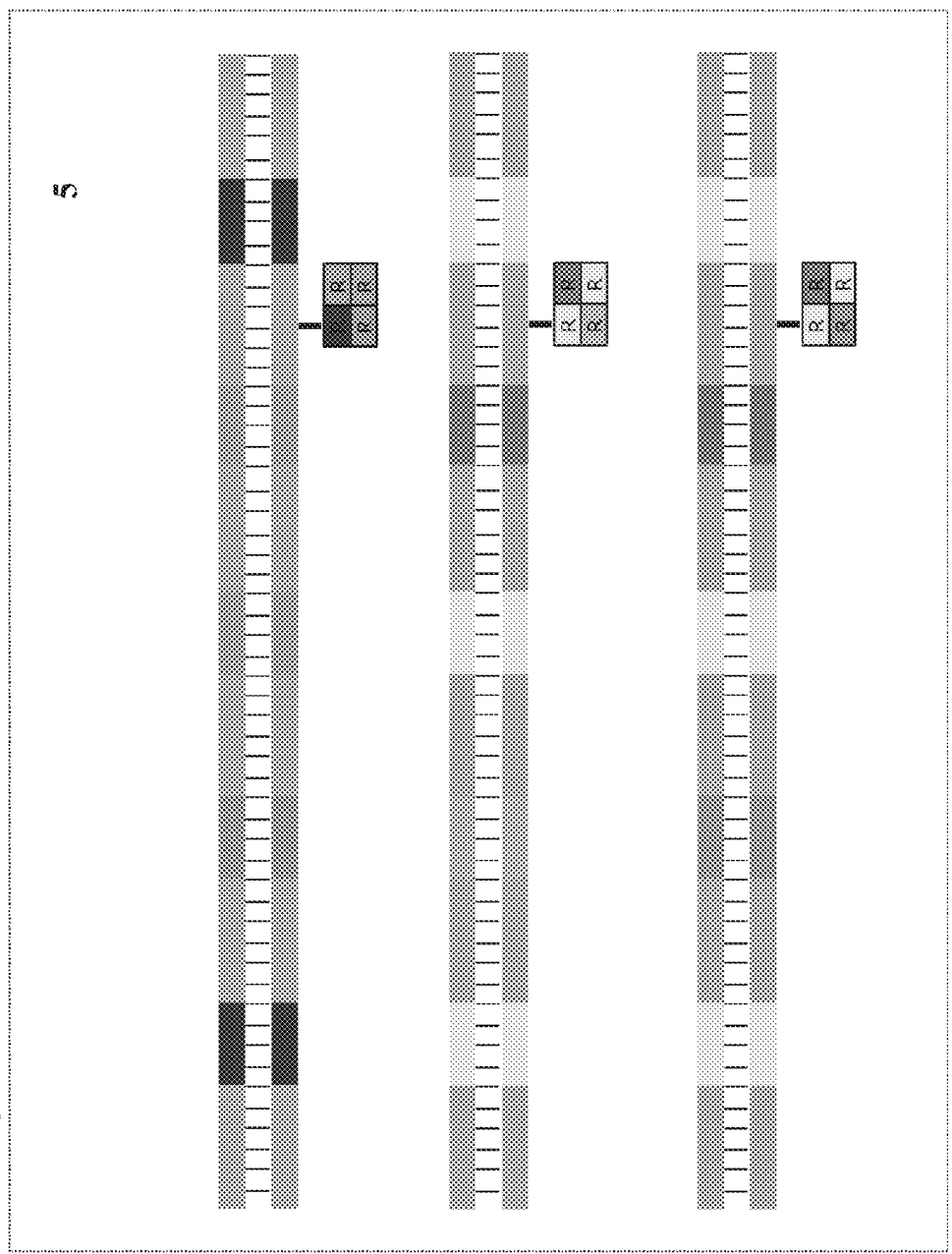
Figure 2a, continued

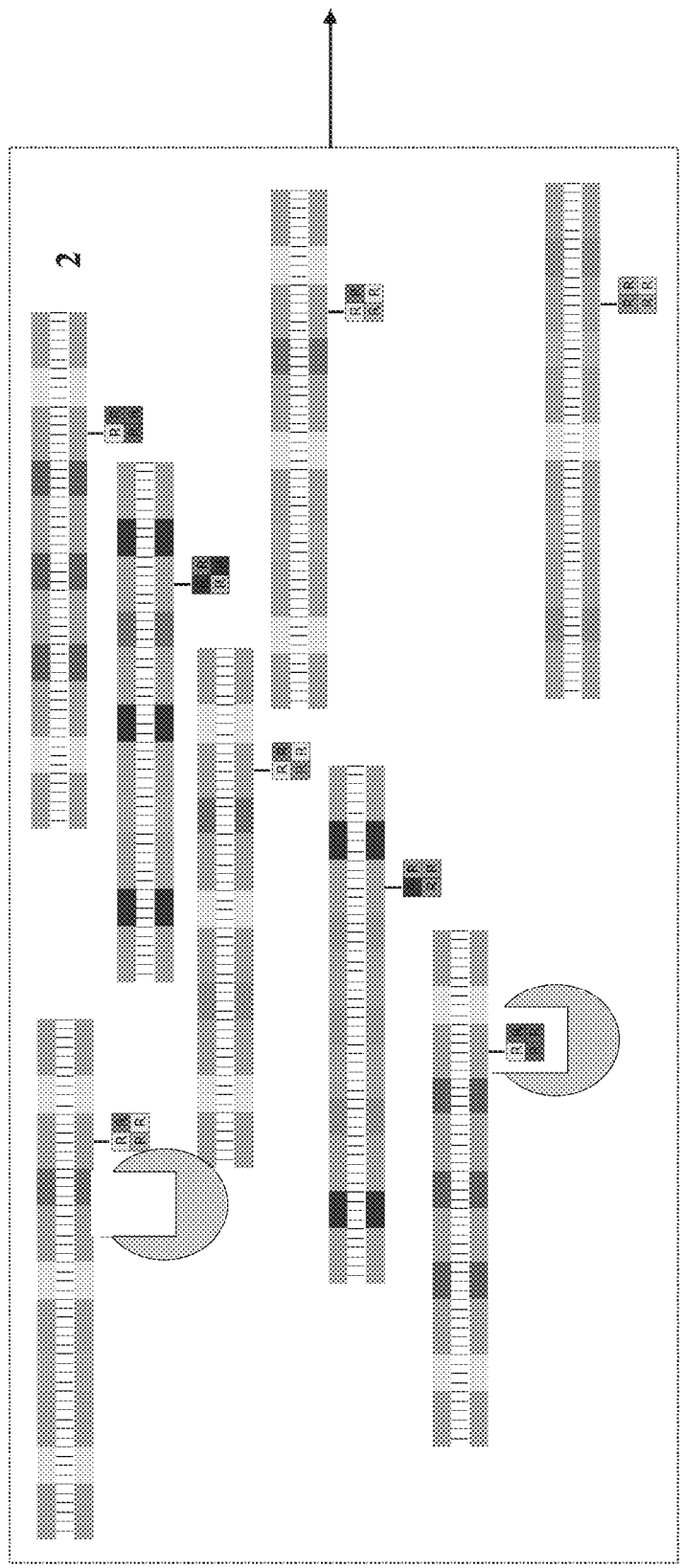
Figure 3, continued

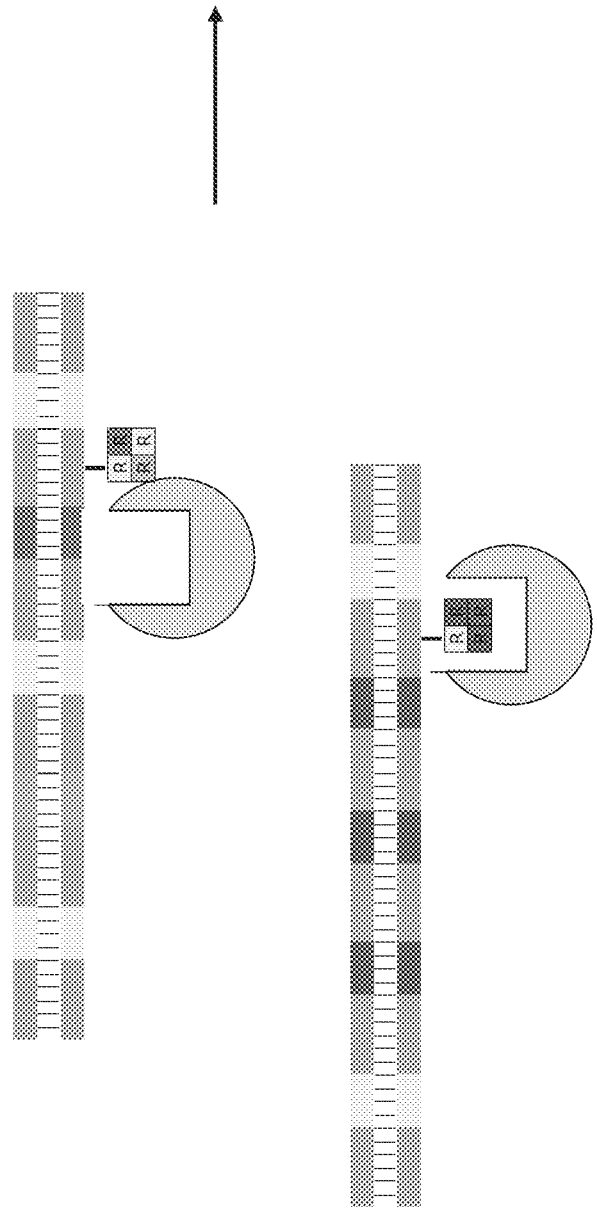
Figure 3, continued

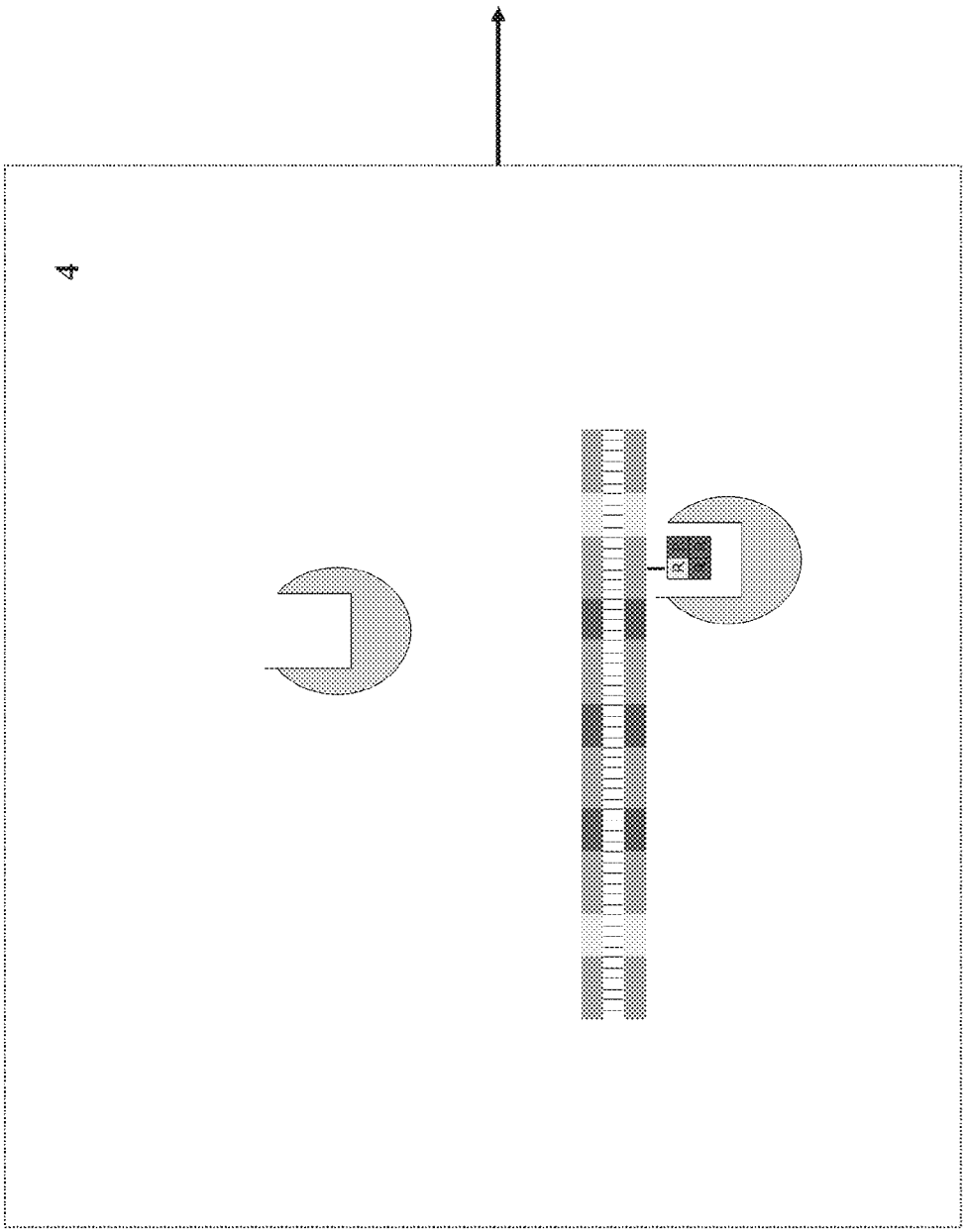
Figure 3, continued

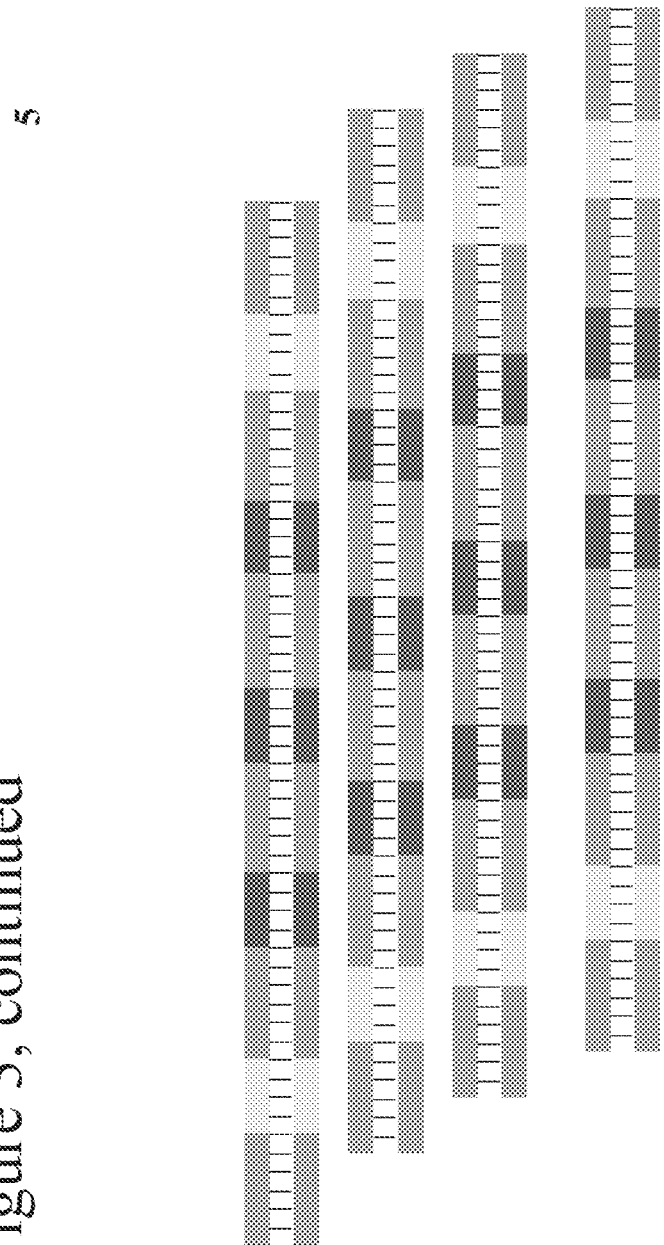
Figure 3, continued

R1 PCR product.
R2 Strand separation - top strand.
R3 Digest left stem with Bsa I.
R4 Ligate position 1 oligo guided by codon/anti-codon
R5 Digest upper stem with N. Alw I.
R6 Denaturation/re-naturation.

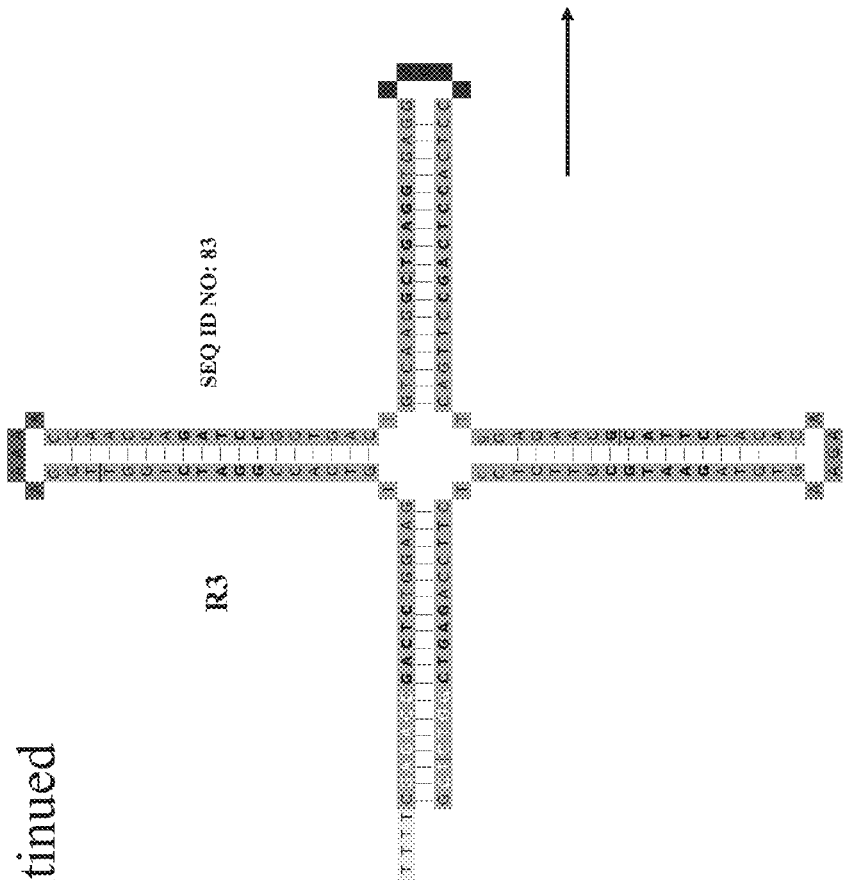
Figure 4a, continued
R1 PCR product.
R2 Strand separation - top strand.
R3 Digest left stem with Bsa I.
R4 Ligate position 1 oligo guided by codon/anti-codon
R5 Digest upper stem with N. Alw I.
R6 Denaturation/re-naturation.

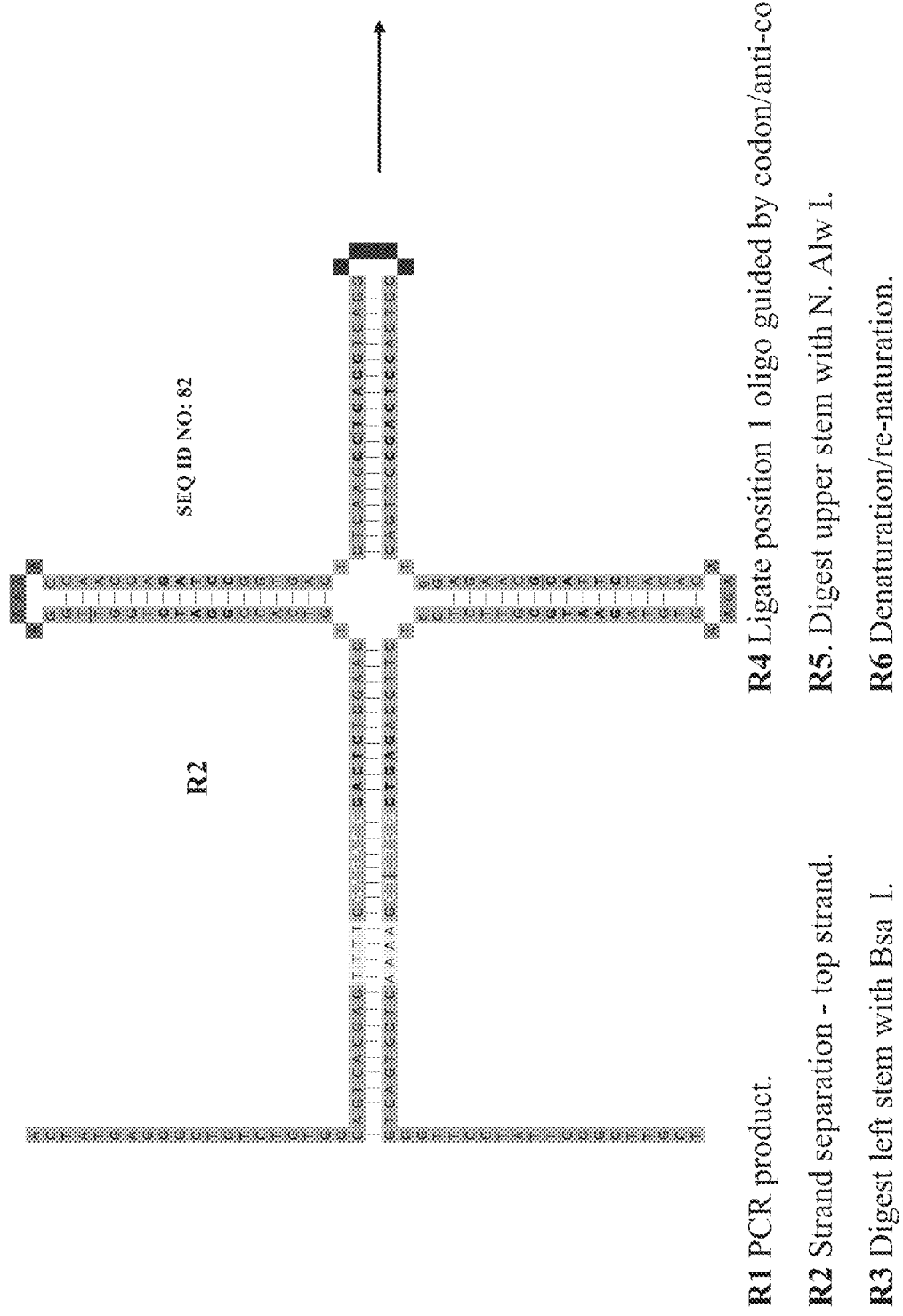
Figure 4a, continued
R1 PCR product.
R2 Strand separation - top strand.
R3 Digest left stem with Bsa I.
R4 Ligate position 1 oligo guided by codon/anti-codon
R5 Digest upper stem with N. Alw I.
R6 Denaturation/re-naturation.

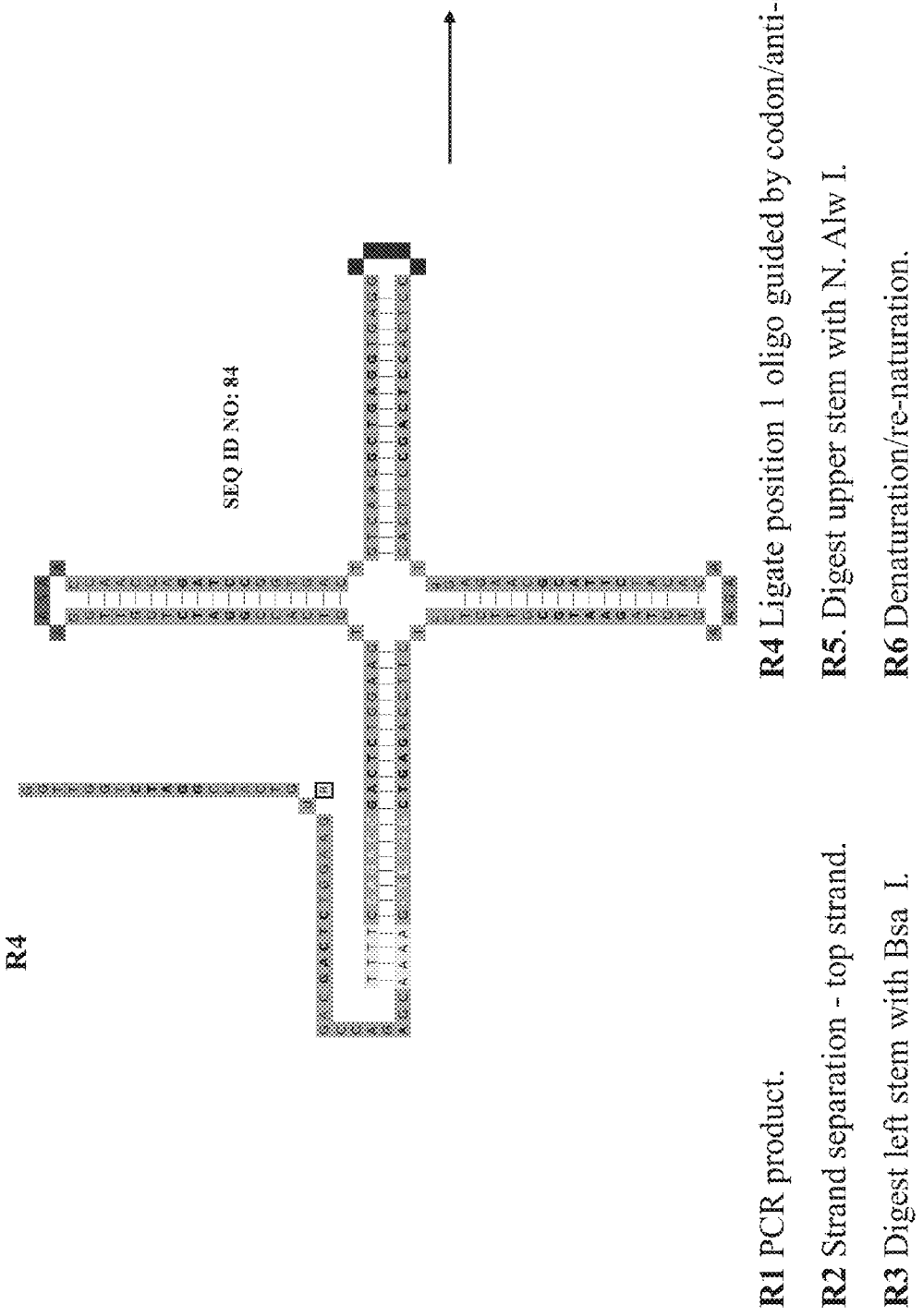
Figure 4a, continued
R1 PCR product.
R2 Strand separation - top strand.
R3 Digest left stem with Bsa I.
R4 Ligate position 1 oligo guided by codon/anti-codon
R5 Digest upper stem with N. Alw I.
R6 Denaturation/re-naturation.

Figure 4a, continued
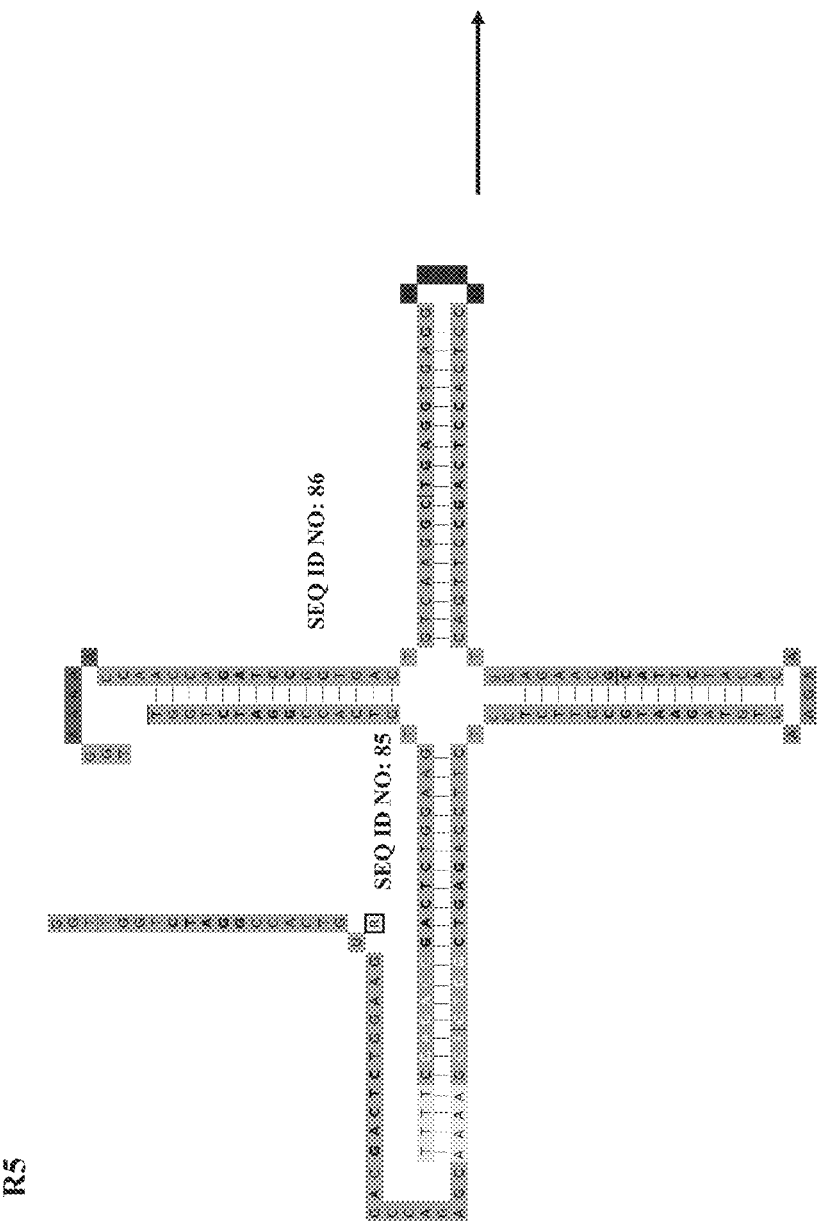
R1 PCR product.
R2 Strand separation - top strand.
R3 Digest left stem with Bsa I.
R4 Ligate position 1 oligo guided by codon/anti-codon
R5 Digest upper stem with N. Alw I.
R6 Denaturation/re-naturation.

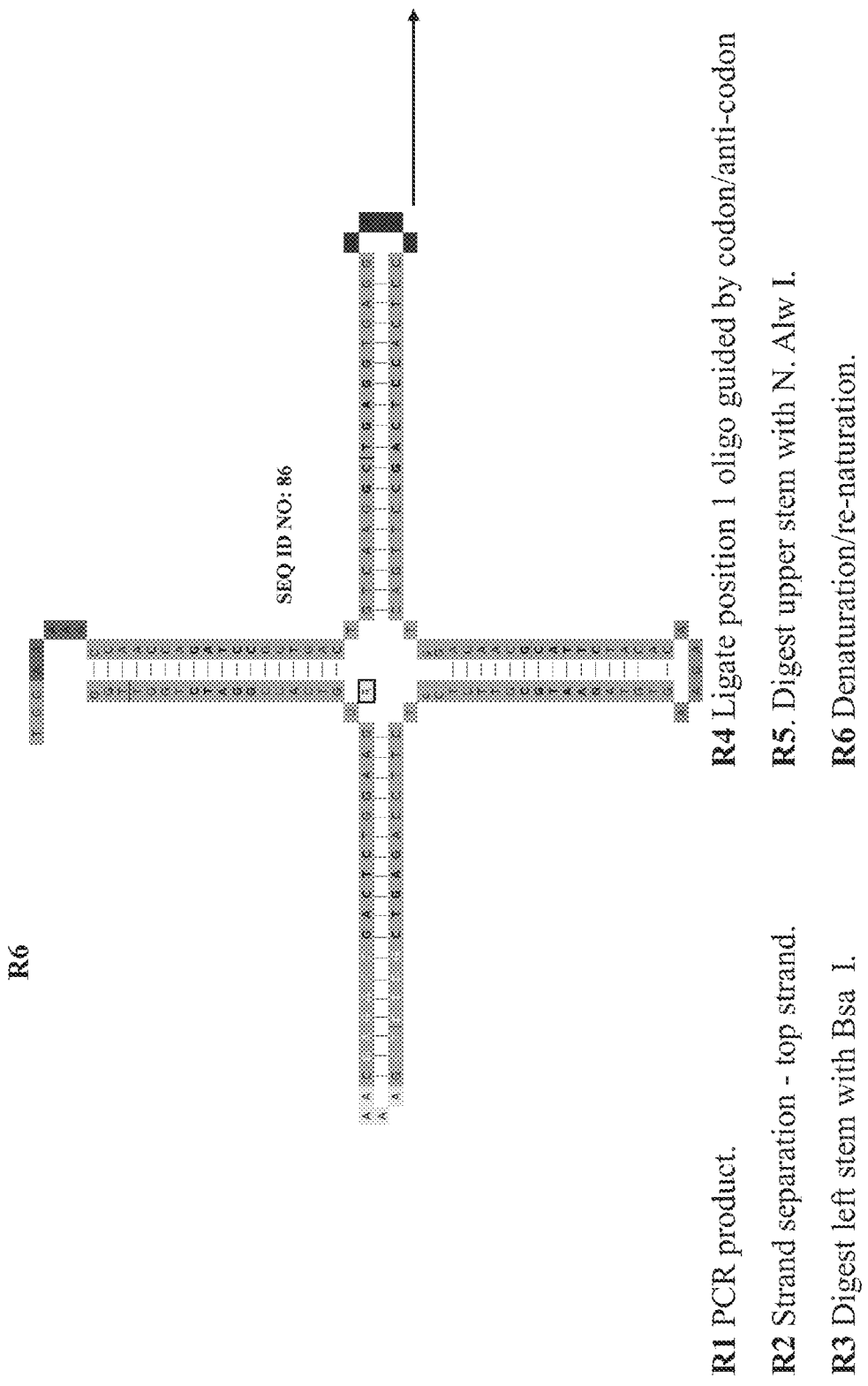
Figure 4a, continued
R1 PCR product.
R2 Strand separation - top strand.
R3 Digest left stem with Bsa I.
R4 Ligate position 1 oligo guided by codon/anti-codon
R5. Digest upper stem with N. Alw I.
R6 Denaturation/re-naturation.

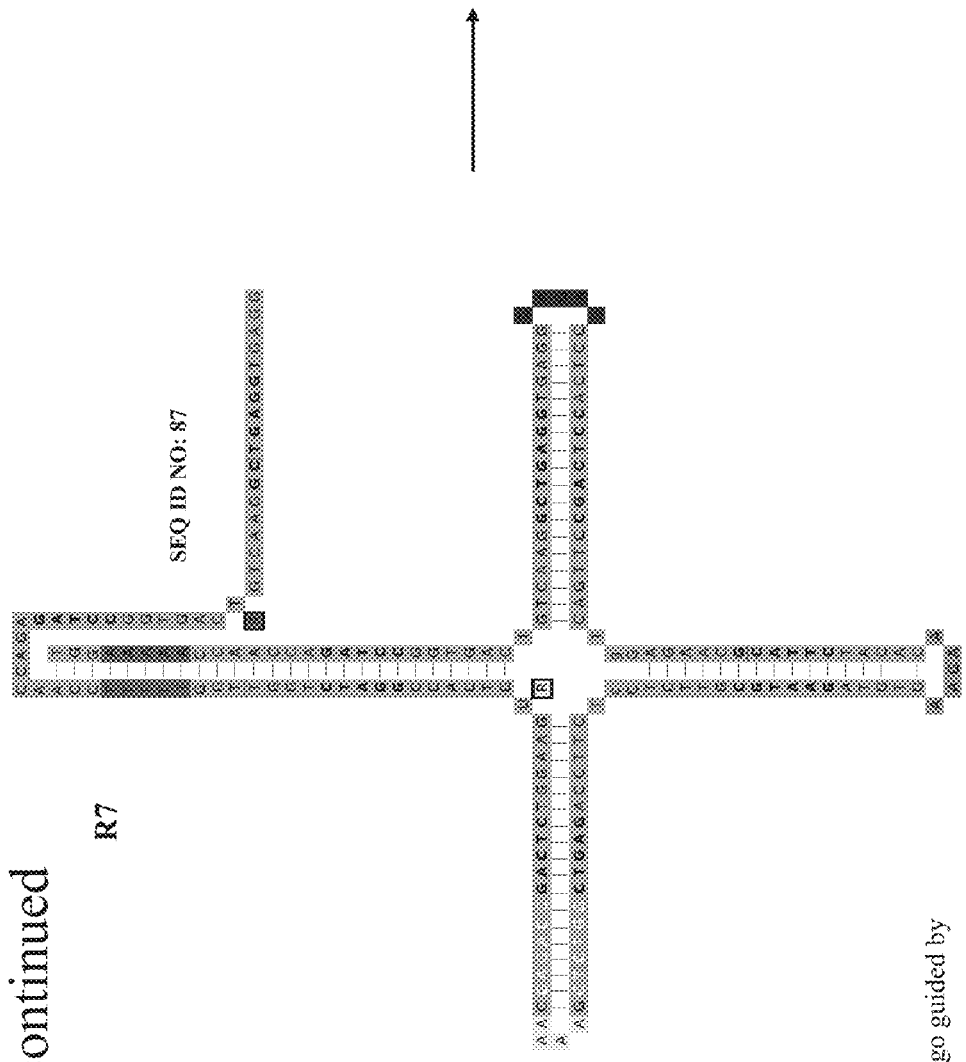
Figure 4a, continued

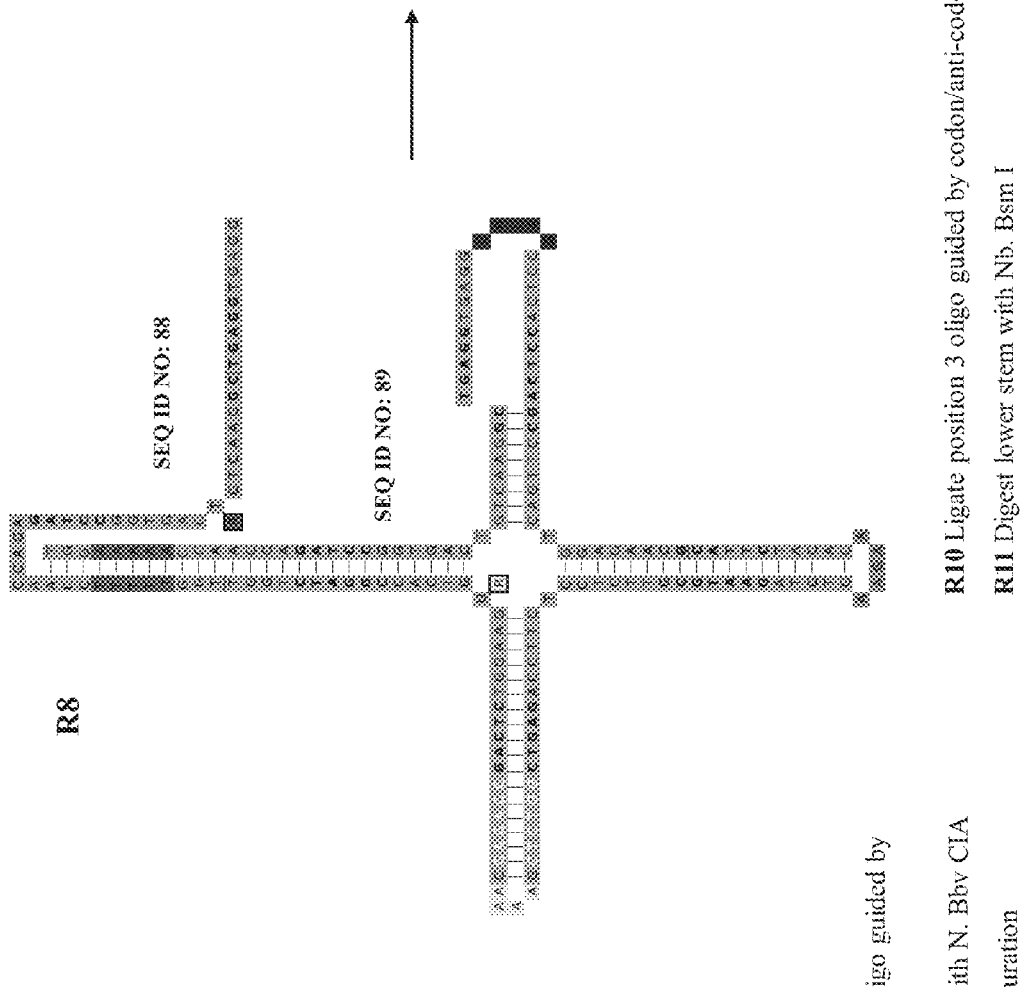
Figure 4a, continued

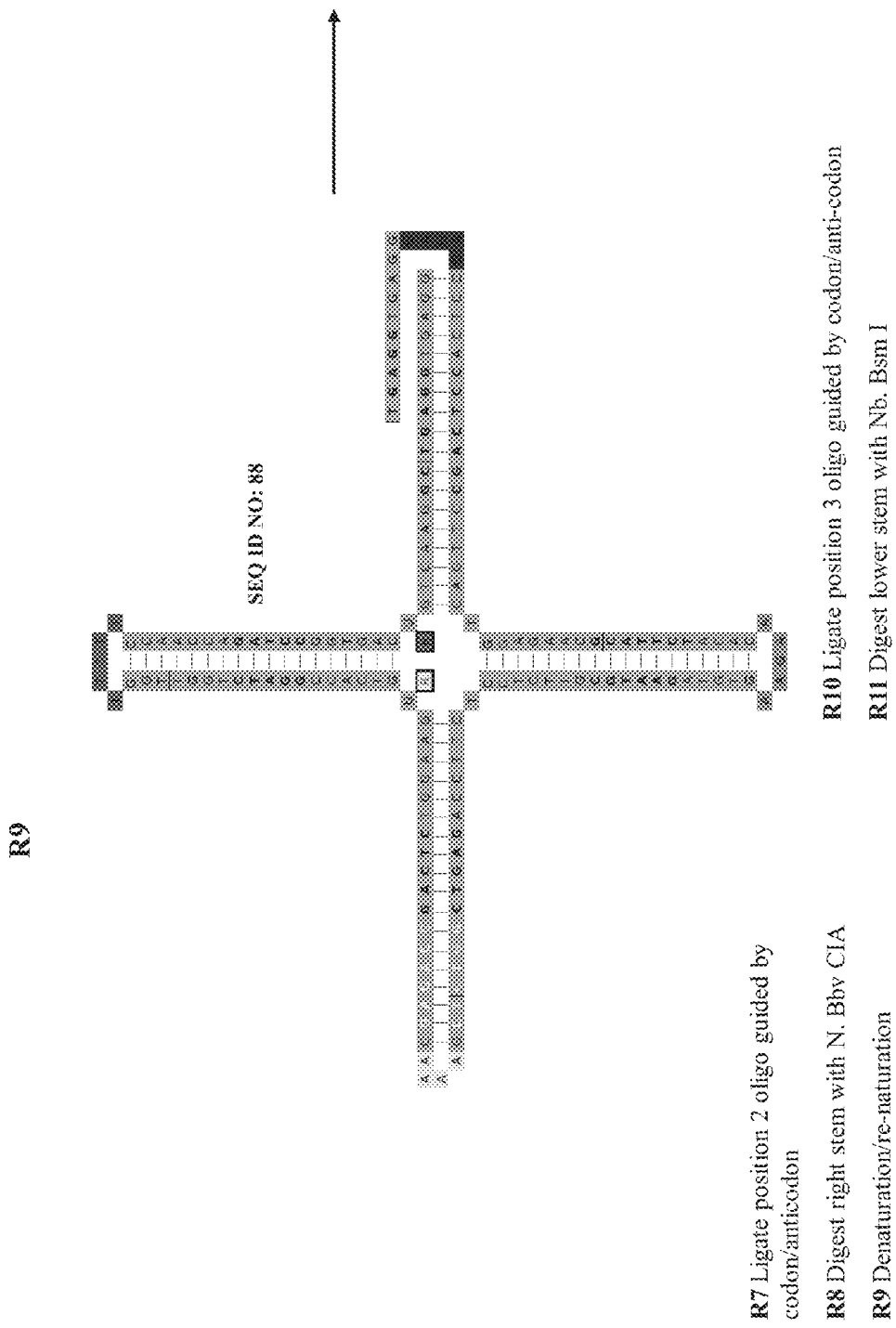
Figure 4a, continued

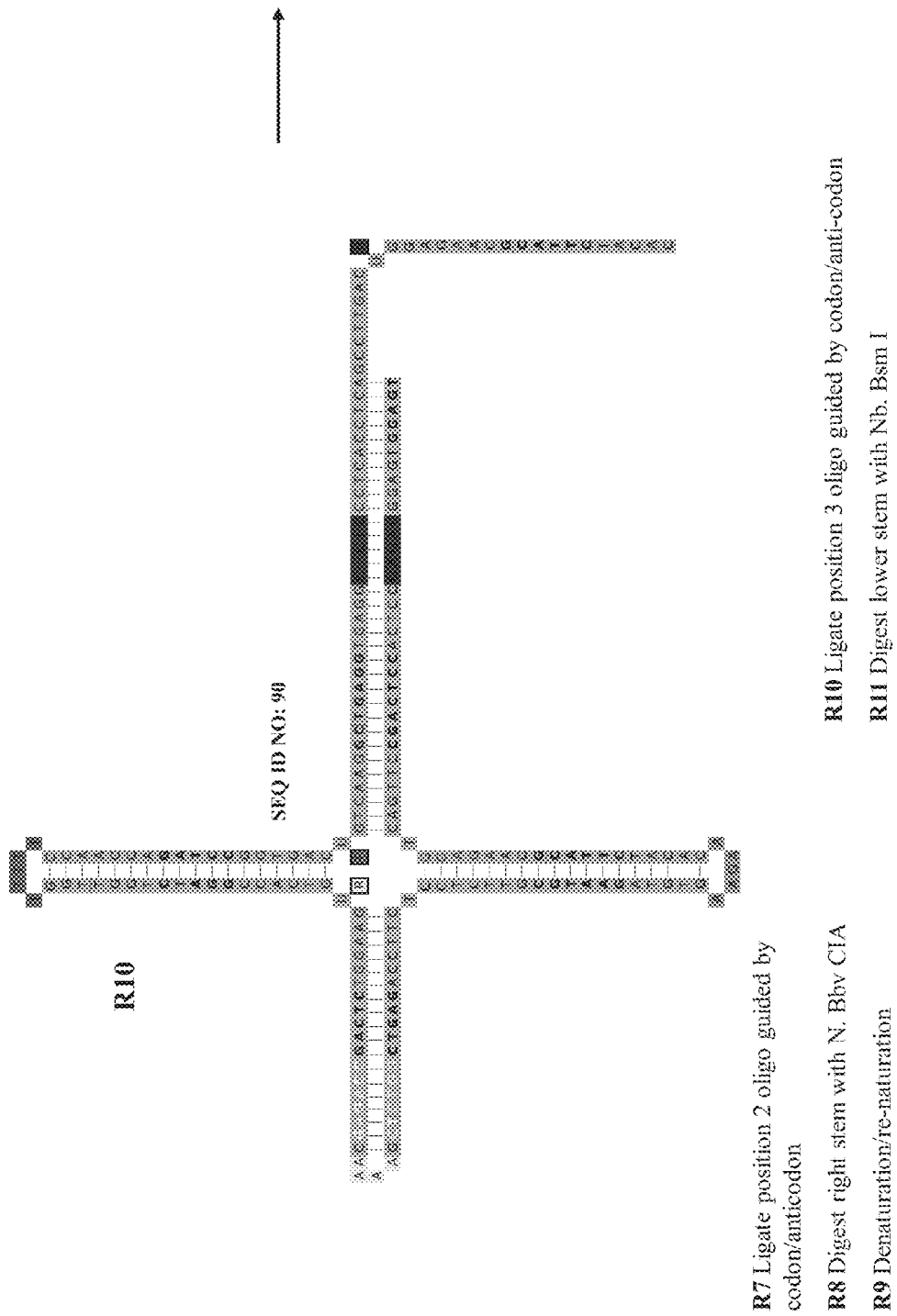
Figure 4a, continued

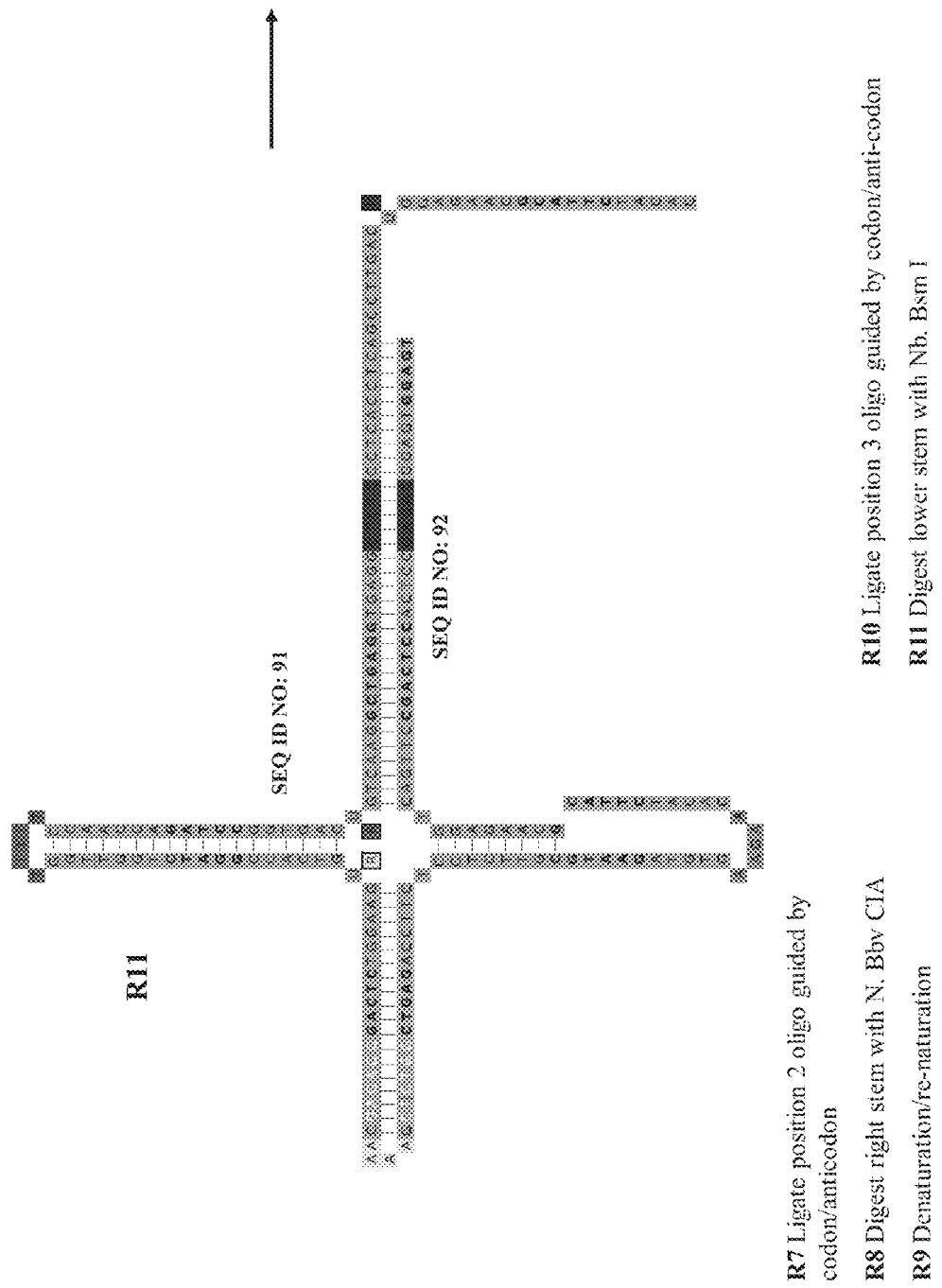
Figure 4a, continued

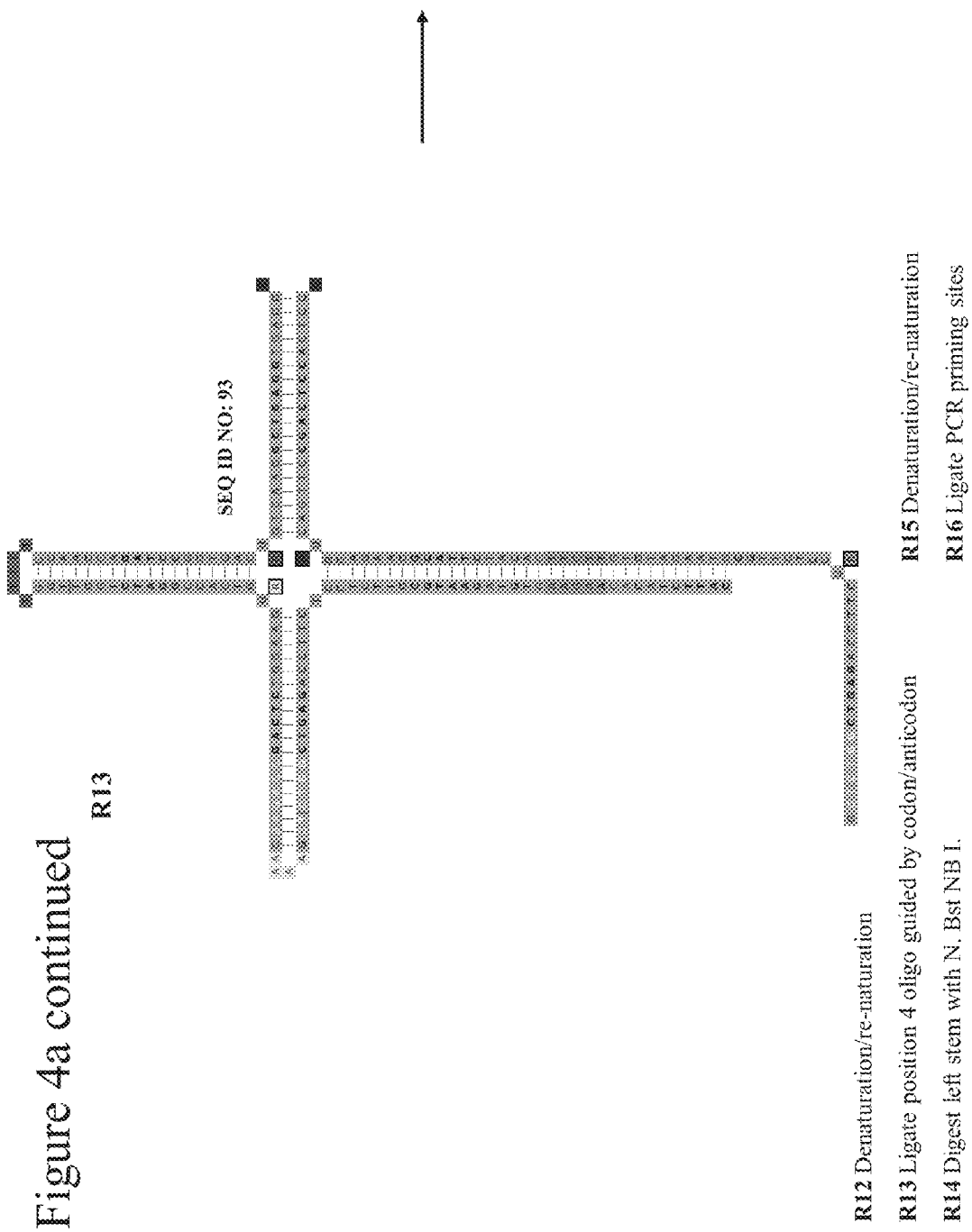

R12 Denaturation/re-naturation
R13 Ligate position 4 oligo guided by codon/anticodon
R14 Digest left stem with N. Bst NB I.
R15 Denaturation/re-naturation
R16 Ligate PCR priming sites Lane 1: vip076 and vip017.
Lane 2: vip076 and vip078.
Lane 3: vip017 and vip078
Lane 4: vip076, vip17 and vip078.

All oligonucleotides were in equimolar concentrations (2uM).

Figure 12
native PAGE
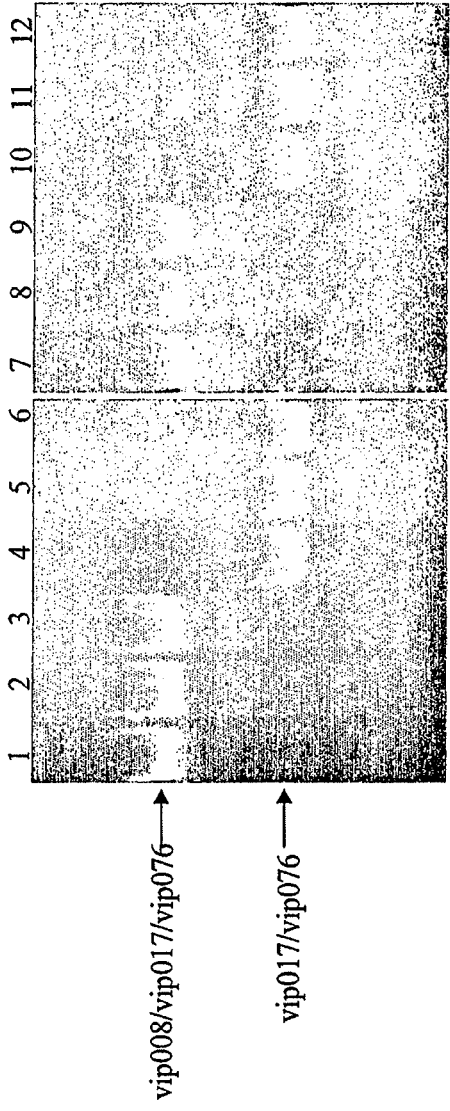
vip008/vip017/vip076 →
vip017/vip076 →
non-native PAGE
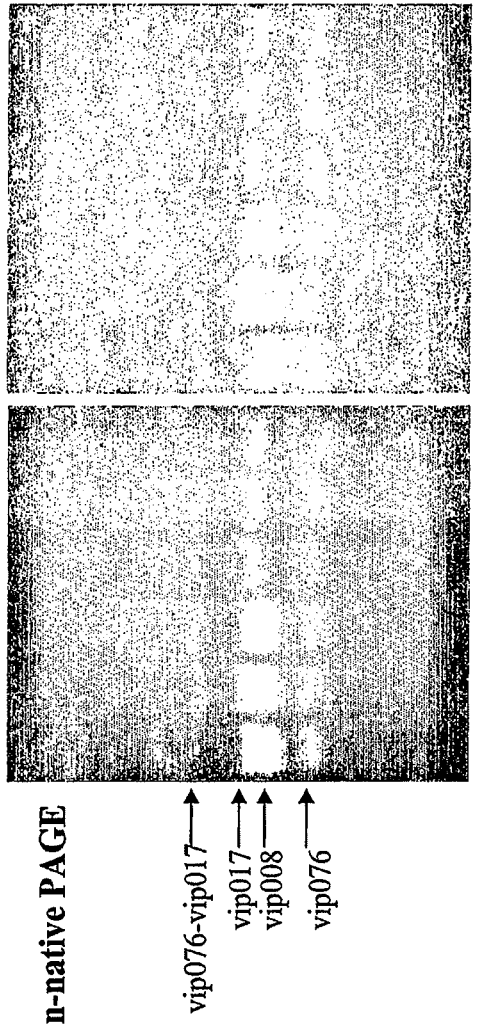
vip076-vip017 →
vip017 →
vip008 →
vip076 →
Lanes 1-6: EDC/sNHS activation
Lane 1: vip008, vip076 and vip17.
Lane 2: vip008, vip076 and vip17-Gly.
Lane 3: vip008, vip076 and vip17-Leu.
Lane 4: vip076 and vip17.
Lane 5: vip076 and vip17-Gly.
Lane 6: vip076 and vip17-Leu.
Lanes 7-12: Equivalent to lanes 1-6 without EDC/sNHS activation.
In all reactions each DNA oligo concentration was 2.5 uM.

| REACTION | REACTION TIME |
|---|---|
| 1 | 0 MIN |
| 2 | 5 MIN |
| 3 | 30 MIN |
| 4 | 60 MIN |
| 5 | 120 MIN |
| 6 | 240 MIN |
| 7 | OVER NIGHT |
| 8 | MORE ACTIVATOR (DMT_MM) ADDED AFTER 2h; INCUBATED OVER NIGHT. |
| 9 | MORE ACTIVATOR (DMT-MM) ADDED AFTER 2h AND 4h; INCUBATED OVER NIGHT. |
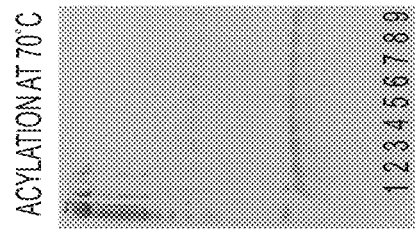
ACYLATION AT 70°C
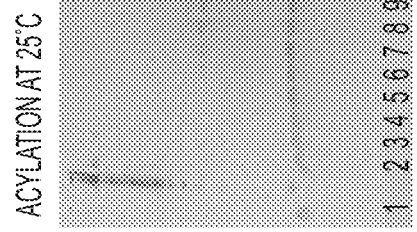
ACYLATION AT 25°C
FIG. 20

| LANE | |
|---|---|
| 1 | LADDER |
| 2 | BLANK REACTION MIXTURE |
| 3 | REACTION 1, pH 5.2 |
| 4 | REACTION 2, pH 5.5 |
| 5 | REACTION 3, pH 6.0 |
| 6 | REACTION 4, pH 6.5 |
| 7 | REACTION 5, pH 7.0 |
| 8 | REACTION 6, pH 7.5 |
| 9 | REACTION 7, pH 8.0 |
| 10 | BLANK REACTION MIXTURE |
| 11 | ssDNA ref |

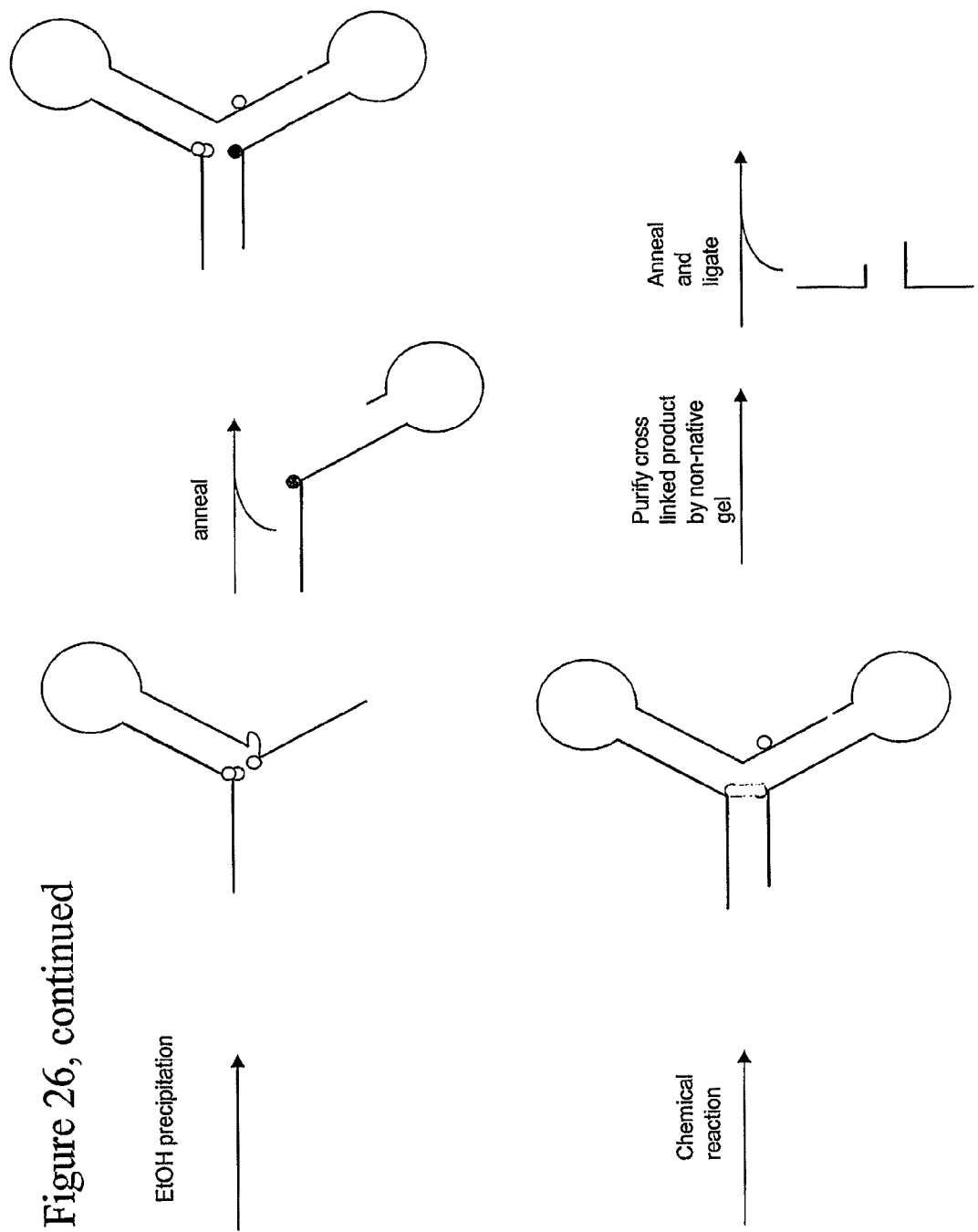
Figure 26, continued

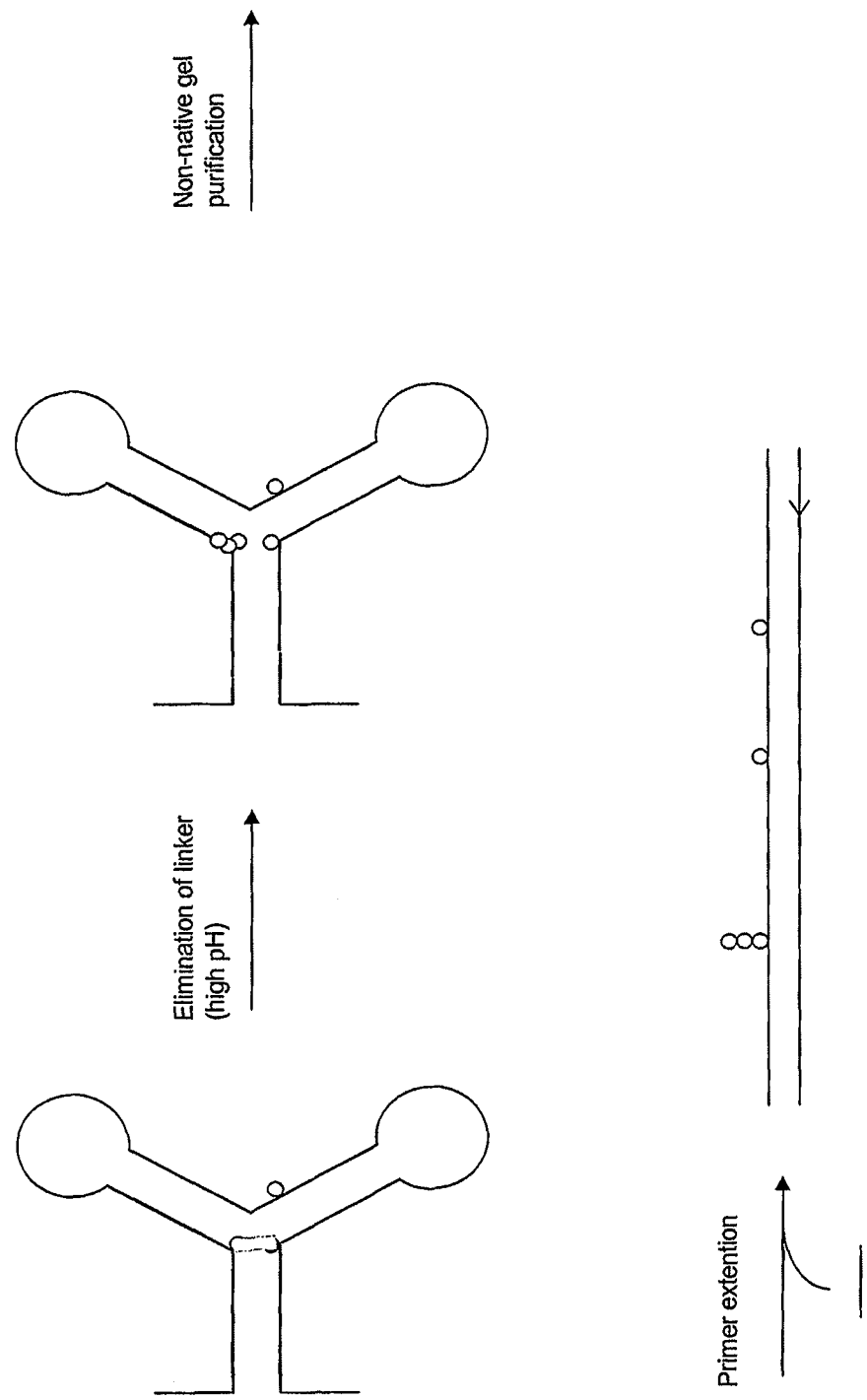
Figure 26, continued

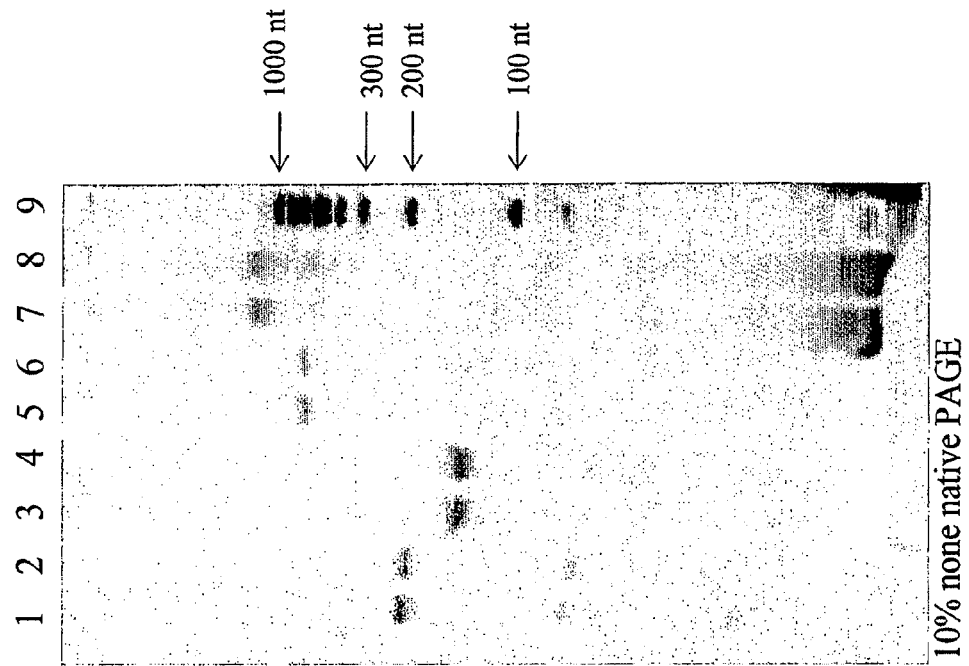
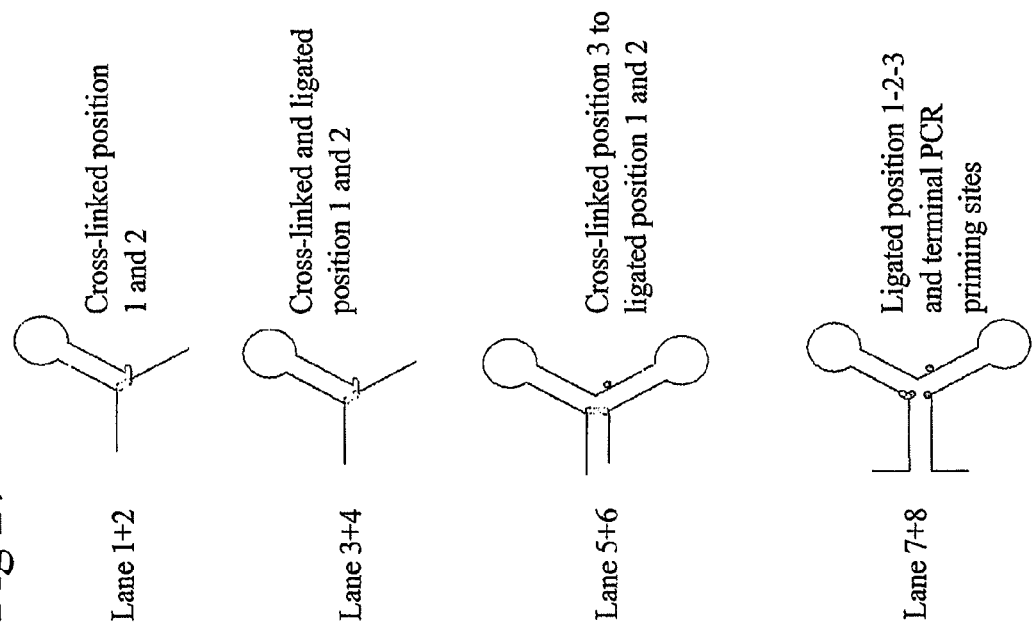
Fig 27

Figure 29: PCR amplification of gel-purified bands from EMSA assay

Figure 30    DNA Star Structure direction of Reductive amination

Figure 31 – Structural DNA directed Urea Formation

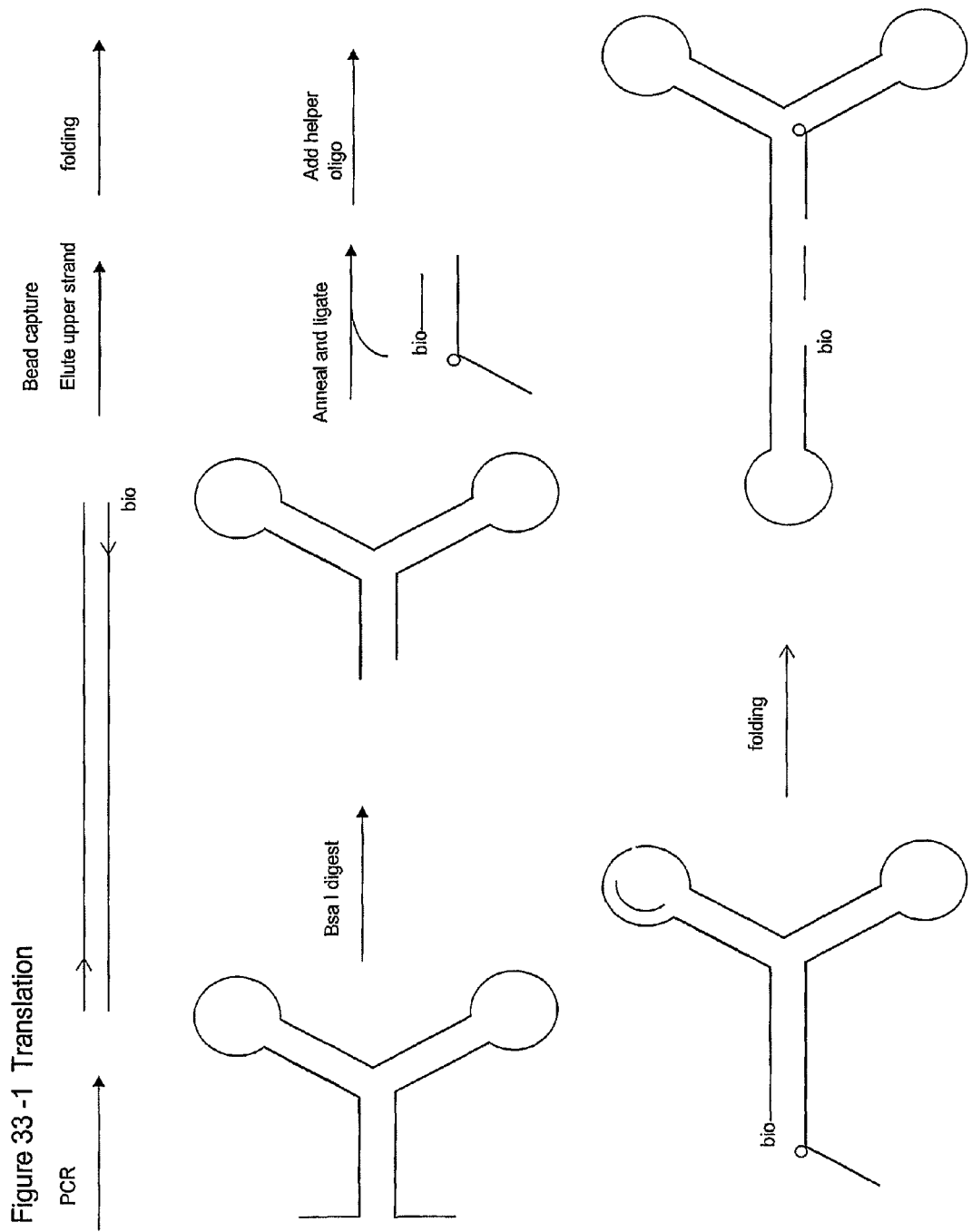
Figure 33-1 Translation

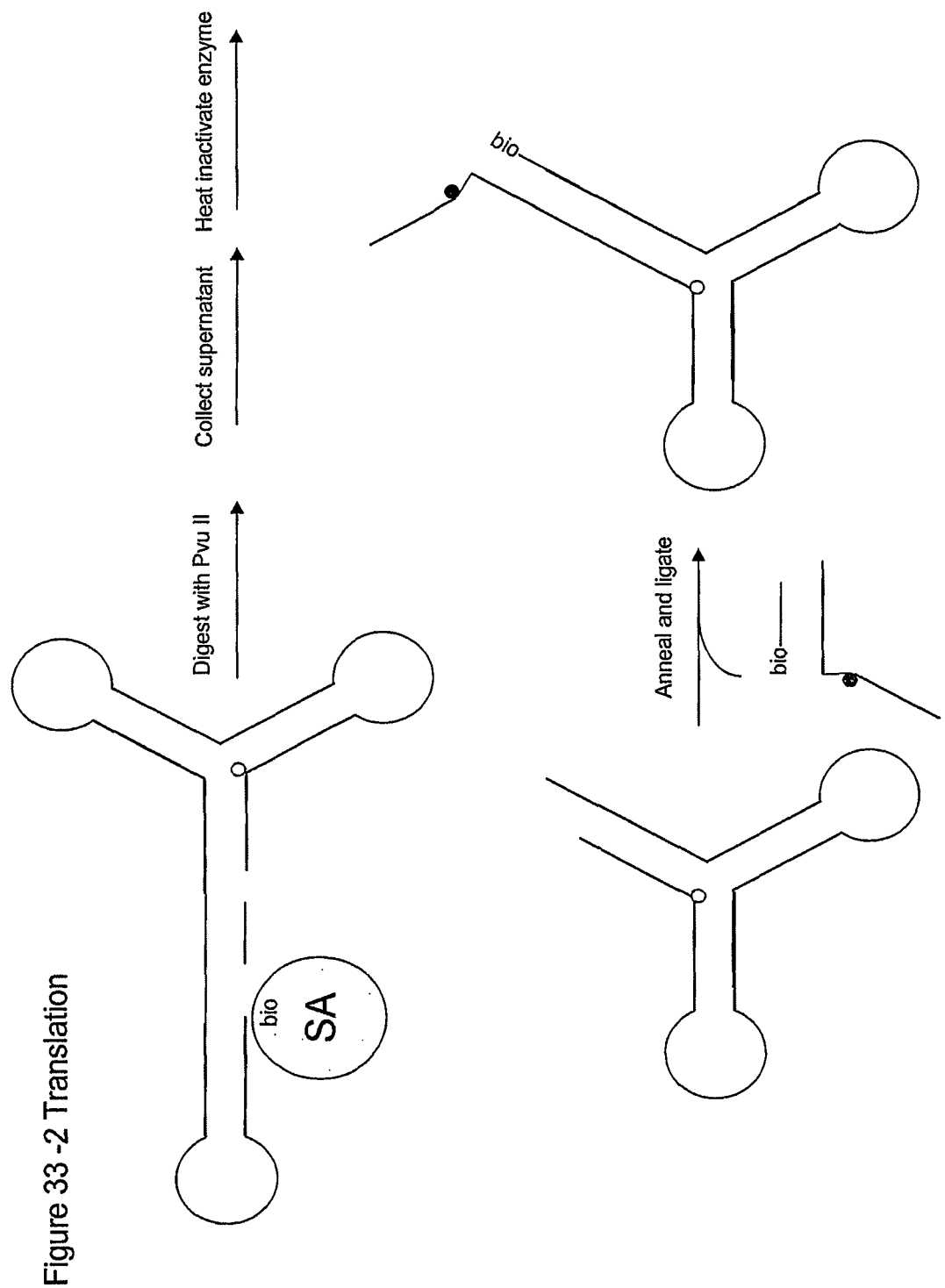
Figure 33 -2 Translation

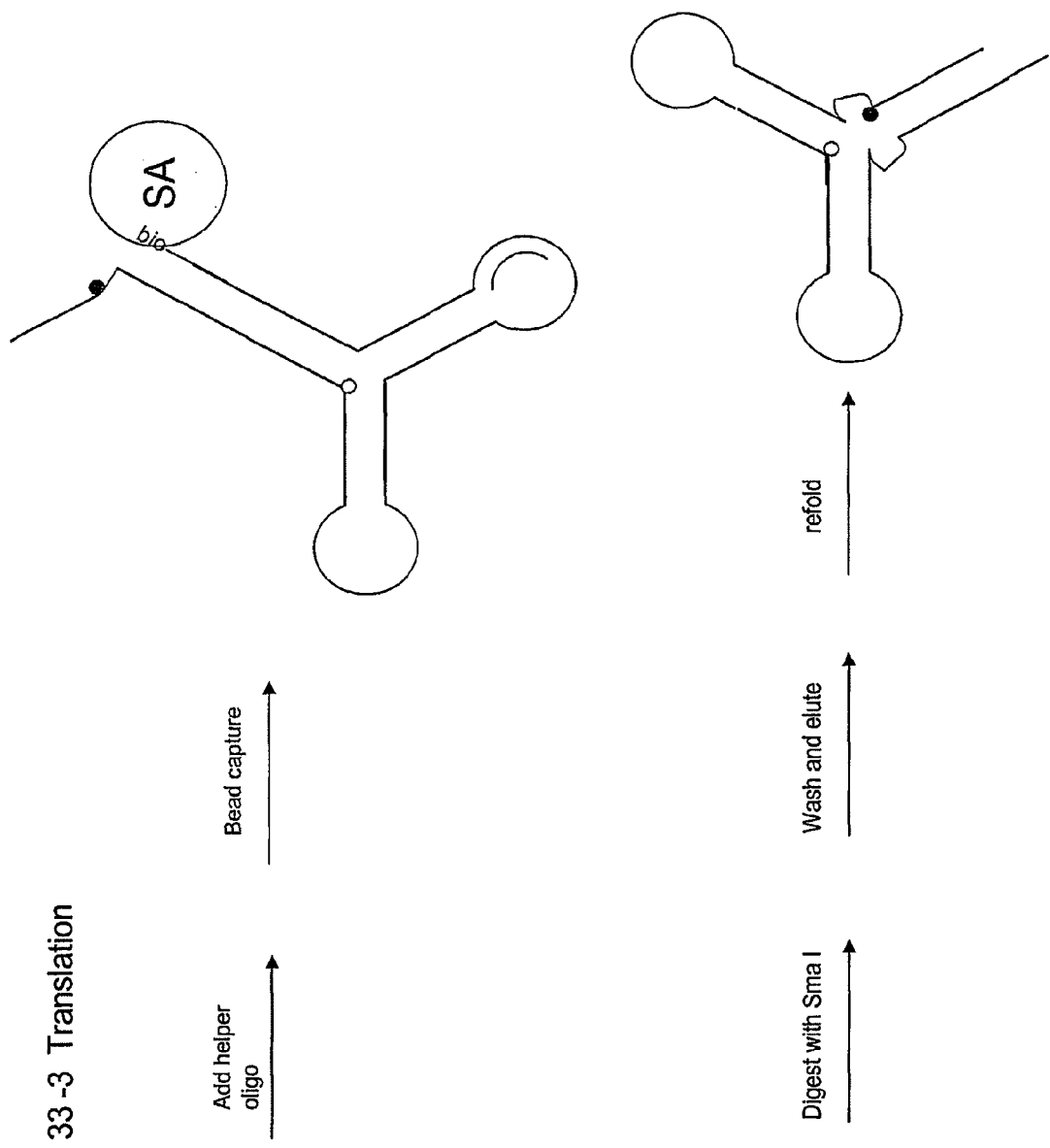
Figure 33-3 Translation

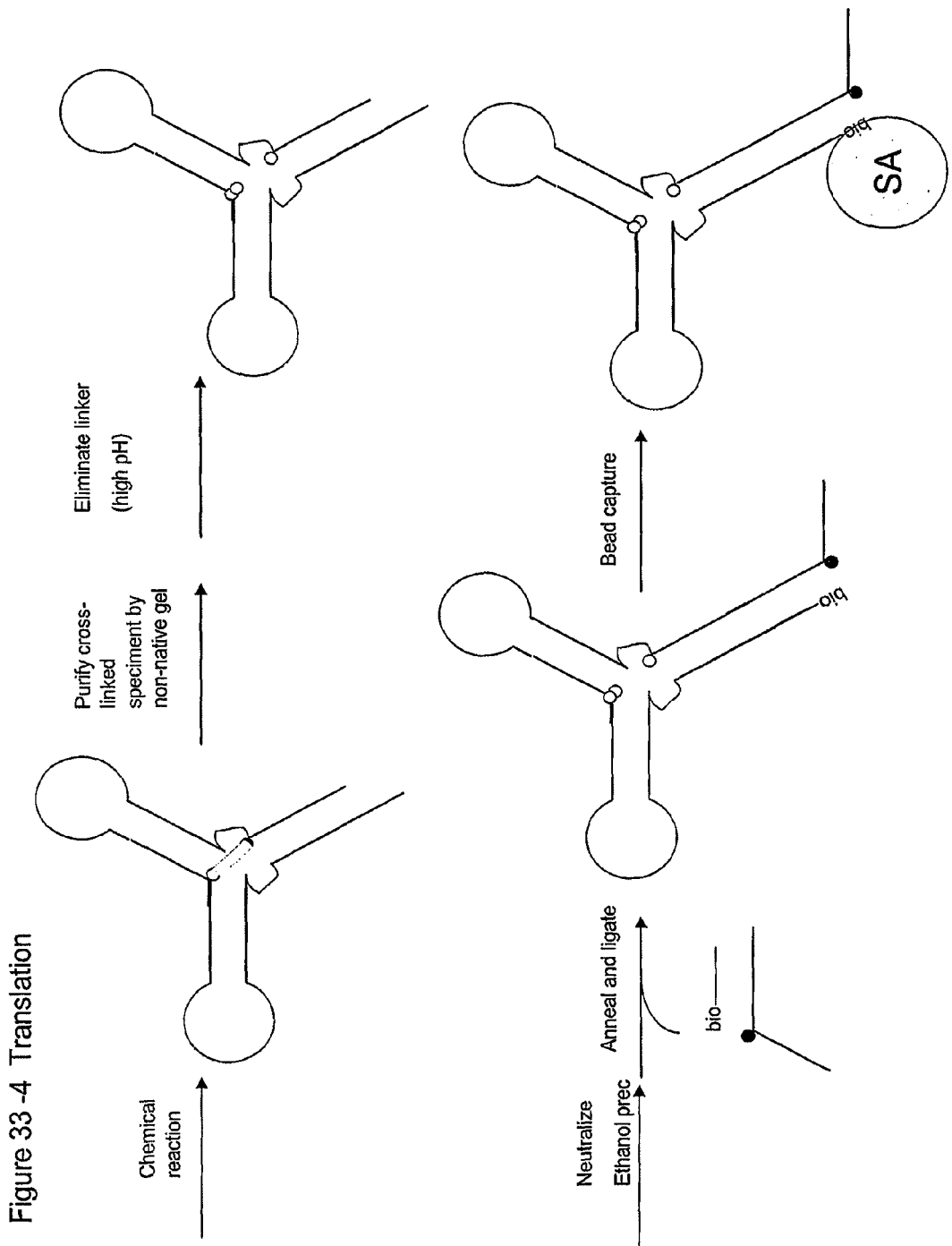

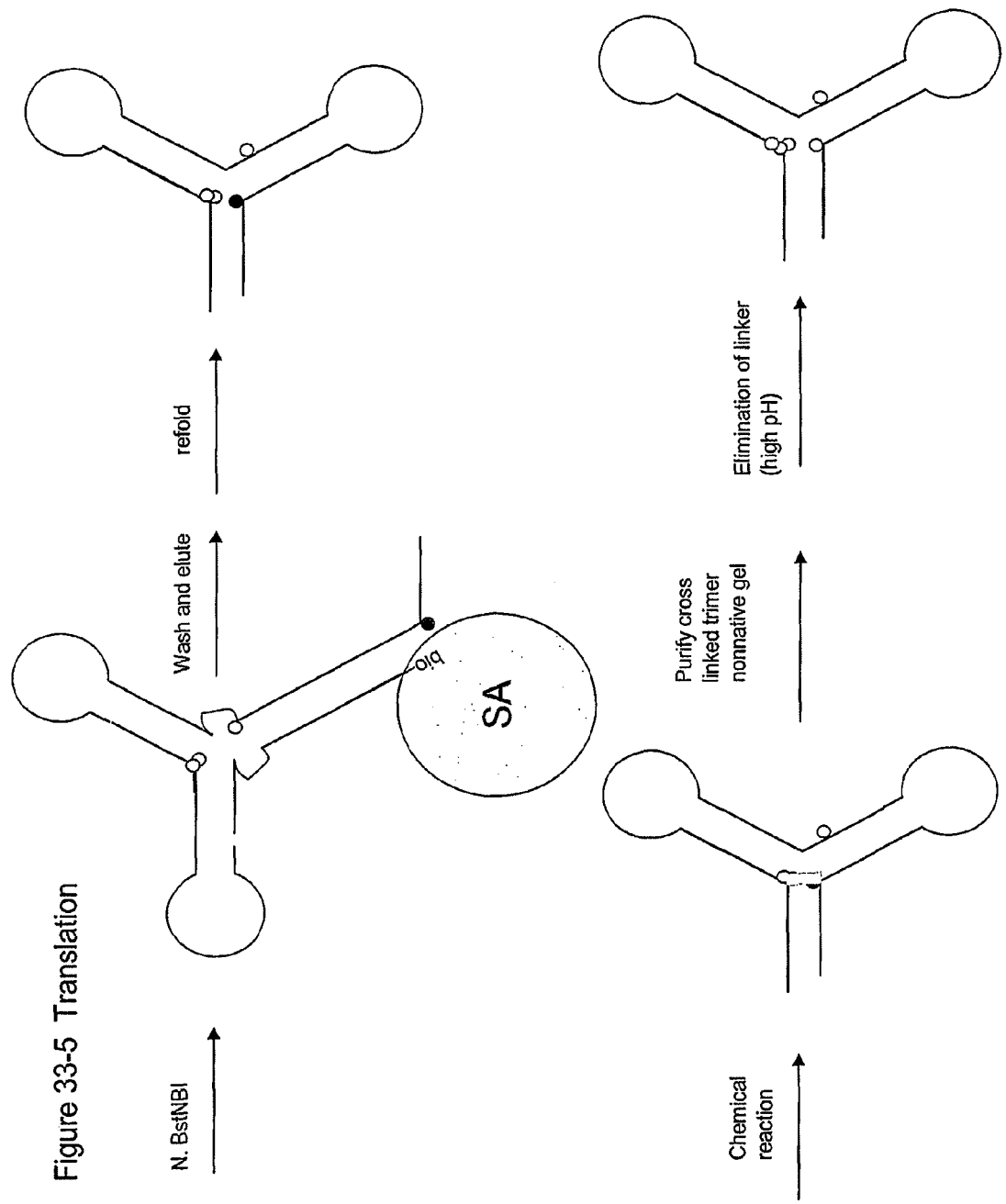
Figure 33-5 Translation

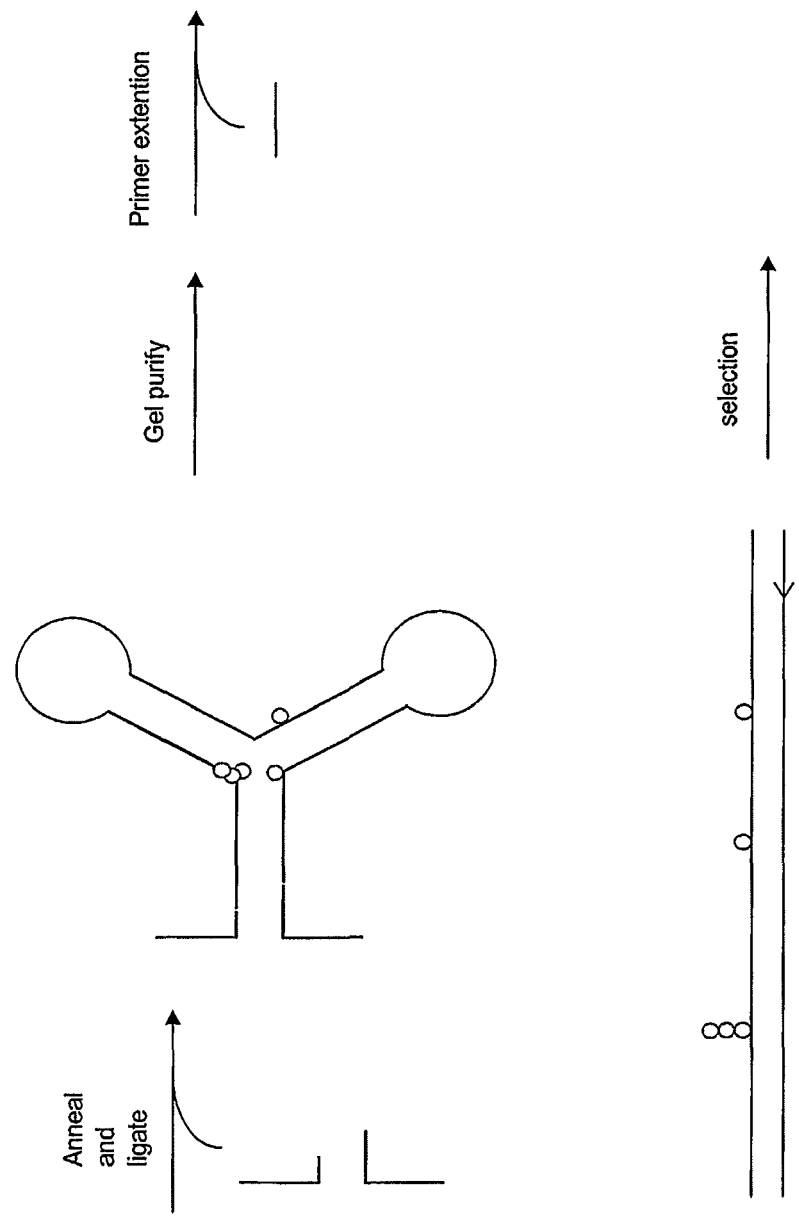
Figure 33-6 Translation 1. uncut starting material
M: 100 bp ladder (Fermentas SM0248)
2-7. Bsa I digest Boxed Gel piece isolated

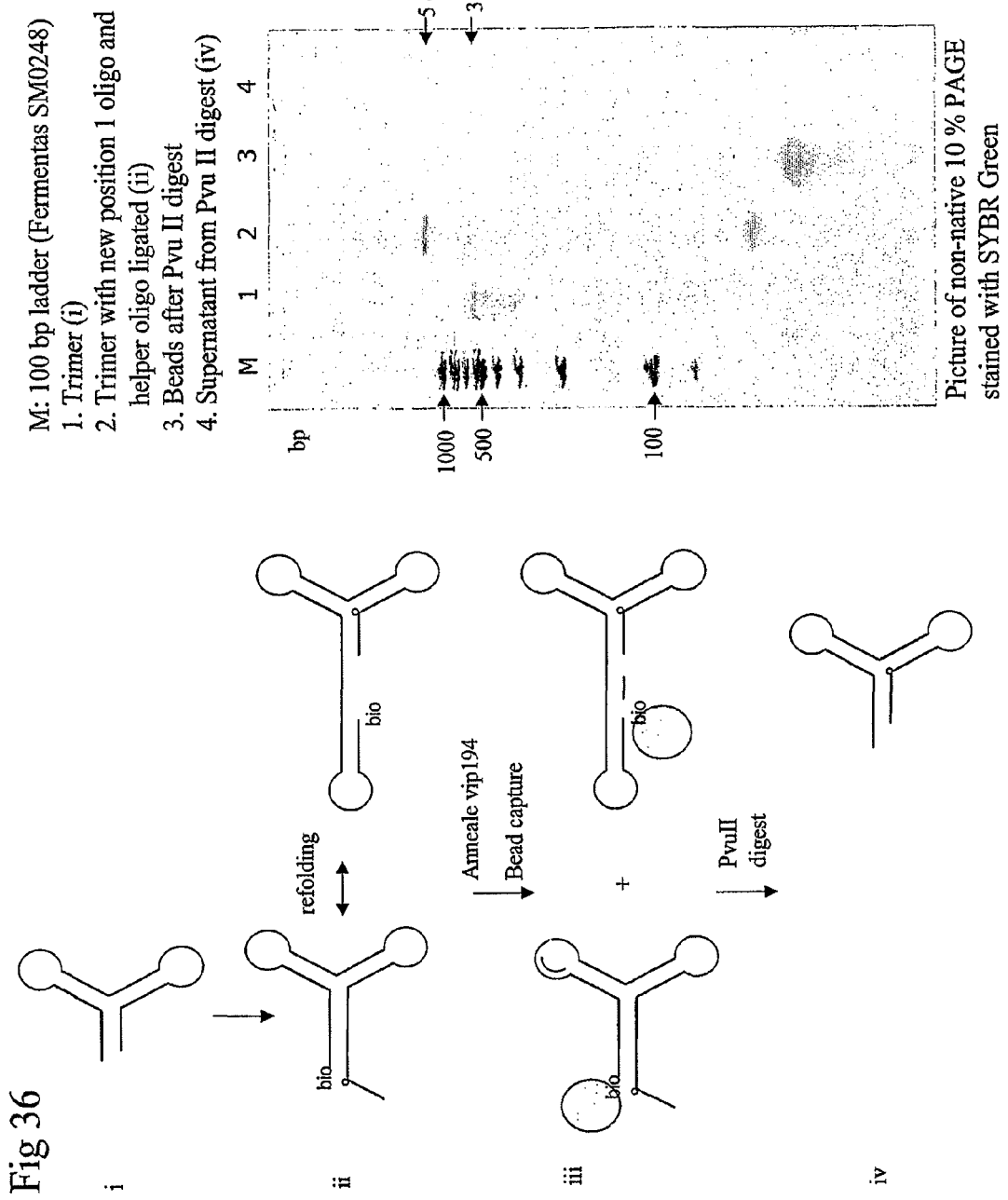

STRUCTURAL NUCLEIC ACID GUIDED CHEMICAL SYNTHESIS

CROSS-REFERENCE TO RELATED APPLICATIONS

This a divisional of U.S. patent application Ser. No. 11/577,649 (now U.S. Pat. No. 8,202,823), which is a 371 National Stage Entry of PCT/DK2005/000714, filed Nov. 8, 2005, which claims benefit from U.S. Provisional Application Nos. 60/687,849, filed Jun. 7, 2005, and 60/725,347, filed Oct. 11, 2005. The entire disclosures of the prior applications are considered part of the disclosure of the accompanying application and are hereby incorporated by reference.

FIELD OF THE INVENTION

The present invention provides compositions and methods for in vitro DNA display technology, allowing display of variety of molecules, such as non-natural polymers and small molecules. Advantages of such methods are that combinatorial libraries can be constructed and subjected to rounds of selections for desired activities, amplification and diversification, thus allowing molecular evolution.

BACKGROUND

Display technologies have been developed to combine information storage and amplification capabilities of nucleic acids with the functional activities of other compound. Display technologies rely on an association between a functional entity and a nucleic acid sequence informative about the structure of the functional entity. An advantage of such methods is that very large libraries can be constructed and probed for a desired activity of the functional entities. Library members having the desired activity can then be partitioned from library members not having the desired activity, thus creating an enriched library with a higher fraction of members having the desired activity. This process is called selection. The structures of the library members in the enriched library can then be identified by their cognate nucleic acid sequence, thus allowing identification even from minute amounts of material.

Some display technologies further allow the enriched library to be amplified without knowing the identity of its members; not merely the nucleic acid sequences but the functional entities too. Such display technologies are called "amplifiable display technologies". These technologies are especially advantageous when dealing with large libraries, because iterative rounds of selection and amplification can be performed allowing increased enrichment of desired activities. Another advantage of amplifiable display technologies is that rounds of selection, amplification and diversification can be performed, thus using the same principle as in natural selection, to evolve molecules with desired function. This process is called molecular evolution.

Display technologies utilizing biological systems have been developed, the most notable of which is phage display (Smith, Science, 228, 1315-7, 1985). However, such systems are limited to the display of natural occurring products such as proteins and peptides.

In vitro display technologies exploiting the flexibility of organic chemistry has been described. One example is described in U.S. Pat. No. 5,723,598. The method uses a bifunctional molecule; one functionality capable of accepting a chemical group and one functionality capable of accepting a nucleic acid sequence. The method for synthesizing such a library is commonly known as "split and mix", consisting of rounds of mixing and splitting the bifunctional molecules into compartments. A compartment specific pair of chemical group and nucleic acid sequence is added. The nucleic acid sequences are thus encoding the chemical groups. All bifunctional molecules are then mixed and the process iterated to create a large combinatorial library. The library is then subjected to selection and the selected nucleic acid sequences amplified by PCR, which may be used for identification by conventional molecular biology; cloning and DNA sequencing.

Another example is described in WO04/039825A2, where a combinatorial library is created, by rounds of proximity-guided addition of cognate pairs of chemical group and nucleic acid code to a bifunctional molecule; one functionality capable of accepting a chemical group and one functionality capable of accepting a nucleic acid sequence. Furthermore repertoires of so-called transfer units are used, where a chemical group is attached to an oligonucleotide, containing a coding segment and a segment capable of annealing to the bifunctional molecule. A repertoire of transfer units is annealed to the bifunctional molecules, which allows the code to be transferred enzymatically to the bifunctional molecule, as well as guiding the chemical group to react with the very same bifunctional molecule. This process can be reiterated to create a large combinatorial library.

The libraries described above can be subjected to selections to form an enriched library. The enriched libraries members' synthetic history can subsequently be deduced through the encoding nucleic acid. A limitation of these approaches is however that the enriched library cannot be amplified.

In vitro display technologies taking advantage of the flexibility of organic chemistry and rounds of selections, amplification and diversification has been described. These methods rely on the use of templates.

One example is described in WO00/23458, using a "split and mix' principle. A library of ssDNA templates is used, each containing a chemical reaction site and several positions of codon segments. The templates are compartmentalized by virtue of hybridizing to a repertoire of anti-codon sequences for a given codon position. Then, a compartment specific chemical reaction is performed modifying the reaction site on the templates. The templates are then mixed and the process reiterated by using other codon positions to form a combinatorial library.

Another example is described in WO02/074929A2, using a "single-pot" principle. A library of oligonucleotide templates is used, each containing a chemical reaction site and several positions of codon segments. Furthermore, using a repertoire of transfer units, the method consists of an oligonucleotide anti-codon sequence and a chemical reactive group. The library of templates are hybridized with a repertoire of transfer units for a given codon position. This brings the chemical group on a hybridized transfer unit in proximity to the reaction site on the hybridized template, which consequently guides the chemical reaction of cognate pairs. This process is then reiterated using other codon positions to form a combinatorial library.

A limitation of the above proximity guiding of cognate pairs of code and chemical group is given by the linear structure of the template oligonucleotide. As a consequence of the linearity the distance between codon and the chemical reaction site will differ from codon position to codon position. For codon positions longer away from the reaction site the proximity guiding becomes compromised, as the local concentration drops to the power of three as a function of the distance.

This disadvantage becomes more pronounced for complex libraries, with more codon positions and more complex codons.

This problem is sought solved in WO04/016767A2, where the transfer units besides from an anti-codon segment also contain a constant segment, which is complementary to a constant sequence on the template close to the reactive site. Thus, by hybridizing a transfer unit to a template results in that the template sequence between the codon position in question and the constant segment is bulging out, to form a so-called omega structure. The concept is that the codon segment is responsible for the specificity and the constant segment responsible for the proximity. Also suggested in WO04/016767A2, is a so-called T-architecture of the templates, where the reactive site on the template is situated in the middle of the template, with the codon positions spread out on each side. Consequently, the distance problem is so called "cut in half".

WO 2004/056994A2 discloses a method similar to WO02/074929A2 or WO04/016767A2 with the difference that the template is cut into minor sequences, termed connecting polynucleotides in the application. The connecting polynucleotides connect transfer units to bring these into reaction proximity. In certain embodiments the connecting polynucleotides may comprise a reactive chemical group. To obtain an encoded molecule the method is dependent upon codon/anti-codon recognition prior to reaction.

The template directed libraries described above are subsequently subjected to selections to form enriched libraries. The enriched libraries members' synthetic history can then be deduced through the encoding nucleic acid. The enriched libraries can also be amplified and diversified by for example error prone PCR, thus allowing for molecular evolution.

A limitation in these approaches is that a large number of templates have to be created, which is cumbersome, as the templates have to be of considerable length to ensure proper codon/anti-codon hybridization. In methods using a plurality of minor sequences to make up the final directed synthesis the number of sequences to be synthesized is even higher than the actual library size.

The prior art methods using templates suffer from the disadvantage that the encoding is dependent upon hybridization of codon and anti-codon sequences. Sometimes hybridization between single stranded oligonucleotides will happen without perfect complementarities. In the case of library construction the result is loss of the association between the encoding and the synthetic history. Consequently, upon selection positive codes may be de-selected and negative codes may be selected. For more complex libraries this disadvantage becomes more significant as the complexity of the single stranded oligonucleotides also increases, both with respect to numbers, length and sequences. This makes the processes more difficult to control.

As described above in vitro display technologies allowing display of a variety of compound classes, selections, amplifications and diversifications have been developed. However, there is still an ongoing need for improvement, especially with respect to the quality in library construction and of diversification. The present invention offers a method for producing an encoded molecule in which the method does not require the pre-synthesis of a large number of templates. Furthermore, the present method is not dependent upon codon/anti-codon recognition for an encoded molecule to be formed.

SUMMARY OF THE INVENTION

The present invention relates to in vitro display technology taking advantage of the flexibility of organic chemistry, and permitting rounds of selection, amplification and diversification.

In particular, the present invention relates to a composition comprising a nucleic acid and a chemical compound, said composition forming a star structure defining 3 or more stems extending from a reaction center, wherein the stems are formed by a nucleic acid duplex and the chemical compound has been formed in the reaction center as the reaction product of 3 or more chemical groups.

The nucleic acid forms a super structure, in which different segments hybridizes to each other so as to form a structure resembling a star. The star structure comprises a reaction center and a plurality of stems. In the reaction center, the chemical compound has been prepared as the reaction product of 3 or more chemical groups. The stems are nucleic acid duplexes, i.e. a stem comprises two hybridizing segments complementing each other sufficiently for a duplex to be formed under conditions favoring the reaction of the chemical groups so as to form the chemical compound.

At least one of the stems extent radially from the center. Suitably, the 3 or more stems extent radially outwards from the reaction center. The duplex nucleic acid of the stems is believed to bring the chemical groups together so as to obtain a reaction proximity. The proximity established between the chemical groups increases the local concentration and enhances the chances for a reaction to proceed. The presence of 3 or more stems in the star structure creates a strong super structure, which is stable even at conditions where a single duplex will separate into two discrete single stranded nucleic acids. Thus, the star structure enables versatile reaction conditions to be used in order to promote reaction between the chemical groups. Experiments reported herein shows that the a three-stem star structure is stable enough for directing organic synthesis in medias containing in the excess of 35% acetonitril and tetrahydrofuran and in the excess of 40% DMF. In certain embodiments of the invention, the star structure encompasses 4, 5, 6, 7 or more stems connected to a mutual reaction center. When the number of stems is increased the stability of the star structure is also increased.

The nucleic acid is segmented into various parts with certain functions. In certain aspect of the invention, the nucleic acid comprises one or more codons identifying the one or more chemical groups, which have participated in the formation of the formed chemical compound. The presence of a codon segment makes it possible not only to use the nucleic acid to promote reaction proximity but also to use the nucleic acid to code for one or more of the chemical groups which have participated in the formation of the chemical compound. The presence of one or more codons is especially useful for decoding purposes. When the formed chemical compound is present in a small amount or is present in a mixture with other compounds, easy identification can be performed through molecular biological techniques.

A codon identifying a chemical group may be present anywhere in the nucleic acid forming the star structure, i.e. the codon may be present at or in the vicinity of the reaction center, in the hybridization segments or in other parts of the star structure. In a certain aspect of the invention a codon is situated at the extremity of a stem. A codon placed at the end of the stem pointing away form the center allows for more liberty in the design of the nucleic acid star structure as the codon at the extremity does not necessarily need for take part in the formation of a duplex or in the formation of the environment for the reaction center.

The stems may be blunt ended, sticky ended or a loop may be present. A blunt ended or sticky ended stem may be preferred when it is intended to ligate the stem to another nucleic acid. In a certain embodiment, a loop is formed at the end of the stem. The loop forms a physical link between the two strands thus forming a covalent linkage between the various parts of the nucleic acid super structure. In a certain embodiment loops are present at all extremes of the stems so as to form a circular nucleic acid. In another embodiment, a loop is present at all extremes of the stems except one, so as to form a contiguous nucleic acid sequence. Suitably, the contiguous sequence comprises a priming site to enzymatically extend the nucleic acid using a polymerase or another nucleic acid active enzyme. In appropriate instances the priming site is present at the stem not having a loop. Suitably, the nucleic acid comprises a priming site for a DNA polymerase, RNA polymerase or reverse transcriptase. Thus, the loops make it possible to prepare a double stranded extension product displaying the formed chemical compound.

Importantly, the extension product comprises a generally linear duplex, i.e. a complementing strand has been formed by the extension reaction. The extension reaction destroys the reaction center so the chemical compound previously formed by reaction in the reaction center is displayed in the media. The display of the chemical compound enables the use of various selection strategies on a library of extension products, as discussed later in this description.

Subsequent to the selection, the possibility of amplifying the nucleic acid is of particular relevance for identification purposes, because the chemical compound can be identified even in cases in which it occurs only in minute concentrations. The contiguous nucleic acid sequent suitably comprises codons of all the reactants, which has participated in the formation of the encoded chemical compound.

In a particularly preferred embodiment of the present invention a codon is situated in the non-base pairing part of the stem-loop structure. The presence in the loop of the codon allows for the use of any combination of nucleotides in the design, as the specific sequence of a codon does not have material influence on the hybridization and reaction capabilities.

In some aspects of the invention an enzymatic restriction site is present in the stem-loop structure. Depending on the specific endonuclease used, one or both strands of the stem-loop structure may be broken. In a certain embodiment only one of the strands close to the loop is nicked, thereby forming a single stranded nucleic acid segment. The single stranded nucleic acid segment suitably contains the codon. A useful enzyme for this purpose is N. Bbvc IA. In another embodiment both strands are broken and a sticky end, i.e. a single stranded nucleic acid overhang, is formed. Suitably, the codon is present in the single stranded overhang. In an aspect of the invention it is preferred to add a helper oligonucleotide complementary to at least to a part of the nucleic acid sequence of the loop. Under suitable conditions, the helper oligonucleotide hybridizes to the loop sequence and forms a substrate for a restriction enzyme.

The stems of the star structure may have any suitable length. Generally, a stem comprises two hybridisation segments having at least 80% complementarity and each hybridisation segment consists of 12 or more nucleotides. The complementarity is generally 90% or above, such as 95% or above. The hybridization segments may contain less than 12 nucleotides for certain applications in which the stability of the star structure may be dispensed with, such as 11, 10, 9, 8, 7, or 6 nucleotides. However, in general a high stability is desired. A suitable stability under most conditions is generally obtained when each hybridisation segment comprises 18 or more nucleotides. When conditions are used which disfavor hybridization, i.e. temperatures well above ambient, high salt concentrations, or presence of organic solvents, hybridization segments of 20 or more nucleotides are usually utilized.

After the reaction of the individual chemical groups, the formed chemical compound is preferably covalently attached to the nucleic acid. In certain applications it may be desired to use hybridization to attach the formed chemical compound to the nucleic acid of the star structure; however a covalent attachment ensures that the chemical compound and the nucleic acid part remains together during a subsequent selection.

A chemical group to be reacted in the reaction center may be associated with the nucleic acid in any appropriate way. As an example, the chemical groups prior to reaction are covalently attached to the nucleic acid. Usually, one or more of the covalent attachments are cleaved simultaneously with or subsequent to reaction. The covalent link may be designed to be cleavable or durable. Furthermore a cleavable linkage may be designed to be cleaved immediately upon reaction or designed to be cleaved in a step subsequent to a reaction.

Usually, the chemical compound is formed by reaction of the chemical groups attached to the nucleic acid and optionally one or more further reactants. The reactants may originate from any source, including be a compound added to the media as a free reactant not associated with a nucleic acid. The further reactant(s) may be scaffolds, cross-linking agents, activating agent, deprotecting agents etc.

The star structures according to the present invention are useful in the generation of libraries of different chemical compounds associated with a genetic code. Accordingly, the present invention also relates to a library of star structures. Each of the star structures may be present in several copies in the media and the media generally comprises star structures containing different chemical compounds. As an example, a library of the present invention may comprise at least 1000 different chemical compounds, preferably $10^6$ different chemical compounds, and more preferred $10^9$ different chemical compounds.

In another aspect, the present invention may be described as relating to e.g. a method for synthesizing large libraries associated with encoding nucleic acids through a "star-structure" formed by mutually complementary oligonucleotides. This is obtained by hybridizing oligonucleotides containing two segments, where a segment towards the 3' end of one oligonucleotide hybridizes to a segment towards the 5' in the next and so forth. Finally, the segment towards the 3' end of the last hybridizes to a segment towards the 5' end of the first oligonucleotide. Consequently, the mid section between the two hybridization segments on each oligonucleotide is pointing towards the center of the formed ring, whereas the termini are pointing outwards, giving the star-structure. So, when three types of oligonucleotides are used three stems are formed, when four types of oligonucleotides are used four stems are formed etc. A chemical reactive group is associated to the mid section on each oligonucleotide, thus allowing proximity guided chemical reactions to occur in the center. Furthermore, a codon is conveniently situated external to the hybridized segment on each oligonucleotide, thus allowing encoding of the chemical groups participating in the creation of the reaction product. The oligonucleotides with associated chemical groups are called carrier modules herein. Consequently, a carrier module has a chemical group, two position specific segments and a codon. The formation of encoded combinatorial libraries is allowed when repertoires of carrier modules for each position are used. According to a certain embodiment, the assembled oligonucleotides are made extendable or amplifiable when the termini in each stem, except one, are ligated via loop formations to form a continuous oligonucleotide with a 5' and 3' termini. Thus, consisting of one stem and a number of stem-loops, the star structure can be amplified by PCR or extended with a suitable enzyme. Consequently, the combinatorial display library can be subjected to selection and the enriched library members identified through their encoding oligonucleotide. Accordingly, an aspect of the invention relates to a method for creating one or more chemical structures comprising the steps of:

(i) providing N(N=3-100) carrier modules comprising:
  (1) a first position carrier module having
    i) a nucleic acid segment capable of hybridizing to a nucleic acid segment of the N position carrier module, and
    ii) a nucleic acid segment capable of hybridizing to a segment of a second position carrier module,
  (2) n position carrier module(s) (n=from 2 to N−1) having a nucleic acid segment capable of hybridizing to said nucleic acids segment of the n−1 carrier module, and a nucleic acid segment capable of hybridizing to a segment of the n+1 carrier module, and
  (3) a N position carrier module having a nucleic acid segment capable of hybridizing to said nucleic acid segment of said N−1 carrier module, and a nucleic acid segment capable of hybridizing to a segment of said first carrier module, wherein
    at least three of said carrier modules comprise an associated chemical group (CG) situated in the mid section between the hybridization segments or in the vicinity hereof and optionally a codon segment situated external to one of the hybridization segments;
(ii) contacting said carrier modules under conditions allowing hybridization of said hybridization segments, thus bringing said chemical groups into proximity, where the formed chemical compound is associated with at least one of said carrier module.

N denotes the total number of carrier modules used in the formation of the chemical structure. Thus, when three carrier modules are used in the formation of the chemical structure, N is 3, when four carrier modules are used in the formation of the chemical structure, then N is 4 etc. n denotes the specific position of the carrier module.

Thus, when N is 3, a (1) first position carrier module is used having a nucleic acid segment capable of hybridizing to a nucleic acids segment of the third position carrier module, and a nucleic acid segment capable of hybridizing to a segment of a second position carrier module; (2) second (n=2) position carrier module is used having a nucleic acid segment capable of hybridizing to said nucleic acids segment of the first carrier module, and a nucleic acid segment capable of hybridizing to a segment of third carrier module; and (3) a third position carrier module is used having a nucleic acid segment capable of hybridizing to said nucleic acids segment of said second carrier module, and a nucleic acid segment capable of hybridizing to a segment of said first carrier module.

When N is 4, a (1) first position carrier module is used having a nucleic acid segment capable of hybridizing to a nucleic acids segment of the fourth position carrier module, and a nucleic acid segment capable of hybridizing to a segment of a second position carrier module; (2) (n=2) second position carrier module is used having a nucleic acid segment capable of hybridizing to said nucleic acids segment of the first carrier module, and a nucleic acid segment capable of hybridizing to a segment of third carrier module; and (n=3) third position carrier module is used having a nucleic acid segment capable of hybridizing to said nucleic acid segment of the second carrier module and a nucleic acid segment capable of hybridizing to a segment of fourth carrier module; and (3) a fourth position carrier module is used having a nucleic acid segment capable of hybridizing to said nucleic acids segment of said third carrier module, and a nucleic acid segment capable of hybridizing to a segment of said first carrier module.

When N is 5, a (1) first position carrier module is used having a nucleic acid segment capable of hybridizing to a nucleic acids segment of the fifth position carrier module, and a nucleic acid segment capable of hybridizing to a segment of a second position carrier module; (2) (n=2) second position carrier module is used having a nucleic acid segment capable of hybridizing to said nucleic acids segment of the first carrier module, and a nucleic acid segment capable of hybridizing to a segment of third carrier module; and (n=3) third position carrier module is used having a nucleic acid segment capable of hybridizing to said nucleic acid segment of the second carrier module and a nucleic acid segment capable of hybridizing to a segment of fourth carrier module and (n=4) fourth position carrier module is used having a nucleic acid segment capable of hybridizing to said nucleic acid segment of the third carrier module and a nucleic acid segment capable of hybridizing to a segment of fifth carrier module; and (3) a fifth position carrier module is used having a nucleic acid segment capable of hybridizing to said nucleic acids segment of said fourth carrier module, and a nucleic acid segment capable of hybridizing to a segment of said first carrier module.

The above method may be followed by the step of providing conditions allowing ligation of the termini of module n−1 to module n and module N−1 to module N, thereby forming a continuous nucleic acid molecule with stem-loop structures and a chemical compound associated. Thus, when N is 3, a terminus of the fist module is allowed to ligate to a terminus of the second modules and a terminus of the second module is allowed to ligate to the third module. When N is 4, (n=2) a terminus of the fist module is allowed to ligate to a terminus of the second module, (n=3) a terminus of the second module is allowed to ligate to the third module, and a terminus of a third module is allowed to ligate to the fourth module. When N is 5, (n=2) a terminus of the fist module is allowed to ligate to a terminus of the second module, (n=3) a terminus of the second module is allowed to ligate to the third module, (n=4) a terminus of a third module is allowed to ligate to the fourth module, and a terminus of the fourth module is allowed to ligate to a terminus of the fifth module.

According to a further aspect of the present invention, the N position carrier modules may be ligated to the first carrier module, so as to form a circular nucleic acid.

A composition comprising a structure of nucleic acid and associated chemical compounds made according to the method indicated above is novel since carrier modules creates a novel "star structure" that are different from the structures created in the prior art. See e.g. the prior art discussed in the Background section above.

In a preferred aspect of the invention a method is provided, which ensures a high proximity between the reaction chemical groups and amplification of the entire genetic code of the synthesis history of the formed chemical compound. Thus, in a preferred aspect, the present method comprises contacting carrier modules under conditions allowing hybridization of hybridization segments, thus bringing reactive groups into reactive proximity; and providing conditions allowing reaction of reactive groups, where the formed chemical compound is associated with at least one carrier module; and conditions allowing ligation of the termini of module n−1 to module n and module N−1 to module N and thereby forming continuous nucleic acid molecule with stem-loop structures and a chemical compound associated.

According to a preferred embodiment, N is 3, 4, 5, 6, 7. It is also preferred that each of the carrier modules comprise an associated chemical group (CG) situated in the mid section between the hybridization segments or in the vicinity hereof and a codon segment situated external to one of the hybridization segments.

The contacting of the carrier modules may performed sequentially, i.e. the carrier modules may be contacted in any order between the individual carrier modules or the contacting may be performed simultaneously, i.e. all the carrier modules, or at least a substantial amount of the carrier modules, are mixed together at hybridisation conditions so as to form a supermolecular complex. When sequential reaction of the chemical groups is performed and only a fraction of the total amount of carrier modules required for assembling the entire star structure is used, an auxiliary oligonucleotide may be used to assemble a star structure, whereby the reaction center is formed. Thus, when a step in the formation of the chemical compound involves the assembling of two carrier modules by hybridization of the respective hybridization segments, an auxiliary oligonucleotide having segments rovers complementary to the non-hybridised hybridization segments may be added to form the star structure.

After the chemical groups attached the carrier modules have been brought into close proximity in the reaction center, reaction is effected. The chemical groups may be designed such that a reaction occurs immediately when the groups come into reaction distance of each other or the groups may be designed such that an external component is necessary for the reaction to occur. The external component may be a reactant, a photon, electromagnetism or any other stimuli, which effects reaction. In a certain aspect of the present invention orthogonal chemistry is used, i.e. the chemical groups are designed such that the order of reaction is directed.

The reaction center is defined by the stems surrounding said center. It has been suggested, that the distance between two reactants in the reaction center is less than 10 nm. Assuming the reaction center is spherical; the concentration of the reactants can be calculated to 1 mM. In a biological context a concentration of this size is regarded as high and a reaction can be assumed to proceed within a reasonable time. Furthermore, the concentration of free reactant in the media is very low, when the carrier modules have been dosed in adjusted molar amounts, so the reaction in the reaction center is greatly favored over non-directed reaction.

The mid section of the carrier module can contain any suitable chemical groups. To allow for enzymatic extension by e.g. a polymerase, the mid section of a carrier module suitably comprises a chemical bond or 1 to 20 nucleotides. The nucleotides may be modified to obtain certain reaction conditions in the reaction center. As an example, the nucleotides of the mid section may be modified with lipophilic groups to provide for a high mobility and reactivity of the associated chemical groups. The chemical group may be associated with the carrier molecule at various positions. In one aspect, the chemical group is associated with a nucleobase of the mid section. In another aspect, the chemical group is associated with a phosphodiester linkage of the midsection.

When the chemical group is attached to the backbone the point of attachment is generally at the phosphor of the internucleoside linkage. When the nucleobase is used for attachment of the chemical group, the attachment point is usually at the $7^{th}$ position of the purines or 7-deaza-purins or at the $5^{th}$ position of pyrimidines. The nucleotide may be distanced from the reactive group of the chemical group by a spacer moiety. The spacer may be designed such that the conformational space sampled by the reactive group is optimized for a reaction with the reactive group of another chemical group in the reaction center. In general, the chemical group is associated to the midsection through one or more covalent bonds.

The ligation may be effected prior to, simultaneously with or subsequent to reaction and the ligation maybe performed enzymatically or chemically at the choice of the experimenter. To reduce the amount of free non-hybridising carrier modules in the media, it is generally desired to ligate the carrier modules prior to reaction.

The formed chemical compound may be associated with the nucleic acid through a variety of chemical interactions. According to a preferred aspect the formed chemical compound is covalently associated with at least one of said carrier molecules or the continuous nucleic acid molecule. The relatively strong association between formed chemical compound and the nucleic acid, such as a covalent link, is useful during the screening of a library as it may be desired to us harsh conditions, which may disrupt weaker bonds, such as hydrogen bondings.

In a preferred aspect of the invention one or more carrier modules are provided with a priming site for DNA polymerase, RNA polymerase or reverse transcriptase. The presence of a priming site assists in the amplification of the genetic code for the chemical group, which have reacted in the formation of the chemical compound. When ligation is absent, i.e. the genetic code for each of the chemical groups remains separate entities kept together by hybridisation, it is preferred that each carrier module contains a priming site. After a selection of a library has been performed, it is possible to gain information concerning which chemical groups that has participated in the formation of successful chemical compounds, i.e. chemical compounds with a desired property. One way of obtaining this information is to quantify the amplification product, through well-know methods such as QPCR or standard PCR combined with microarray. The information may be used in the formation of a second-generation library with a reduced diversity, as it is only necessary to include carrier modules in the library, which are successful. A reduced diversity library is also a focused library because the abundance of chemical compounds with a desired property is higher.

When two or more carrier modules are ligated together, it is possible to obtain information of the reactants, which together have participated in the formation of chemical compounds with a desired property. Preferably all, carrier modules are ligated together so as to form a linear nucleic acid or a circular nucleic acid. Thus, when two or more carrier modules are ligated together, a single priming site is necessary to amplify the contiguous nucleic acid comprising the two codons. According to a preferred embodiment, the method of the invention comprises a priming site for a DNA polymerase, RNA polymerase or reverse transcriptase site in at least the first carrier module and/or at least in the N carrier module. When all the carrier modules are ligated together, i.e. the first carrier module is ligated to carrier module n (n=2 to N−1), which is ligated to the carrier module N, a nucleic acid can be extended when a priming site is situated at one of the ends. To reduce the risk that the formed chemical compound remains hidden in the reaction center, an extension is preferably performed prior to the selection process. The extension of the contiguous nucleotide effectively displays the formed chemical compound to the media and any target, which may be present therein.

Preferably, a priming site for hybridisation of a forward primer is situated at one end and a priming site for hybridisation of a reverse primer is situated in the other end, so as to allow for amplification according to the protocol of the polymerase chain reaction (PCR). PCR amplification is suitably performed after the selection has been performed to generate more copies of the genetic material of the structures having the desired properties.

Accordingly, a second aspect of the invention relates to a composition comprising a structure of nucleic acid and associated chemical compound or a library of more than one of such structures obtainable by the method indicated above.

A library of chemical compounds associated with a nucleic acid coding for the chemical groups, which have participated in the formation of the chemical compound, can be form by using a repertoire of carrier modules on one or more positions.

The library as described herein may be used to screen for a compound of interest. It is generally desired to have a library as large as possible to increase the possibility of finding a compound with desired properties. In a certain aspect of the invention the property of the compound of interest is the ability to bind to a target. Generally, it is assumed that the possibility of finding a compound with high affinity and specificity towards a target is increasing with increasing library size. Thus, a library according to the present invention suitably comprises more than $10^3$, $10^4$, $10^5$, $10^6$, $10^7$, $10^8$, $10^9$, $10^{10}$, $10^{11}$, $10^{12}$, $10^{13}$, or $10^{14}$ different chemical compounds associated with a nucleic acid encoding the synthetic history.

To obtain a library a repertoire of carrier modules may be used at a number of positions. In an aspect of the invention, the repertoire on at least one position comprises at least 10 different carrier modules. In a certain aspect, the repertoire on at least two positions comprises at least 10 different carrier modules. To obtain a library of one million different chemical compounds in the same container, the multiple structures of the invention can be formed with 100 carrier modules at 3 different positions. In other words, synthesis of just 300 carrier modules enables the formation of a library of a million compounds. Similarly, a library of 100 million compounds can be formed with 100 carrier modules at 4 different positions.

The invention also relates to a method for performing module substitution. The method comprises the steps of:
a) providing a single stranded contiguous nucleic acid sequence comprising N hybridisation segments and complementing hybridisation segments as well as N−1 non-hybridising segments between the hybridisation segments and complementing hybridisation segments,
b) hybridizing the nucleic acid under conditions favoring intramolecular hybridization, thereby forming a continuous nucleic acid, at least containing N−1 stem-loops and one stem;
c) introducing a break in said stem or loop thereby creating an overhang which at least contains a codon segment;
d) providing a first group of carrier modules having at least: a nucleic acid segment capable of hybridizing to said stem, a nucleic acid segment capable of hybridizing to the stem of an adjacent stem-loop, optionally an associated reactive group, and an anti-codon segment;
d) providing conditions allowing hybridization of codon and anti-codon segments; and
e) providing conditions allowing enzymatical or chemical ligation of said hybridized carrier module to the recessive termini of said overhang; and perform the steps of:
  i) digest with a restriction enzyme the stem or loop of the stem-loop adjacent to said codon sequence thereby making overhangs which at least contain a next codon segment; and
  ii) denaturate the nucleic acids; and
  iii) hybridize under conditions favoring intramolecular hybridization thereby forming N−1 stem-loops and one stem with overhang at least containing said next codon segment; and
  iv) optionally provide conditions allowing reaction of said reactive groups, where the formed chemical compound is associated with at least one of said carrier module; and
  v) provide a next group of carrier modules having at least; a nucleic acid segment capable of hybridizing to said stem, and a nucleic acid segment capable of hybridizing to the stem of the adjacent stem-loop, and optionally having a reactive group associated, and having an anti-codon segment; and vi) provide conditions allowing enzymatically or chemical ligation of hybridized carrier module to the recessive termini of said overhang; and repeat steps i) through vi) N−1 times; and
f) introducing a break in said stem-loop structure consisting partial of said first group of carrier modules at least leaving said anti-codon segment connected to said first carrier module; and
g) denaturating the nucleic acids; and
h) hybridizing under conditions favoring intramolecular hybridization thereby forming N−1 stem-loops and one stem; and
i) optionally, providing conditions allowing reaction of said reactive groups, where the formed chemical compounds are associated with at least one of said carrier module.

The contiguous nucleic acid sequence used in step a) may be provided from a number of sources. According to a first aspect, the nucleic acid is provided by the above method, however using dummy carrier modules not carrying chemical groups. When these nucleic acids representing the carrier modules are ligated together, a linear or circular nucleic acid is formed. According to a second aspect, the contiguous nucleic acid sequence of step a) is obtainable by performing an enzymatic extension reaction to display the formed chemical compound. Thus, after the formation of the star structure, the single stranded extension product or a strand complementing the extension product may be used in step a). If desired, the extension product may be subjected to polynucleotide amplification, such as PCR, to amplify the number of copies of the nucleic acid.

In a certain aspect, the contiguous nucleic acid sequence in step a), b), or c) is obtained by immobilizing the sense strand of the PCR product on a solid support, isolating the solid support, allowing the sense stand to self-hybridize so as to form the star structure, and, optionally, breaking the stem attaching the self-hybridized star structure with the solid support, thereby liberating the star structure from the solid support.

A suitable method of immobilizing the sense strand is to attach biotin to the primer producing the sense strand. The sense strand may then be attached to solid supports, such as beads, covered with streptavidin. Depending on the property of the solid support it may be isolated from the remainder of the media in a number of ways. Presently, it is preferred to use magnetic beads, which easily can be isolated by a magnet.

After the solid support has been washed a number of times, the sense strand is allowed to self-hybridize to form the star structure anew. In a preferred aspect, the re-folding is performed by instant cooling. The star structure may be maintained on the solid support throughout the module substitution process or the star structure may be cleaved from the solid support. Suitably a cleavage of the stem attaching the solid support and the re-folded star structure is performed with a restriction enzyme. The ability of the restriction enzyme to perform the cleavage is actually a test confirming the intramolecular folding.

In certain aspects of the invention it may be suitable to cleave the star structure in the loop. As most restriction enzymes recognize double stranded nucleic acids only as substrates it is not immediately possible to cleave in the loop using a restriction enzyme. Therefore, the present invention comprises the further step of adding a helper oligonucleotide complementary to a sequence of a loop, prior to a digesting step, to create a double stranded substrate for the restriction enzyme in the loop.

The invention also relates to a method for screening a library of more than one chemical compound comprising:
probing the library for library members having a chemical compound of desired property; partitioning the library members having desired property from library members not having desired property; and
thereby obtaining an enriched pool of library members having desired property.

The enriched pool of library members having the desired property may be isolated and characterized if desired. However, one of the advantages of this method is that it is not necessary to isolated the enriched pool. In a preferred embodiment, the enriched pool is subjected to a nucleic acid amplification method to increase the genetic material indicative of the synthetic history of the chemical compounds having the desired property. The pool of amplified nucleic acid representing the enriched library of compounds with a desired property may be decoded in order to identify the reactants, which have been involved in the synthesis of the chemical compound with the desired property. However, if the enriched pool is larger than it is feasible easy to decode the entire amount of nucleic acid, the present invention offers the possibility of reassembling the chemical compounds encoded by the enriched library members or the nucleic acid representing such enriched library using the above method of performing module substitution.

In one embodiment, the present invention provides a method for amplification of an enriched pool of library members having the desired property. The method include that the PCR amplified oligonucleotides are allowed to hybridize under conditions favoring intramolecular hybridization, whereby the star-structure, consisting of a stem and a number of stem-loops are recreated. The stem without a loop preferably contains a recognition site for a restriction enzyme, which cuts outside its recognition sequence and generates an overhang upon digest. The redundancy of the sequence in the created overhang may conveniently be utilized to contain a codon. Restriction enzyme digestion of the stem then generates codon specific overhangs for this first position. The restriction enzyme digested star-structures are subsequently hybridized with a repertoire of carrier modules containing the two constant segments for the first position and a cognate pair of the chemical group and the anti-codon. Consequently, codon/anti-codon hybridizations allow appropriate pairs of carrier modules and star-structures to be ligated by a DNA ligase. The neighboring stem-loop also contains a recognition site for another restriction enzyme capable of leaving a codon specific overhang for this second position. Digestion with this second restriction enzyme thus eliminates the covalent linkage of the PCR amplified first module to the rest of the structure. The star-structures are denatured and subsequently allowed to hybridize under conditions favoring intramolecular hybridization. The star-structures are thereby recreated, but now with a new carrier module on position one (with an associated chemical group) and the stem, without a loop is now located on position two. Rounds of this process may be performed to substitute all positions, to allow for proximity guided chemical reactions of the proper combinations of chemical groups. Consequently, rounds of selection and amplifications can be performed until desired enrichment has been achieved.

The breaks in the stems may be introduced by a number of methods, such as by restriction enzymes, e.g. RNase, Endonuclease III, endonuclease VIII, APE1, Fpg, or by chemical cleavage or photo cleavage.

The contiguous nucleic acid sequence used in step a) of the module substitution method described above can be provided by "breeding". In a certain embodiment, a breeding method include the steps of:
digesting intermolecular hybridized nucleic acid structures derived from an enriched library with two consecutive restriction enzymes, which eliminate the covalent linkages between the module in question and the remaining structure,
denaturing the digested structures,
allowing rehybridization of the nucleic acid fragments from the digested structures, thus allowing for exchange of a nucleic acid fraction specifying the module in question to obtain breeding, and
ligation of the appropriate termini.

According to this method, carrier modules or nucleic acid parts representing carrier modules can be shuffled. The shuffling allows for a diversification of the gene pool similar to breeding in a meiotic biological system. The method may be modified when nucleic acid fragments representing carrier modules, not present in the formation of the first generation library is added before allowing rehybridisation. Alternatively, the carrier module as such can be added before allowing rehybridisation. When new genetic material is added to the gene pool this is similar to mutation in a biological system. The possibilities of performing breeding and mutation operations between generations of libraries allow for an evolution strikingly similar to the natural evolution process in the search for new drug candidates.

Thus, in a certain embodiment, the present invention provides a method for diversification of an enriched library, thus allowing molecular evolution. In the process described above for the amplification of a display library, a fraction of the library in each round for module substitution, is digested with two consecutive restriction enzymes, which eliminate the covalent linkages between the module in question and the remaining structure. The star-structures are denaturated and hybridized with a repertoire of carrier modules for the position in question. The position specific constant segments are thus guiding the hybridizations, equivalently to the creation of the primary library. The appropriate termini are ligated and the formed product pooled with the codon guided assembled fraction of the library, leading to a diversification. Consequently, rounds of selection, amplification and diversification can be performed, thus allowing for molecular evolution.

In another embodiment, the present invention provides a method for breeding of an enriched library, thus allowing molecular evolution. In the process described above for the amplification of a display library, a fraction of the library in each round for module substitution, is digested with two consecutive restriction enzymes, which eliminate the covalent linkages between the module in question and the remaining structure. The star-structures are denatured and hybridized. The position specific constant segments are thus guiding the hybridizations and allowing exchange of the module in question, i.e. breeding. The appropriate termini are ligated and the formed product pooled with the codon guided assembled fraction of the library, leading to a diversification. Consequently, rounds of selection, amplification, diversification and breeding can be performed, thus allowing for molecular evolution.

In another embodiment, the present invention provides a method for creating combinatorial display libraries of polymers or small molecules. The chemical reactions may either be performed simultaneously or sequentially, by use of e.g. orthogonal chemistries, protective/masking groups, sequentially mixing of carrier modules, or carrier modules without a CRG.

In one embodiment, the present invention provides a method for creating combinatorial display libraries of catalytic activity. In this aspect the carrier modules are associated with reactive site functionalities and the star structure provides a framework for a three dimensional arrangement of these functionalities.

The above-described aspects and embodiments show clear advantages over the prior art. To name some, the various possible embodiments of the present invention show one or more of the following advantages: 1) a unique method for assembly of a combinatorial display library, 2) a unique structure for proximity guiding of chemical reactions, 3) the chemical reactions are highly independent of codon sequences because these are separated from the reactive site by constant segments, 4) high accuracy in amplification of display library as only codons on a relevant position are capable of guiding fresh carrier modules as only these contain a termini to facilitate ligation, and 5) if accidentally an incorrect codon/anti-codon guiding has occurred, the association between encoding and display will still exist as the fresh carrier modules provides both the CRG and the code.

BRIEF DESCRIPTION OF THE DRAWINGS

FIG. 1a discloses steps in the formation in the star structure, in which the chemical groups are simultaneously reacted.

FIG. 12 shows gels obtained in the experiments described in example 5.

FIG. 20 shows two gel resulting form experiments disclosed in example 12

FIG. 27 shows a non-native PAGE gel of he individual steps in the process used in example 18.

FIG. 33 shows a schematic representation of the translation process.

FIG. 36 shows the result of the experiments reported in example 22.

DETAILED DESCRIPTION OF THE INVENTION

Nucleic Acid

Figure 1B:
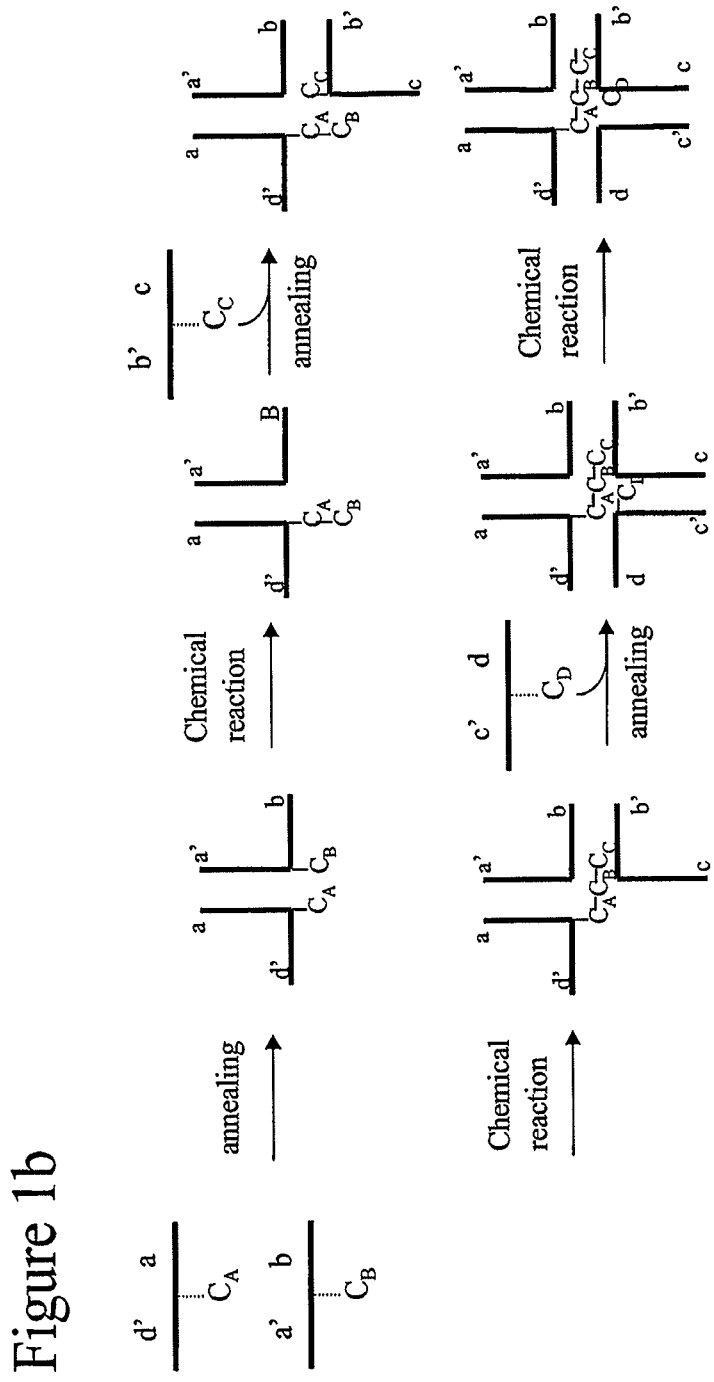
FIG. 1b shows steps in the formation of the star structure, in which chemical groups are sequentially reacted.

Nucleic acid encoded chemical synthesis as described herein permits the production of combinatorial display libraries and the performance of selection, amplification and evolution of a broad variety of chemical compounds such as small molecules and non-natural polymers. The nucleic acid serves multiple functions, for example, it brings chemical reactants together, guides the three-dimensional arrangement of chemical reactants, stores information regarding the chemical synthesis history, guides for proper matching of selected combinations of chemical reactants and allows diversification and breeding of chemical compounds.

The method may be used to assemble one molecule, trillions of molecules, or even more at a time.

The method allows the isolation of ligands or drugs with properties superior to those isolated by traditional rational design and combinatorial drug discovery methods, as the chemical space can be systematically searched for ligands having desired properties.

Nucleic acid guided chemical synthesis has been shown to be a wide-ranging phenomenon, not only limited to compounds of nucleic acid nature, but also applicable to guiding a broad range of chemical reactions under a broad range of conditions (WO 2004/016767, WO 2002/074929A2). This is of particular importance, as most molecules of interest do not resemble nucleic acid or nucleic acid analogs. The chemical groups participating in the formation of the final chemical compound may be transferred in one step to a receiving chemical entity on a scaffold or a chemical group may be transferred in two steps, in which the first step includes a cross link between the chemical group and the receiving entity and the second step include a cleavage of the chemical group from the carrier module to complete the transfer. An example of the former type of reaction of a reaction is a carrier module having attached a 5-membered substituted N-hydroxysuccinimid (NHS) ring serving as an activator, i.e. a labile bond is formed between the oxygen atom connected to the NHS ring and the chemical group to be transferred. The chemical groups can be transferred to a recipient nucleophilic group, typically an amine group, which may be present on a scaffold. The remainder of the fragment is converted into a leaving group of the reaction. When the chemical group is connected to the activator through a carbonyl group and the recipient group is an amine, the bond formed on the scaffold will an amide bond.

An example of a two-step reaction is the so-called allylglycin reaction. In a first step a chemical group comprising a carboxylic acid or a derivative there of is reacted with a nucleophilic group, such as an amine. The chemical group is attached to an allylglycin group, which in a second step may be cleaved with iodine to release the chemical group. The two-step reaction method is disclosed in more detail in WO 2004/039825, the content thereof being incorporated herein by reference. Another example of a two-step reaction strategy is shown in more detail in example 10.

Of pivotal importance for nucleic acid guided synthesis of combinatorial display libraries is the proximity guiding of reactants, which ensures reaction efficiency and proper association of encoding and display. Proximity of reactants is obtained by associating together the reactants, by some sort of linker. Proximity can also be described as a local concentration, which is dependent on the length and flexibility of the linker. If free flexibility of the linker is assumed, the local concentration can be calculated by using the volume of a sphere with the linker length as radius. The formula to calculate the volume of a sphere is; $v=4/3*pi*r^3$. Consequently, the proximity or local concentration drops in the $3^{rd}$ power as a function of the linker length. For example a linker length around 10 nm, will be equivalent to a concentration around 1 millimolar, whereas a 100 nm linker will be equivalent to a concentration around 1 micromolar. Efficient organic chemistries are typically performed in the millimolar to molar concentration range. Consequently, to ensure efficiency in the chemical reactions the linker length should not be significantly longer than 10 nm.

Preferably, the reactive groups are brought into reactive proximity of less than 100 nm, more preferably less than 50 nm, even more preferably less than 25 nm, even more preferably less than 10 nm and most preferably less than 5 nm.

In the prior art for single-pot synthesis of DNA encoded display libraries allowing amplification, single stranded DNA templates with codons spread out over the length of template are used (WO 2004/016767, WO 2002/074929A2). The templates are responsible for recruiting transfer units having proper anti-codon sequences from a repertoire of transfer units and thereby bringing together chemical groups on the template and the transfer unit. Consequently, the single stranded template acts also as a linker between the chemical group on the template and the chemical group on the transfer unit hybridized to the template. Hence, the linker length and thereby the local concentration of reactants will depend on which codon position is employed. An unfolded (extended) oligonucleotide having for example 20 nucleosides will have a length around 10 nm, (the six-bond backbone spacing is around 0.63 nm) and an oligonucleotide having 200 nucleosides will have a length around 100 nm. Consequently, unfolded oligonucleotides considerably longer than 20 nucleosides (10 nm, equivalent to a concentration around 1 millimolar) will in general not be suitable to create proximity guiding of chemical reactions.

In one embodiment the present invention circumvents the lengthened structure of nucleic acid in use to bring reactants into reaction proximity. This is achieved by choosing appropriate sequences of oligonucleotides capable of folding into stable three dimensional structures and thereby allowing proximity guiding by sequence positions separated by many nucleosides. As shown in FIG. 1a this is achieved by using bi-specific oligonucleotides (mutually complementary), which can hybridize into a "star-structure". The bi-specific oligonucleotides contain two segments: a segment towards the 3' end of one oligonucleotide hybridizes to a segment towards the 5' in the next and so forth. Finally, the segment towards the 3' end of the last hybridizes to a segment towards the 5' end of the first oligonucleotide. Consequently, the mid section between the two segments on each oligonucleotide is pointing towards the center. This mid section can be a bond or a segment. In contrast, the termini are pointing outwards, thus giving the star-structure. So, when three types of oligonucleotides are used three stems are formed, when four types of oligonucleotides are used four stems are formed etc. A chemical reactive group (CRG) is conveniently associated to or in the vicinity of the mid section on each oligonucleotide. The chemical reactive groups are thus brought into reaction proximity, as the diameter of the DNA double helix is around 2 nm, thus allowing proximity guided chemical reactions to occur in or in the vicinity of the center.

The chemical reaction is performed such that the formed product is associated to at least one oligonucleotide. Furthermore, a codon is conveniently situated external to one or both of the hybridized segments on each oligonucleotide, thus allowing encoding of the chemical groups. The oligonucleotides with associated chemical group, two position specific hybridisation segments and a codon are called carrier modules.

To make the created combination of oligonucleotides amplifiable by e.g PCR, the termini in each stem, except one, are ligated via loop formations to form a continuous oligonucleotide with a 5' and 3' termini. In one aspect, the structure consists of one stem and a number of stem-loops, which can be amplified by having PCR priming sites at the termini (FIGS. 1d and 1e). Alternatively, all termini are ligated forming a closed ring, which may be amplified by primer extension by a DNA polymerase without strand displacement activity.

A method using stepwise reaction of the chemical groups are shown in FIG. 1b. Initially, two carrier modules are contacted under hybridisation conditions. Carrier module A comprises a hybridisation segment a, which anneals to hybridisation segment a' of carrier module B. Following the annealing step, a chemical reaction between chemical group $C_A$ on carrier module A and $C_B$ on carrier module B is allowed. In a third step, carrier module C is added under hybridisation conditions. Carrier module C comprises a hybridisation segment b', which complements the hybridisation segment d of carrier module B. The reaction proximity of the product $C_A$-$C_B$ to the chemical group $C_C$ enables the chemical reaction to proceed so as to produce the product $C_A$-$C_B$-$C_C$. A fourth carrier module D is added under hybridisation conditions. Carrier module D is allowed to hybridize to the growing star structure, so as to bring reactant $C_D$ into close proximity of reaction product of the preceding reaction, whereby a reaction is promoted to produce the final chemical compound $C_A$-$C_B$-$C_C$-$C_D$.

Figure 1C:
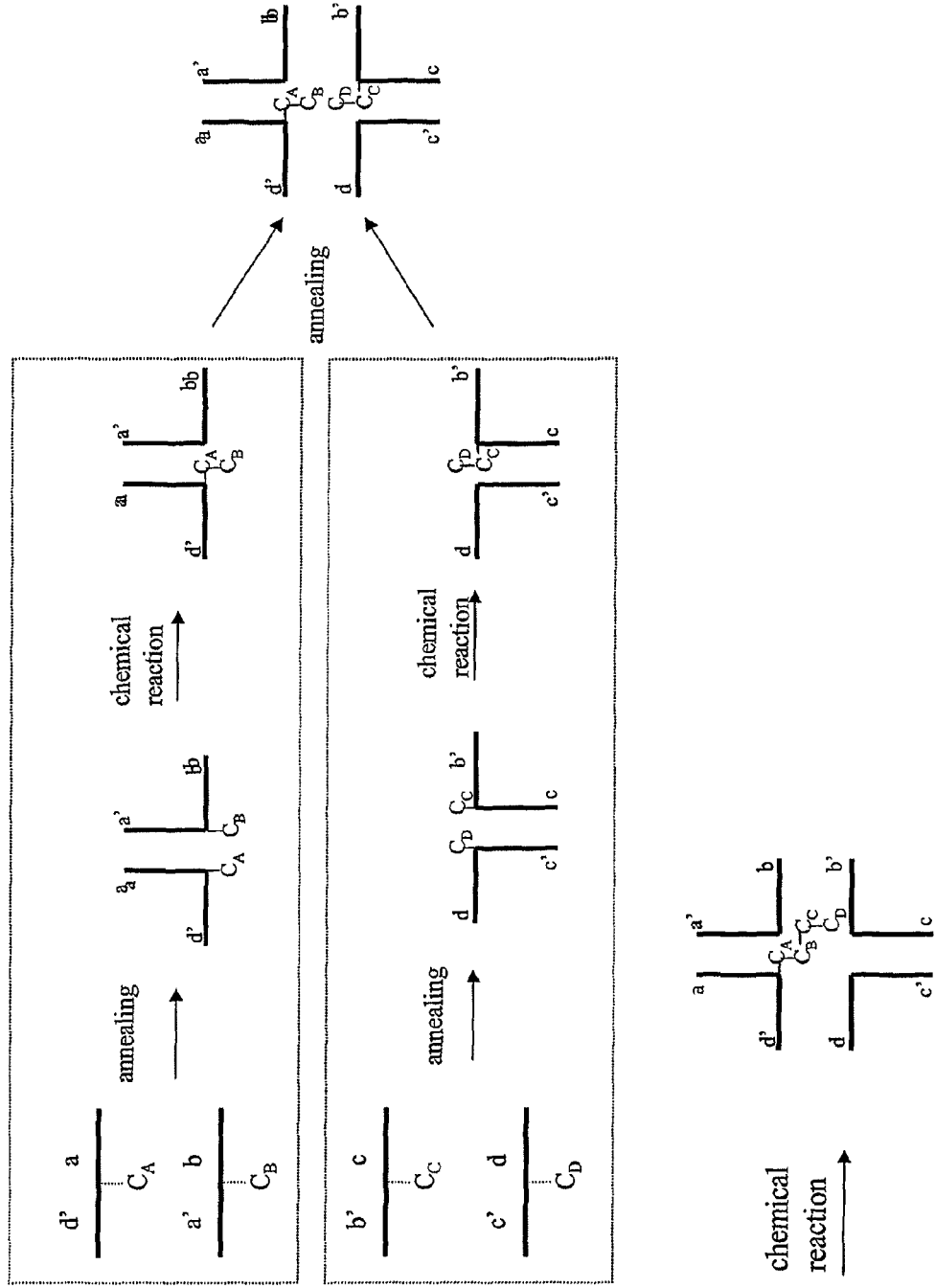
FIG. 1c discloses a method which uses convergent synthesis of the chemical compound.
Figure 1D:
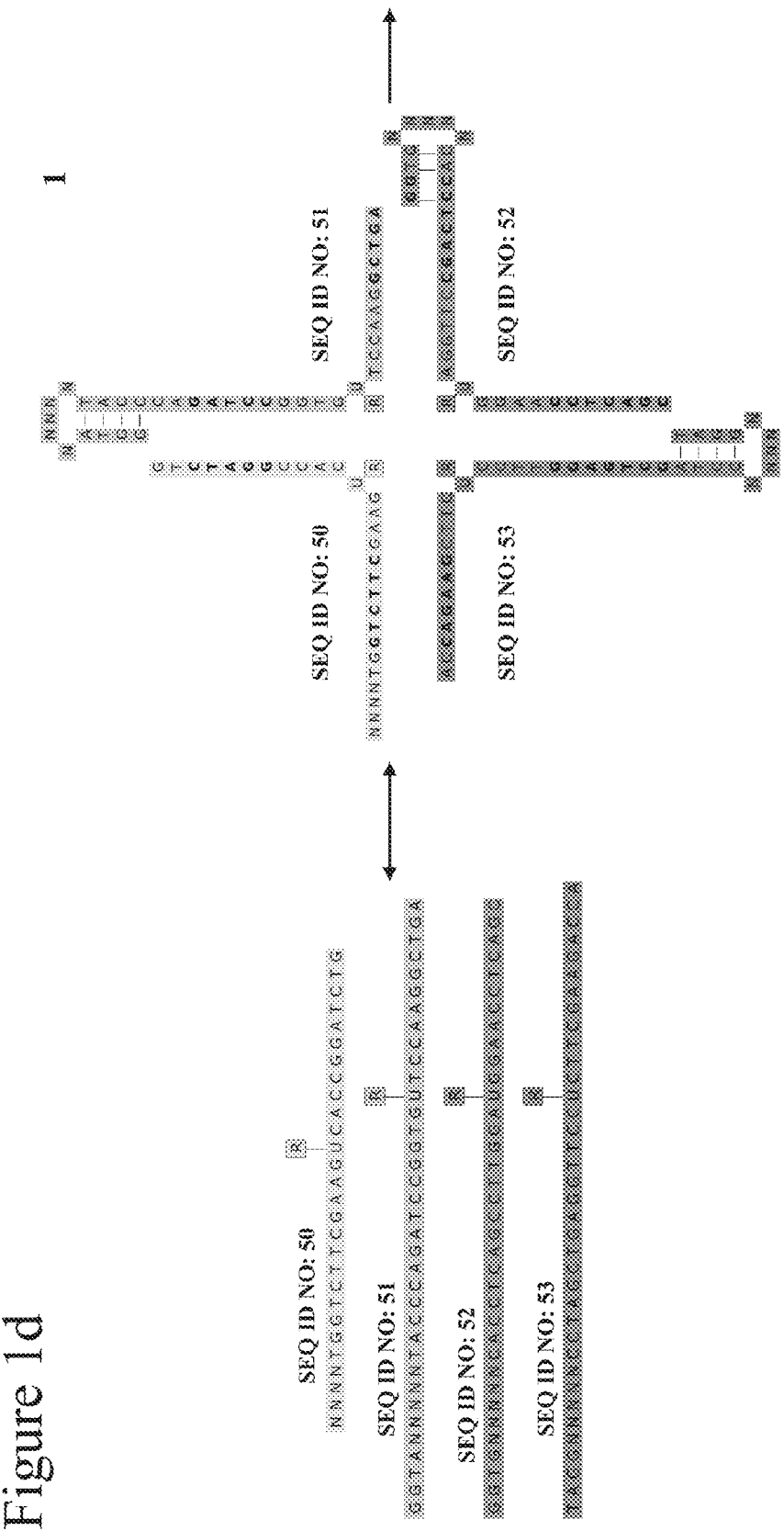
FIG. 1d shows a method in 5 steps for forming a library in which each members displays the formed chemical compound efficiently.
Figure 1E:
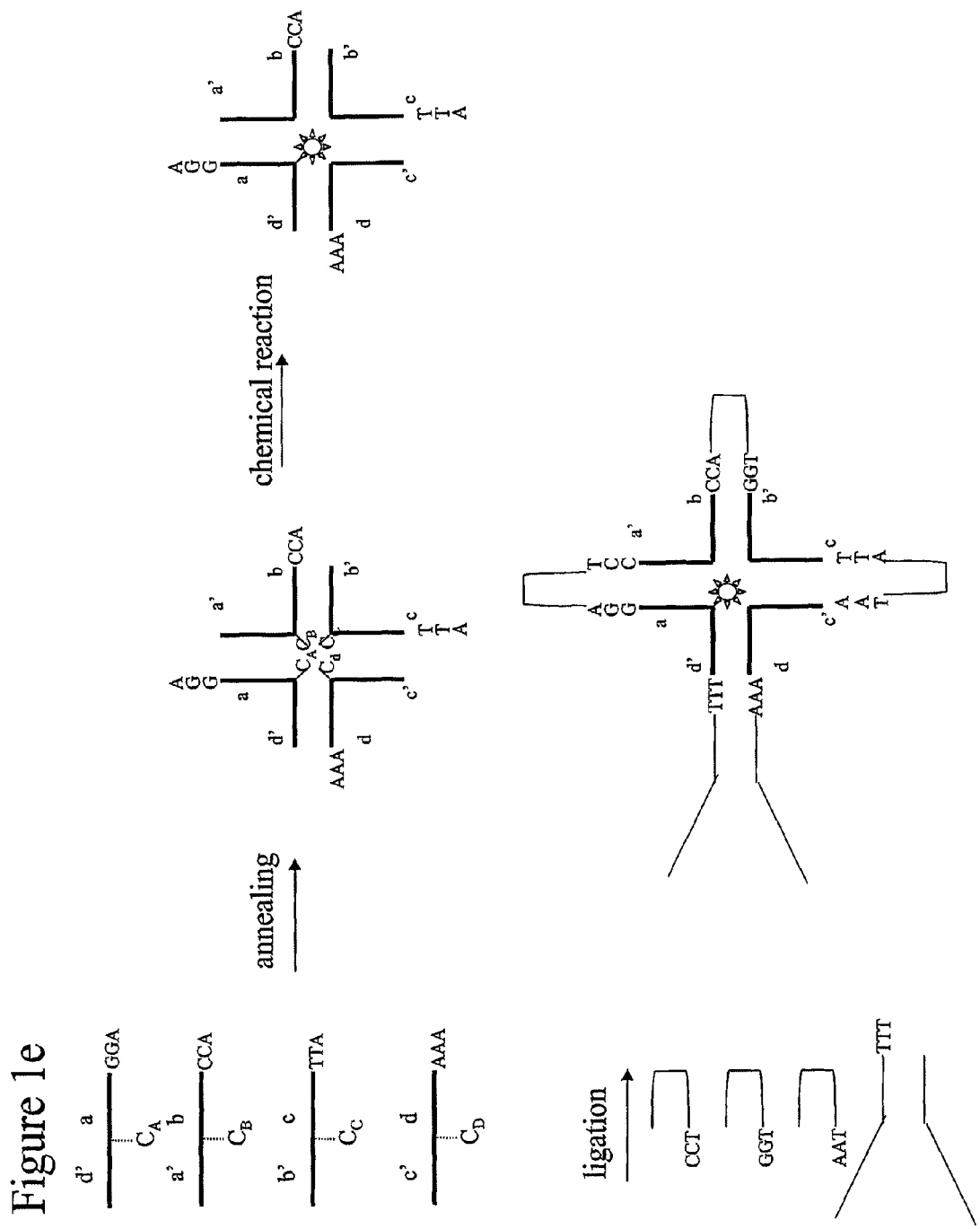
FIG. 1e discloses a method in which the loops are added after reaction of the chemical groups.

FIG. 1c discloses a convergent synthesis method, in which the initial reaction steps follow two separate pathways. In a first series of reactions carrier modules A and B are contacted separately under hybridisation conditions in a first container. Hybridisation segment a of carrier module A and hybridisation segment a' of carrier module B will anneal to each other and a reaction between the chemical groups $C_A$ and $C_B$ is effected. In a second container carrier modules C and D are mixed under hybridisation conditions so as to form a hybridisation product in which hybridisation segment c of carrier module C is annealed to hybridisation segment c' of carrier module D. Subsequently, reaction occurs between chemical group $C_C$ and chemical groups $C_D$ to produce intermediate product $C_C$-$C_D$. The intermediate products are allowed under hybridisation conditions to anneal to each other, whereby the start structure is formed. Subsequently, or simultaneously with the formation of the star structure, reaction between the two intermediate reaction products $C_A$-$C_B$ and $C_C$-$C_D$ is allowed to produce the final chemical compound $C_A$-$C_B$-$C_C$-$C_D$. When performing stepwise or convergent synthesis it may be useful prior to reaction of the chemical groups to provide an auxiliary oligonucleotide to form the reaction center.

In one embodiment, the present invention relates to the formation of the loop in the stem-loop structures as provided by carrier modules as shown in FIG. 1d. Alternatively, the loops are formed by ligation of stem-loops provided by other oligonucleotides as shown in FIG. 1e or any combination hereof of the embodiments shown in FIGS. 1d and 1e. The terminal carrier modules may contain PCR priming sites or the priming sites may be provided by ligating other oligonucleotides.

The embodiment disclosed in FIG. 1d is shown in five steps. In the first step, four carrier modules, each carrying a reactive groups R and bi-specific oligonucleotides are contacted under hybridisation conditions. The carrier modules are in equilibrium with the star structure. In the second step the hybridisation complex is ligated at the termini of the carrier modules so as to form a continuous nucleic acid. The proximity of the chemical groups at the center of the star structure promotes the reaction and in step 3a product is formed, which is attached with a linking entity to the nucleic acid coding for the chemical groups which have participated in the formation of the chemical compound. In step 4a priming site for a polymerase is ligated to the star structure to enable extension of the nucleic acid. The last step shows the extension product in which a double stranded DNA has been formed using the nucleic acid of the star structure as a template.

In FIG. 1e, a variant of the embodiment of FIG. 1d is shown, as the stem-loop is added separately and ligated to the star structure. In a first step, four carrier modules are mixed. Due to the existence of hybridisation segments, the star structure is formed under hybridisation conditions. Subsequent to formation of the hybridisation complex, reaction is effected to form the chemical compound. After formation of the compound by reaction of the four chemical groups, 3 stem-loops and a priming site for a polymerase is added. The stem-loops and the priming site comprise an overhang which complements an overhang of the star structure. When a ligase is added, the stem-loops and the priming site are ligated to the start structure, so as to form a continuous nucleic acid.

In certain embodiments the present invention relates to ligation of carrier modules, for example using enzymes such as T4 DNA ligase, Taq DNA ligase, T4 RNA ligase or *E. coli* DNA ligase or by chemical ligation (Shabarova et al., Nucleic Acids Res, 19, 4247-51, 1991).

Carrier Modules—Oligonucleotide Portion

Oligonucleotides are used to guide the chemical reactions in the present invention. The oligonucleotides in this context are called carrier modules, which contain at least two position specific hybridization oligonucleotide segments, optionally an oligonucleotide codon segment, and a reactive chemical group.

In one embodiment the present invention relates to carrier modules, where the oligonucleotide portion consists of DNA, RNA or analogs hereof and in any combinations hereof. The oligonucleotide portion is capable, at least after modification, of being an appropriate template in standard protocols for nucleic acid replication and/or amplifications.

The carrier modules may be synthesized using methodologies known in the art. For example the oligonucleotide may be prepared by any method known in the art for synthesizing oligonucleotides, e.g. solid phase synthesis using an automated synthesizer. Oligonucleotides following synthesis may be associated when desired (for example, covalently or non-covalently coupled) with a CRG of interest using standard coupling chemistries known in the art.

In one embodiment the present invention relates to carrier modules, where the association of the CRG to the oligonucleotide is to the mid section between the hybridization segments or in the vicinity hereof. The mid section may be a phosphordiester linkage, derivatives thereof or a nucleic acid segment. In vicinity of the mid section relates to locations on the duplex nucleic acid stem, preferentially to locations close to the mid section. Preferably, the vicinity of the mid section relates to less than 20 nucleotides, more preferably less than 10 nucleotides, even more preferably less than 5 nucleotides and most preferably less than 2 nucleotides.

In one embodiment the present invention relates to carrier modules, where an association of a CRG to an oligonucleotide occurs via linkers or spacers, which are long and flexible enough to allow the reactants to come into reaction proximity. The linkers preferentially have a length and composition to permit reactions between reactants paired by oligonucleotides, but yet minimizing reactions with unpaired entities. Moreover, the association between the oligonucleotide and the CRG may be through a covalent bond. In certain embodiments, the covalent bond may be more than one.

The linkage can be cleavable by for example light, oxidation, hydrolysis, exposure to acid, exposure to base, or reduction. A variety of linkages useful in the practice of the invention is described in the prior art (Fruchtel and Jung, Angew Chem Int Ed Engl, 35, 17, 1996). The linker assists contact of the reactants and in certain embodiments, depending on the desired reaction, positions DNA as a leaving group, where the linker is cleaved as a natural consequence of the reaction. In certain embodiments depending on the desired circumstances reaction of one reactive group is followed by cleavage of the linker attached to a second reactive group to yield products without leaving behind additional atoms capable of providing chemical functionality.

In one embodiment the present invention relates to carrier modules, where the association of the CRG to the oligonucleotide occurs through the backbone of the nucleic acid In one embodiment the present invention relates to carrier modules, where the association of the CRG to the oligonucleotide is through the base. In a preferred embodiment the CRG is associated to the non-Watson-Crick hydrogen bonding parts.

In one embodiment the present invention relates to carrier modules, where the association of the CRG to the oligonucleotide allows read through by a DNA polymerase, at least after its removal.

In one embodiment the present invention relates to carrier modules, where the association of the CRG to the oligonucleotide is non-covalent. For example if biotin is attached to the oligonucleotide and streptavidin is attached to the CRG, hence an interaction between biotin and streptavidin associates the oligonucleotide and the CRG with each other non-covalently.

Carrier Modules—Chemistry

A broad range of compounds and/or libraries of compounds can be prepared using the methods described herein. In certain embodiments, compounds that are not, or do not resemble, nucleic acids or analogs thereof, are synthesized according to the method of the invention. In certain other embodiments, compounds that are not or do not resemble, proteins or analogs thereof, are synthesized according to the method of the invention.

In one embodiment the present invention relates to sequential chemical reactions of proximity guided reactants. For example, by use of orthogonal chemistries or the use of orthogonal protective/masking groups, or by sequential assembly and reaction of carrier molecules.

The assembly of carrier modules without ring formation, i.e. formation of a contiguous nucleic acid, may by itself bring appropriately located CRGs into proximity, as the diameter of a double helix is around 2 nm thus allowing positioning of several consecutive CRGs within reaction proximity. The reaction conditions, linkers, reactants and reaction site are chosen to avoid non-oligonucleotide guided reactions and accelerate oligonucleotide guided reactions. Sequential or simultaneously contacting of carrier molecules can be employed depending on the particular compound to be synthesized. In a certain embodiment of special interest, the multi-step synthesis of chemical compounds is contemplated in which three or more carrier molecules are contacted sequentially to facilitate multi-step synthesis of complex chemical compounds.

In one embodiment the present invention relates to annealing of carrier modules, which allows the use of carrier modules at concentrations lower than concentrations used in many traditional organic synthesis. Thus carrier modules may be used in submillimolar concentrations. Preferably, the carrier module concentrations may be used in submillimolar concentrations of less than 100 micromolar, more preferably less than 10 micromolar, even more preferably less than 1 micromolar, even more preferably less than 100 nanomolar and most preferably less than 10 nanomolar In one embodiment the present invention relates to CRG forming small molecules or polymers. Known chemical reactions for synthesizing polymers or small molecules can be used in the practice of the present invention. The chosen reactions preferably are compatible with nucleic acids, such as DNA and RNA or analogs thereof. Reactions useful include, for example, substitution reactions, carbon-carbon bond forming reactions, elimination reactions, and addition reactions.

The CRG or reactants include a variety of reagents and can be any chemical group or reactive moiety (e.g. electrophiles, nucleophiles) known in the chemical art.

In synthesizing small molecules using the method of the present invention a carrier module may have a scaffold associated upon which the small molecule is to be assembled. The scaffold can be any chemical compound with two or more sites for functionalization. The sites may be protected by methods and protecting groups known in the art. The protecting groups may be orthogonal to each other so that they can be removed individually. The reactants to modify a scaffold may be, for example electrophiles (e.g. acetyl, amides, acid chlorides, esters, imines), nucleophiles (e.g. amines, hydroxyl groups, thiols) or side chains.

In certain embodiments, polymers, specifically unnatural polymers, are synthesized according to the method of the present invention. The unnatural polymers that can be synthesized using the inventive method and system include any unnatural polymers. For example unnatural polymers include, but are not limited to, peptide nucleic acid (PNA) polymers, polycarbamates, polyureas, polyesters, polyacrylate (e.g. polyethylene, polypropylene), polycarbonates, polypeptides with unnatural stereochemistry, polypeptides with unnatural amino acids, and combination thereof. In certain embodiments, the polymers comprise at least 3, 4, 5, 6, 7, 8, 9, 10, 25 monomer units or more. In certain embodiments the monomer units may comprise di-mers, tri-mers or tetramers or oligomers. The polymers synthesized using the inventive system may be used, for example, as catalysts, pharmaceuticals or diagnostic affinity ligands. In preparing certain unnatural polymers, the monomer units are attached to the carrier module. The monomer units may be, for example, carbamates, D-amino acids, unnatural aminoacids, PNAs, ureas, hydroxy acids, esters, carbonates, acrylates, or ethers. In certain embodiments, the monomer units have two reactive groups used to link the monomer unit into the growing polymer chain. Preferably, the two reactive groups are not the same so that the monomer unit may be incorporated into the polymers in a directional fashion, for example, at one end may be an electrophile and at the other end a nucleophile. Reactive groups may include, but are not limited to, esters, amides, carboxylic acids, activated carbonyl groups, acid chlorides, amines, hydroxyl groups, and thiols. In certain embodiments, the CRGs are masked or protected. (Green et al (1999) Protective Groups in Organic Synthesis $3^{rd}$ Edition, Wiley) so that polymerization may not occur until a desired time when the CRGs are deprotected. Once the monomers are brought together via carrier module assembly, initiation of the polymerization results in a cascade of polymerization and deprotection steps wherein the polymerization results in deprotection of a reactive group to be used in the subsequent polymerization step. The monomer units to be polymerized can include two or more monomers.

The monomer units may contain any chemical groups known in the art. Reactive chemical groups especially those that would interfere with polymerization, hybridization, etc., are preferably masked using known protecting groups ((Green et al (1999) Protective Groups in Organic Synthesis 3rd Edition, Wiley). In general, the protective groups used to mask these reactive groups are orthogonal to those used in protecting the groups used in the polymerization steps.

In one embodiment the present invention relates to carrier modules, where the reactive site is associated with the same carrier module for all chemical reactions. For example a small molecule scaffold is associated with one carrier module and the remaining carrier modules provide entities modifying the scaffold.

In one embodiment the present invention relates to carrier modules, where the reactive site will shift positions during the chemical reactions In one embodiment the present invention relates to the association of the formed chemical compound to the oligonucleotide while maintaining read through by a DNA polymerase for example at least after its removal.

Preparation of Combinatorial Library

An important practical difference between traditional and nucleic acid guided library synthesis is the scale of each manipulation. Due to the amounts of material needed for screening and compound identification, traditional combinatorial syntheses typically proceed on nanomol-micromol scale per library member. In contrast, nucleic acid guided library synthesis can take place on the femptomol-picomol scale because only minute quantities (e.g. about $10^{-20}$ mol) of each nucleic acid-linked synthetic molecule are needed for selection and PCR amplification. The vast difference in scale, combined with the single-solution format in nucleic acid guided library synthesis simplifies significantly the preparation of materials required.

Figure 2A:
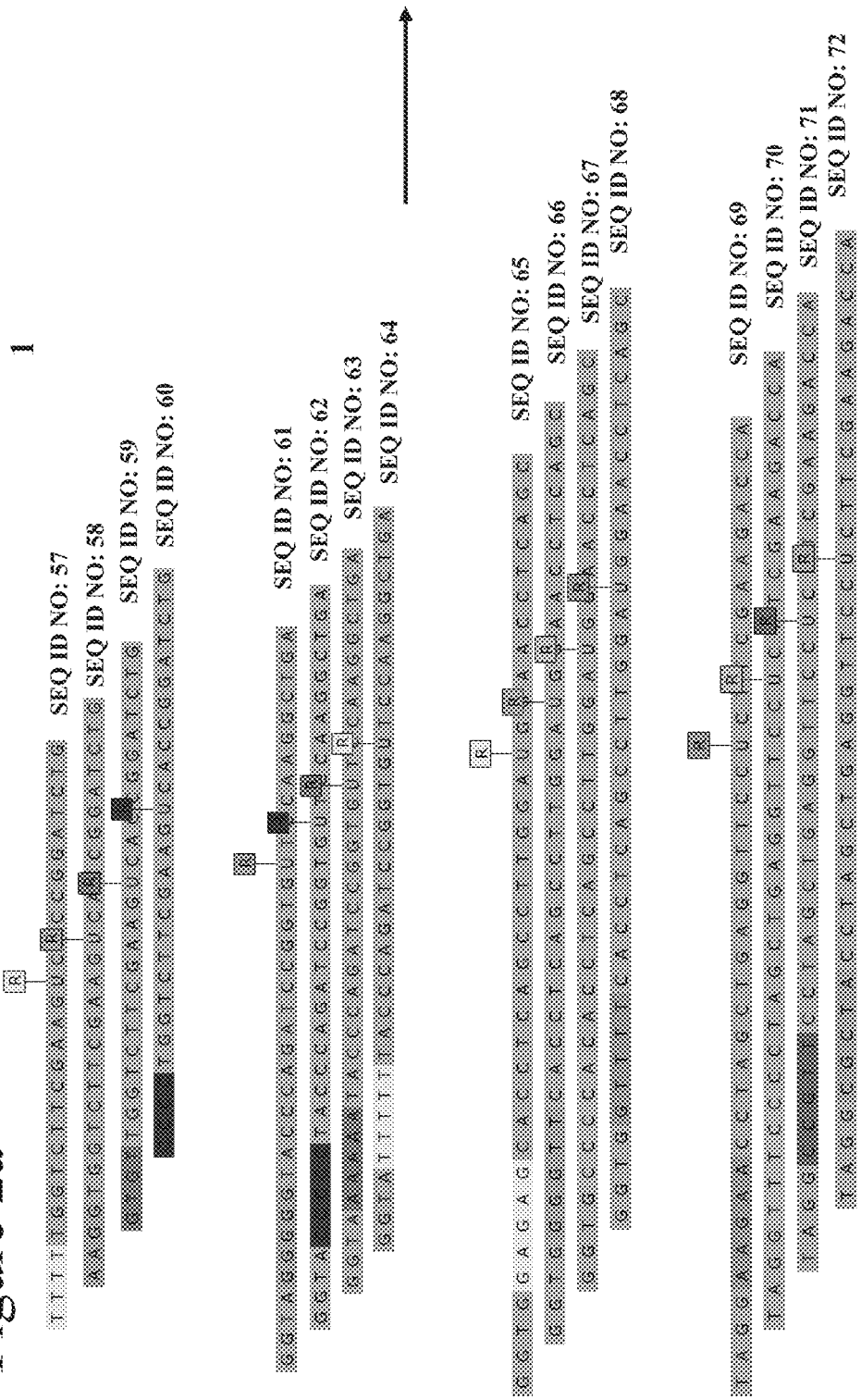
FIG. 2a discloses a method for self-assembling of combinatorial library by repertoires of bi-specific oligonucleotides.

In one embodiment, the present invention relates to the formation of a combinatorial display library. Libraries can be produced by use of repertoires of carrier modules on some or on all positions (FIG. 2a). In a first step a repertoire of carrier modules for each position is provided. When the carrier modules are mixed under hybridisation conditions, they will assemble into the star structure, directed by the sequence of the hybridisation segments. After assembling of the carrier modules ligation and reaction is effected in any order. In an aspect of the invention, the ligation is performed before the reaction to increase the stability of the star structure. Subsequent to the proximity guided reaction, a polymerase priming site is ligated to the star structure and an extension reaction is preformed to display the formed chemical compound to the exterior environment.

As would be appreciated by one skilled in this art, libraries of small molecules and polymers can be synthesized using the principles disclosed herein. Consequently, the combinatorial display library can be subjected to selection and the enriched library's members identified through their encoding oligonucleotide.

Depending upon the circumstances repertoires of carrier modules for two or more positions are initially combined and subjected to a nucleic acid guided chemical reactions between the attached CRGs. Depending upon the circumstances the library can be formed by multiple chemical reactions, wherein each intermediate product is purified before the subsequent round of reactions. Preferably less than 20 chemical reactions steps are required to create a library. In other embodiments, less than 10 chemical reaction steps are needed, and more preferably between 3 and 9 steps are needed to create a the library Selection Selection and/or screening for reaction products with desired activities (such as catalytic activity, binding affinity, binding specificity, or a particular effect in an activity assay) might be performed according to any standard protocol. For example, affinity selections (see FIG. 3) may be performed according to the principles in library-based methods such as phage display (Smith, Science, 22S, 1315-7, 1985), ribosome display (Hanes et al., Proc Natl Acad Sci USA, 95, 14130-5, 1998), mRNA display (Roberts and Szostak, Proc Natl Acad Sci USA, 94, 12297-302, 1997) or DNA encoded chemical libraries (WO 2004/016767, WO 2002/074929A2). Selection for catalytic activities may for example be performed by affinity selection on transition state analog affinity columns (Baca et al., Proc Natl Acad Sci USA, 94, 10063-8, 1997) or by function based selection schemes (Pedersen et al., Proc Natl Acad Sci USA, 95, 10523-8, 1998). Since minute quantities of DNA (~100 molecules) can be amplified by PCR, these selections can thus be conducted on a scale of this magnitude allowing a truly broad search for desired activities, both economical and efficient.

The display library can be selected or partitioned for binding to a target molecule. In this context, selection or partitioning means any process whereby a library member bound to a target molecule is separated from library members not bound to target molecules. Selection can be accomplished by various methods known in the art. In most applications, binding to a target molecule preferable is selective, such that the binding to the target is favored over other binding events. Ultimately, a binding molecule identified using the present invention may be useful as a therapeutic reagent and/or diagnostic agent.

The selection strategy can be carried out to allow selection against almost any target. Importantly, the selection strategy does not require any detailed structural information about the target molecule or about the members of the display library. The entire process is driven by the binding affinities and specificities involved in library members binding to a given target molecule.

Selected library members can easily be identified through their encoding nucleic acid, using standard molecular biology. The present invention broadly permits identifying binding molecules for any known target molecule. In addition, novel unknown targets can be discovered by isolating binding molecules of selected library members and use these for identification and validation of a target molecule.

Selection of binding molecules from a display library can be performed in any format to identify binding library members. Binding selection typically involve immobilizing the desired target molecule, adding the display library, allowing binding, and remove non-binders/weak-binders by washing. The enriched library remaining bound to the target may be eluted with, for example acid, chaotropic salts, heat, competitive elution with known ligand, high salt, base, proteolytic release of target, enzymatic release of nucleic acids. In some embodiments the eluted library members are subjected to more rounds of binding and elution, using the same or more stringent conditions or using a different binding format, which will increase the enrichment. In other embodiments the binding library members are not eluted from the target. To select for library members that bind to a protein expressed on a cell surface, such as an ion channel or a transmembrane receptor, the cells themselves can be used as selection agents. A selection procedure can also involve selection for binding to cell surface receptors that are internalized so that the receptor together with the binding molecule passes into the cytoplasm, nucleus, or other cellular compartment, such as the Golgi or lysosomes. Isolation of the compartment in question leads to partitioning of library members being internalized from non-internalized library members (Hart et al., J Biol Chem, 269, 12468-74, 1994). A selection procedure may also involve in vivo selection. For example by in vivo organ targeting, where a library is injected into an animal and the organ of interest is subsequently isolated and thereby obtain an enriched pool of library members targeted to that organ (Pasqualini and Ruoslahti, Nature, 380, 364-6, 1996). The enriched library's nucleic acid portion may be amplified by, for example PCR, leading to many orders of amplification, allowing identification by e.g cloning and DNA sequencing.

Figure 3:
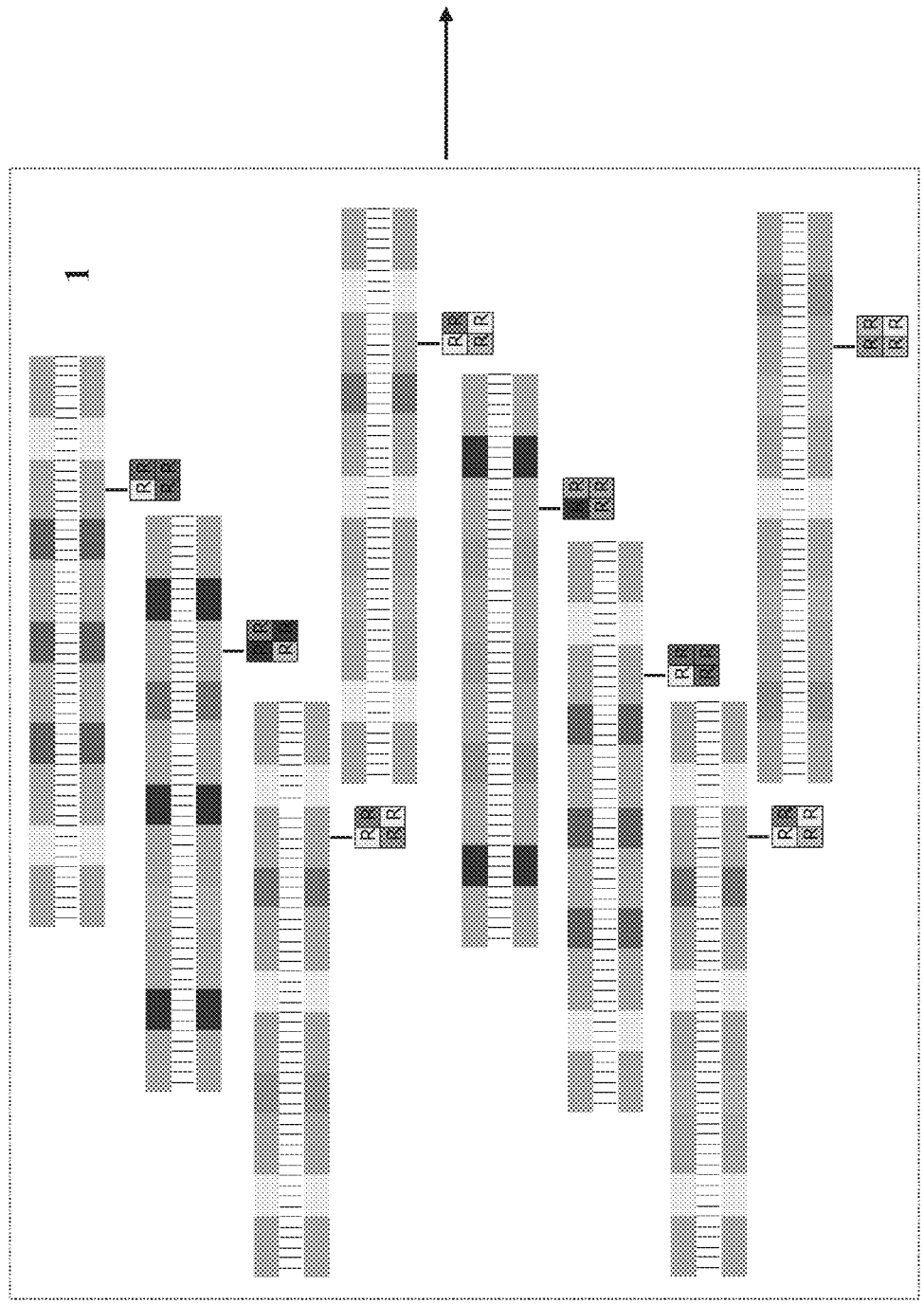
FIG. 3 shows 5 steps in an affinity selection.

According to the specific embodiment for affinity selection shown in FIG. 3, a library of reaction products resulting from the embodiment shown in FIG. 2a, is contacted with a target under binding conditions. If one or more of the formed chemical compounds have affinity towards the target a binding will result. In a subsequent step, binding library members or a nucleic acid derived therefrom are partitioned. The nucleic acid attached to the formed chemical compound is subsequently amplified by e.g. PCR to produce multiple copies of the nucleic acid, which codes for the synthesis history of the compound displaying the desired affinity. The amplified nucleic acid can be sequenced by a number of well-known techniques to decode which chemical groups that have participated in the formation of the successful compound. Alternatively, the amplified nucleic acid can be used for the formation of a next generation library.

Other Selections

Selections for other properties, such as catalytic or other functional activities, can also be performed. Generally, the selection should be designed such that library members with a desired activity can be separated from other library members. For example, selection for library members with capacity for catalyzing bond cleavage can be performed by having biotin attached to each library member by the bond in question. Partitioning using streptavidin can then separate library members having the catalytic activity from others. Another example is selection for library members with bond formation capabilities. This can be performed, by attaching a substrate to each library member and subsequently adding a substrate to which biotin is attached. A reaction between the two substrates forming a bond will attach biotin to catalytic library members. Partitioning using streptavidin can then separate library members having the catalytic activity from others. Selection for other properties, such as dimerization and/or polymerization may also be performed. In this case library members can be partitioned by size of the formed complex, using for example, HPLC, acrylamid or agarose gels or size exclusion columns.

Nucleic Acid Amplification

Amplification of the nucleic acid portion of enriched library members may be performed by standard protocols for nucleic acid amplification. These methods include, for example, polymerase chain reaction (PCR) (Saiki et al., Science, 230, 1350-4, 1985), nucleic acid sequence-based amplification (NASBA) (Compton, Nature, 350, 91-2, 1991), strand displacement amplification (Nycz et al., Anal Biochem, 259, 226-34, 1998), self-sustained sequence replication (Mueller et al., Histochem Cell Biol, 108, 431-7, 1997), primer extension, and plasmid amplification (see for example Sambrook, J., Fritsch, E F, and Maniatis, T. (1989) in: Molecular Cloning: A Laboratory Manual, Cold Springs Harbor Laboratory.

Assembly of Display Library by Module Substitution

Figure 4A:
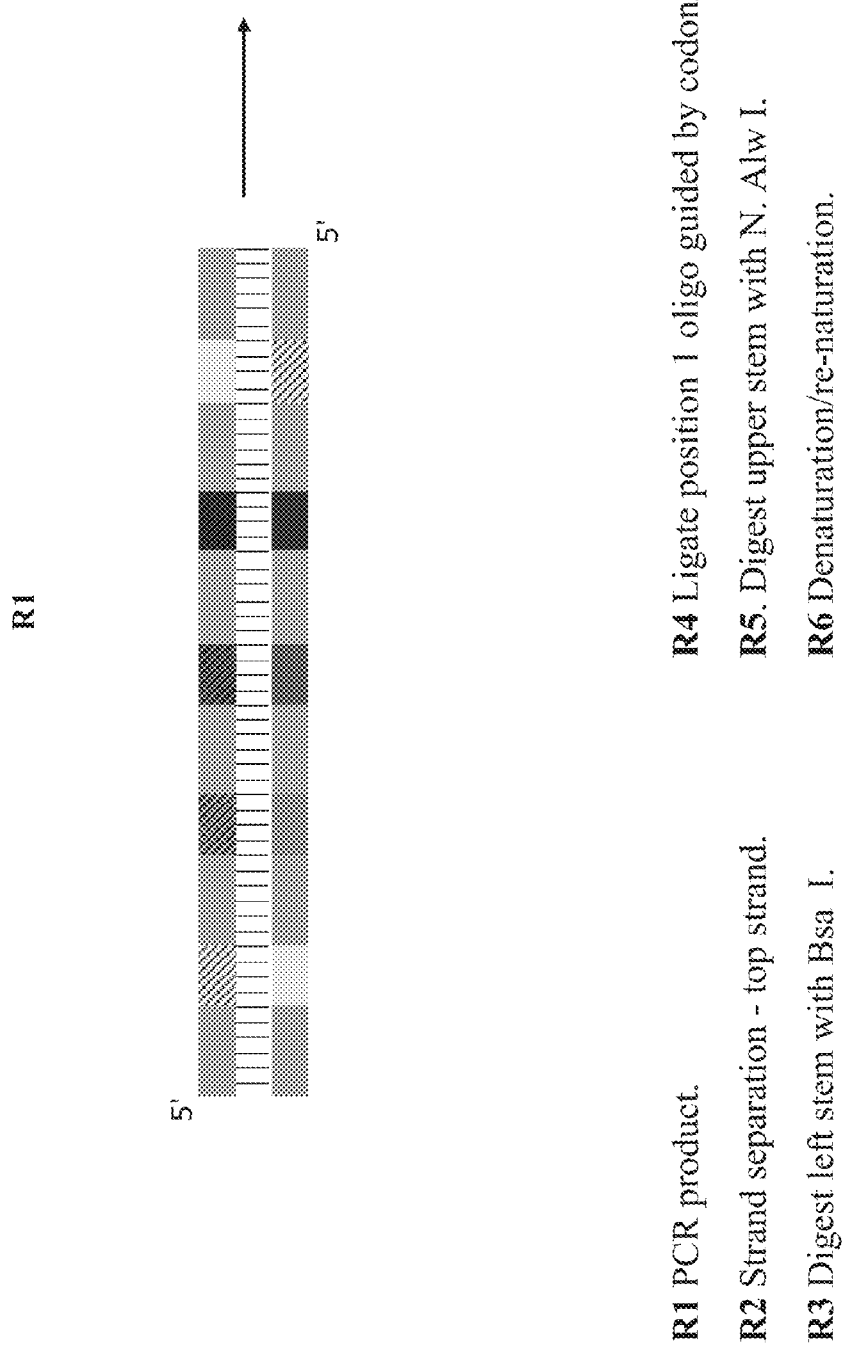
FIG. 4a discloses steps in the formation of a library.
Figure 4A:
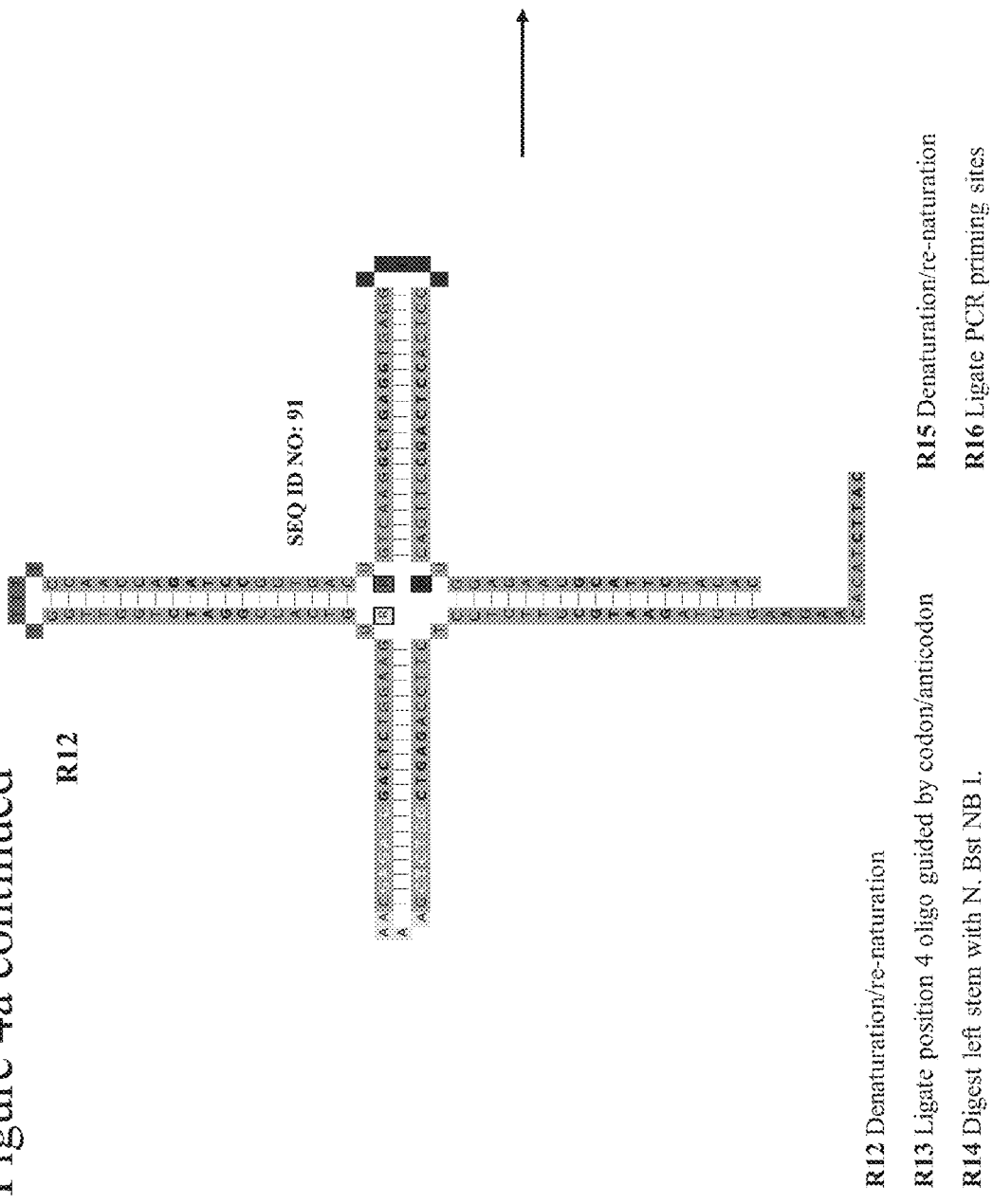
Figure 4A:
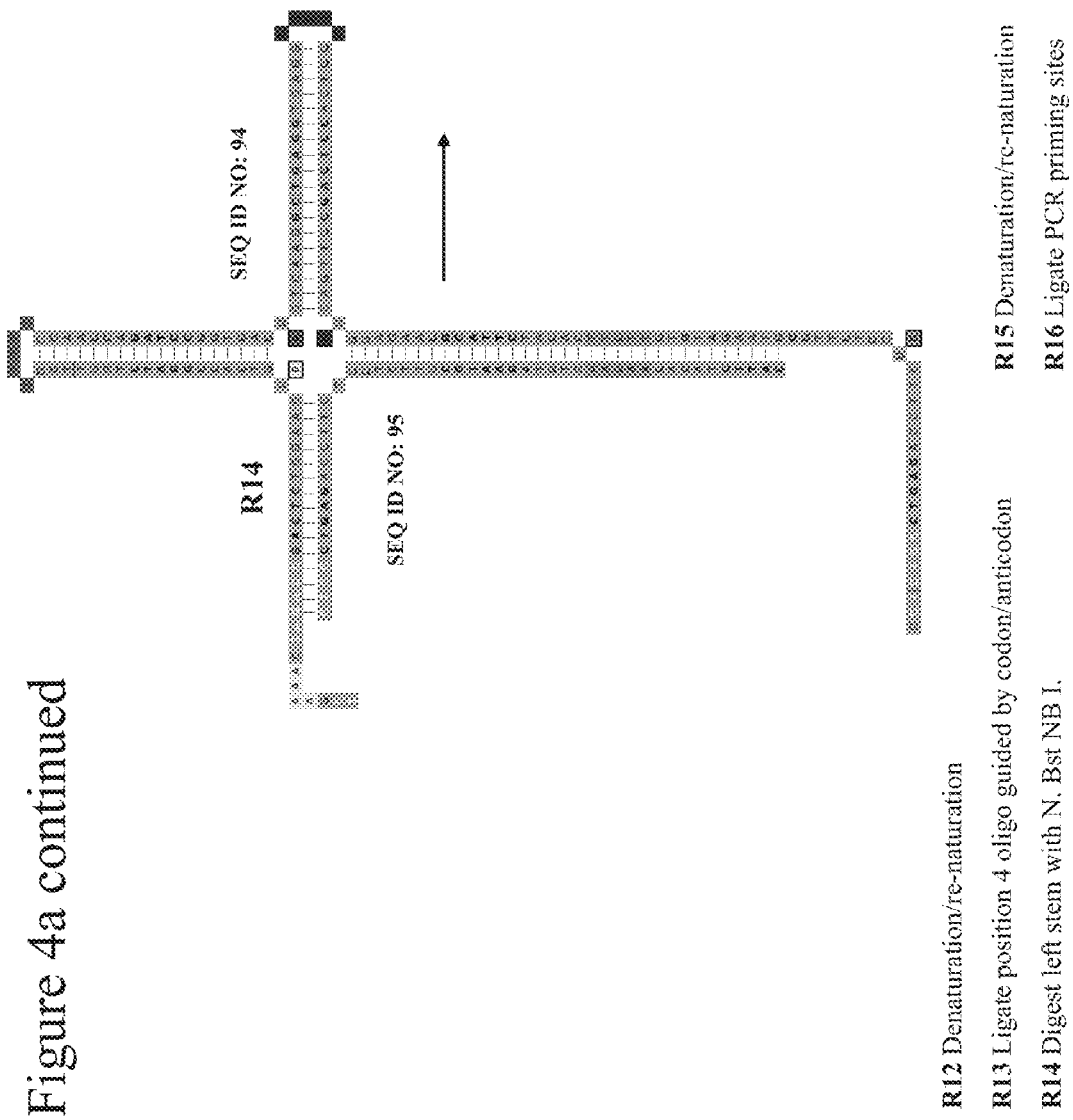
Figure 4A:
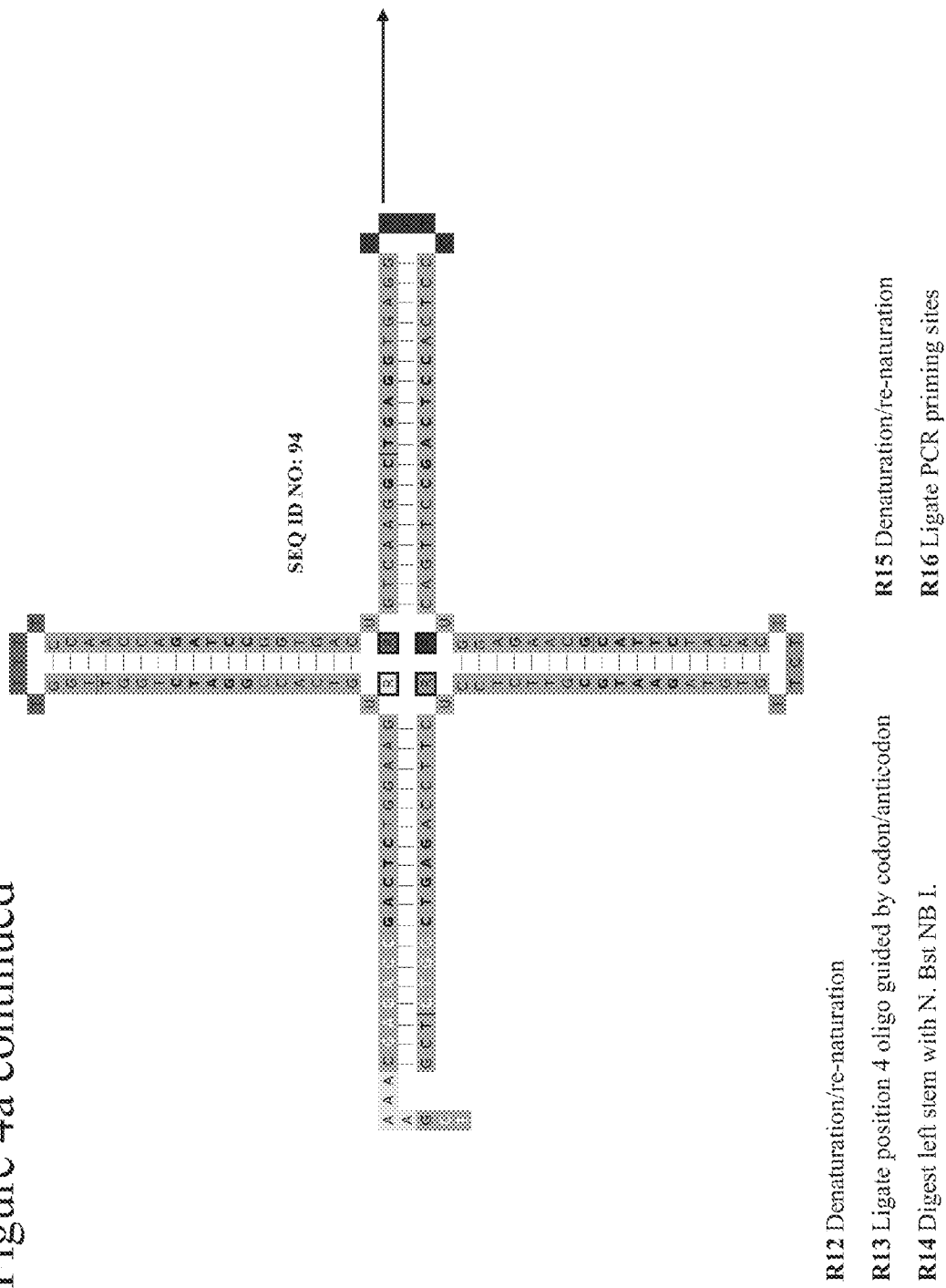
Figure 4A:
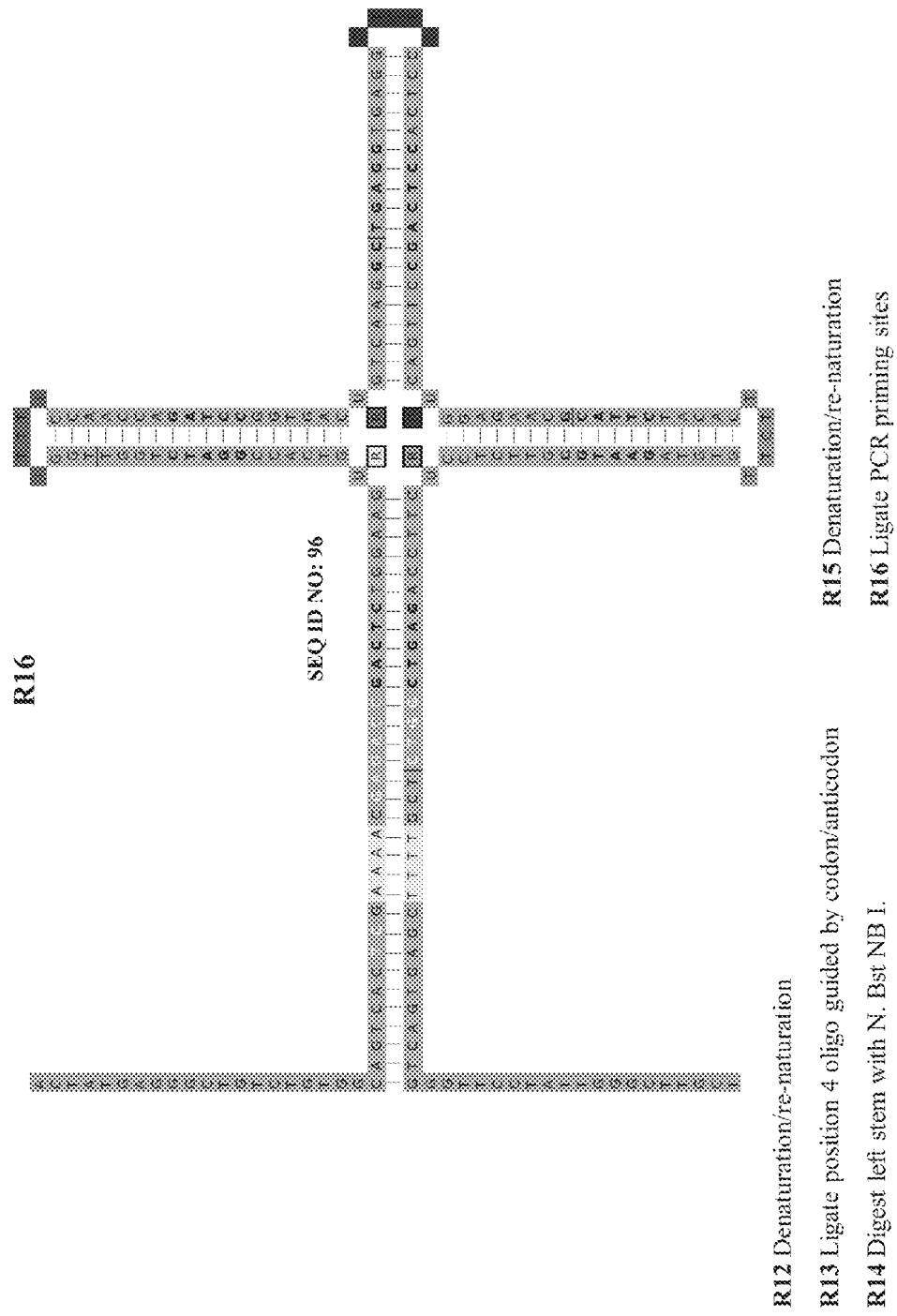
Figure 5:
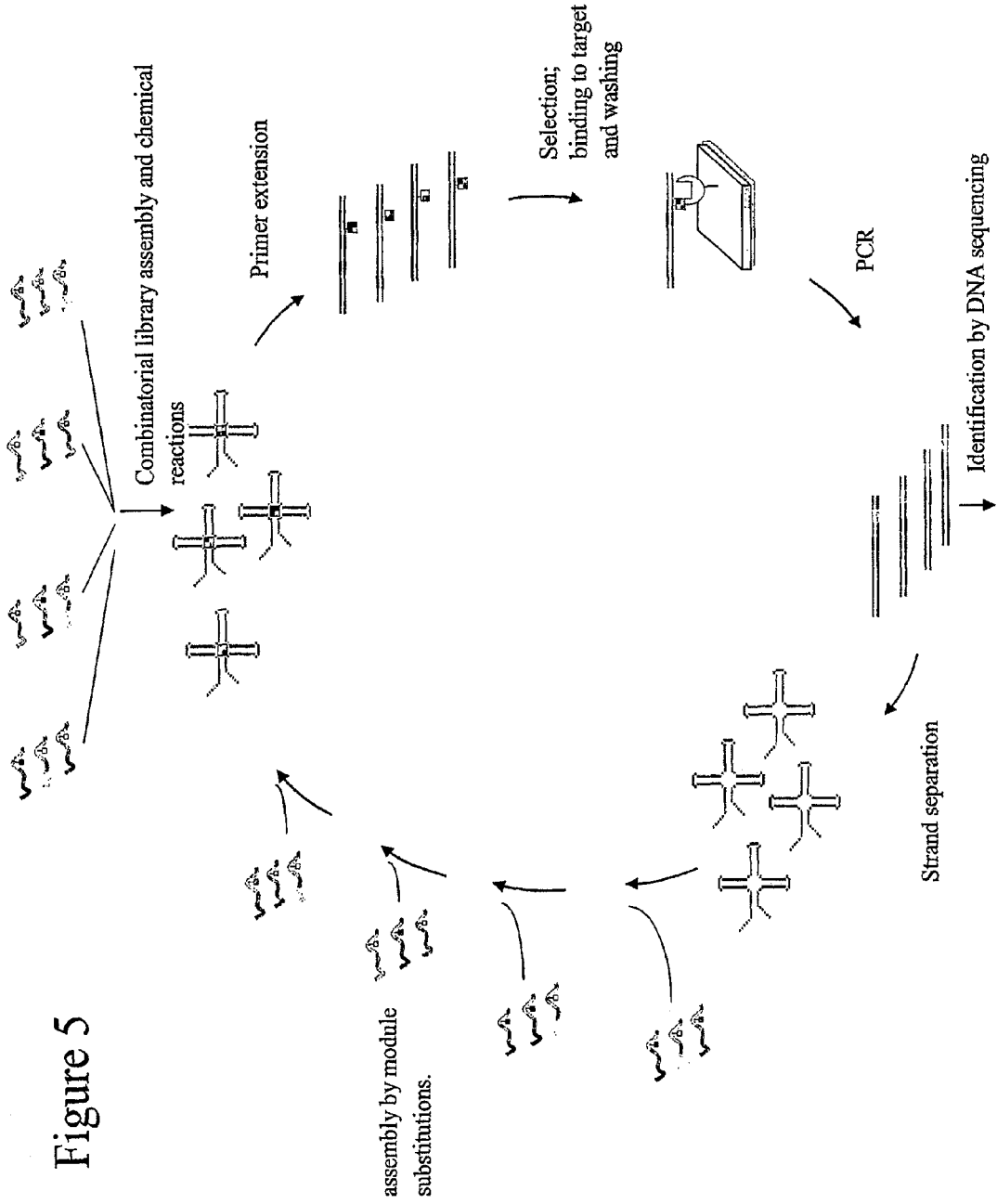
FIG. 5 discloses steps in a method leading to the formation of an enriched library.

In one embodiment, the present invention relates to re-assembly/amplification of an enriched library member or a second generation library of enriched library members to re-create the display. In the case of an enriched library an enriched display library is formed, thus, allowing rounds of selection and amplification and re-assembly. For example, as shown in FIG. 4a, the above described PCR amplified oligonucleotides of enriched library members are allowed to hybridize under conditions favoring intramolecular hybridization, whereby the star-structure, consisting of a stem and a number of stem-loops is recreated. The stem without a loop may contain a recognition site for a restriction enzyme, which generate an overhang with ambiguous base(s). The ambiguous base(s) of the sequence in the created overhang is conveniently utilized to contain a codon. Restriction enzyme digestion of the stem thus generates codon specific overhangs for this first position. The restriction enzyme digested star-structures are then hybridized with a repertoire of carrier modules containing the two constant segments for the first position and a cognate pair of CRG and anti-codon. Consequently, codon/anti-codon hybridization allows for appropriate pairs of carrier modules and star-structures to be ligated. The neighboring stem-loop may also contain a recognition site for another restriction enzyme capable of leaving a codon specific overhang for this second position. Digestion with this second restriction enzyme thus eliminates the covalent linkage of the PCR amplified first module to the rest of the structure. The star-structure is denaturated, and subsequently allowed to hybridize under conditions favoring intramolecular hybridization. The star-structures are thereby recreated, but now with a new carrier module on position one (with a CRG), and the stem, without a loop, is now located on position two. Rounds of this process are performed to substitute all positions, to allow for proximity guided chemical reactions of the proper combinations of CRGs; the display library is thereby amplified and re-assembled. Finally PCR priming sites may be ligated to the star-structure. Consequently, rounds of selection and amplifications and re-assembly can be performed until desired enrichment has been achieved (see FIG. 5).

In one embodiment, the present invention relates to the formation of codon specific overhangs created by restriction enzymes. Suitable restriction enzymes are capable of forming overhangs with more than one specific sequence. Such enzymes include i) restriction enzymes with ambiguous bases in their recognition sequence, ii) restriction enzymes cutting outside their recognition sequence and iii) restriction enzymes performing nicks (nicking endonucleases). Examples of such restriction enzymes; AlwNI, ApaBI, Asul, BbvI, BbvII, BccI, Bce831, Bcefl, BciVI, BglI, BinI, BseMII, BseRI, BsgI, BsiYI, BsmAI, BspMI, BsrDI, BstEII, BstXI, BtgZI, DdeI, DraII, DraIII, DrdI, Earn1105I, EciI, Eco31I, Eco57I, Eco57MI, EcoNI, EspI, Esp3I, Fnu4HI, Fold, GsuI, Hinfl, Hpy178III, Hpy188I, Ksp632I, MaeIII, MboII, MmeI, MwoI, PflMI, PfoI, PleI SapI, SauI, ScrFI, SecI, SfaNI, SfiI, Sth132I, Tsp4CI, TspDTI, TspGWI, TspRI, Tth111I, Tth111II, XcmI, N.AlwI, N.BstNBI, N.BbvCIA and N.BbvCIB.

The encoding capacity (the number of different codons possible) of an overhang is given by the number of ambiguous bases in the overhang created by the restriction enzyme. Hence, for every N(N=A, T, G or C) four different residues can be chosen, for every H (H=A, C or T), V (V=A, C or G), B (B=C, G or T) and D (D=A, G or T) three different residues can be chosen and for every R(R=A or G), K (K=G or T), Y (Y=C or T), S(S=C or G) and M (M=A or C) and W (W=A or T) two different residues can be chosen. Consequently, the encoding capacity is calculated by multiplying the number of different residues on each position with each other. For example Sfi I;

```
                                              (SEQ ID NO: 1)
         5'- . . . GGCCNNNN/NGGCC . . . -3'

(SEQ ID NO: 1)
         3'- . . . CCGGN/NNNNCCGG . . . -5'
``` is creating the overhang 5'-NNN-3', thus consisting of three Ns, thus having an encoding capacity of 64 (=4×4×4).

Another example, Ava II;

```
5'- . . . G/GWCC . . . -3'
3'- . . . CCWG/G . . . -5'
``` creating the overhang 5'-GWC-3', thus having an encoding capacity of 2.

Another example is Bbs I;

```
                                         (SEQ ID NO: 2)
5'- . . . GAAGACNN/NNNN . . . -3'

(SEQ ID NO: 3)
3'- . . . CTTCTGNNNNNN/ . . . -5'
``` creating an overhang consisting of four Ns, thus having an encoding capacity of 256 (=4×4×4×4).

A special group of restriction enzymes are those restriction enzymes cutting only one strand (nicking endonuclease). These enzymes may in principle have indefinite encoding capacity; for example, when i) the recognition sequence is located in the stem of a stem-loop structure, or ii) used to create a terminal overhang, or iii) in the combination with another restriction enzyme. This is because the length of the created overhang can in principle be of indefinite length.

For example, N. BbvC IA located in the stem of a stem-loop structure;

```
        (SEQ ID NO: 4)
5'-...CC/TCAGCNNN
                  ⊃
        (SEQ ID NO: 5)
3'-...GGAGTCGNNN
``` a digest results in;

```
5'- . . . CC -3'

(SEQ ID NO: 6)
3'- . . . GGAGTCGNNNNNNCGACT-5'
``` in this example six Ns are present in the formed overhang, thus giving an encoding capacity of 1024 (=4×4×4×4×4×4). However, it's apparent that the number of Ns can be chosen arbitrarily thus giving an indefinite encoding capacity. A small fraction of the total number of possible sequences in this example can't be used. Namely those sequences forming a recognition sequence of the restriction enzyme in use.

Furthermore a nicking endonuclease can create a terminal overhang of arbitrary length, for example
N. BbvC IA

```
                                         (SEQ ID NO: 7)
5'- . . . CC/TCAGCNNNNNNNN- 3'

(SEQ ID NO: 8)
3'- . . . GGAGTCGNNNNNNNN- 5'
``` a digest results in;

```
5'- . . . CC -3'

(SEQ ID NO: 8)
3'- . . . GGAGTCGNNNNNNNN- 5'
``` and

```
                                         (SEQ ID NO: 9)
5'-TCAGCNNNNNNNN- 3'
```

In this example eight Ns are present in the formed overhang, thus giving an encoding capacity of 65536 (=4 in the $8^{th}$ power). However, it's apparent that the number of Ns can be chosen arbitrarily thus giving an indefinite encoding capacity. A small fraction of the total number of possible sequences in this example can't be used. Namely those sequences forming a recognition sequence of the restriction enzyme in use.

Furthermore a nicking endonuclease in combination with a restriction enzyme can be used to create overhangs of arbitrary length without any requirements for a stem-loop structure. For example
N. BbvC IA combined with Eco RI;

```
                                         (SEQ ID NO: 10)
5'- . . . CC/TCAGCNNNNNNNNG/AATTC . . . -3'

(SEQ ID NO: 11)
3'- . . . GGAGTCGNNNNNNNNCTTAA/G . . . -5'
``` a digest results in;

```
5'- . . . CC -3'

(SEQ ID NO: 12)
3'- . . . GGAGTCGNNNNNNNNCTTAA- 5'
and;

(SEQ ID NO: 13)
5'- TCAGCNNNNNNNNG -3'
and

5'- AATTC -3'
3'- G -5'
``` in this example eight Ns are present in the formed overhang, thus giving an encoding capacity of 65536 (=4 in the $8^{th}$ power). However, it's apparent that the number of Ns can be chosen arbitrarily thus giving an indefinite encoding capacity. A small fraction of the total number of possible sequences in this example can't be used. Namely those sequences forming a recognition sequence of the restriction enzyme in use.

Although the length of the codon segments may vary, the codon segments may range from 1 to 50 nucleotides, from 1 to 40, from 1 to 30, from 1 to 15, from 1 to 10 Codon segments, however, preferentially are 2, 3, 4, 5, 6, 7, 8, 9 or 10 nucleotides long.

Although the length of the stem forming segments may vary, the stem segments may preferentially range from 5 to 50 nucleotides, from 5 to 40, from 5 to 30, from 5 to 15, from 5 to 10. Stem segments, however preferentially are 10, 11, 12, 13, 14, 15, 16, 17, 18, 19, 20, 21, 22, 23, 24, 25, 26, 27, 28, 29 or 30 nucleotides long The length of the mid section between the stem forming segments may vary. The mid section may preferentially range from a single phosphodiester bond (or analogue bond) to a stretch of 20 nucleotides. However, the mid section is preferentially a single phosphodiesterbond or 1, 2, 3, 4, 5, or 6, nucleotides long.

In one embodiment the present invention relates to a method for re-assembly/-amplification of a display library, where the star-structures following restriction enzyme digest further are treated with a phosphatase, which removes the 5' phosphate and thus prevent ligation of two star-structures.

Several suitable phosphatases are known in the art, for example antarctic phosphatase and calf intestinal alkaline phosphatase.

In one embodiment the present invention relates to a method for re-assembly/-amplification of a display library, where the carrier modules contain a 5' phosphate to facilitate ligation to the star-structure.

In one embodiment the present invention relates to a method for re-assembly/amplification of a display library, where the carrier modules are phosphorylated after ligation to a star-structure. This prevents ligation between free carrier modules.

In certain embodiments the present invention relates to a method for re-assembly/amplification of a display library, where the PCR amplified star-structure's 5' terminus may be created by other means than restriction enzymes for example; RNase, Endonuclease III, endonuclease VIII, APE1, Fpg, chemical cleavage or photo cleavage. A PCR product consists of a primer in the 5' end and the remaining sequence formed by a DNA polymerase. The primer may contain residues not found in the segment formed by the DNA polymerase, such as dUTP or RNA. Such residues may be specifically recognized and cleaved by appropriate means, which will create a defined terminus (Smith et al., PCR Methods Appl, 2, 328-32, 1993).

In one embodiment the present invention relates to a method for re-assembly/amplification of a display library. The PCR amplified enriched library termini may be modified before the formation of a star-structure, by any of the above mention methods.

Diversification

Figure 4B:
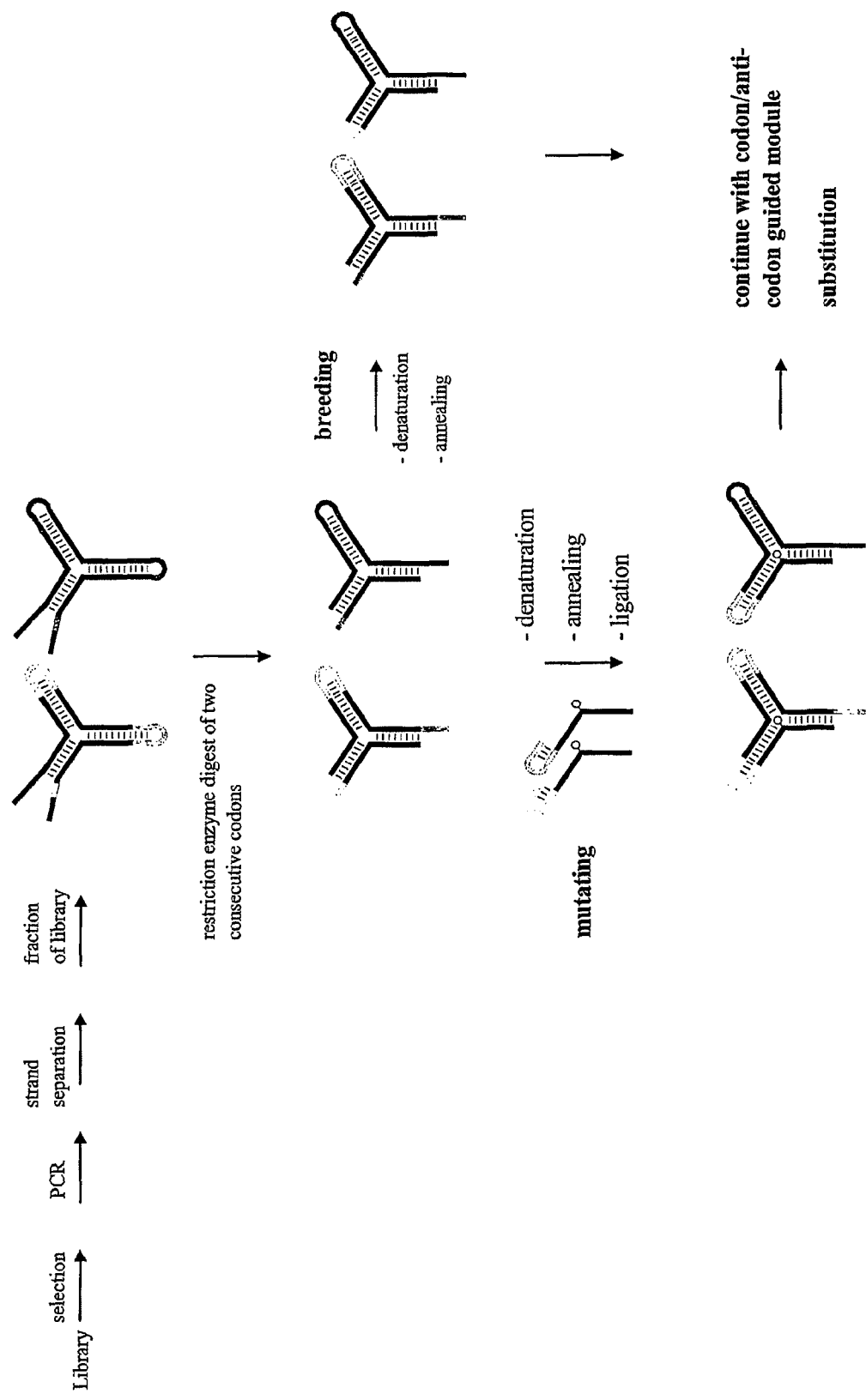
FIG. 4b discloses the principles of breeding and mutation of an enriched library.

In one embodiment, the present invention contemplates a method for diversification of a displayed compound or library of displayed compounds, thus allowing molecular evolution. This can be achieved in a number of ways without going beyond the scope of the present invention. For example (see FIG. 4b), a fraction of the molecules in a round for module substitution is digested with two consecutive restriction enzymes, which eliminate the covalent linkages between the module in question and the remaining structure. The star-structures are denaturated and hybridized with a repertoire of carrier modules for the position in question. The position specific constant segments are thus guiding the hybridizations, in the same way as the primary library was created. The appropriate termini are ligated and the formed product pooled with the codon guided assembled fraction, leading to diversification. This may be done in one, some or all rounds of module substitution. In another example, a fraction of the molecules in a round for module substitution is subjected to removal of codon specific overhangs for the position in question, e.g. by an exonuclease. Subsequently a repertoire of carrier modules for the position in question is hybridized and ligated. The then formed non-codon guided products are pooled with the codon guided assembled fraction, leading to diversification. This may be done in one, some or all rounds of module substitution.

Figure 6:
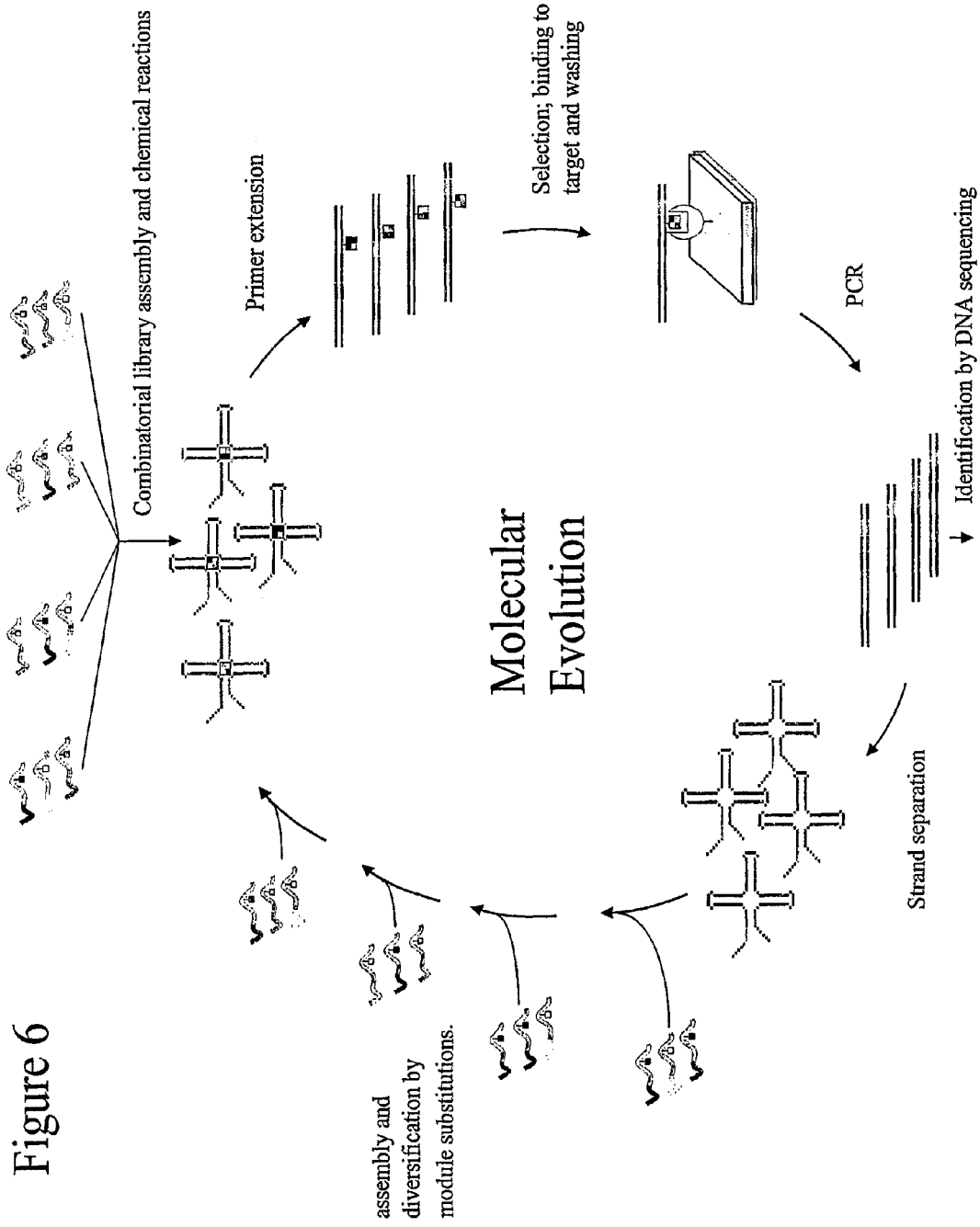
FIG. 6 shows the principle of molecular evolution.

The diversification may also be performed by shuffling/recombination (breeding) of modules between library members before the module substitution process. For example, the enriched library members' nucleic acid portion is amplified and digested with a restriction enzyme cutting in constant segment(s), thus creating two or more fragments. The fragments can be ligated with fragments originating from other library members to form a full length product, whereby shuffling/recombinations have occurred. Another example of methods for shuffling/recombinations is by using the star-structures (see FIG. 4b). The star-structures are digested by two consecutive restriction enzymes, denaturated and allowed to hybridize leading to exchange of the module in question. Consequently, rounds of selection, amplification and diversification can be performed, thus allowing for molecular evolution (see FIG. 6).

Selection for Catalytic Activity

The principle described can also be applied to select for catalytic activity. In this case the carrier modules include reactive site functionalities and the star structure provides a framework for a three dimensional arrangement of these functionalities, thus mimicking protein enzymes.

Figure 7:
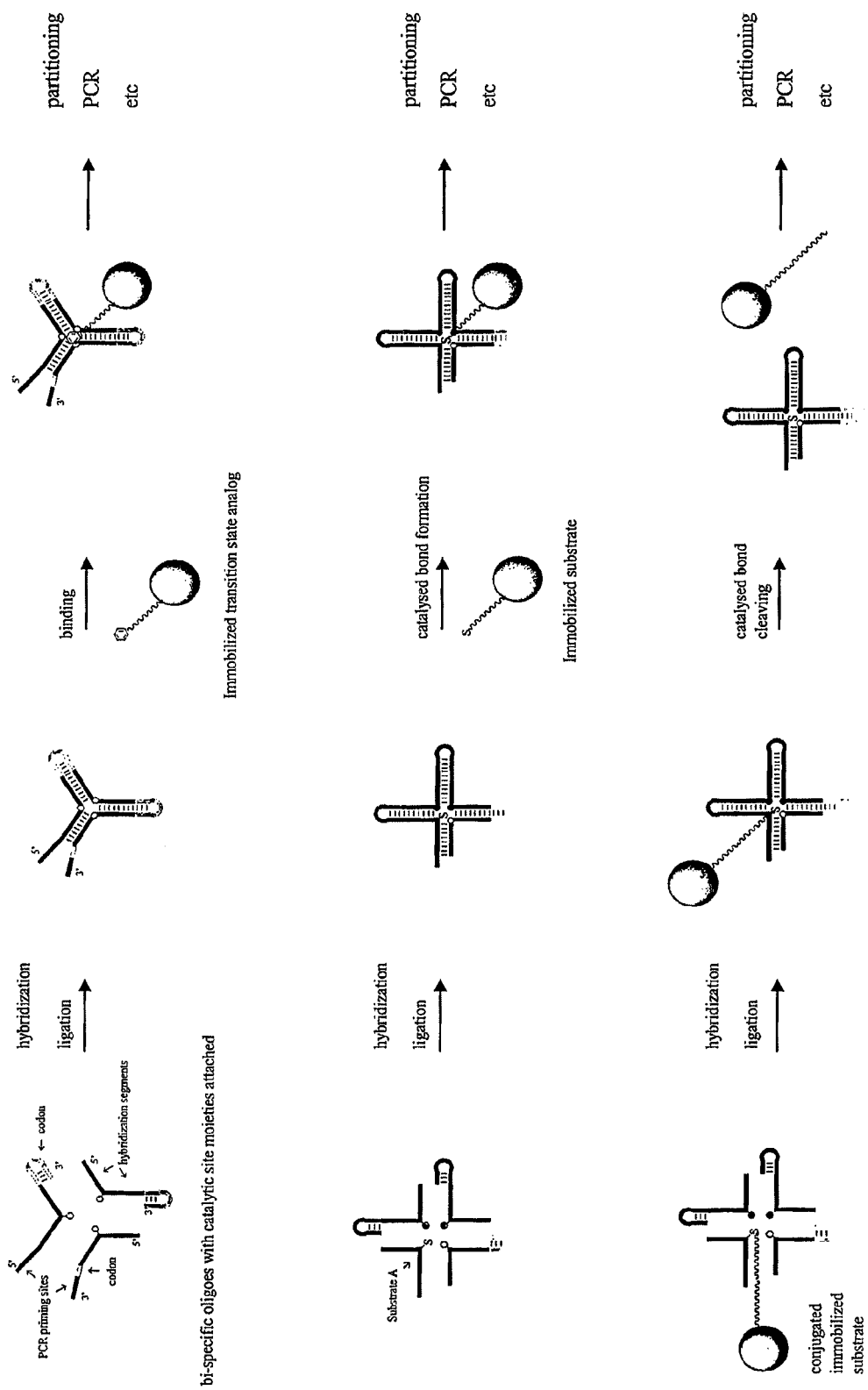
FIG. 7 shows an embodiment of the invention involving an immobilized substrate.

Selection schemes for various catalytic activities are contemplated. For example i) selection for binding to a transition state analog, ii) selection for bond formation by associating one substrate to the star structures while the other substrate is immobilized to e.g. beads. (Consequently library members associated to the beads are capable of bond formation), or iii) selection for bond cleavage by having the substrate associated to both the star structure and a bead. (Consequently library members not associated to the bead are capable of bond cleavage.) (see FIG. 7).

Codon Specific Compartmentalization

The star-structure allows any codon position to become terminal and single stranded by use of for example a suitable restriction enzyme, thus allowing highly specific compartmentalization by hybridization and optionally ligation for a particular codon position. Various methods for compartmentalization are known in the art, for example, microarrays of anti-codon sequences (Lockhart et al., Nat Biotechnol, 14, 1675-80, 1996), columns of anti-codon sequences (Halpin and Harbury, PLoS Biol, 2, E173, 2004) or using beads, where the individual beads contain an anti-codon sequence and a fluorescence tag, which subsequently allows for sorting by e.g. fluorescence activated cell sorted (Iannone et al., Cytometry, 39, 131-40, 2000).

Such compartmentalization may be useful in the practice of the present invention, for example; i) during library synthesis for post chemical reaction modifications, ii) analysis of single clones, iii) analysis of progression in selections, or iv) analysis of diversity. Consequently, compartmentalization in situation ii)-iv) may be a rapid and economical alternative to DNA sequencing for deconvolution of a single sequence or a library of sequences.

Throughout the description, where compositions are described as having, including, or comprising specific components, or where processes are described as having, including, or comprising specific process steps, it is contemplated that compositions of the present invention also consist essentially of, or consist of, the recited components and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

The method and compositions of the present invention represent new ways to generate molecules with desired properties. This approach combines extremely sensitive and powerful molecular biology, with the flexibility of organic chemistry. The ability to prepare, amplify, and evolve unnatural polymers and small molecules by molecular evolution may lead to new classes of catalysts, novel ligands, or drugs with superior properties to those isolated with slower traditional discovery methods.

The present invention also provides kits and composition for the use in the inventive methods.

DEFINITIONS

The terms, "nucleic acid" or "oligonucleotide" as used herein refer to a polymer of nucleotides. The polymer may include, without limitation, natural nucleosides (i.e. adenosine, thymidine, guanosine, cytidine, uridine, deoxyadenosine, deoxythymidine, deoxyguanosine; and deoxycytidine), nucleoside analogs, (eg., 2-aminoadenosine, 2-thiothymidine, inosine, pyrrolo-pyrimidine, 3-methyl adenosine, 5-methylcytidine, C5-bromouridine, C5-fluorouridine, C5-urouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g. methylated bases), intercalated bases, modified sugars (e.g., 2'-fluororibose, ribose, 2'-deoxyribose, arabinose and hexose), or modified phosphate groups (e.g., phosphorothioates and 5', -N-phosphoramidite linkages). Nucleic acids and oligonucleotides may also include other polymers of bases having a modified backbone, such as a locked nucleic acid (LNA), a peptide nucleic acid (PNA), a threose nucleic acid (TNA) and any other polymers capable of serving as a template for an amplification reaction, using an amplification technique, for example, a polymerase chain reaction or a ligase chain reaction.

The term "segment" as used herein, refers to a continuous section of an oligonucleotide sequence.

The terms, "codon" and "anti-codon" as used herein, refer to an oligonucleotide sequence that code for a certain chemical group associated with the said codon or anti-codon. A series of codons codes for the combination of specific chemical reactants, which have participated in the formation of the encoded molecule.

The term "Stem-loop" structure as used herein, refers to any secondary structure involving at least a nucleotide portion within which a strand of a nucleic acid sequence, via intramolecular hydrogen bonds, with another portion of the same nucleic acid molecule in order to constitute a "self-paired" region termed "stem" of mostly double-stranded nature and an unpaired "loop" region located at one end of the said stem. When the length of the loop is zero, it produces the special case of stem-loop called "hair pin" or palindrome.

The term "small molecule" as used herein refers to an organic compound either synthesized in the laboratory or found in nature having a molecular weight less than 10,000 grams per mole, optionally less than 5,000 grams per mole, and optionally less than, 2,000 grams per mole, such as less than 1000 grams per mole. Preferred small molecules are suitable for oral administration.

The terms, "small molecule scaffold" or "molecular scaffold" as used herein, refer to a chemical compound having at least one site or chemical moiety suitable for functionalization. The small molecule scaffold or molecular scaffold may have two, three, four, five or more sites or chemical moieties suitable for functionalization. These functionalization sites may be protected or masked as would be appreciated by one skilled in this art. The sites may also be found on an underlying ring structure or backbone.

The terms "chemical reactive group" or "chemical groups" or "reactive unit" as used herein, refer to any chemical moiety capable of modifying, adding to, or taking away from another chemical moiety. Including, for example, but not limited to, a building block, monomer, monomer unit, molecular scaffold, or other reactant useful in proximity mediated chemical synthesis. In some instances the chemical group is not a nucleotide or a derivative thereof. In another aspect at least one of the chemical groups which have participated in the synthesis of the formed chemical compound is not a naturally occurring amino acid.

The term, "associated with" as used herein describes the interaction between or among two or more groups, moieties, compounds, monomers, etc. When two or more entities are "associated with" one another as described herein, they are linked by a direct or indirect covalent or non-covalent interaction. Preferably, the association is covalent. The covalent association may be, for example, but without limitation, through an amide, ester, carbon-carbon, disulfide, carbamate, ether, thioether, urea, amine, or carbonate linkage. The covalent association may also include a linker moiety, for example, a photocleavable linker. Desirable non-covalent interactions include hydrogen bonding, van der Waals interactions, dipole-dipole interactions, pi stacking interactions, hydrophobic interactions, magnetic interactions, electrostatic interactions, etc. Also, two or more entities or agents may be "associated" with one another by being present together in the same composition.

The term, "carrier module" as used herein, refers to a chemical group associated to an oligonucleotide, and a segment towards the 3' end which can hybridize to a segments towards the 5' in a second oligonucleotide and a segment towards the 5' end which can hybridize to a segment towards the 3' end of a third oligonucleotide. The carrier module optionally contains a codon or anti-codon segment. The term "hybridization segment" as used herein refers to said oligonucleotide segment.

The term "star-structure" as used herein, refers to any secondary structure involving at least three stems of mostly double stranded nature. 0, 1, 2, 3, 5, 6, 7, 8, 9 or more nucleotide residues may separate the stems. In the special case where zero nucleotide residues are separating four stems the junction is called a Holliday junction. A star structure may consist of one nucleic acid molecule, or it may consist of a plurality of nucleic acid molecules.

The term "reaction proximity" as used herein, refers to a distance between reactants by which the reaction of said reactants can occur in a controlled, efficient and timely manner.

The term "proximity guided chemical reaction" as used herein, refers to chemical reactions between reactants, which are brought into reaction proximity by hybridization of nucleic acid to which the reactants are associated.

EXAMPLES

Example 1

Figure 8:
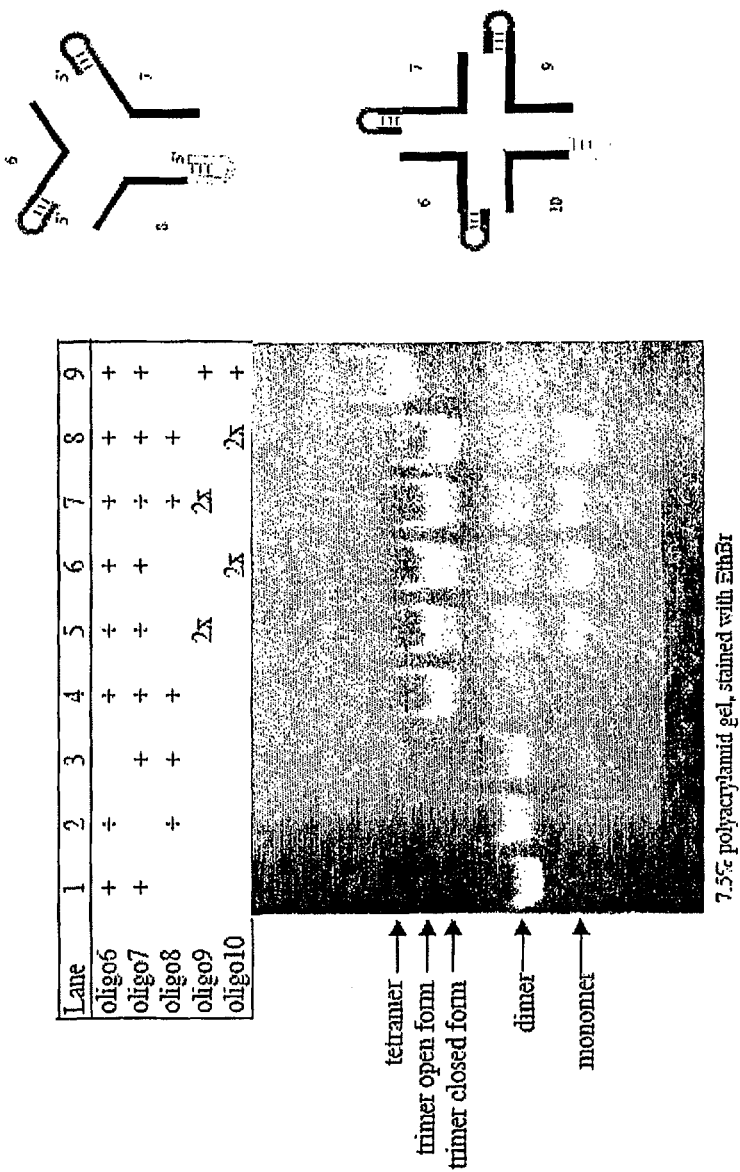
FIG. 8 discloses the experimental results of example 1.

The Formation of Trimeric and Tetrameric DNA Star Structures by Mutual Complementary Bi-Specific Oligonucleotides is Demonstrated DNA oligonucleotides (prepared by DNA Technology Århus, Denmark) were mixed as indicated in the table shown in FIG. 8 in 2 uM concentrations each in 1× Ligase Buffer (New England Biolabs), 50 mM NaCl. The mixtures were incubated at 80 degrees C. for 2 minutes and slowly cooled to room temperature in a water bath. The products were analyzed by PAGE native (7.5% polyacrylamide), followed by staining with ethidium bromide, using standard protocols (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.).

Oligo6 and oligo7 (corresponding to Vip006 and vip007, respectively), oligo6 and oligo8 (corresponding to vip006 and vip008) and oligo7 and oligo8 (corresponding to vip007 and vip008, respectively) each have a mutual complementary segment, thus capable of forming an annealed dimer. Accordingly, a band corresponding to dimers were observed in lane 1-3. Vip006, vip007 and vip008 each have a mutual complementary segment to two neighboring oligoes, thus capable of forming a closed annealed trimeric structure (see FIG. 8). Accordingly, a band corresponding to a trimer was observed in lane 4. Oligo6, oligo7, and oligo9 (corresponding to Vip006, vip007 and vip009, respectively) each have a mutual complementary segment to a neighboring oligo, thus capable of forming an annealed trimeric structure. However, the structure is open because vip008 and vip006 do not have complementary segments (see FIG. 8). Accordingly, a band corresponding to a trimeric was observed in lane 5. The open trimer is expected to have a slightly lower mobility in the gel than the more compact closed trimer form. The mobility difference is in fact observed when comparing lane 4 with 5.

An equivalent observation of a slow migrating trimeric band was obtained by using oligo6, oligo7, and oligo 10 (corresponding to vip006, vip007 and vip010, respectively), where vip006 and vip010 do not anneal directly to each other (compare lane 4 and 6). To assess the efficiency of formation of the closed trimeric form oligo6, oligo7, and oligo8 (corresponding to vip006, vip007, and vip008, respectively) were annealed in the presence of two-fold excess of oligo9 or oligo10 (corresponding to vip009 or vip010, respectively). Interestingly, the major band in both lanes 7 and 8 correspond to the closed trimeric fast migrating species consisting of vip006, vip007 and vip008. The successful formation of a closed tetramer was accomplished by annealing oligo6, oligo7, oligo9 and oligo10 (corresponding to vip006, vip007, vip009 and vip010, respectively) and observed as one major band in lane 9. Note that the intended valency in all chases were obtained with high efficiency; observed as a single major band.

Example 2

Conversion of Trimer DNA Star Structure into a Single Contiguous Strand of DNA by T4 DNA Ligase The successful creation of a tri-stemmed DNA star structure consisting of a single uninterrupted strand of DNA was demonstrated in this example. Mutual complementary bi-specific oligonucleotides were annealed, and subsequently ligated to form a continuous strand of DNA.

Figure 9:
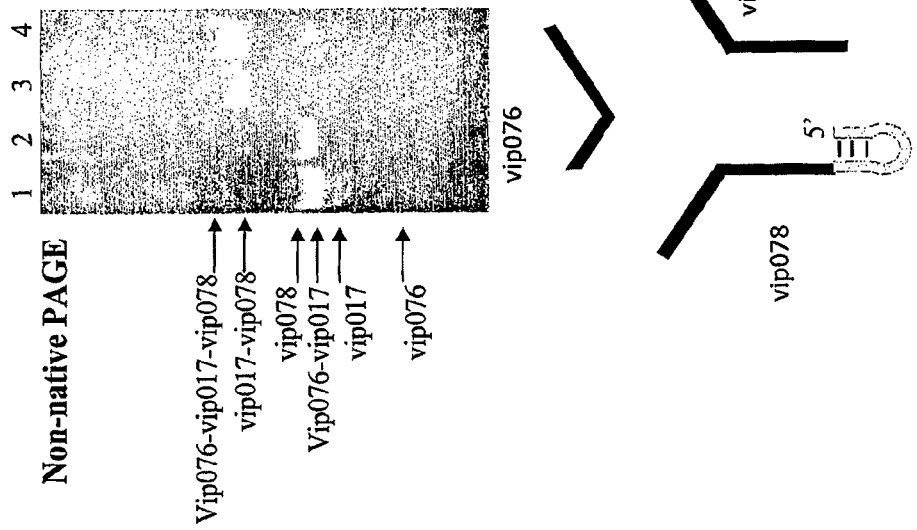
FIG. 9 depicts the results of experiments reported in the example 2.

DNA oligoes (prepared by DNA Technology Århus, Denmark) were mixed as indicated in FIG. 9 in 2 uM concentrations each in 1× Ligase Buffer (New England Biolabs), 50 mM NaCl. The mixtures were incubated at 80 degrees C. for 2 minutes and slowly cooled to room temperature in a water bath.

The 5' termini of the oligonucleotides were phosphorylated by T4 DNA polynucleotide kinase. A mixture consisting of 1.67 uM star structure, 1×DNA ligase Buffer (New England Biolabs), 50 mM NaCl and 0.2 u/ul T4 DNA polynucleotide kinase (New England Biolabs, cat# M0201), was prepared and incubated for 30 minutes at 37° C.

A phosphodiester bond between juxtaposed ends of annealed oligonucleotides was formed by T4 DNA ligase (New England Biolabs, cat# M0202). ⅓× Volume of ligase mix, 1×DNA ligase Buffer (New England Biolabs), 50 mM NaCl, and 100 u/ul T4 DNA ligase (New England Biolabs, cat# M0202), were added to the above described kinase treated mixture and incubated for 2 hours at room temperature. The products were analyzed by non-native PAGE (7.5% polyacrylamide, 8M urea), followed by staining with ethidium bromide, using standard protocols (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.).

Vip076 (25 nt) and vip017 (42 nt) each have a mutual complementary segment which upon annealing places the 3' end of vip076 adjacent to the 5' end of vip017, thus making a substrate for T4 DNA ligase. Accordingly, a prominent band corresponding to vip076-vip017 (67 nt) was observed in lane 1 (non-native PAGE). Similarly, the formation of a prominent band corresponding to vip017-vip078 (100 nt) was observed in lane 3. In contrast, vip076 and vip078 (58 nt) each have a mutual complementary segment but do not form annealed adjacent ends and are not expected to be ligated. Accordingly, only bands corresponding to monomers of vip076 and vip078 were observed in lane 2. Note the band corresponding to vip076 is fainter, which is expected as vip076 is smaller and the oligonucleotides are in equimolar concentrations. Moreover, vip078 (58 nt) migrates slower than vip076-vip017 (67 nt) in the gel, which is not unexpected as vip076-vip017 contains sequences for creation of a stem-loop structure giving a more compact fold, thus higher mobility in the gel.

Vip076, vip017 and vip078 each have a mutual complementary segment, which upon annealing places the 3' end of vip076 adjacent to the 5' end of vip017, and the 3' end of vip017 adjacent to the 5' end of vip078, thus making two substrates for T4 DNA ligase. Accordingly, a prominent band corresponding to vip076-vip017-vip078 was observed in lane 4.

Consequently, creation of a trimeric DNA star structure consisting of one contiguous strand of DNA was hereby demonstrated.

Example 3

Amplification of Tri-Stemmed DNA Star Structure

The successful amplification of trimeric DNA star structure consisting of one contiguous strand of DNA was demonstrated in this example. Mutual complementary bi-specific oligonucleotides were annealed, ligated and subsequently used as a template in a primer extension reaction.

DNA oligoes (prepared by DNA Technology Århus, Denmark) were mixed as indicated below in 2 uM concentrations each in 1× Ligase Buffer (New England Biolabs), 50 mM NaCl. The mixtures were incubated at 80 degrees C. for 2 minutes and slowly cooled to room temperature in a water bath.

The 5' termini of the oligonucleotides were phosphorylated by T4 DNA polynucleotide kinase. A mixture consisting of 1.67 uM star structure, 1×DNA ligase Buffer (New England Biolabs), 50 mM NaCl and 0.2 u/ul T4 DNA polynucleotide kinase (New England Biolabs, cat# M0201), was prepared and incubated for 30 minutes at 37 C A phosphodiester bond between juxtaposed ends of annealed oligonucleotides was formed by T4 DNA ligase (New England Biolabs, cat# M0202). ⅓× Volume of ligase mix, 1×DNA ligase Buffer (New England Biolabs), 50 mM NaCl, and 100 u/ul T4 DNA ligase (New England Biolabs, cat# M0202), were added to the kinase treated mixture and incubated overnight at room temperature.

A primer extension reaction was performed by adding 3 volume extension mix, 1.33× Vent Buffer (New England Biolabs), 1.33 uM vip038, 2.67 mM dNTP and with or without 1.33 u/ul Vent(exo-) DNA polymerase (New England Biolabs, cat# M0257) to 1 volume ligation reaction. The solution was incubated for 1 minutes at 92 C, 1 minute at 50 C and 10 minutes at 74 C and put on ice.

The reactions were analyzed by native PAGE (7.5% polyacrylamide) followed by staining with ethidium bromide, using standard protocols (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.).

Figure 10:
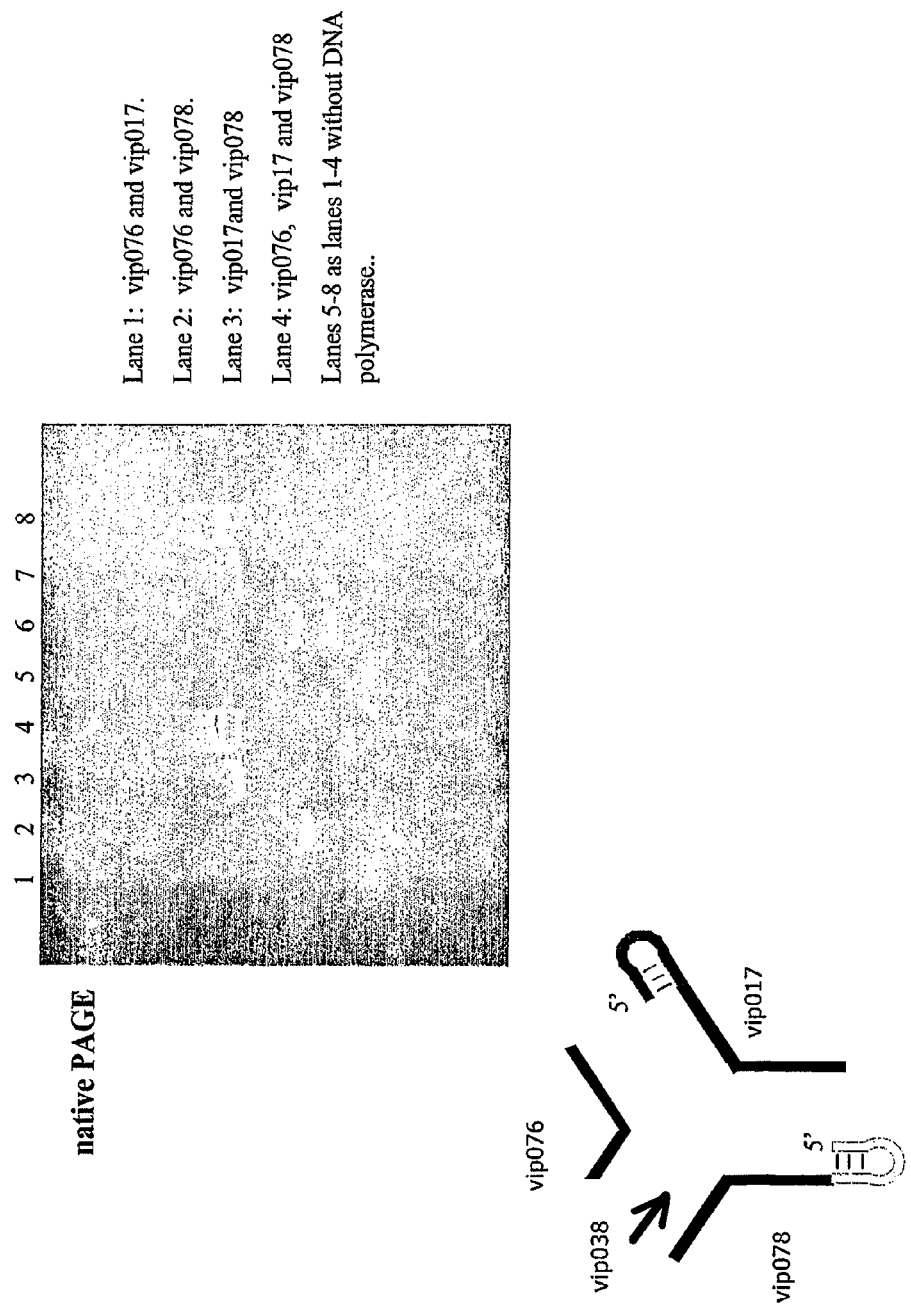
FIG. 10 shows the result of the experiments according to example 3.
Figure 11:
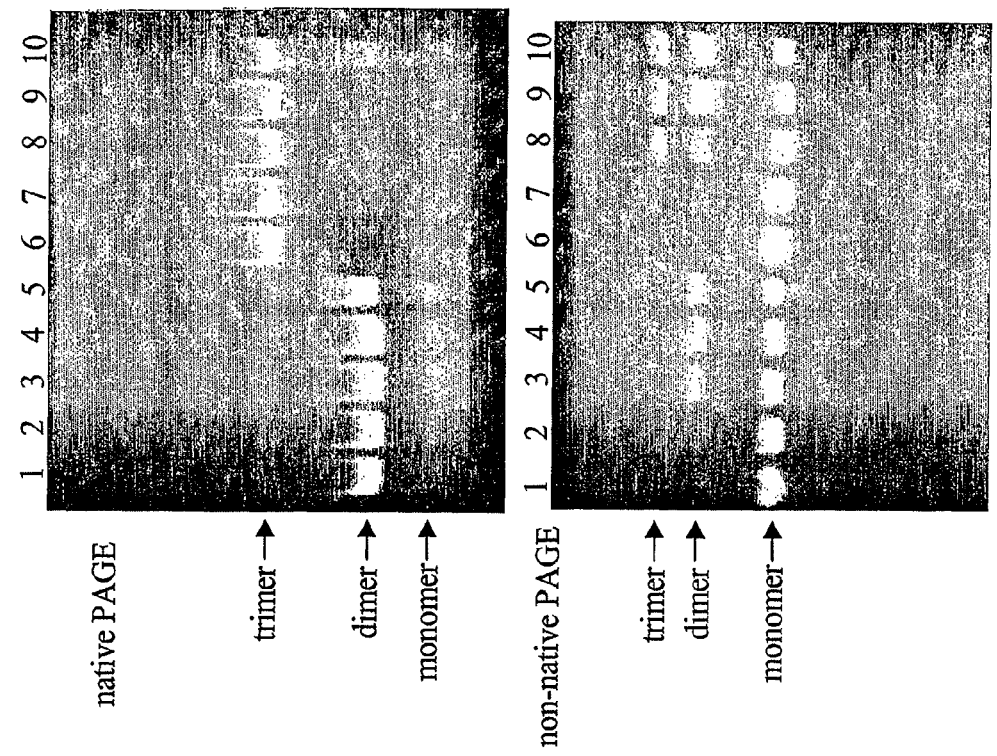
FIG. 11 discloses the results of experiments reported in example 4.

The results of the experiments are shown in FIG. 10. Vip038 is reverse complementary to the 20 most 5' terminal bases in vip078 and can therefore prime an extension reaction using vip078 or vip078 fusions as templates. Accordingly, a single prominent band corresponding to double stranded vip073 was obtained in the extension reaction containing vip038, vip076 and vip078 (lane 2). Note that this band is not present in lane 6, which is equivalent but without the DNA polymerase included. In contrast, lane 6 contains two bands, which presumably consists of annealed vip076/vip078/vip038 and annealed vip078/vip038.

The specificity of the reaction was demonstrated by vip038, vip076 and vip017, where no visible difference between with or without the DNA polymerase was observed, compare lane 1 and 5.

A successful primer extension was also observed using the ligation reaction vip017-vip078 illustrated by the prominent band in lane 3. Note a fainter band corresponding to double stranded vip078 also is observed illustration that not all vip078 was ligated to vip017. In the corresponding lane 7 without DNA polymerase a fainter band with almost the same mobility as double stranded vip017-vip078 is observed. The band presumably consists of annealed vip038/vip017-vip078.

A successful primer extension was also observed using vip076-vip017-vip078 ligation reaction as template. Two bands with lower mobility in the gel than double stranded vip017-vip078 were observed. The lower band corresponds to annealed vip038/vip076-vip017-vip078 as seen when comparing to the equivalent lane 8 without DNA polymerase. However, the upper band in lane 4 is unique and therefore consisting of double stranded vip076-vip017-vip078. Consequently, this example demonstrates that DNA structures can be converted into double stranded DNA and therefore amplifiable.

Example 4

Chemical Reactivity in the Center of Star Structures

The chemical reactivity in the center of star structures was accomplished by using the following tri-functional crosslinker (TSAT, Tris-succinimidyl aminotriacetate, Pierce cat. No 33063):

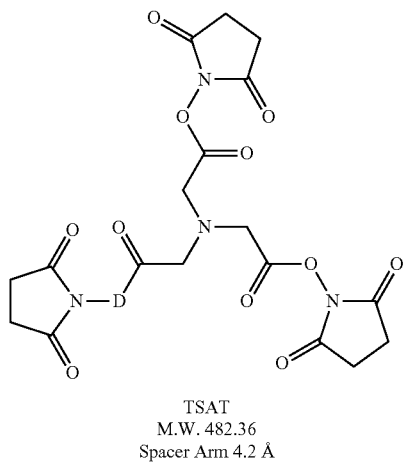

TSAT
M.W. 482.36
Spacer Arm 4.2 Å

The DNA oligoes: vip016/vip017 or vip016/vip017/vip018 (prepared by DNA Technology Århus, Denmark), all having an internal amino modified dT (GlenResearch, cat. No.: 10-1038-xx) were mixed in 150 mM NaCl, 100 mM sodium phosphate, pH 7.2 giving 20 uM total oligo concentration. The mixtures were incubated at 80 degrees C. for 2 minutes and slowly cooled to room temperature in a water bath. TSAT was dissolved in DMF. A 10 fold serial dilution in DMF was prepared. 1 volume DMF or TSAT dilution was mixed with 9 volume buffer giving a final buffer concentration of 150 mM NaCl, 100 mM sodium phosphate, pH 7.2. 1 volume buffered DMF or buffered TSAT dilution was mixed with 1 volume annealed DNA oligo mixture giving final oligo:TSAT ratios; 1:0, 1:10, 1:100, 1:1000, 1; 10000, and allowed to incubate for 2 hours at room temperature. The reactions were analyzed by PAGE; both native (7.5% polyacrylamide), as well as by non-native PAGE (7.5% polyacrylamide, 8M urea), followed by staining with ethidium bromide, using standard protocols (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.).

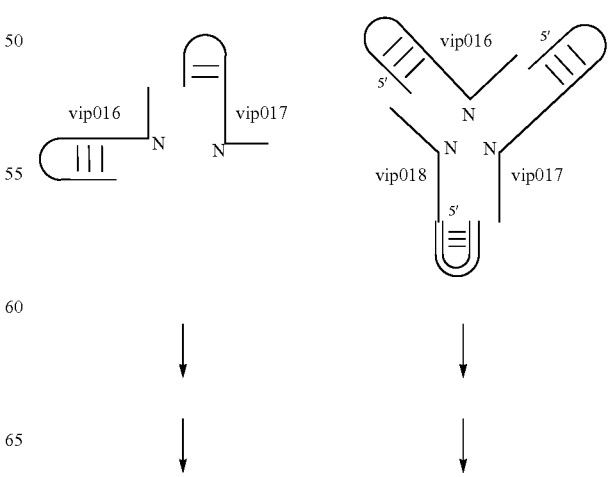

-continued

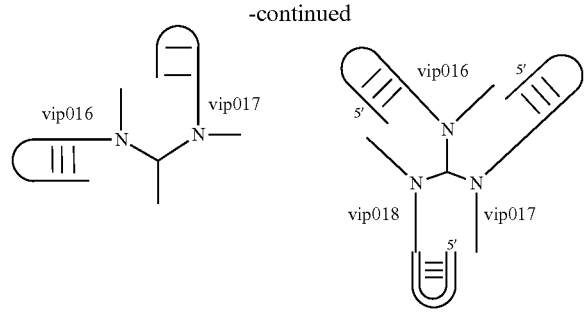

Vip016 and vip017 each have a mutual complementary segment, thus capable of forming an annealed dimeric structure. Vip016, vip017 and vip018 each have a mutual complementary segment to the neighboring oligo, thus capable of forming a closed annealed trimeric structure (see FIG. 12).

As expected in lanes 1-5, native gel, the major band corresponds to a dimeric structure, whereas the major band in lanes 6-10 in the native gel corresponds to a trimeric structure. In a non-native gel the annealing is disrupted. As expected a band in lanes 1 and 6 in the non-native gel corresponding to a monomer was observed. However, when TSAT was included higher order structures were observed (lanes 2-5, 7-10, non-native gel) indicating that TSAT did cross-link the oligoes. Interestingly, when only vip016 and vip017 were present the highest order cross-linked structure was dimeric (non-native gel, lanes 2-5), whereas when vip016, vip017, vip018 were present an additional trimeric structure was observed (non-native gel, lanes 7-10), thus indicating that cross-linking is dependent on annealing of the DNA oligonucleotides. Noteworthy is also that as expected a bell-shaped dose response was observed; at low TSAT concentration the reaction will be slow leading to poor yields, as the TSAT concentration increases the reaction will proceed faster leading to more cross-linked product, however at higher
TSAT concentrations the cross-linking will be competed by TSAT molecules reacting with only one DNA oligo leading to lower cross-linked product. Hence, the highest yield of cross-linked product was observed using 1000 TSAT equivalents (lanes 4 and 9, non-native gel). Moreover, the advantageous in a closed annealed structure for cross-linking was illustrated by the much higher overall yields obtained in lanes 7-10 when compared to their counterparts in lanes 2-5 with the same TSAT concentration.

Example 5

Chemical Reactions Directed by DNA Star Structure

The oligonucleotide, vip017, was functionalized by cross-linking an amino acid (L-Leu or Gly Fluka, #61820 and #50052) through the alfa-amine to the primary amine on an internal modified dT in vip017, by the homobifuntional linker BSOCOES ((Bis[2-(succinimidooxycarbonyloxy)ethyl]sulfone), Pierce cat#21600) by treatment of the oligonucleotide (5 nmol) in a 200 mM pH 7.4 sodium phosphate solution (200 uL) with 0.1 volumes of a 100mM BSOCOES solution in DMF for 10 min at 25° C., followed by 0.3 volumes of a 300 mM amino acid (Leu or Gly) solution in 300 mM NaOH for 2 hrs at 25° C. The total volume of the reactions was 200 uL. The crude linked amino acid reagents were isolated by EtOH precipitation and used without further purification. DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in water.

The oligonucleotides were annealed by preparing: 3.125 uM of each oligonucleotides, 125 mM MES pH 6.0, 187.5 mM NaCl. The mixtures were incubated at 80 degrees C. for 2 minutes followed by slow cooling to room temperature in a water bath. The DNA directed chemical reaction (amide bond formation) were performed by adding EDC and sNHS to the pre-annealed oligonucleotedes; 2.5 uM preformed star structures, 100 mM MES pH 6.0, 150 mM NaCl, 20 mM EDC and 15 mM sNHS (final concentrations). The mixture was incubated overnight at room temperature and EtOH precipitated as described above.

The reactions were analyzed by PAGE; both native (7.5% polyacrylamide), as well as by non-native PAGE (7.5% polyacrylamide, 8M urea), followed by staining with ethidium bromide, using standard protocols (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.).

The oligonucleotide, vip017, was functionalized by cross-linking a amino acid, Leu or Gly, through the alfa-amine to the primary amine on a modified internal dT in vip017, by the homobifuntional linker BSOCOES. The modified dT is positioned between the two hybridization segments in vip017. Vip076 has a modified dT containing a primary amine followed by a 3' hybridization segment complementary to the 5' hybridization segment in vip017. Consequently, by annealing vip017 and vip076 proximity is created between the amino acid conjugated to vip017 and the primary amine on vip076. Accordingly, a band corresponding to a dimer was observed in lane 4-6 in the native gel. Vip008 has complementary segments to both vip076 and vip017 thus capable of forming a closed trimer star structure and arranging the chemical functionalities of vip017 and vip076 in the reaction chamber in the center of the star structure. Accordingly, a band corresponding to a trimer was observed in lanes 1-3 in the native gel.

Upon activation by EDC/sNHS an amide bond can be formed between the amino acid conjugated to vip017 and the primary amine in vip076, and thereby cross-linking vip017 and vip076. As expected when star structures were formed (vip008 present), a unique band corresponding to cross-linked vip076/vip017 did appear both with vip017-Gly and vip017-Leu (none-native PAGE, lanes 2 and 3, respectively), which was not present without EDC/sNHS activation (none-native PAGE, lanes 8 and 9) or with non-acetylated vip017 (non-native PAGE, lane 1). Interestingly, the unique band was not detectable when vip008 was not present (non-native PAGE, lanes 5 and 6). This illustrates that a chemical reaction can be directed by a star structure and that the star structure seems more efficient in guiding chemical reactions than two annealed oligoes.

Example 6

Assembling and Ligation of a Star Structure

Figure 13:
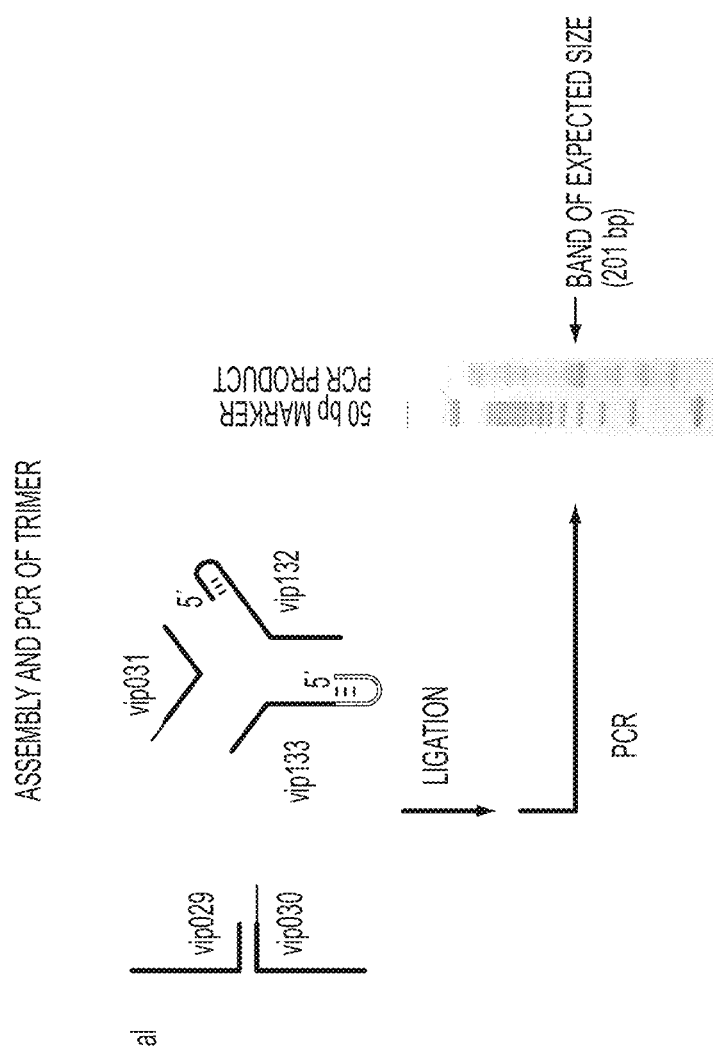
FIG. 13 depicts a native PAGE gel from example 6

The successful amplification of trimeric DNA star structure consisting of dsDNA was demonstrated in this example. Mutual complementary bi-specific oligonucleotides were annealed, ligated and subsequently used as a template in a PCR reaction. The following oligonucleotides were used: vip029-vip031-vip0132-vip0133-vip030. FIG. 13 shows schematically the hybridization of the oligonucleotides.

DNA oligonucleotides (prepared by DNA Technology Århus, Denmark) were mixed in 2 µM concentrations each in 1× Ligase Buffer (New England Biolabs), 50 mM NaCl. The mixtures were incubated as follows: 94° C. for 5 minutes, 80° C. for 30 seconds, 65° C. for 30 seconds, 50° C. for 30 seconds, 35° C. for 30 seconds, 20° C. for 30 seconds, 10° C. until next step. The annealing procedure was performed on an Applied Biosystems AB2720 PCR machine.

The 5' termini of the oligonucleotides were phosphorylated by T4 DNA polynucleotide kinase. A mixture consisting of 1.5 µM star structure, 1×DNA ligase Buffer (New England Biolabs), 50 mM NaCl and 0.17 U/µl T4 DNA polynucleotide kinase (New England Biolabs, cat# M0201), was prepared and incubated for 30 minutes at 37° C.

A phosphodiester bond between juxtaposed ends of annealed oligonucleotides was formed by T4 DNA ligase (New England Biolabs, cat# M0202), in 1×DNA ligase Buffer (New England Biolabs), 50 mM NaCl, and 200 U T4 DNA ligase (New England Biolabs, cat# M0202) in a volume of 10 µl and incubated overnight at 16° C.

PCR amplification was performed using the following conditions:

Reactions were performed in 1× ThermoPol buffer (New England Biolabs B9004S), with 0.2 mM dNTPs (New England Biolabs O447S), 8 mM MgSO4, 0.2 µM sense primer and 0.2 µM antisense primer, 1 M Betaine (Sigma B0300), 1 U/100 µl of Vent (exo-) (New England Biolabs M0257L). Primers used were vip027 and vip028. Biotinylated versions of these two primers are vip034 and vip038, respectively. PCR amplification was performed using the following cycling conditions: 2 minutes at 95° C., and 20 cycles of 95° C./30 sec, 60° C./30 sec, 74° C./30 sec. PCR product to be used for folding and ssDNA purification reported in example 7 below, was made with vip034 and vip028 primers. The PCR product was analyzed by native PAGE. A band of 201 bp is clearly seen on the gel depicted on FIG. 13.

Example 7

Re-Folding of PCR Product

Folding of PCR products were performed as follows. A PCR cleanup procedure was performed using PerfectPrep (Eppendorf, cat#0032 007.740) according to kit instructions. Folding was performed in 0.1 M NaCl, 0.1% Triton X-100, 0.1 µM vip027, 0.1 µM vip028, in a volume of 10 µl (5 µl per product mixed with 5 µl 2× buffer/primer mix). The PCR product was used in 4 different concentrations (ranging from 1:2 dilution to 1:20 dilution). In one series, the mixture was incubated for 2 minutes in boiling water, and subsequently cooled in an ice/water bath. In the second series, the mixture was heated and cooled using the following program on an ABI2720 PCR machine: 94° C. for 5 minutes, 80° C. for 30 seconds, 65° C. for 30 seconds, 50° C. for 30 seconds, 35° C. for 30 seconds, 20° C. for 30 seconds, 10° C. until next step. In the third series, no heating or cooling was performed.

The products were analyzed on 20% TBE urea gel (Invitrogen). The gel was stained with SYBR green (Molecular Probes 57563, 1:10.000 dilution in 1×TBE buffer, according to instructions).

Figure 14:
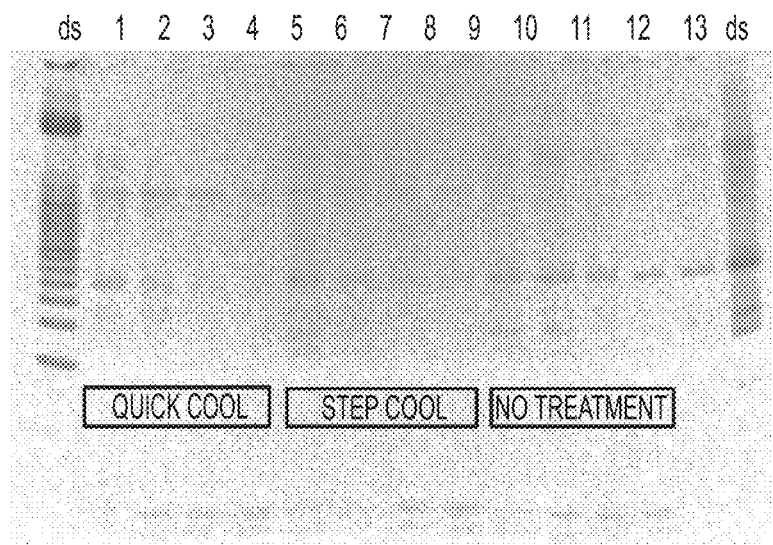
FIG. 14 shows a gel from the experiments reported in example 7

In FIG. 14 the lanes of the gel comprise the following content:
Lane 1: PCR product diluted 1:2, quick cool
Lane 2: PCR product diluted 1:4, quick cool
Lane 3: PCR product diluted 1:10, quick cool
Lane 4: PCR product diluted 1:20, quick cool
Lane 5: PCR product diluted 1:2, step cool
Lane 6: PCR product diluted 1:4, step cool
Lane 7: PCR product diluted 1:10, step cool
Lane 8: PCR product diluted 1:20, step cool
Lane 9: PCR product diluted 1:2, no treatment
Lane 10: PCR product diluted 1:4, no treatment
Lane 11: PCR product diluted 1:10, no treatment
Lane 12: PCR product diluted 1:20, no treatment
Lane 13: PCR product only The experiment shows that single stranded star structure DNA is migrating at app. 1000 bp, in contrast to the 201 bp dsDNA product. In appears that the optimal condition for star structure formation is heating followed by quick cooling of the reactions.

Example 8

Purification of Re-Folded Star Structure

The ssDNA star structure was purified using streptavidin-coated magnetic beads (Dynal, Cat#650.02). 10 pa beads were washed two times with 2×BWT (2 M NaCl, 10 mM Tris-HCl, pH 8.0, 1 mM EDTA, 0.2% Triton X-100). After the final wash, the beads were suspended in one volume 2×BWT and added one volume refolded PCR product. The suspension was incubated for 15 minutes at room temperature, mixing every once in a while. The tube was placed in the magnet, and after the beads had been collected the supernatant was removed. The beads were suspended in 50° C. warm wash buffer (2 M urea, 0.1% Triton X-100), and incubated for 2 minutes at 50° C. The tube was placed on the magnet, and the wash procedure was performed three times in total. One final wash was performed in 1×BWT (1 M NaCl, 5 mM Tris-HCl, pH 8.0, 0.5 mM EDTA, 0.1% Triton X-100). Following removal of the final wash buffer, the beads were suspended in 1.5 ml NT (10 mM NaCl, 0.1% Triton X-100), and incubated at 50° C. for 5 minutes. The tube was transferred to an ice/water bath for rapid cooling, and this procedure resulted in formation of the star structure immobilized on the streptavidin-coated magnetic beads. The tube was after the rapid cooling placed in the magnet, and the supernatant was removed. The beads were suspended in 50 µl NT, ready for digest with BsaI for release of the ssDNA from the beads.

17 µl beads were added 2 µl 10×NEB3 buffer and 1 µl BsaI (10 U/µl; NEB R0535L). The reaction was incubated 1½ h at 50° C. The digest was analyzed by denaturing polyacrylamide gel electrophoresis (10% TBE-urea gel, Invitrogen), by adding denaturing loading buffer to the samples, and loading the whole mixture including the beads in the wells of the gel. The gel was stained with SYBR green (Molecular Probes S7563, 1:10.000 dilution in 1×TBE buffer, according to instructions).

Figure 15:
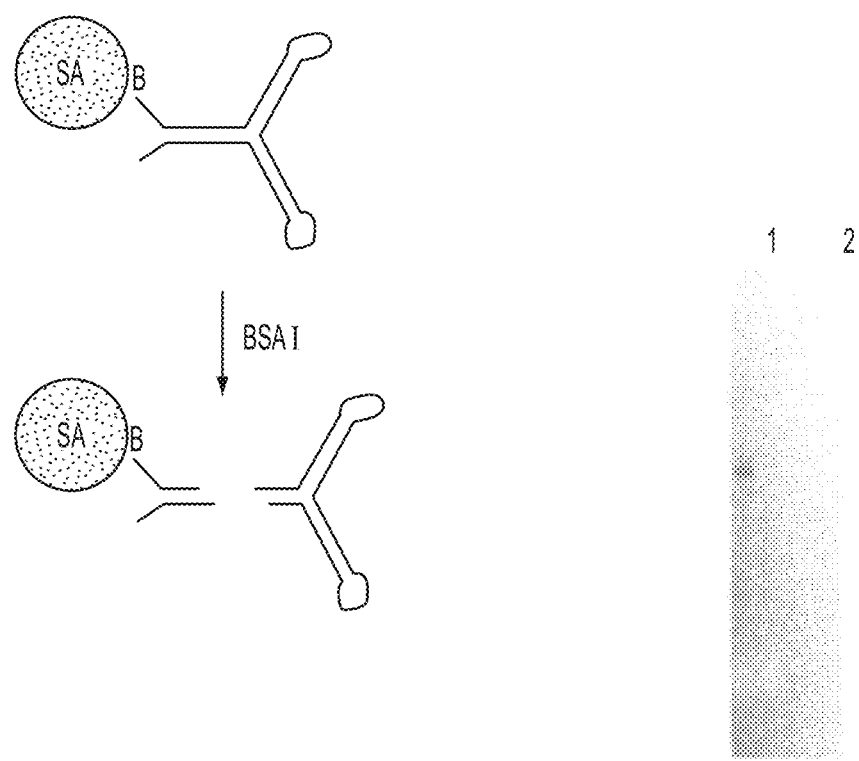
FIG. 15 discloses a gel of a re-folding experiment of example 8

On FIG. 15 one band is observed in lane 1 (+BsaI) lane and no band is seen in lane 2 '-BsaI' lane. Thus, the ssDNA was folded on the streptavidin-coated magnetic beads thus forming the substrate for BsaI demonstrated by the ability of the enzyme to cleave off the single stranded product.

Example 9

Digest Loop Format

Figure 16:
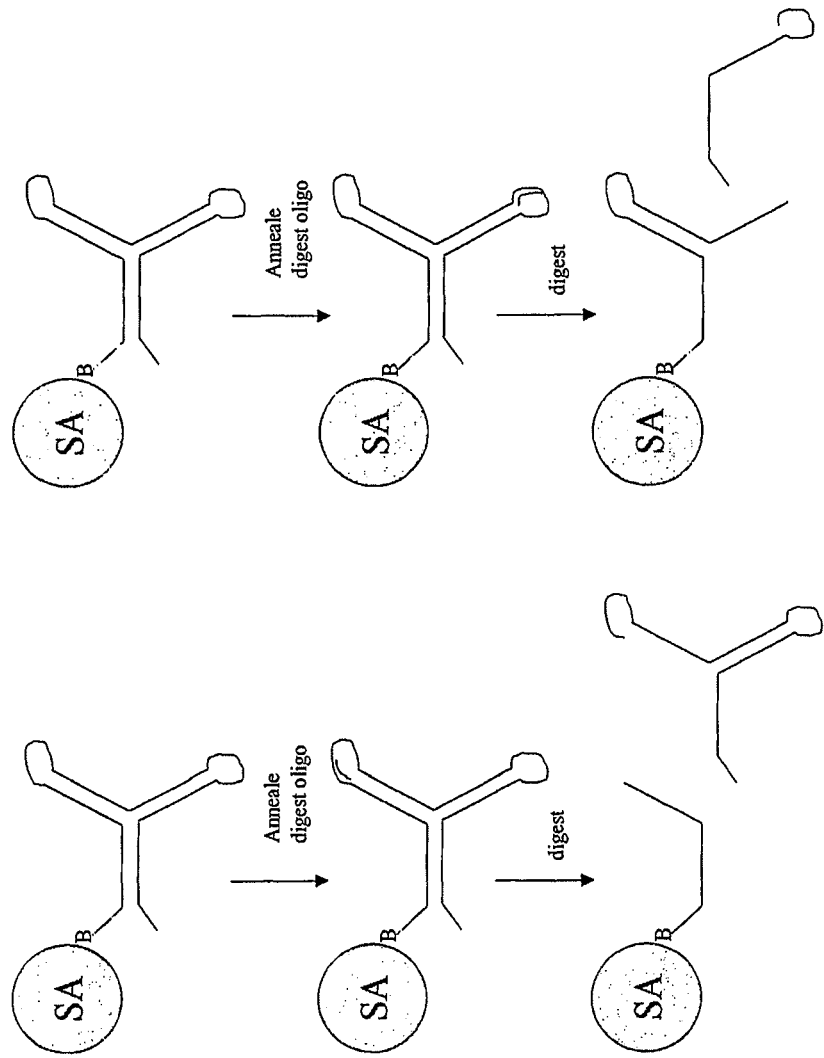
FIG. 16 is a schematic diagram of the design of example 9.

Two genomes were designed, both enabling digest in the loops of the star structures. Restriction enzymes are in general not capable of digesting ssDNA. However, annealing of 10-mer oligonucleotides to the loops generates substrates for the enzymes, and thereby the recognition sequences for the enzymes will become double-stranded. The design of the experiment is schematically shown on FIG. 16.

Two structures were assembled, s129 and s149. s129 was composed of the following oligonucleotides: vip029-vip161-vip162-vip163-vip070. s149 was composed of the following oligonucleotides: vip029-vip161-vip192-vip193-vip070. Vip162, vip163, vip 192 and vip 193 all contain recognition sequences for two restriction enzymes (vip 162: ApaI and BamHI, vip163: EcoRI and KpnI, vip192: PvuII and SacL vip193: SmaI and VspI)

DNA oligoes (prepared by TAGC, Copenhagen, Denmark) were mixed in 2 µM concentrations each in 1× Ligase Buffer (New England Biolabs), 50 mM NaCl. The mixtures were incubated as follows: 94° C. for 5 minutes, 80° C. for 30 seconds, 65° C. for 30 seconds, 50° C. for 30 seconds, 35° C. for 30 seconds, 20° C. for 30 seconds, 10° C. until next step. The annealing procedure was performed on an Applied Biosystems AB2720 PCR machine.

The 5' termini of the oligonucleotides were phosphorylated by T4 DNA polynucleotide kinase. A mixture consisting of 1.5 µM star structure, 1×DNA ligase Buffer (New England Biolabs), 50 mM NaCl and 0.17 U/µl T4 DNA polynucleotide kinase (New England Biolabs, cat# M0201), was prepared and incubated for 30 minutes at 37° C.

A phosphodiester bond between juxtaposed ends of annealed oligonucleotides was formed by T4 DNA ligase (New England Biolabs, cat# M0202), in 1×DNA ligase Buffer (New England Biolabs), 50 mM NaCl, and 200 U T4 DNA ligase (New England Biolabs, cat# M0202) in a volume of 10 µl and incubated overnight at 16° C.

PCR amplification was performed using the following conditions:

Reactions were performed in 1× ThermoPol buffer (NEB B9004S), with 0.2 mM dNTPs (NEB O447S), 8 mM MgSO4, 0.2 µM sense primer and 0.2 µM antisense primer, 1 M Betaine (Sigma B0300), 1 U/100 µl of Vent (exo-) (NEB M0257L). Primers used were vip027 and vip028. Biotinylated versions of the primers are vip034 and vip038, respectively. PCR amplification was performed using the following cycling conditions: 2 minutes at 95° C., and 20 cycles of 95° C./30 sec, 60° C./30 sec, 74° C./30 sec.

Figure 17:
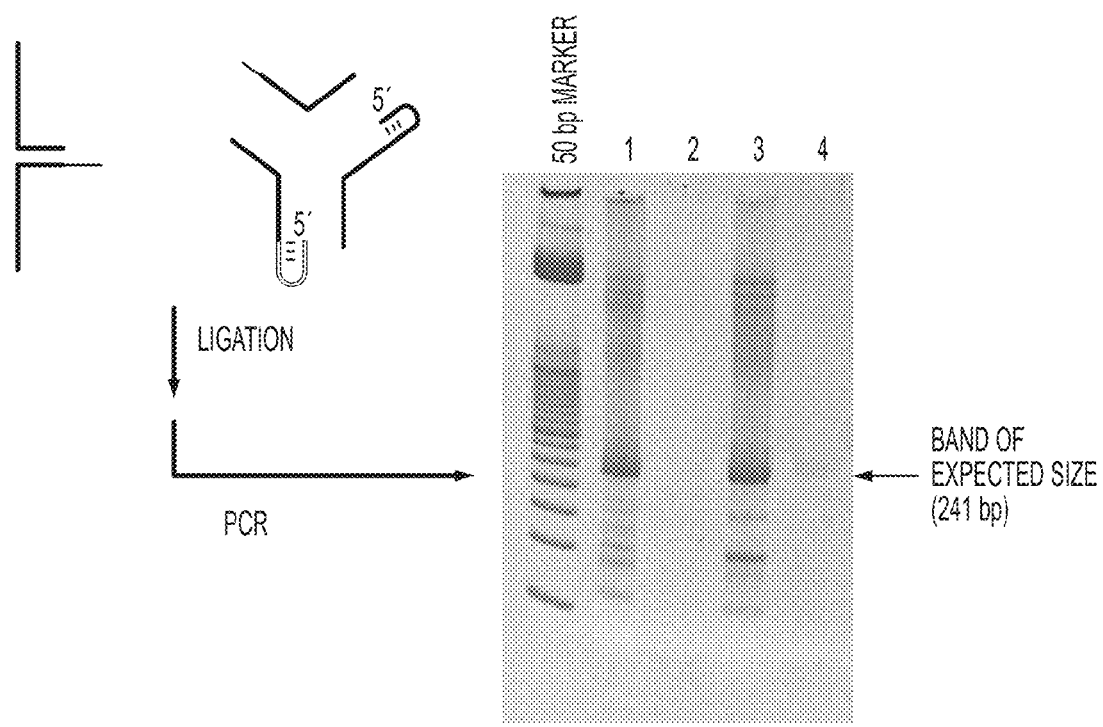
FIG. 17 shows the gel resulting from the experiments reported in example 9

The result of the experiment is shown in FIG. 17.

In lane 1 and 3 it is seen that both genomes were amplified successfully. Lanes 2 and 4 are negative controls without ligase added for the two genomes.

Purification of ssDNA structures of s129 and s149.

80 µl PCR product (made using vip034 and vip028 primers) of each genome was purified using PerfectPrep (Eppendorf, cat#0032 007.740) according to kit instructions. Elution was done in 40 µl elution buffer. For refolding of the PCR products, the following was performed: to 40 µl PCR product, add 750 µl 0.2 M NaCl, 0.2% Triton X-100, 7.5 µl vip027 and 7.5 µl vip028 and 695 µl H2O. Incubate the mix in boiling water for 5 minutes, and cool quickly in an ice-water bath.

20 µl Streptavidin beads (Dynal, 650.02) were washed two times with 2×BWT (2 M NaCl, 10 mM Tris-HCl, pH 8.0, 1 mM EDTA, 0.2% Triton X-100). After the final wash, the beads were suspended in one volume 2×BWT and added one volume refolded PCR product. The suspension was incubated for 15 minutes at room temperature, mixing every once in a while. The tube was placed in the magnet, and after the beads had been collected the supernatant was removed. The beads were suspended in 50° C. warm wash buffer (2 M urea, 0.1% Triton X-100), and incubated for 2 minutes at 50° C. The tube was placed on the magnet, and the wash procedure was performed three times in total. One final wash was performed in 1×BWT (1 M NaCl, 5 mM Tris-HCl, pH 8.0, 0.5 mM EDTA, 0.1% Triton X-100). After separation on the magnet, the beads were suspended in 50 µl 10 mM NaCl, 0.1% Triton X-100.

20 µl of the beads of each prep were separated on the magnet, and suspended in 10 µl 100 mM NaCl, 0.1% Triton X-100. Each preparation was split into two tubes of 5 µl each, and digest oligoes were added as follows:
1: s129-vip164-ApaI
2: s129-vip165-KpnI
3: s149-vip194-PvuII
4: s149-vip195-VspI 0.25 µl oligo (20 µM stock) was added, resulting in a final conc. of 1 µM. Annealing was performed on AB2720 PCR machine using the program: 50° C.-2 minutes; 40° C.-2 minutes; 35° C.-2 minutes; 30° C.-2 minutes; 30° C.-2 minutes; 25° C.-2 minutes; 20° C.-2 minutes.

The beads were washed in 100 µl 100 mM NaCl, 0.1% Triton X-100. The beads were subsequently suspended in 18 µl 1.1× digest buffer. The reactions were split into two tubes, 9 µl each, and 1 µl enzyme (10 Units) were added to each tube, resulting in 1× digest buffer for the digest. One set of digests was incubated at 30° C. and the other set was incubated at 37° C. Incubation was done for 5 h, mixing every once in a while to suspend the beads from the bottom of the tubes.

Following digest, the products were analyzed on 10% TBE-urea gel (Invitrogen). Loading buffer was added to the digests, and the whole reaction mix including the beads was loaded on the gel. The gel was stained with SYBR green (Molecular Probes S7563, 1:10.000 dilution in 1×TBE buffer, according to instructions).

Figure 18:
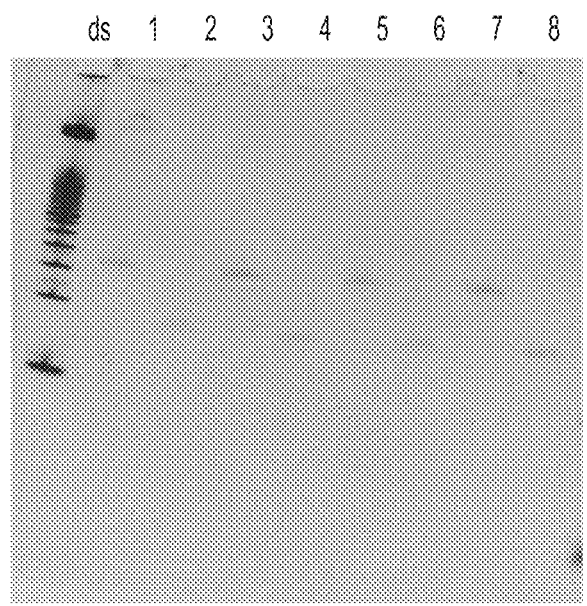
FIG. 18 discloses the gel resulting from the experiments reported in example 9

The result of the experiment is shown in FIG. 18.
Lane 1 shows ApaI digest of s129 at 37° C.
Lane 2 shows KpnI digest of s129 at 37° C.
Lane 3 shows PvuII digest of s149 at 37° C.
Lane 4 shows VspI digest of s149 at 37° C.
Lane 5 shows ApaI digest of s129 at 30° C.
Lane 6 shows KpnI digest of s129 at 30° C.
Lane 7 shows PvuII digest of s149 at 30° C.
Lane 8 shows VspI digest of s149 at 37° C.
Expected Band Sizes are as Follows:
ApaI: 163 nt, KpnI: 80 nt, PvuII: 165 nt, VspI: 83 nt.

On the gel, bands of the expected sizes do appear for all four enzymes. Note that the fragments containing biotin will not enter the gel as they are bound to the beads. Both temperatures give a product, showing the robustness of the procedure.

Example 10

DNA Directed Formation of Amide Bonds in Various Topologies

The oligonucleotide, vip017, was functionalized by cross-linking an amino acid (Glycine, Fluka cat #50052) through the alfa-amine to the primary amine on an internal modified dT in vip017, by the homobifuntional linker BSOCOES ((Bis [2-(succinimidooxycarbonyloxy)ethyl]sulfone), Pierce cat#21600) by treatment of the oligonucleotide (5 nmol) in a 200 mM pH 7.4 sodium phosphate solution (200 uL) with 0.1 volumes of a 100 mM BSOCOES solution in DMF for 10 min at 25° C., followed by 0.3 volumes of a 300 mM amino acid (Glycine) solution in 300 mM NaOH for 2 hrs at 25° C. The total volume of the reaction was 200 uL. The crude linked amino acid reagents were isolated by EtOH precipitation and used without further purification.

DNA was precipitated by NaOAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in water.

The oligonucleotides were annealed by preparing: 0.556 uM of each oligonucleotide, 111 mM MOPS pH 6.5 (Fluka 69947), 1.11 M NaCl (Fluka 71376), and subsequently incubated as follows: 94° C. for 5 minutes, 80° C. for 30 seconds, 65° C. for 30 seconds, 50° C. for 30 seconds, 35° C. for 30 seconds, 20° C. for 30 seconds, 10° C. until next step. The annealing procedure was performed on an Applied Biosystems AB2720 PCR machine.

The DNA directed chemical reaction (amide bond formation) were performed by adding 100 mM DMTMM (Acros, cat #A017657001) to the pre-annealed oligonucleotides. DMTMM was dissolved in water at a concentration of 1 M. Before adding DMTMM, the reaction mixtures were preheated to 50° C. Final concentration of each oligonucleotide was 0.5 µM. The reactions were performed in 100 mM MOPS pH 6.5, 1 M NaCl, 100 mM DMTMM (final concentrations), in a volume of 20 µl, at 50° C. for 3 h.

Figure 19:
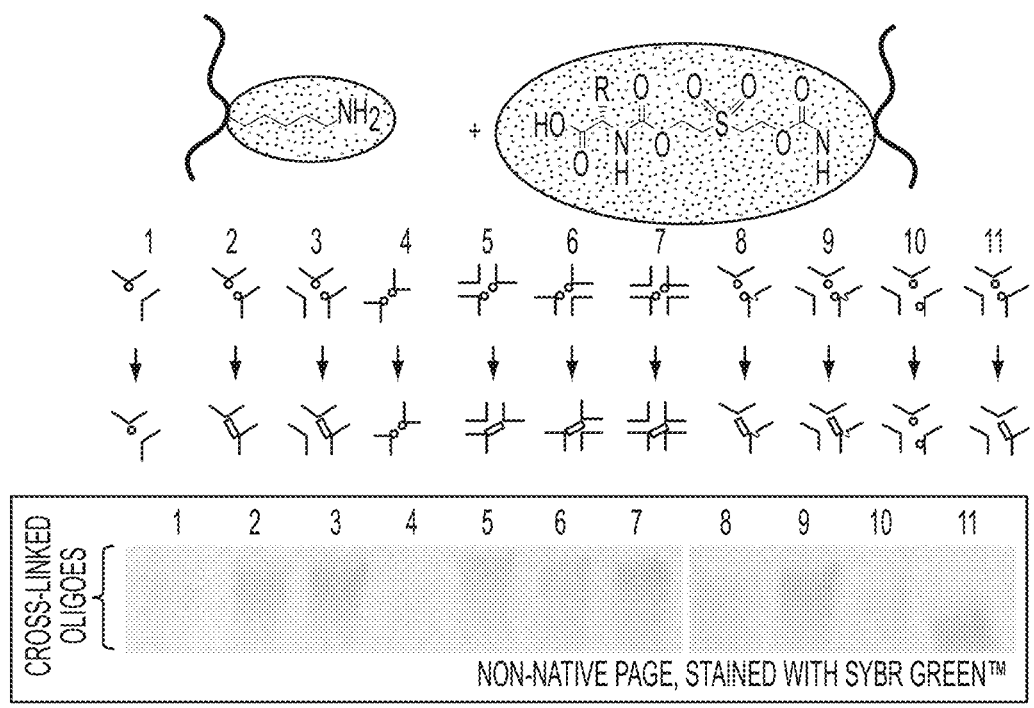
FIG. 19 shows various architectures of reaction design reported on example 10.

The reactions were analyzed by PAGE; both native (20% polyacrylamide, Invitrogen), and by denaturing PAGE (10% polyacrylamide, 7 M urea, Invitrogen), followed by staining with SYBR green (Molecular Probes 57563, 1:10.000 dilution in 1×TBE buffer, according to instructions). All results are shown in FIG. 19.

The oligonucleotide, vip017, was functionalized by cross-linking an amino acid (Glycine) through the alfa-amine to the primary amine on a modified internal dT in vip017, by the homobifuntional linker BSOCOES. The modified dT is positioned between the two hybridization segments in vip017. Vip008 does not contain an acceptor amine on a modified dT, it contains one hybridization segment with which it will hybridize to Vip017, and thus it will not be covalently cross-linked to Vip017-Gly upon the addition of DMTMM. Accordingly, no visible band was observed in lane 1.

Vip018-NH2 has a modified dT containing a primary amine followed by a 3' hybridization segment complementary to the 5' hybridization segment in vip017. Consequently, by annealing vip017-Gly and vip018-NH2 proximity is created between the amino acid conjugated to vip017 and the primary amine on vip018. Accordingly, a band corresponding to a dimer composed of cross-linked vip017-Gly/vip018-NH2 was observed in lane 2.

Vip006 has complementary segments to both vip017-Gly and vip018-NH2, and it is thus capable of forming a closed trimer star structure and arranging the chemical functionalities of vip017-Gly and vip018-NH2 in the reaction chamber in the center of the star structure. Accordingly, a band corresponding to a dimer composed of cross-linked vip017-Gly/vip018-NH2 was observed in lane 3. Furthermore, lane 3 contained more stain than lane 2, indicating that the closed trimer star structure creates better reaction conditions than an open dimer structure does.

Vip020-N112 has a modified dT containing a primary amine, but it contains no hybridization segments to vip017-Gly. Consequently, no bands appear in lane 4 because the reactants of vip020-NH2 and vip017-Gly are not brought into proximity by base airing.

Vip006 has one hybridization segment capable of hybridizing to a segment of vip017-Gly, and another hybridization segment capable of hybridizing to vip020-NH2, which has a modified dT containing a primary amine between its two hybridization segments. Thus, vip006 brings the functional groups into proximity, and a band is visible on in lane 5, constituting cross-linked vip017-Gly and vip020-NH2.

Vip009 has one hybridization segment capable of hybridizing to a segment of vip017-Gly, and another hybridization segment capable of hybridizing to vip020-NH2, which has a modified dT containing a primary amine between its two hybridization segments. Thus, vip009 brings the functional groups into proximity. Accordingly, a band was observed in lane 6, constituting cross-linked vip017-Gly and vip020-NH2.

Vip006 has one hybridization segment capable of hybridizing to a segment of vip017-Gly, and another hybridization segment capable of hybridizing to vip020-NH2, which has a modified dT containing a primary amine between its two hybridization segments. Vip009 has one hybridization segment capable of hybridizing to a segment of vip017-Gly, and another hybridization segment capable of hybridizing to vip020-NH2, which has a modified dT containing a primary amine between its two hybridization segments. Hybridizing these four oligonucleotides result in the formation of a tetramer star structure. In lane 7 a band was observed, showing that the functional groups on vip017-Gly and vip020 are brought into proximity of each other by the hybridization of the four oligonucleotides. Furthermore, lane 7 contained more stain than both lane 5 and 6, indicating that the closed tetrameric star structure creates better reaction conditions than open trimer structures do.

Vip048-NH2 has a modified dT containing a primary amine and one hybridization segment capable of binding to vip017-Gly. Between the modified dT with the primary amine and the hybridization segment capable of annealing to vip017-Gly is inserted 6 nucleotides not involved in hybridization (wobble nucleotides). A band was observed in lane 8, thus indicating cross-linking of the two oligonucleotides. However, the 6 extra nucleotides introduced did lower the amount of cross-linked product obtained as seen by comparing lane 8 and lane 2.

Vip006 has one hybridization segment capable of hybridizing to a segment of vip017-Gly, and another hybridization segment capable of hybridizing to vip048. Vip048-NH2 has a modified dT containing a primary amine and one hybridization segment capable of binding to vip017-Gly. Between the modified dT with the primary amine and the hybridization segment capable of annealing to vip017-Gly is inserted 6 nucleotides not involved in hybridization (wobble nucleotides).

The presence of vip006 brings the two reactive groups into proximity, and a product is formed as seen in lane 9. The band intensity was stronger than that seen in lane 8, indicating that vip006 stabilizes the structure (trimer star structure) and the reaction proceeds better than that found in the dimer format of the reaction.

Vip048-NH2 has a modified dT containing a primary amine and one hybridization segment capable of binding to vip017-Gly. Between the modified dT with the primary amine and the hybridization segment capable of annealing to vip017-Gly is inserted 6 nucleotides not involved in hybridization (wobble nucleotides). Vip056 contains one hybridization segment capable of hybridizing to vip017-Gly, and another hybridization segment capable of hybridizing to the segment of vip048-NH2 containing the 6 wobble-nucleotides. Thus, upon annealing of these three oligonucleotides, the primary amine on the modified dT on vip048 is moved 6 nucleotides away for the reaction chamber and are now located in the double stranded arm. Double stranded DNA is in contrast to single stranded DNA very rigid thus preventing the conjugated moiety to move freely and thereby decreasing its reactivity. Accordingly, only a very faint stain was observed in lane 10.

Vip018-NH2 has a modified dT containing a primary amine followed by a 3' hybridization segment complementary to the 5' hybridization segment in vip017-Gly.

Vip056 contains one hybridization segment capable of hybridizing to vip017-Gly, and another hybridization segment capable of hybridizing to the segment of vip018-NH2. Between the two hybridization segments, vip056 contains 6 extra nucleotides (wobble nucleotides). A dimer band is seen in lane 11, indicating that the reactive groups are brought into proximity of each other for a chemical reaction to occur, and the 6 wobble nucleotides in vip056 does not impair the proximity with the current architecture in this experiment.

Example 11

Chemical Preparation of Various Oligonucleotides

Example 11.1

Acetylation of an Oligonucleotide Having Internal Modified dT (Amine-C6-dT) (Position n=1)

Acetylation with Fmoc-AA-OH promoted by DMT-MM.

The oligonucleotide Vip068 having an internal amine-C6-dT, was acylated with Fmoc-Leu-OH promoted by DMT-MM (4-(4,6-Dimethoxy-1,3,5-triazin-2-yl)-4-methylmorpholinium chloride, Fluka #74104) by treatment of the oligonucleotide (500 pmol) dissolved in a 1:1 mixture of DMF and 300 mM NaCl together with one of the following buffers: sodium phosphate 400 mM, pH 7.0, MOPS 400 mM, pH 7.5, HEPES 400 mM pH 8.0, sodium phosphate 400 mM, pH 8.8, with DMT-MM 50 mM. Total reaction volume was 20 µL. Reactions were incubated 16 hrs at 25° C. The reaction mixture was diluted to 50 µL and purified on a spin column (Amersham Biosciences #27-5325-01) according to manufactures protocol followed by purification by HPLC and mass spectrometry analysis.

General Purification Method:

Functionalized oligonucleotides were purified by a Hewlett Packard Agilent HPLC instrument with auto sampler and fraction collector on an XTerra C18 column (Waters #186000602) using acetonitrile/TEAA 100 mM pH 7.0 mixtures as eluent. Appropriate fractions were lyophilized and diluted to 20 mM with water.

General Mass Spectrometry Analysis:

Functionalized oligonucleotides were analyzed by MALDI-TOF mass spectrometry on a Bruker AutoFlex instrument in a HPA/ammonium citrate matrix using negative ion reflector mode.

| DNA | Calculated mass | Found mass |
| --- | --- | --- |
| vip068-LeuFmoc | 6843.340 | 6844.5 |

Example 11.2

Acetylation of an Oligonucleotide Having Internal Modified dT (Amine-C6-dT) (Position n=1)

Acetylation with Fmoc-AA-OSu

The oligonucleotide Vip046 was acylated with Fmoc-AA-OSu (AA=Gly or Leu) by treatment of the oligonucleotide (125 pmol) dissolved in a 1:1 mixture of DMF and sodium phosphate buffer 100 mM, pH 7.4 with 25 mM Fmoc-Gly-OSu (ChemImpex #02420) or Fmoc-Leu-OSu (ChemImpex #02429) for 2 hrs at 25° C. The functionalized oligonucleotide was precipitated by NH4OAc/EtOH according to (Sambrook, J., Fritsch, E. F. and Maniatis, T. (1989) in "Molecular Cloning: a Laboratory Manual", Second Edition, Cold Spring Harbor Laboratory Press, Cold Spring, Harbor, N.Y.). The pellet was resuspended in water and analyzed by MALDI-TOF mass spectrometry.

| DNA | Calculated mass | Found mass |
| --- | --- | --- |
| vip046-LeuFmoc | 6932.3642 | 6932.1 |
| vip046-GlyFmoc | 6876.3016 | 6876.1 |

Example 11.3

Acetylation of Oligonucleotides Having Internal Modified dT (Amine-C6-dT) (Position n=1)

Synthesis of peptide-oligonucleotide conjugates (single letter abbreviation used for amino acid): YGGFL-Vip068, GLFYG-Vip068, YGGFL-PEG-Vip068, GLFYG-PEG-Vip068, GFL-Vip016 and GFL-PEG-Vip016: Acetylation with Fmoc-AA-OSu with subsequent deprotection on Sepharose.

The peptides were synthesized from the primary amine on an internal modified dT on the oligonucleotides absorbed on DEAE Sepharose (Sigma #DFF100). Amino acids were coupled by rounds of acylation with Fmoc-AA-OSu (AA=Gly, Leu, Phe, Tyr, C6, PEG) (Fmoc-L-Glycine N-hydroxysuccinimide ester, ChemImpex #02420; Fmoc-L-leucine N-hydroxysuccinimide ester, ChemImpex #02429; Fmoc-L-phenylalanine N-hydroxysuccinimide ester, ChemImpex #02446; Fmoc-L-tyrosine N-hydroxysuccinimide ester, ChemImpex #11972; Fmoc-6-aminohexanoic acid N-hydroxysuccinimide ester, ChemImpex #7296; Fmoc-8-amino-3,6-dioxaoctanoic acid hydroxysuccinimide ester, synthesized from Fmoc-8-amino-3,6-dioxaoctanoic acid (ChemImpex #7310) by EDC coupling with N-hydroxysuccinimide) followed by Fmoc deprotection according to the procedure of Halpin and Harbury (Plos Biology 2004, 2, 1-8). After elution of the DNA from the sepharose the mixture was desalinated on a spin column (Amersham Biosciences #27-5325-01) according to manufactures protocol followed by purification by HPLC. Yields were determined by HPLC.

| DNA | Isolated yield |
| --- | --- |
| YGGFL-Vip068 | 19% |
| YGGFL-PEG-Vip068 | 32% |
| GLFYG-Vip068 | 11% |
| GLFYG-PEG-Vip068 | 18% |
| GFL-Vip016 | 30% |
| GFL-PEG-Vip016 | 36% |

Example 11.4

Acetylation of Oligonucleotides Having Internal Modified dT (Amine-C6-dT) (Position n=1)

Synthesis of acceptor oligonucleotide with a C6-NH2, PEG-NH2 and Gly-NH2 linker.

Oligonucleotide, vip016, absorbed on DEAE Sepharose (Sigma #DFF100) was acylated at the primary amine on an internal modified dT in vip016 with FmocNH-C6-CO2Su (Fmoc-6-aminohexanoic acid N-hydroxysuccinimide ester, ChemImpex #7296), FmocNH-PEG-OSu (Fmoc-8-amino-3,6-dioxaoctanoic acid hydroxysuccinimide ester, synthesized from Fmoc-8-amino-3,6-dioxaoctanoic acid (ChemImpex #7310) by EDC coupling with N-hydroxysuccinimide) or Fmoc-Gly-OSu (Fmoc-L-Glycine N-hydroxysuccinimide ester, ChemImpex #02420) followed by cleavage of the Fmoc protecting group according to the procedure of Halpin and Harbury (Plus Biology 2004, 2, 1-8) Reactions were performed on 1 nmol DNA. After elution of the DNA from the sepharose the mixture was desalted on a spin column (Amersham Biosciences #27-5325-01) according to manufactures protocol followed by purification by HPLC. Yields were determined by HPLC.

| DNA | Isolated yield |
| --- | --- |
| H2N-PEG-vip016 | 39% |
| H2N-C6-vip016 | 39% |
| H-G-vip016 | 45% |

Example 11.5

Conjugation of Amino Acids to Oligonucleotides Having Internal Modified dT (Amine-C6-dT) via BSOCOES or DSS at Position n≠1

The oligonucleotides, vip046, vip017, vip047 and vip048, were functionalized by cross-linking an amino acid (Gly, L-Leu, L-Phe, L-Tyr, Fluka, #50052, #61820, #78020, #93829) through the alfa-amine to the primary amine on an internal modified dT in the oligonucleotide, by the homobifunctional linkers BSOCOES ((Bis[2-(succinimidooxycarbonyloxy)ethyl]sulfone), Pierce cat#21600) and DSS (Disuccinimidyl suberate, Pierce #21655) by treatment of the oligonucleotide (0.5 nmol) and the amino acid (15 mM) in a 1:1 mixture of DMF and 400 mM pH 8.4 sodium phosphate buffer with the linker (10 mM). Total volume of the reactions was 20 µL. The reactions were incubated 4 hrs at 25° C. The reaction mixture was diluted to 50 µL and purified on a spin column (Amersham Biosciences #27-5325-01) according to manufactures protocol followed by purification by HPLC. Yields were determined by HPLC. Identity was determined by MALDI-TOF mass spectrometry.

| DNA | Isolated yield | Calculated mass | Found mass |
| --- | --- | --- | --- |
| vip046-BSOCOES-Gly | 32% | 6878.2325 | 6879.3 |
| vip046-BSOCOES-Leu | 48% | 6934.2951 | 6936.1 |
| vip046-BSOCOES-Phe | 49% | 6968.2795 | 6969.0 |
| vip046-BSOCOES-Tyr | 51% | 6984.2744 | 6985.5 |

Example 12

Stability of Acylation Reaction in Reaction Center at Different Temperatures

In this example it is demonstrated how transfer of one amino acid can be effected at elevated temperatures in a trimer star structure. Results are shown in FIG. 20.

Oligos vip006, vip018, and vip017-Leu (DNA Technology Arhus, Denmark, vip017 derivatized as described in example 11 as 20 mM stock solutions were mixed in buffer solution containing a final composition of morpholinopropanesulfonic acid (MOPS, 100 mM, pH 7.0) and NaCl (1M). Solutions were subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). Each reaction was added chemical activator (DMTMM, Fluka #74104, 100 mM aq. sol, final concentration of 5 mM) and incubated for indicated time at 25° C. or 70° C.

Reaction mixtures were analyzed by denaturing (10%) PAGE and bands were visualized by SYBR Green stain (fixation of gel in 50% EtOH for 5 min, wash in water bath 5 min, then incubated for 10 min in 10.000 fold diluted DMSO stock of SYBR Green in 1×TBE buffer).

For reactions run at 25° C., an indetectable amount of product was observed after the first 2 h (reactions 1-5). In the 4 h reaction (reaction 6), a small amount was observed. Significant amounts were observed after an over night incubation with highest intensity observed where more activator was added.

For reactions run at 70° C., the first trace of product was observed after 5 min (reaction 2). Increasing amounts were observed up to 240 min, then decreasing amounts for over night reactions.

The desired cross-linked product of vip017-Leu and vip018 was clearly formed at both 25° C. and 70° C., thus demonstrating that star structures are able to mediate reactions run at elevated temperatures. The rate of reaction is clearly different at the two temperatures used in this experiment. However, this would be expected as the initial activation of the amino acid carboxylic acid by DMTMM is controlled by intermolecular collisions only, not dirigation by DNA.

Example 13

Stability of Acylation Reaction in Reaction Center at Different pH's

Figure 21:
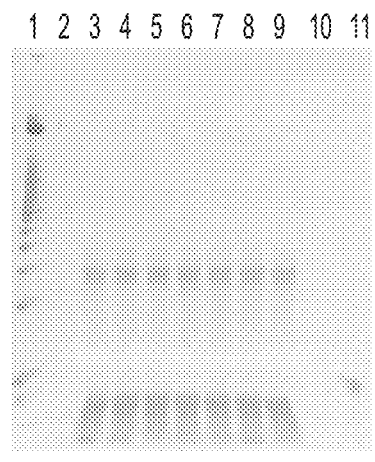
FIG. 21 Discloses a gel from an experiment reported in example 13.

In this example it is demonstrated how one amino acid can be transferred in a trimer star structure in a pH span of 5.2 to 8.0. At low pH, the acceptor amino group may be partially protonated, thus inactivating it as a potent nucleophile. At higher pH, reactive intermediates produced by activation of the amino acid carboxylic acid can be hydrolyzed, thus deactivating it and destroying the chemical activator. Both may hamper formation of the desired amide bond. Results are shown in FIG. 21.

Oligos vip016, vip008, and vip017-Tyr (DNA Technology Arhus, Denmark, vip017 derivatized as described in example 11) as 20 mM stock solutions were mixed in 2M NaCl and subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted into buffer solutions to a final composition of morpholinopropanesulfonic acid (MOPS, 100 mM, pH 5.2, 5.5, 6.0, 6.5, 7.0, 7.5, or 8.0), NaCl (1M) and chemical activator (DMTMM, Fluka #74104, 1.0M aq. sol, final concentration of 75 mM) and incubated for 1 h at 50° C. Final DNA concentration was 0.5 mM. Reaction mixtures were analyzed by denaturing PAGE (10% gel), which was incubated with SYBR green (10.000 dilution in TBE-EtOH (96%) 1:1 from DMSO stock) for 10 min.

All seven lanes covering pH between 5.2 and 8.0 showed a strong band for the cross-linked oligos vip016-vip017-Tyr indicating a broad pH window in which to operate. Thus, protonation of acceptor amine or hydrolysis of reactive intermediates is not a significant problem using the above conditions.

Example 14

Stability of Acylation Reaction in Reaction Center at Different Levels of Organic Solvent To demonstrate the stability of DNA star structures, the transfer of one amino acid was carried out in a mixture of $H_2O$ and an organic solvent, thus resembling conditions used in organic chemical synthesis. If base pairing and star structure was destroyed under these conditions, no cross linked product can be formed. The solvents dioxan, acetonitrile, and tetrahydrofuran were chosen with regard to miscibility with water and general applicability in organic synthesis.

Figure 22:
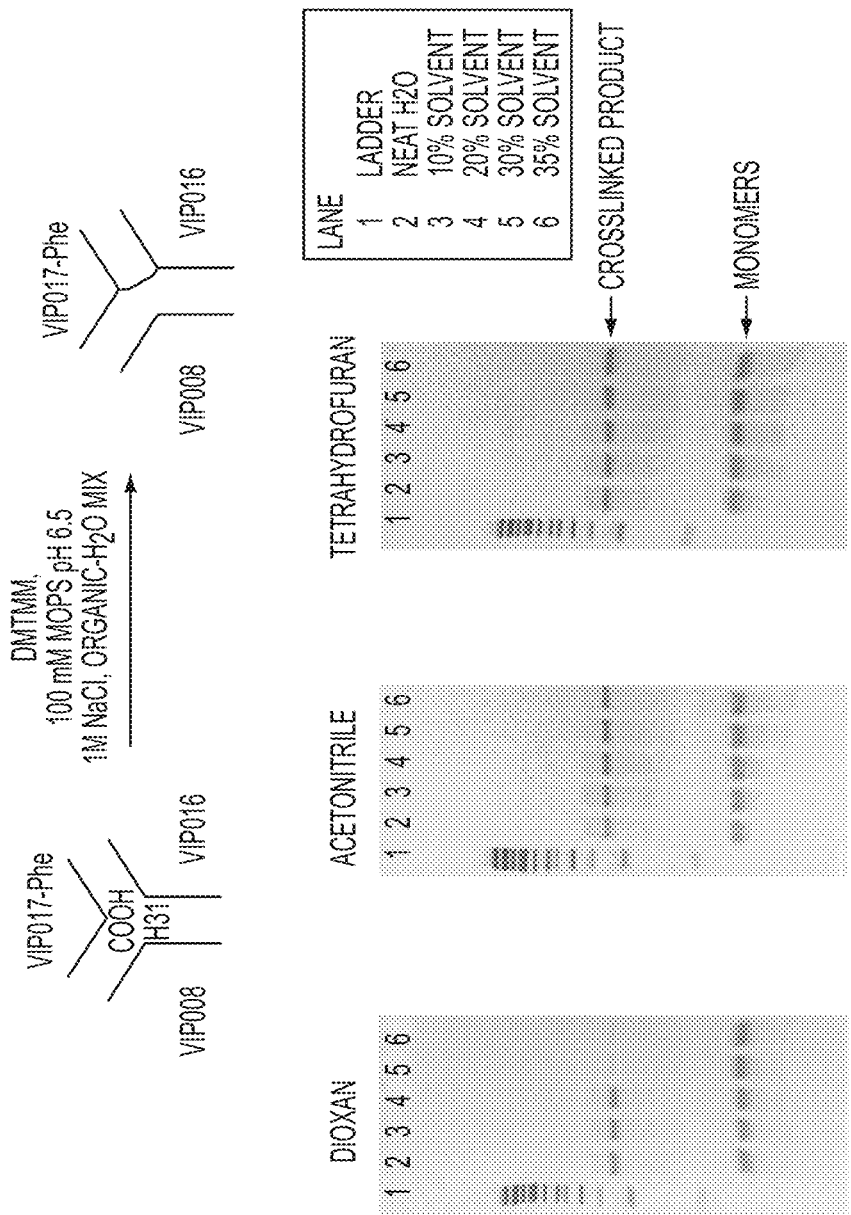
FIG. 22 shows a gel from an experiment reported in example 14.

Oligos vip016, vip008, and vip017-Phe (DNA Technology Arhus, Denmark, vip017 derivatized as described in example 11) as 20 µM stock solutions were mixed in a buffer of MOPS (200 mM, pH 6.5; Fluka #69947) and NaCl (2M; Fluka #71376), and subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted into mixtures of solvent and water to a final composition of morpholinopropanesulfonic acid (MOPS, 100 mM, pH 6.5), NaCl (1M), solvent (0, 10, 20, 30, or 35 vol %), and chemical activator (DMTMM, Fluka #74104, 1.0M aq. sol, final concentration of 75 mM), which was incubated at 50° C. for 1 h. Final DNA concentration was 0.5 µM. Reaction mixtures were analyzed by denaturing PAGE (10% gel), which was stained with SYBR green (Molecular Probes, #S7563) according to manufactures instructions. The results are shown in FIG. 22

For dioxan, cross linked product was formed with up to 20% solvent. On the other hand, for all reactions containing acetonitrile or tetrahydrofuran similar amounts of product was formed, thus indicating that the presence of at least up to 35% of the organic solvent was well tolerated and DNA base paring was intact.

Example 15

Stability of Reaction Center at Different Levels of DMF

To demonstrate the stability of DNA star structures, the transfer of one amino acid was carried out in a H2O-DMF mixture, thus resembling conditions used in organic chemical synthesis. If base pairing and star structure was destroyed under these conditions, no cross linked product can be formed.

Figure 23:
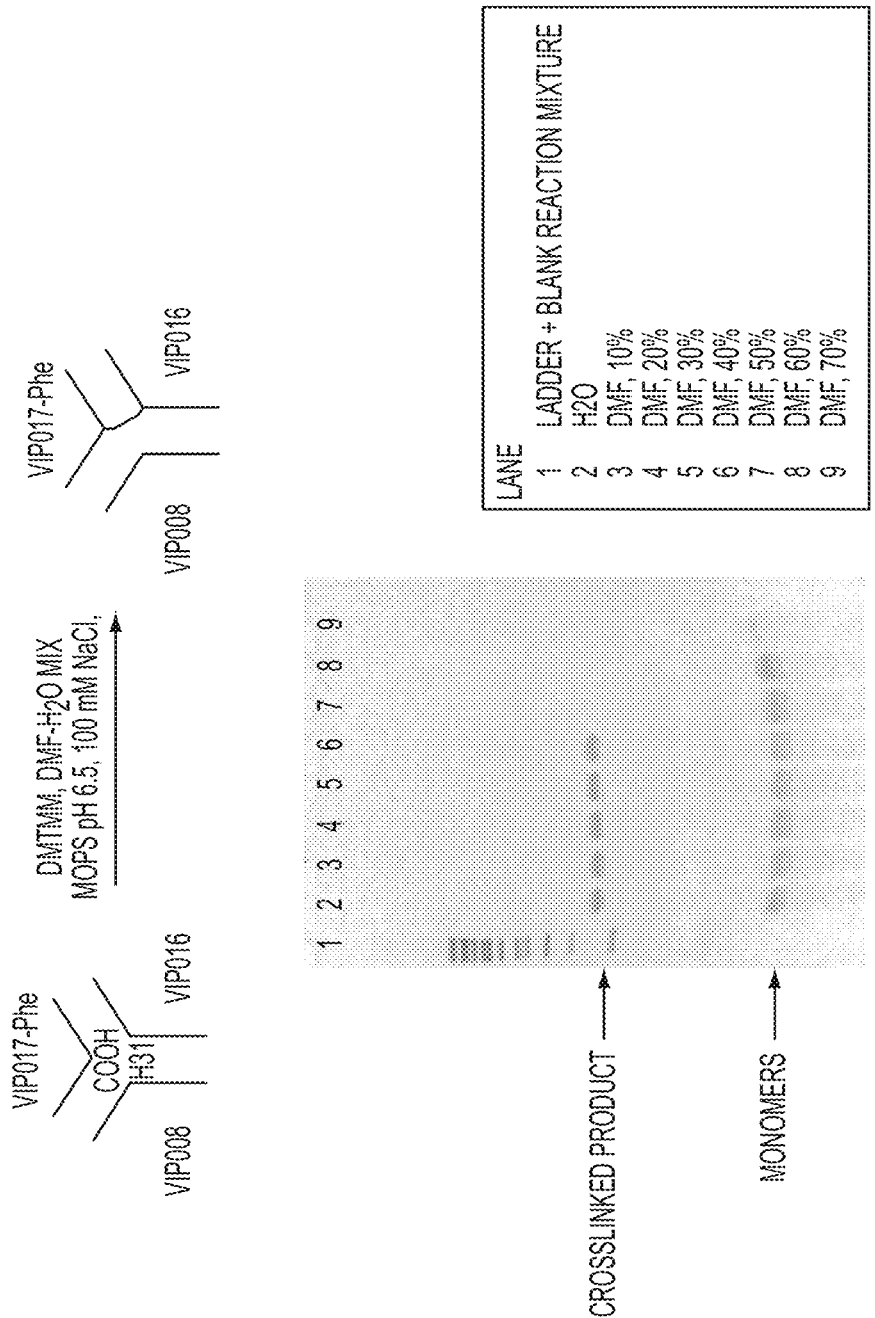
FIG. 23 shows a gel from an experiment reported in example 15.

Oligos vip016, vip008, and vip017-Phe (DNA Technology Arhus, Denmark, vip017 derivatized as described in example 11) as 20 µM stock solutions were mixed in a buffer of MOPS (500 mM, pH 6.5; Fluka #69947) and NaCl (4M; Fluka #71376), and subjected to an annealing program (PCR machine: 5 mM @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted into mixtures of DMF and water to a final composition of morpholinopropanesulfonic acid (MOPS, 12.5 mM, pH 6.5), NaCl (100 mM), DMF (0, 10, 20, 30, 40, 50, 60, or 70 vol % DMF), and chemical activator (DMTMM, Fluka #74104, 1.0M aq. sol, final concentration of 75 mM), which was incubated over night at 25° C. Final DNA concentration was 0.5 µM. Reaction mixtures were analyzed by denaturing PAGE (10% gel), which was stained with SYBR green (Molecular Probes, #S7563) according to manufactures instructions. The results are shown in FIG. 23

The product band produced in the first five lanes were of similar intensity, thus indicating that the presence of at least up to 40% of the organic solvent, DMF, was well tolerated and DNA base paring was intact. At 50% DMF, a weak band was still observed, but from 60% and above no cross linked product was detected.

Example 16

Different Activators for Mediating Chemical Reaction

This example serves to illustrate how various chemical activators and auxiliary nucleophiles can be used to mediate the acylation of an acceptor amine with an amino acid. It is known from peptide chemistry that addition of an axiliary nuclephile can greatly enhance the rate of acylation and/or change the final outcome of the reaction. In this example reactions were nm using no axiliary nucleophile, N-hydroxysuccinimide (NHS, e.g. Fluka #56480), N-hydroxysulfosuccinimide sodium salt (s-NHS, Fluka #56485), or N-hydroxybenzotriazole hydrate (e.g. Fluka #54804) were used with DMTMM (Fluka #74104) or EDC (e.g. Fluka #03449) as activators.

Oligos vip016, vip008, and vip017-Tyr (DNA Technology Arhus, Denmark, vip017 derivatized as described in example 11) as 20 mM stock solutions were mixed in a buffer of MOPS (200 mM, pH 6.5) and NaCl (2M), and subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted with water and solutions of additives to a final composition of morpholinopropanesulfonic acid (MOPS, 100 mM, pH 6.5), NaCl (1M), auxiliary nucleophile (final conc. 25 mM), and chemical activator (DMTMM or EDC, 0.5M aq. sol, final concentration of 75 mM). Final DNA concentration was 0.5 mM. Reactions were incubated for 1 h at 50° C.

Figure 24:
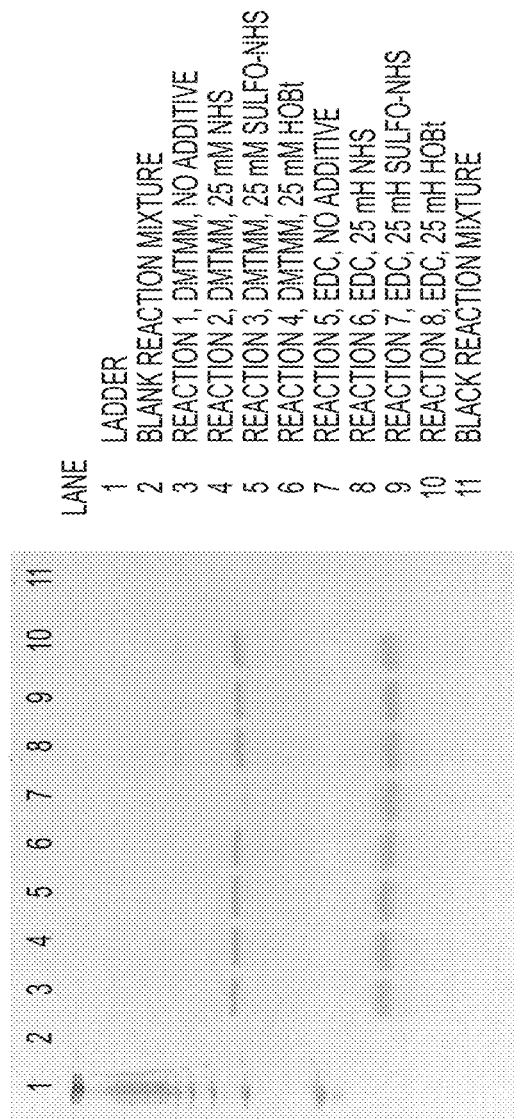
FIG. 24 discloses a gel from the experiment disclosed in example 16.

Reaction mixtures were analyzed by denaturing PAGE (10% gel), which was incubated with SYBR green (10.000 dilution in TBE-EtOH (96%) 1:1 from DMSO stock) for 10 min. Results are shown on FIG. 24.

Reactions 1-4 using DMTMM as activator, no difference was observed by using additive or none. Most clearly was observed for EDC only, in which case no, or only faintly, product was observed. However, addition of either auxiliary nucleophile gave a comparable amount of cross linked product again. This demonstrates that auxiliary nucleophile us needed when using EDC as activator and otherwise it is well tolerated in the reaction mixture.

Example 17

Transfer of Amino Acid to Other Acceptors

This example demonstrates how an amino acid can effectively be transferred to a number of acceptor amine linked in various ways. Vip016 carrying a C6-NH2 served as control as before. Other acceptors were tripeptide GFL-vip016, PEG linked tripeptide GFL-PEG-vip016, amino functionalized NH2-PEG-vip016, amino functionalized NH2-C6-vip016, and glycine in G-vip016 (all prepared as described in example XX)

Oligos vip016-X-NH2, vip008, and vip017-Gly (DNA Technology Arhus, Denmark, vip017 derivatized as described in example XX) as 20 mM stock solutions were mixed in a buffer of MOPS (200 mM, pH 6.5) and NaCl (2M), and subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). This annealing mixture was diluted with water and solution of activator to a final composition of morpholinopropanesulfonic acid (MOPS, 100 mM, pH 6.5), NaCl (1M), and chemical activator (DMTMM, Fluka #74104, 1.0M aq. sol, final concentration of 75 mM). Final DNA concentration was 0.5 mM. Reactions were incubated for 1 h at 50° C.

Figure 25:
FIG. 25 shows the results of the experiment shown in example 17.

Reaction mixtures were analyzed by denaturing PAGE (10% gel), which was incubated with SYBR green (10.000 dilution in TBE-EtOH (96%) 1:1 from DMSO stock) for 10 min. Results are shown in FIG. 25.

All six reactions show a strong band from cross linked product. Lane 4 and 5 were observed to run marginally slower compared to others because of larger peptide (tetrapeptide). Thus, transfer of one glycine to amino group linked via tripeptide +/−PEG linker, PEG linker itself, C6 linker, or glycine directly gives consistent results. This demonstrates robustness in the reactor formed by star structures. Increasing size of acceptor has little or no effect of the outcome of the crosslinking.

Example 18

Assembly and Subsequent Binding of Two Structural DNA Display Products

Figure 26:
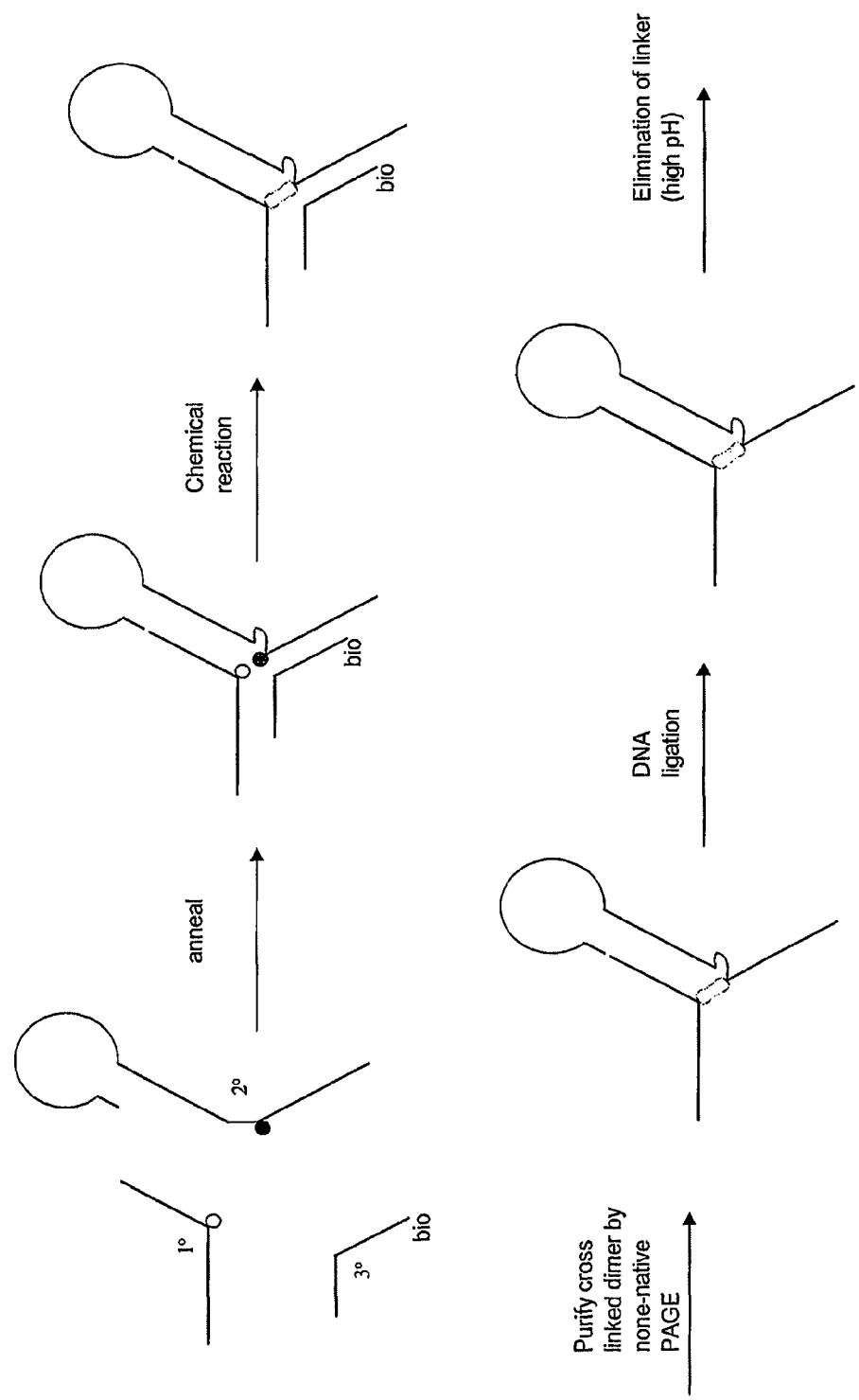
FIG. 26 discloses the outline of the experimental strategy used in example 18

Two Structural DNA display products were formed: Leu-enkephalin (Tyr-Gly-Gly-Phe-Leu-DNA) and scrambled Leu-enkephalin (Gly-Leu-Phe-Tyr-Gly-DNA). The latter was included as a negative control for the partitioning assay using the Leu-enkephalin specific monoclonal antibody 3E7. Key steps of the process are illustrated in FIG. 26.

DNA oligonucleotides were purchased by DNA Technology (Aarhus, Denmark) and functionalized as described in Example 11.

First step of the process involved annealing of the following oligoes, in two separate reactions to form Leu-Enkephalin-DNA and scramble Leu-Enkephalin respectively. In reaction 1 (R1); Gly-Phe-Leu-PEG-vip231, Gly-BSOCOES-vip262 and vip088 (position 1, 2 and 3 in a 3-way DNA Star Structure, respectively) and in reaction 2 (R2): Gly-Tyr-Phe-PEG-vip238, Leu-BSOCOES-vip269 and vip088 (position 1, 2 and 3 in a 3-way DNA Star Structure, respectively). The three oligoes in the reactions will hybridize to each other, thus forming a three-way junction, where the attached amino acids are located in the centre of the structure. Note that vip088 does not have a chemical functionality attached. Vip088's function is simply to hybridize to the two other oligoes to form the closed three-way junction.

200 pmoles of each oligo were mixed in 100 mM morpholinopropanesulfonic acid (MOPS, Fluka #69947) pH 6.5 and 1 M NaCl in a total volume of 370 µl. The annealing of the oligoes was performed by incubation for five minutes at 95° C., before cooling to room temperature over approximately 30 minutes. The activator DMT-MM (Fluka #74104) was dissolved in water and added to a final concentration of 75 mM. The final reaction volume was 400 µl. The chemical reaction was incubated for 1 hour at 50° C. Then, the product was ethanol precipitated by adding 2.5 volumes ethanol and 1 µl GenElute (Sigma 56575) to each reaction, and centrifuging the tubes 30 minutes, 20000×g at 4° C. The pellets were washed with 70% ethanol, before they were air-dried, and re-suspended in water.

Then, the samples were subjected to preparative non-native polyacrylamide gel electrophoresis (PAGE); 10% TBE-urea gel (Invitrogen) according to manufactures instructions. The band corresponding to the cross-linked product was cut out and the product extracted by the "crush and soak" method (Sambrook, J., Fritsch, E F, and Maniatis, T. (1989) in: Molecular Cloning: A Laboratory Manual, Cold Springs Harbor Laboratory); the gel piece was crushed and soaked overnight in 400 TBE Buffer. The samples were ethanol precipitated as described above. The precipitates were dissolved in 1× Ligase buffer (New England Biolabs), 50 mM NaCl. Then, the 5' ends were phosphorylated by Polynucleotide Kinase; 50 units Polynucleotide Kinase (NEB M0201) were include in a total of 200 µl reaction volume. The reactions were incubated for 30 min at 37° C.

Then, the two cross-linked oligoes were transformed into a continuous DNA strand by a DNA ligase, which formed a phosphordiesther bond between the juxtaposed 3' end of vip231 and 5' end of vip262 for R1 and the juxtaposed 3' end of vip238 and 5' end of vip269 for R2. T4 DNA ligase (NEB M0202L) was added in 1× Ligase buffer, 50 mM NaCl, and 5 units/µl enzyme was added, giving a final reaction volume of 300 µl. The ligation was incubated overnight at 16° C.

Then, the cleavable BSOCOES linker was eliminated. 3-(Cyclohexylamino)-1-propanesulfonic acid (CAPS, Fluka#29338) (pH 11.8) buffer and 2-mercaptoethanol (Fluka#63689) were added giving final concentrations of 100 and 60 mM, respectively, in a final reaction volume of 600 µl. The reactions were incubated for 2 hours at 37° C. The reactions were then neutralized by adding 200 µl 1 M MOPS buffer, pH 6.5. Then, the DNA was ethanol precipitated according to the standard procedure. After air drying of the pellets, the DNA was ready for the next step, which was introduction of functionalized oligonucleotides on the position 3. Note that by the elimination of the BSOCOES linker two primary amines are formed: one is at the terminus of the growing peptide chain on the original position 1 oligonucleotide and the other is located on the original position 2 oligonucleotide. The so called "wobbling" strategy was used to favour a subsequent reaction between the growing peptide chain and the incoming amino acid on position 3 in the next step: the oligoes on position 2 contain upstream of the modified base a stretch of bases (wobbling bases), which are unpaired during the first chemical transfer, however in the second transfer process they are base paired with the position 3 oligo. Consequently, the primary amine on the original position 2 oligonucleotide is now separated from the centre of structure by a stretch of dsDNA which will decrease its reactivity with moieties in the centre of the Star Structure because dsDNA is rigid.

R1 product was annealed to Tyr-BSOCOES-vip263 and R2 product was annealed to Gly-BSOCOES-vip270 under the following conditions: 200 pmoles oligo, in 100 mM MOPS, pH 6.5, 1 M NaCl in a total volume of 240 µl. The mixture was incubated 5 minutes at 95° C., before cooling to room temperature over a period of approximately 30 minutes. Then, the activator DMT-MM (Fluka #74104) was added to a final concentration of 75 mM, for promoting the chemical reaction between the amino acids. The chemical reaction was incubated for 1 hour at 50° C. The samples were precipitated by ethanol and subsequently subjected to preparative non-native PAGE (as described above) where the band corresponding to the cross-linked product was excised from the gel. Then, each cross-linked product were transformed into a continuous DNA strands by a DNA ligase, which formed a phosphordiesther bond between the juxtaposed 3' end of the original vip232 and 5' end of vip263 for R1 and the juxtaposed 3' end of the original vip269 and 5' end of vip270 for R2, respectively.

Furthermore terminal PCR priming sites were introduced in the same reaction by the DNA ligase. The DNA oligoes having the PCR priming sites vip029/vip070 and vip029/vip030 for R1 and R2, respectively, were pre-annealed under the following conditions: 200 pmoles of each oligo in 1× Ligase buffer and 50 mM NaCl in total volume of 40 µl and incubated in a PCR machine for 5 minutes at 95° C. and for 30 seconds steps at the following temperatures: 80° C., 65° C., 50° C., 45° C., 30° C., 20° C.

When vip070 is annealed to vip029 the four most 5' terminal nucleotides of vip070 are protruding. These four are reverse complementary to the four most 5' terminal nucleotides in vip231 which also are protruding when vip231 is annealed to vip263. Consequently, the protruding ends can anneal and form a substrate for a DNA ligase. Likewise, when vip030 is annealed to vip029 the four most 5' terminal nucleotides of vip070 are protruding. These four nucleotides are reverse complementary to the four nucleotides most 5' in vip238 which also are protruding when vip238 is annealed to vip270. The cross-linked, gel-purified products were re-suspended in 1× Ligase buffer, 50 mM NaCl, and mixed with the pre-annealed PCR sites containing DNA oligoes; vip029/vip070 and vip029/vip030 for R1 and R2, respectively. The DNA 5' ends were first phosphorylated by 50 units Polynucleotide Kinase (NEB 0201L) in a final volume of 200 µl. The reaction was allowed to incubate for 30 minutes at 37° C.

Then, the DNA was by a T4 DNA ligase transformed into a continuous DNA strand consisting of vip029-vip231-vip262-vip263-vip070 and vip029-vip238-vip269-vip270-vip030 in R1 and R2 respectively. 1500 units T4 DNA Ligase (NEB 0201L) in 1× Ligase buffer, 50 mM NaCl were added to the reactions giving a final reaction volume of 300 µl. The ligation reactions were incubated at 16° C. overnight. Then, the BSOCOES linker was eliminated as described above. The samples were precipitated by ethanol and subsequently subjected to preparative non-native PAGE, ethanol precipitated again and dissolved in 20 µA water as described above. The assembled products were now ready for primer extension.

Throughout the above described procedure, small samples were removed for analysis by none-native PAGE as described above. The gel picture is shown in FIG. 27. Lane 1 and 2 show the successful formed cross-linked functionalised oligoes vip-231 (35 nt)/vip262 (68 nt) and cross-linked vip-238 (35 nt)/vip-269 (68 nt) for R1 and R2, respectively. The cross-linked products migrate with an apparent size of approximately 200 bp. The observed difference between actually size and apparent size is not unexpected due to the strong secondary structures in the formed products which are present even in a non-native gel due to the reverse complementary sequences. Furthermore, bands of smaller size were observed which most likely originate from degradation of the full length specie.

Lanes 3 and 4 show the products after both ligation of the two oligoes and elimination of the BSOCOES linker for R1 and R2 respectively. The main products migrate with an apparent size of 150 bp. Furthermore, bands of smaller size were also observed most likely generated by degradation of the full length species. Note that the species in both lane 1 and 3 (and in lane 2 and 4) are of almost equal in size but migrate significantly differently in the gel. This is not unexpected because the species in lane 1 and 2 essentially are branched DNA molecules, whereas the species in lane 3 and lane 4 are linear DNA molecules.

Lane 5 and 6 show the product after cross-linking of the position 3 oligoes for R1 and R2 respectively. In both reactions, the position 3 oligo is 74 nt. Thus, the expected products are 177 nt. However, the apparent size in the gel of cross-linked species is around 600 bp. This is not unexpected because the species consist of cross-linked linear DNA molecules with very strong secondary structures due to the reverse complementary sequences in the arms of the DNA Star Structure. Even a urea containing PAGE are not capable of denature the structure.

Lane 7 and 8, contain the products after both ligation of the position 3 oligoes and PCR sites containing oligoes and elimination of the BSOCOES linker for R1 and R2 respectively. The PCR priming sites containing oligoes add a total of 64 nt, thus the desired products are 241 nt. Two prominent bands of an apparent size in excess of 1000 bp were observed. The upper band most likely contains the full length products, whereas the lower band most likely contains molecules missing one of the two PCR sites containing oligoes. Furthermore, in lane 8, a band migrating with an apparent size of 600 bp was seen. The band most likely represents a specie with no PCR sites containing oligoes ligated (compare lane 8 and 6).

Lane 9 contains the 100 bp DNA ladder (Fermentas, SM0248).

Primer Extension.

The assembled products were subjected to primer extension, which transforms the DNA folded in a star structure with the chemical product in the centre into linear double stranded molecules with the chemical product displayed on the surface. The reaction was primed by vip038 which is reverse complementary to the 3' of the assembled molecules. The reactions were conducted in 1× Thermopol buffer, 0.2 mM dNTPs, 8 mM MgSO4, 1 M betaine (Sigma, B-0300), 0.4 µM vip038, 0.2 U/10 µl Vent (exo-) (NEB M0259L), and 5 µl assemble molecule as template in a 10 µl primer extension reaction. The reaction mix was incubated at 95□C for 2 minutes, 60° C. for 30 seconds and at 74° C. for 5 minutes.

Binding Assay.

The DNA displaying the synthesized peptides was analyzed in a electrophoresis mobility shift assay (EMSA). A demonstration of binding will confirm the capability of correctly synthesize a compound from carrier modules directed by Structural DNA.

Figure 28:
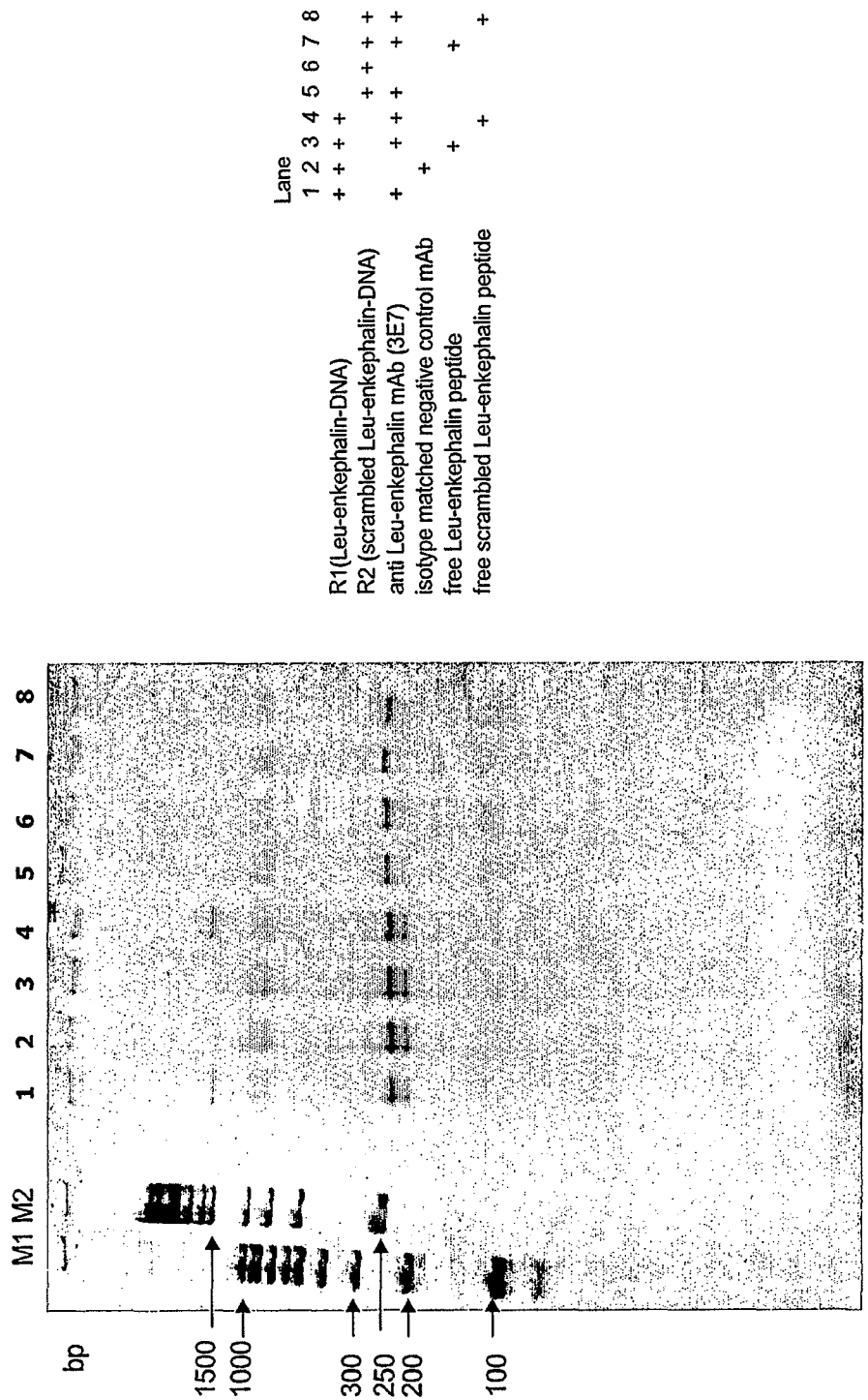
FIG. 28 shows a non-native PAGE gel of the binding assay reported in example 18.

This assay is adapted from the literature (Halpin and Harbury, PLoS Biol, 2, E174, 2004). 10 µL primer extension product of R1 (Leu-enkephalin-DNA) or R2 (scrambled Leu-enkephalin-DNA) were each placed into 4 tubes. To tubes R1-1 and R2-1 1 µL 0.5 mg/ml 3E7 anti Leu-enkephalin monoclonal antibody (Chemicon, cat# MAB5276), 1 µL 1M Tris-HCl pH 7.2 and 1 µL 0.1% Triton-X/PBS were added. To tubes R1-2 and R2-2 1 µL 0.5 mg/ml W6/32 monoclonal antibody (Sigma, H1650), 1 µL 1M Tris-HCl pH 7.2 and 1 µL 0.1% Triton-X/PBS were added. To tubes R1-3 and R2-3 1 µL 0.5 mg/ml 3E7 anti Leu-enkephalin monoclonal antibody, 1 µL 20 µM Leu-enkephalin (Tyr-Gly-Gly-Phe-Leu) (Schafer-N, Denmark) and 1 µL 1M Tris-HCl pH 7.2 were added. To tubes R1-4 and R2-4 1 µL 0.5 mg/ml 3E7 anti Leu-enkephalin monoclonal antibody, 1 µL 20 µM scrambled Leu-enkephalin (Gly-Leu-Phe-Tyr-Gly) (Schafer-N, Denmark) and 1 µL 1M Tris-HCl pH 7.2 were added. All samples were incubated with agitation for one hour at room temperature. 1.4 µL of 10× loading dye (Invitrogen, Cat#10816-015) was added to each sample and the entire amount was loaded onto the gel. 1 µL of both 100 bp and 1 kb ladders were also loaded (Fermentas #SM0248 and #SM0318). The 10% PAGE TBE gel (Invitrogen) was run cold at 220 mV and 15 mA for 45 minutes. The gel was developed for 20 minutes in SYBR Green™ nucleic acid stain (Molecular Probes) according to manufactures instructions. The picture of the gel is shown in FIG. 28. Results: in all lanes two prominent bands having apparent sizes of 200-250 bp are observed. The bands most likely contain species having double stranded DNA (further evidence can be found in e.g. Example 21). The upper band corresponds well with the intended 241 bp full length product, whereas the lower band most likely contains a species missing the vip029 which will give a 30 bp smaller product. Two prominent bands with apparent sizes of around 1000 bp are observed in all lanes. Most likely the bands contain species having star structure folded DNA: the upper band most likely contains the full length products, whereas the lower band most likely contains molecules missing one of the two PCR sites containing oligoes.

In lane 1 containing R1-1 a band of apparent size of around 1500 bp is observed. This band most contain the Leu-enkephalin-DNA product binding to 3E7 antibody which slows the electrophoretic migration of the entire complex. This band is absent when the R1 product is incubated with the IgG2A isotype matched negative control antibody as shown in lane 2 (R1-2). The specificity of the interaction is further enforced by the competition of the binding by free-soluble Leu-enkephalin: In lane 3 the gel-shifted band is absent when the R1 product, 3E7 and the free Leu-enkephalin peptide are co-incubated. The competition is not seen in lane 4 containing R1-4 when the free soluble scrambled Leu-enkephalin is present. Lanes 5-8 containing R2-1, R2-2, R2-3 and R2-4, respectively show that the negative control R2 product (scrambled Leu-enkephalin-DNA) does not bind to 3E7, as expected.

Amplification

To demonstrate that the DNA of the gel-shifted band and other bands are intact gel pieces were excised and DNA was extracted for use as templates for PCR.

Figure 29:
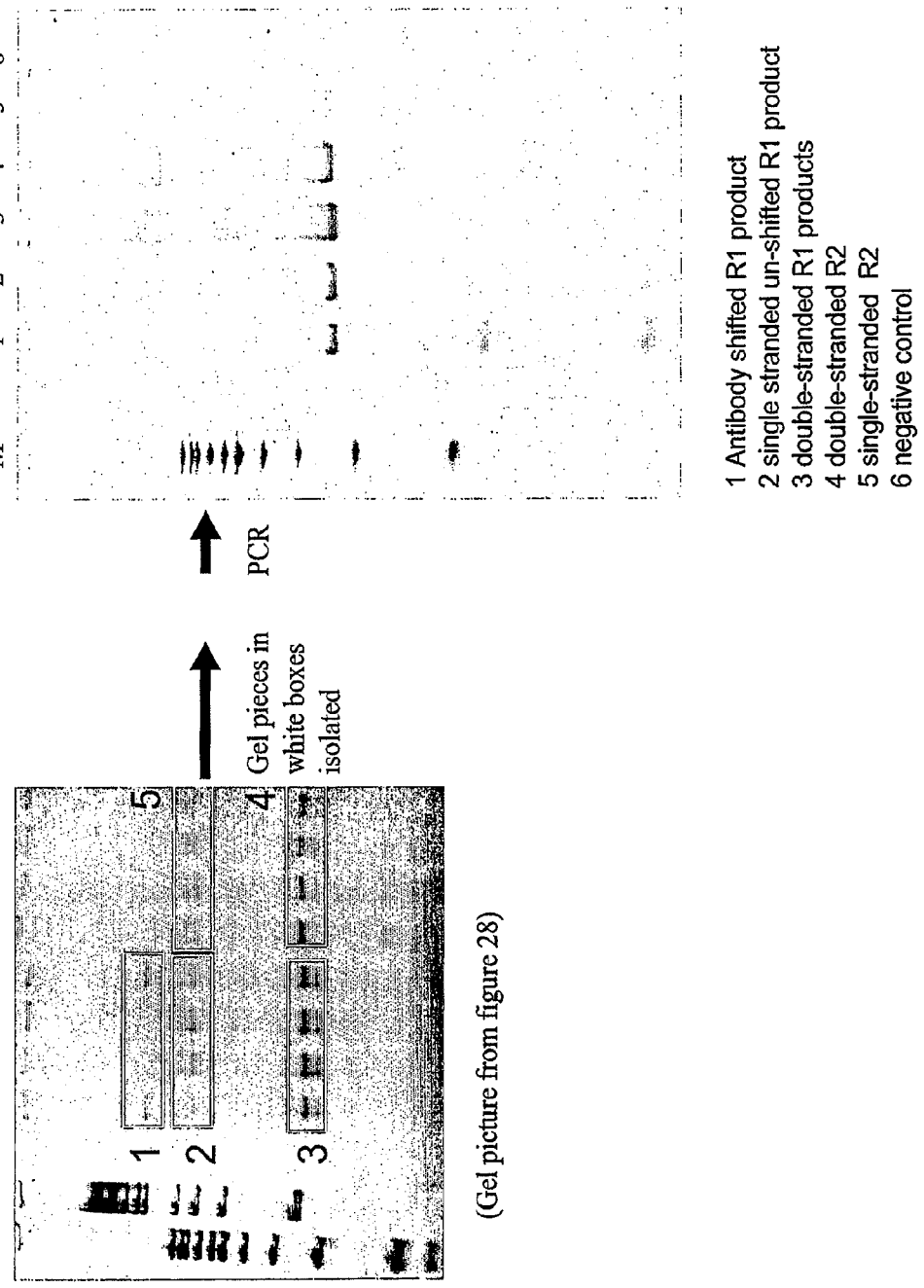
FIG. 29 shows a PCR amplification gel reported in example 18.

The gel pieces boxed in FIG. 29 were cut out and the product extracted by the "crush and soak" method (Sambrook, J., Fritsch, E F, and Maniatis, T. (1989) in: Molecular Cloning: A Laboratory Manual, Cold Springs Harbor Laboratory); the gel piece was crushed and soaked overnight in 4000 µl TE Buffer. The tubes were spun for 10 minutes at 20 000×g and the supernatant transferred to a fresh tube. PCR [1× Polymerase Buffer, 0.2 mM dNTP, 6 mM MgSO4, 0.2 µM vip027, 0.2 µM vip028, 0.5 M betain (Sigma, B-0300), 0.1 mg/ml BSA 0.08 units/µl Vent(exo-)(NEB M0259L)] was then performed using 5 µl of the supernatant diluted 200 fold in a 20 µl reaction. 20 cycles of 30" at 95° C., 30" at 60° C. and 30" at 74° C. in a thermocycler were performed and 2 µl of the samples were analyzed on a native 10% PAGE (Invitrogen) and stained with SYBR Green (Molecular Probes) according to manufactures instructions and a picture was taken. The result is shown in FIG. 29. Lane M contains the 100 bp DNA ladder (Fermentas, SM0248). Lanes 1-5 contain the reactions having the gel purified templates: in all lanes a prominent band around 250 bp is observed corresponding to the expected size of the full length product. In contrast in lane 6 which contain the negative control without template added the band is not observed. Consequently, it is hereby demonstrated that a Structural DNA Display product can be formed, partitioned and amplified.

In conclusion, the specific binding of the R1 product to the 3E7 anti-Leu-enkephalin antibody demonstrates conclusively that the Leu-enkephalin peptide has been correctly assembled by the process. Furthermore, it has been shown that partitioning of a product displaying a ligand from a product not displaying a ligand indeed is doable. For example as illustrated here simply by isolating the gel shifted band.

Furthermore, the partitioned product can be amplified for subsequently identification by e.g. DNA sequencing or used as a template in a translation process, thus allowing cycles of selection and amplification to be performed.

Example 19

DNA Star Structure Direction of Reductive Amination

The present example serves to illustrate that Structural DNA can direct reductive amination. Reductive amination was chosen as an example of an important and widely applicable chemoselective reaction.

Oligos were obtained from DNA Technology (Arhus, Denmark). The oligonucleotide vip046 was acetylated with DST (disuccinimidyl tartrate, Pierce #20589) at the primary amine on an internal modified dT in the oligonucleotide followed by oxidative cleavage with $NaIO_4$ (Aldrich #31, 144-8) to yield the glyoxylate functionalized oligo. The oligonucleotide (2.5 nmol) was treated with DST (10 mM) in a 40% DMF/water mixture containing and 400 mM pH 8.8 sodium phosphate buffer. Total volume of the reaction was 100 µL. The reactions were incubated 2 hrs at 25° C. $NaIO_4$ (50 µL of a 150 mM solution) was then added and incubated for an additional 2 hrs at 25° C. The reaction mixture was diluted to 200 µL and purified on a spin column (Amersham Biosciences #27-5325-01) according to manufactures protocol followed by purification by HPLC and mass spectrometry analysis according to Example 11. Yield: 36%.

| DNA | Calculated mass | Found mass |
|---|---|---|
| vip046-NHCOCHO | 6653.202 | 6656.1 |

Synthesis of a Benzaldehyde-Functionalized Oligo Having Internal Modified dT (Amine-C6-dT) (Position n=1) (Vip046-NHCOC$_6$H$_4$CHO)

The oligonucleotide vip046 was acylated with 4-carboxy-benzaldehyde (Lancaster #8192) promoted by DMT-MM (4-(4,6-Dimethoxy-1,3,5-triazin-2-yl)-4-methylmorpholinium chloride, Fluka #74104) by treatment of the oligonucleotide (2.5 nmol) dissolved in a 40% DMF/water mixture containing 150 mM NaCl, 200 mM sodium phosphate buffer pH 8.8 with DMT-MM 50 mM. Total reaction volume was 100 µL. The reaction was incubated 4 hrs at 25° C. The reaction mixture was purified on a spin column (Amersham Biosciences #27-5325-01) according to manufactures protocol followed by purification by HPLC and mass spectrometry analysis according to Example 11. Yield: 53%

| DNA | Calculated mass | Found mass |
|---|---|---|
| vip046-NHCOC$_6$H$_4$CHO | 6729.233 | 6729.9 |

Structural DNA Directed Reductive Amination.

In reaction 1 and 5 the two derivatives of vip046 carrying an amide of glyoxylic acid and 4-formylbenzoic acid, respectively, were mixed with equimolar amounts (10 pmoles each) of vip017 and vip008 in a buffer solution containing a final composition of morpholinopropanesulfonic acid (Fluka #69947; MOPS, 100 mM, pH 5.2) and NaCl (Fluka #71376, 1M). Solutions were subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @

10° C.). The annealing mixture was added the reductant (NaCNBH$_3$; Sigma #156159, 1M aq. sol, final concentration of 100 mM; total reaction volume 20 µL) and incubated for 2 h at 30° C.

Controls run in parallel for both aldehydes:
Vip017 was exchanged for vip007, which does not carry an amine (reactions 2+6).
Vip008 was omitted in order to test the efficiency of the dimer compared to trimer (reactions 3+7).
Vip046-CHO was attempted cross-linked to vip019, thus performing the reaction between oligoes, which cannot base pair (reactions 4+8).

All eight reaction mixtures were diluted to 50 µl and EtOH precipitated (added GenElute 0.5 µL; Sigma 56575) and 96% EtOH (Biochemika grade; 250 µl). Incubated 15 min on ice, then spun at 14000 rpm for 30 min at 4° C. Supernatant was decanted, tubes spun briefly, remaining liquid removed by pipette, and the pellet was allowed to dry in a stream of air).

Figure 30:
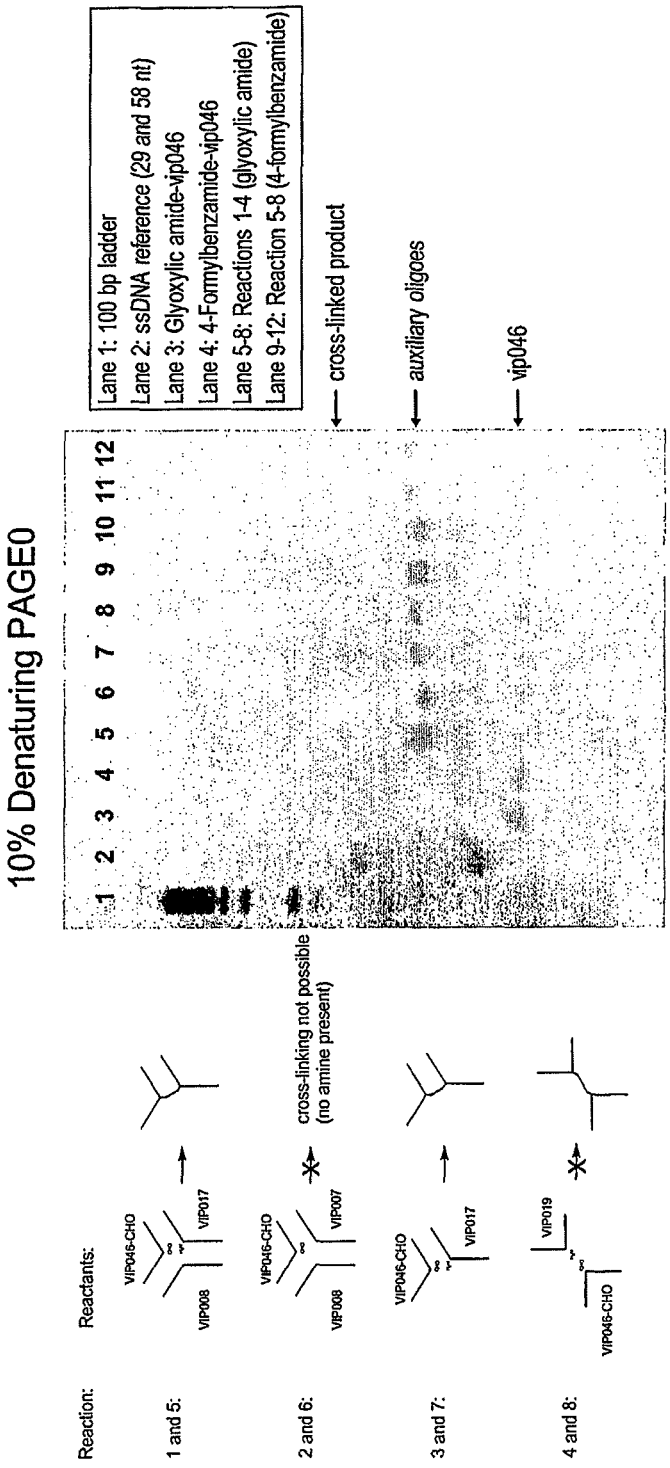
FIG. 30 shows a picture of a gel evidencing the occurrence of a reductive amination.

Crude DNA was dissolved in water and analyzed by denaturing 10% PAGE (Invitrogen) and subsequently stained by SYBR Green (Molecular Probes) according to manufactures instructions. A picture of the gel is shown in FIG. 30. The formation of a new band with a mobility corresponding to 60-70 nt confirms the expected cross-linking of vip046 (21 nt) and vip017 (42 nt) (lanes 5 and 9). No cross-linking was observed in the control experiments with vip007, which is identical to vip017 except that it's without an amine on the internal dT) indicating a selective reaction (lanes 6 and 10). Same product was formed in the dimer, but slightly less intense bands were observed (lanes 7+11). No product was observed for oligoes that cannot base pair indicating that matched sequences are required for product formation (lanes 8+12).

Consequently, Structural DNA is capable of directing reductive amination in a highly specific manner.

Example 20

Structural DNA Direction of Urea Formation

The present example serves to illustrate that Structural DNA can direct urea formation. Urea formation between two amines was chosen as an example of an important, widely applicable reaction. Ureas are known isosters in medical chemistry.

Oligos were obtained from DNA Technology Århus, Denmark.

A DNA Star Structure consisting of a three-way DNA junction was assembled comprising two amino functionalized oligoes and one auxiliary oligo. Oligoes vip046, vip017, and vip008 were mixed in equimolar amounts (10 pmol each) in a buffer solution containing a final composition of morpholinopropanesulfonic acid (Fluka #69947; MOPS, 100 mM, pH 8.0) and NaCl (Fluka #71376, 1M). Solutions were subjected to an annealing program (PCR machine: 5 min @ 94° C., 30 sec @ 80° C., 30 sec @ 65° C., 30 sec @ 50° C., 30 sec @ 35° C., 30 sec @ 20° C., 30 sec @ 10° C.). The annealing mixture was urea forming reagents (N,N'-Disuccinimidyl carbonate, Aldrich #225827 (0.45M in DMF) or bis(4-nitrophenyl)carbonate, Aldrich #161691 (1.0M in DMF)) to a final concentration of 10, 50, or 100 mM (total reaction volume 20 µL) and incubated for 90 min at 37° C.

An aliquot of each reaction mixture was and analyzed by denaturing 10% PAGE (Invitrogen). Bands were visualized by SYBR Green stain (Molecular Probes, #S7563) according to manufactures instructions.

Figure 31:
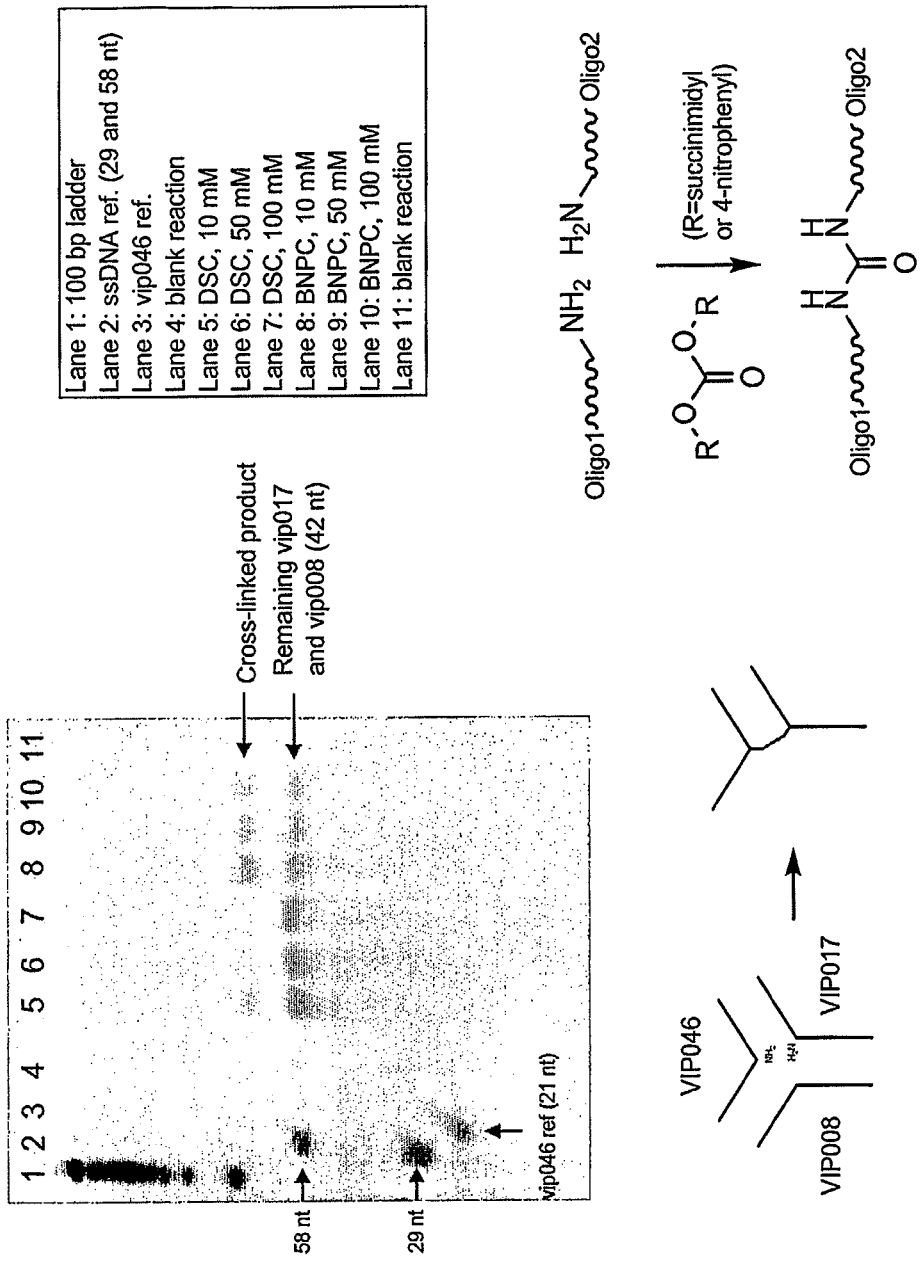
FIG. 31 discloses a picture of a gel evidencing the occurrence of urea attachment

A picture of the PAGE is shown in FIG. 31. The formation of a new band with a mobility corresponding to 60-70 nt confirms the expected cross-linking of vip046 (21 nt) and vip017 (42 nt) in lanes 5-10. Interestingly, a decreasing amount of product was formed with increasing amounts of coupling reagent. This observation, however, can be explained by reactions of reagent molecules with both amino groups, thus transforming both amines into nucleophiles. Thus, a lower concentration of reagent may allow for just one of the amines to form an intermediate carbamate, which rapidly reacts with the other amine to form the expected urea.

Consequently, Structural Star DNA is capable of directing urea formation.

Example 21

DNA Star Structure Electromobility

This example demonstrates Structural DNA's electromobility in native polyacrylamide gels.

Figure 32:
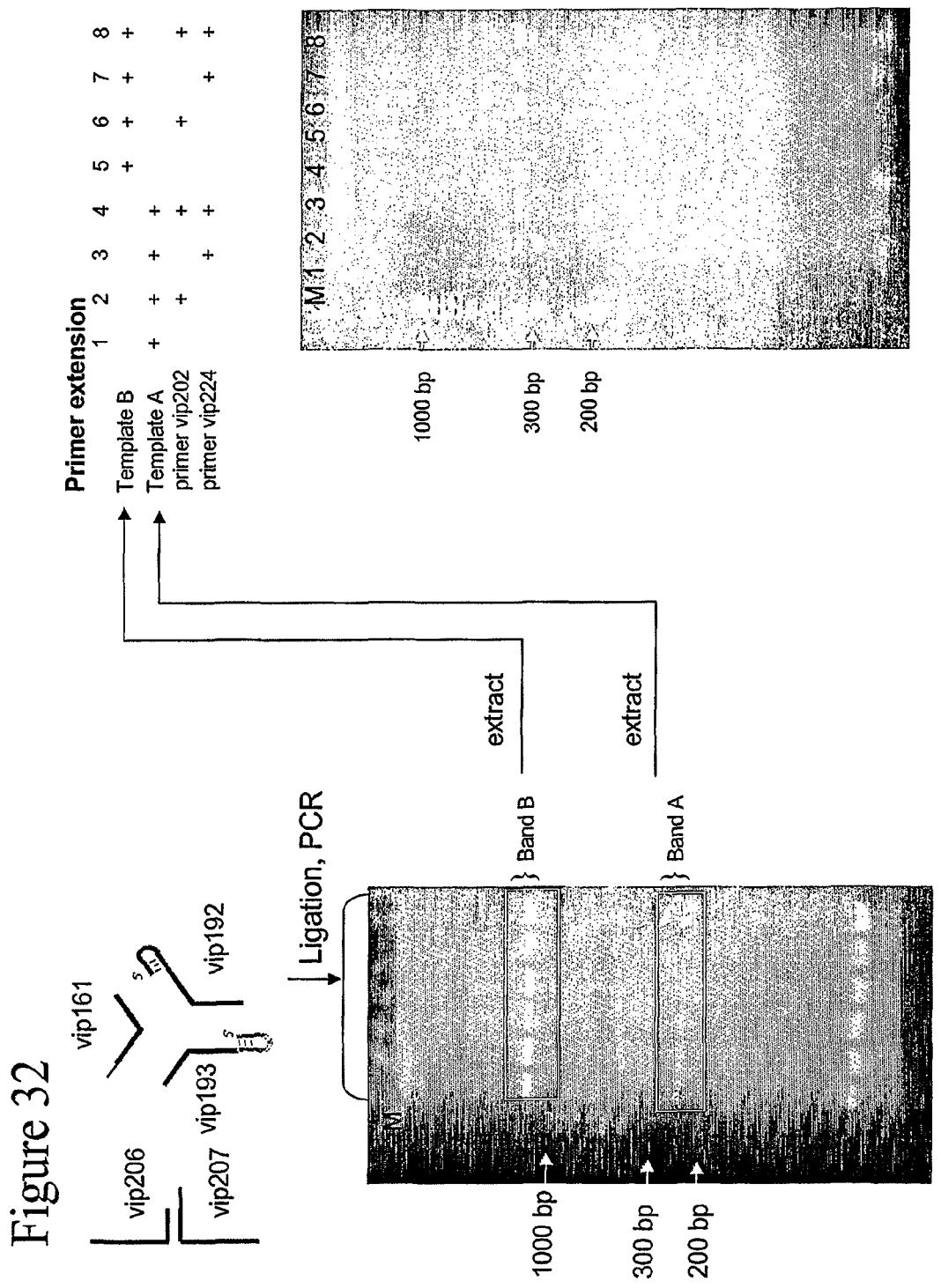
FIG. 32 shows gels of a study on the electromobility of the star structure.

Structural DNA has a distinct different conformation than double stranded DNA. The latter is a linear elongated molecule, whereas Structural DNA has a more globular structure. Consequently, different migration patterns of the two conformations are expected in gels: Structural DNA has an apparent size far exceeding that of the double stranded linear DNA counterpart. To demonstrate this phenomenon the following experiment was performed:

A trimeric DNA Star Structure with terminal PCR priming sites was formed by ligation of five oligoes vip029, vip 161, vip 192, vip 193 and vip207. A schematic drawing of the organization is shown in FIG. 32.

DNA oligoes (prepared by DNA Technology Århus, Denmark) were mixed in 2 µM concentrations each in 1× Ligase Buffer (New England Biolabs), 50 mM NaCl. The mixtures were incubated as follows: 94 µC for 5 minutes, 80 µC for 30 seconds, 65 µC for 30 seconds, 50 µC for 30 seconds, 35 µC for 30 seconds, 20 µC for 30 seconds, 10° C. until next step. The annealing procedure was performed on an Applied Biosystems AB2720 PCR machine. The 5' termini of the oligonucleotides were phosphorylated by T4 DNA polynucleotide kinase. A mixture consisting of 1.5 µM star structure, 1×DNA ligase Buffer (New England Biolabs), 50 mM NaCl and 0.17 u/µl T4 DNA polynucleotide kinase (New England Biolabs, cat# M0201), was prepared and incubated for 30 minutes at 37° C. A phosphodiester bond between juxtaposed ends of annealed oligonucleotides was formed by T4 DNA ligase (New England Biolabs, cat# M0202), in 1×DNA ligase Buffer (New England Biolabs), 50 mM NaCl, and 200 U T4 DNA ligase (New England Biolabs, cat# M0202) in a volume of 10 p. 1 and incubated overnight at 16° C.

PCR Amplification:

0.04 µl of the ligation reaction was used as template in 4000 PCR reaction mix [1× ThermoPol buffer (New England Biolabs B9004S), 0.2 mM dNTPs (New England Biolabs O447S), 8 mM MgSO4, 0.2 µM vip202 and vip224 µM, 0.5 M Betaine (Sigma B0300), 1 U/100 µl of Vent (exo-) (New England Biolabs M0257L). PCR amplification was performed in 50 µl aliquots using the following cycling conditions: 30 seconds at 92° C., and 25 cycles of 92° C./15 sec, 50° C./15 sec, 70° C./30 sec.

The sample was ethanol precipitated by adding 1 ml ethanol and ⅒th 3 M sodium acetate (pH 5.2), incubated 30 minutes on ice and centrifuged 30 minutes at 20 000×g, the supernatant was discarded and the pellet was resuspended in 1× loading buffer (Invitrogen) and subjected to a preparative native 10% PAGE (Invitrogen), and stained with SYBR Green (Molecular Probes, S7563) following manufactures instruction. A picture of the gel is shown in FIG. 32. Lane M contains the 100 bp DNA ladder (Fermentas, SM0248). Two bands were isolated: the band around 250 bp (A) and the band with an apparent size in excess of 1000 bp. The gel pieces boxed in FIG. 32 were cut out and the product extracted by the "crush and soak" method (Sambrook, J., Fritsch, E F, and Maniatis, T. (1989) in: Molecular Cloning: A Laboratory Manual, Cold Springs Harbor Laboratory); the gel piece was crushed and soaked overnight in 400 µl TE Buffer. The tubes were spun for 10 minutes at 20 000×g and the supernatant transferred to a fresh tube and ethanol precipitated as described above and resuspended in 100 µl water.

Primer Extesion

Primer extensions using the isolated DNA as templates was then performed. 2 µl template was used in a 20 µl reaction containing [1× ThermoPol buffer (New England Biolabs B9004S), 0.2 mM dNTPs (New England Biolabs O447S), 8 mM MgSO4, 0.5 M Betaine (Sigma B0300), 1 U/100 µl of Vent (exo-) (New England Biolabs M0257L)]. To reactions 1 and 5 no primer was included, in reactions 2 and 6 0.2 µM vip202 were included, in reaction 3 and 7 0.2 µM vip224 were included and in reactions 4 and 8 0.2 µM vip202 and 224 were included. The primer extensions were performed by incubating the samples at 95□C for one minute, at 50□C for 15 seconds and at 70□C for 30 seconds. 10 µl of the reactions were analyzed by 10% PAGE as described above.

Discussion and Conclusion

First, PCR was performed using a trimeric DNA Star Structure with terminal PCR priming sites as template. Secondly, the sample was subjected to preparative PAGE where two bands were isolated: a band (A) with an apparent size of around 250 bp (the expected size of the double stranded PCR product is 241 bp) and a band (B) with an apparent size in excess of 1000 bp. Finally, the isolated DNA was used as templates in primer extension reactions and analyzed by PAGE. As shown in FIG. 32, both templates give rise to a double stranded product with a size of around 250 bp, with both the forward (lanes 2 and 6) and the backward primer (lanes 3 and 7). Furthermore, when both primers are present more product is formed (lanes 4 and 8). This is illustrating that both band A and B contain the intended 241 bp product and the difference in mobility in the gel are consequently due to folding: A is presumably the double stranded linear product, whereas the B is Star Structure folded DNA.

Interestingly, without any primers present in the primer extension reaction only a limited double stranded band around 250 bp is observed not even when the starting was double stranded DNA as shown in lane 1. This is properly due to the thermal de-naturation and renaturation cycle the sample has undergone, which will lead to the formation of a mixed product of double stranded DNA and Star Structure folded DNA. The same phenomenon is observed in lane 5 where the starting material is band B.

Consequently, it is hereby demonstrated that the 241 nucleotide long DNA molecule can fold into a conformation (Star Structure), which leads to a apparent size in a native gel in the excess of 1000 bp.

Example 22

Translation of DNA Star Structures

This example demonstrates the principle of the translation process of DNA Star Structures. In this context the translation process is the process where the individual modules on various positions are substituted by fresh modules and the substitution process is directed by codon/anticodon recognition. The fresh modules may have a chemical reactant attached in such a way that it will be located in the centre or in the vicinity of the centre upon proper folding of the new DNA Star Structure which the fresh modules will be a part of. Consequently, translation allows the chemical compound encoded by the DNA Star Structure to be synthesized.

The starting material for the translation process may be a PCR product using the output from a selection process as a template for example as shown in Example 18. This will allow iterative cycles of selection and amplification, which in turn will allow a diverse library to convert towards solutions for the applied selection pressure.

Outline of the Translation Process

A schematic drawing of the major steps of a translation process using a PCR product as starting material are shown in FIG. 33.

First, a DNA Star Structure was amplified by PCR using a biotinylated backward primer, which allowed the separation of the two strands. The separation was performed by using magnetic streptavidin beads. The strand of interest (upper strand) was eluted from the beads and folded into the DNA Star Structure having two stem-loops and stem. Then, the position 1 stem (without a loop) was digested by the restriction enzyme Bsa I, which digest outside its recognition sequence and formed a 5' overhang. This overhang was the codon for position 1.

Then a fresh carrier module for position 1 having a suitable 5' anticodon sequence was ligated to the Star Structure. To aid the ligation and downstream purification a biotinylated helper oligo was included. The helper oligo hybridize to the fresh position 1 carrier module in such a way that it created a 5' overhang, which was the anticodon. Consequently, the subsequent ligation (helper oligo/Star Structure/module 1 was guided by the codon/anticodon hybridization.

Then, the original module on position 1 was liberated from the Star Structure by first performing a denaturation step where the fresh carrier module was replacing the original position 1 module in the Star Structure and then a restriction enzyme digest was performed in the sequence which was originally located in the distal loop in the second stem. By this exercise the covalent bond between the original position 1 module as well as the base pairing to the Star Structure were removed. The restriction enzyme digest was performed on Star Structure captured on streptavidin coated magnetic beads. Consequently, Star Structures liberated from the beads were successfully translated for postion 1.

Note that upon folding to the Star Structure, the 3' end of the fresh position 1 module was participating in forming the second stem and the stem ends immediately before the codon on position 2. Consequently the 3' end of the fresh module 1 was lined up for accepting a fresh carrier module for position 2 directed by codon/anticodon interactions for position 2. Consequently, the Structure was ready for the second codon/anticodon directed module substitution. Consequently, by repeating the described substitution process for all positions in the Star Structure a complete translation is accomplished.

Star Structure Formation

Figure 34:
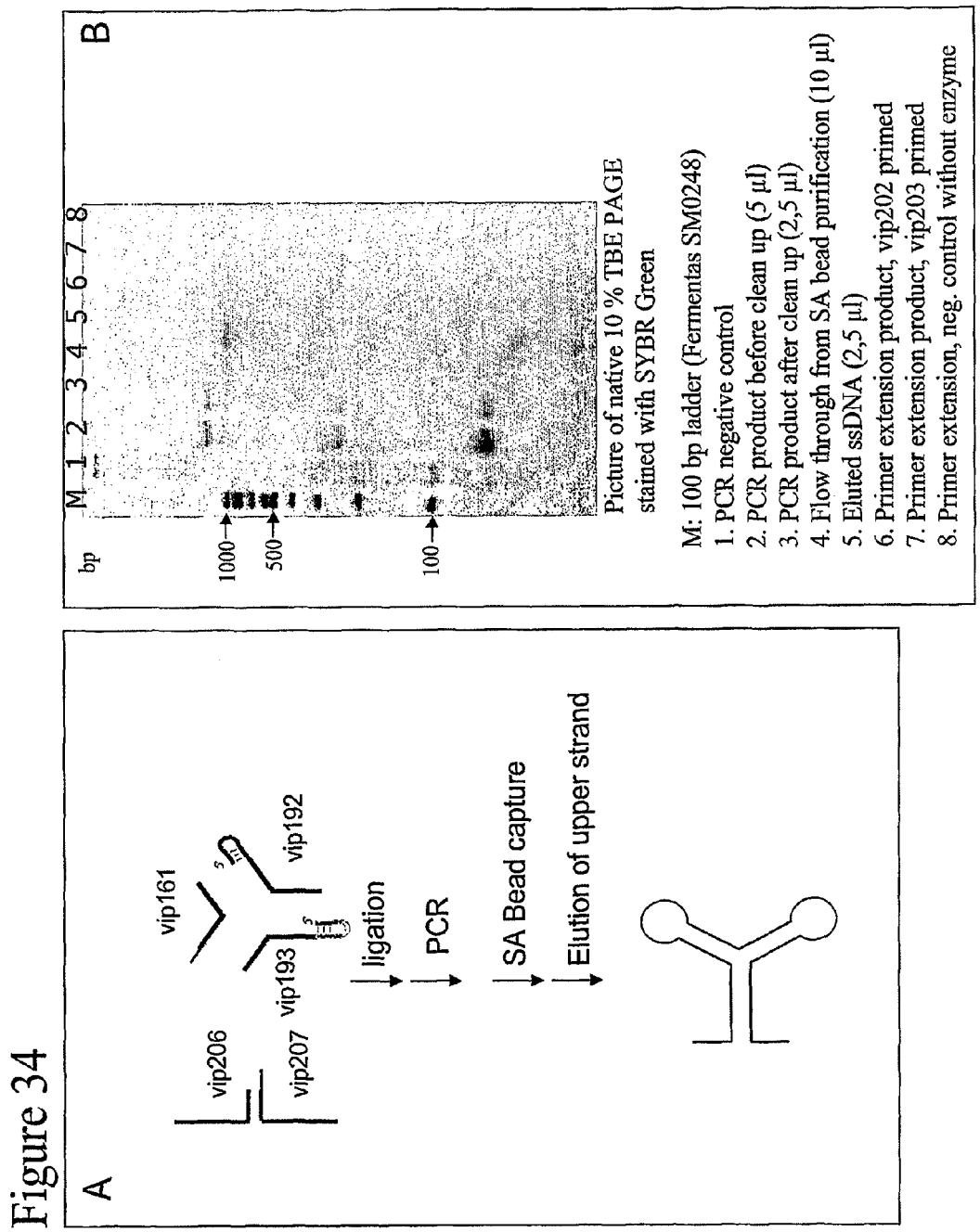
FIG. 34 shows the result of the experiments reported in example 22.

The first step involved annealing of five oligoes: vip206, vip161, vip192 and vip193 vip207. A schematic drawing of the organization is shown in FIG. 34A. The five oligoes in the reaction will hybridize to each other, thus forming a three-way junction, consisting of two stem-loops and one stem with both 5' and 3' un-hybridized sequences at the end distal to the centre of the three-way junction. The un-hybridized sequences represent PCR priming sequences (5' segment of vip206 and 3' segment of vip207). The oligoes were mixed in 1× Ligase buffer (NEB B0202S), 50 mM NaCl, with 20 pmol of each oligonucleotide in a volume of 10 μl. The annealing was performed by incubation in a PCR machine for 5 minutes at 95° C. and for 30 seconds steps at the following temperatures: 80° C., 65° C., 50° C., 45° C., 30° C., 20° C.

Then, the 5' ends were phosphorylated by Polynucleotide Kinase; 2.5 units Polynucleotide Kinase (NEB M0201) were included in a 15 μl reaction volume, in 1× Ligase Buffer, 50 mM NaCl. The reaction was incubated for 30 minutes at 37° C.

The annealed oligoes were transformed into a continuous DNA strand by a DNA ligase, which formed phosphordiesther bonds between the juxtaposed 3' end of vip206 and the 5' end of vip161, and between the juxtaposed 3' end of vip161 and the 5' end of vip192, and between the juxtaposed 3' end of vip192 and the 5' end of vip 193, and between the 3' end of vip 193 and the 5' end of vip207, respectively. T4 DNA ligase (NEB M0202L) was added in 1× Ligase Buffer, 50 mM NaCl, and 20 units/μl enzyme were added, giving a final reaction volume of 20 μl. The ligation was incubated overnight at 16° C. The DNA Star Structure was PCR amplified in a total reaction volume of 400 μl, in 1× Thermopol Buffer (NEB M0257L), 8 mM MgCl$_2$, 0.2 mM dNTPs, 0.5 M Betaine (Sigma B0300), 1 μg/ml BSA (NEB B9001S), 0.1 μM primers (vip202 and vip224) and 32 units Vent(exo-) (NEB M257L). Vip224 had a biotin moiety at the 5' end, enabling capture of the PCR product on streptavidin coated magnetic beads. Amplification was performed with an initial denaturation step for 30 seconds at 92° C., followed by 25 cycles with incubations at 92° C. for 30 seconds, at 60° C. for 15 seconds and at 70° C. for 30 seconds. A final extension at 70° C. for 1 minute was done.

After the PCR amplification, the PCR products were cleaned up using the Eppendorf kit (0032 007.740) according to the instructions. Two columns were used. Elution was done with 150 μl TE for each column. Then, the cleaned up PCR product was added to Streptavidin coated magnetic beads (Dynal MyOne, 605.02). 100 μl beads were washed two times in 2×BWT Buffer (10 mM Tris-HCl, pH 8.0, 1 mM EDTA, 2 M NaCl, 0.1% Triton X-100). The beads were suspended in 300 μl 2×BWT, and 300 μl cleaned up PCR product was added to the beads. The beads were incubated for 15 minutes at RT, shaking slowly. The beads were captured on a magnet, and the supernatant was removed. The beads were washed 3 times with 1×BWT (half strength of 2×BWT). The DNA was eluted from the complementary biotinylated DNA strand captured on the magnetic beads by adding 50 μl 10 mM NaOH, and incubated for 5 minutes at room temperature. The beads were captured on the magnet, the supernatant containing the upper DNA strand was removed and immediately neutralized with 20 μl 1 M Tris-HCl, pH 7.2.

The purity of the eluted DNA was tested by primer extension reactions with the forward and reverse primers in separate reaction. The primer extension reactions was performed using Vent(exo-) (NEB), in reactions of 10 μl, in 1× Thermopol Buffer, 8 mM MgCl$_2$, 0.2 mM dNTPs, 1 M Betaine and 0.2 units Vent(exo-) and 0.2 μl template and 0.4 μM vip202 or 0.4 μM vip203 per reaction. The primer extension reaction was as follows: 95° C. for 2 minutes, 60° C. for 30 seconds, and 74° C. for 5 minutes.

An outline of the procedure is shown in FIG. 34A. Through out the procedure samples were removed for analysis by PAGE. A picture of the gel is shown in FIG. 34B. The gel also contains the quality control primer extension reactions. In lane 2 is observed a band of the expected size of 241 bp, which is not present in the negative control without added template (lane 1). Consequently, the DNA Star Structure has been successfully assembled and amplified. Furthermore, two bands with an apparent size in the excess of 1000 bp are observed in lane 2, which represents folded DNA Star Structure (for reference see Example 21). Lane 3 shows the product after PCR clean up.

The product was captured via the biotin moiety on the lower strand of the PCR product. The flow through is shown in lane 4. The lower of the two bands with an apparent size in the excess of 1000 bp was found here, which consequently did neither contain biotin nor was hybridized to the biotinylated strand. After washing of the beads, the unbiotinylated strand was eluted by high pH which abolished base pairing. The elution product is shown in lane 5. A single band equivalent to the lower of the two bands with an apparent size in the excess of 1000 bp was observed indication successful isolation of the un-biotinylated upper strand of the PCR product. Interestingly, the upper band of the two bands with an apparent size in the excess of 1000 bp was only observed when both strands of the PCR were present (Lanes 1 and 2). Consequently, the upper band most likely represents two hybridized DNA Star Structure molecules—hybridized via the terminal PCR priming sites.

As a quality control of the purified DNA two primer extensions were performed. In one reaction the forward primer (vip202) was used and in the second reaction the backward primer (vip203) was used, which prime on the lower and upper PCR strands, respectively. Consequently, if the isolated DNA is pure only the second reaction should give rise to a primer extension product. Accordingly, only a band corresponding to the expected size of 241 bp was observed in lane 7 whereas no primer extension product was observed in lane 6. Consequently, the successful purification of the desired strand of the PCR product in a highly pure preparation was achieved.

Exposure of the Codon on Position I

The DNA Star Structure contained two stem-loops and one stem. The stem without a loop contained the codon for position 1. The codon was exposed by restriction enzyme digest by Bsa I, which cut outside its recognition sequences and formed a 4 nucleotide 5' overhang, which sequence can be chosen without restrictions, thus ideal for encoding purposes. In this context the overhang is called the codon for position 1.

The Star Structure DNA was subjected to digest with Bsa I. The double stranded substrate for Bsa I was found in the first stem (the stem without a loop) generated by hybridization of the 5' segment of vip 161 and the 3' segments of vip 193. Note that the product obtained after the BsaI digest corresponds to the sequence of vip 161-vip 192-vip193 described at the start of this example.

110 μl purified Star Structure DNA were mixed with 20 μl 10×NEB3 buffer and 200 units of Bsa I (NEB R0535L) in a total volume of 200 μl. The digest was incubated at 50° C. for 2.5 hours. The DNA was subjected to a standard ethanol precipitation, before it was applied to a 10% TBE-urea gel (Invitrogen) for gel purification.

Figure 35:
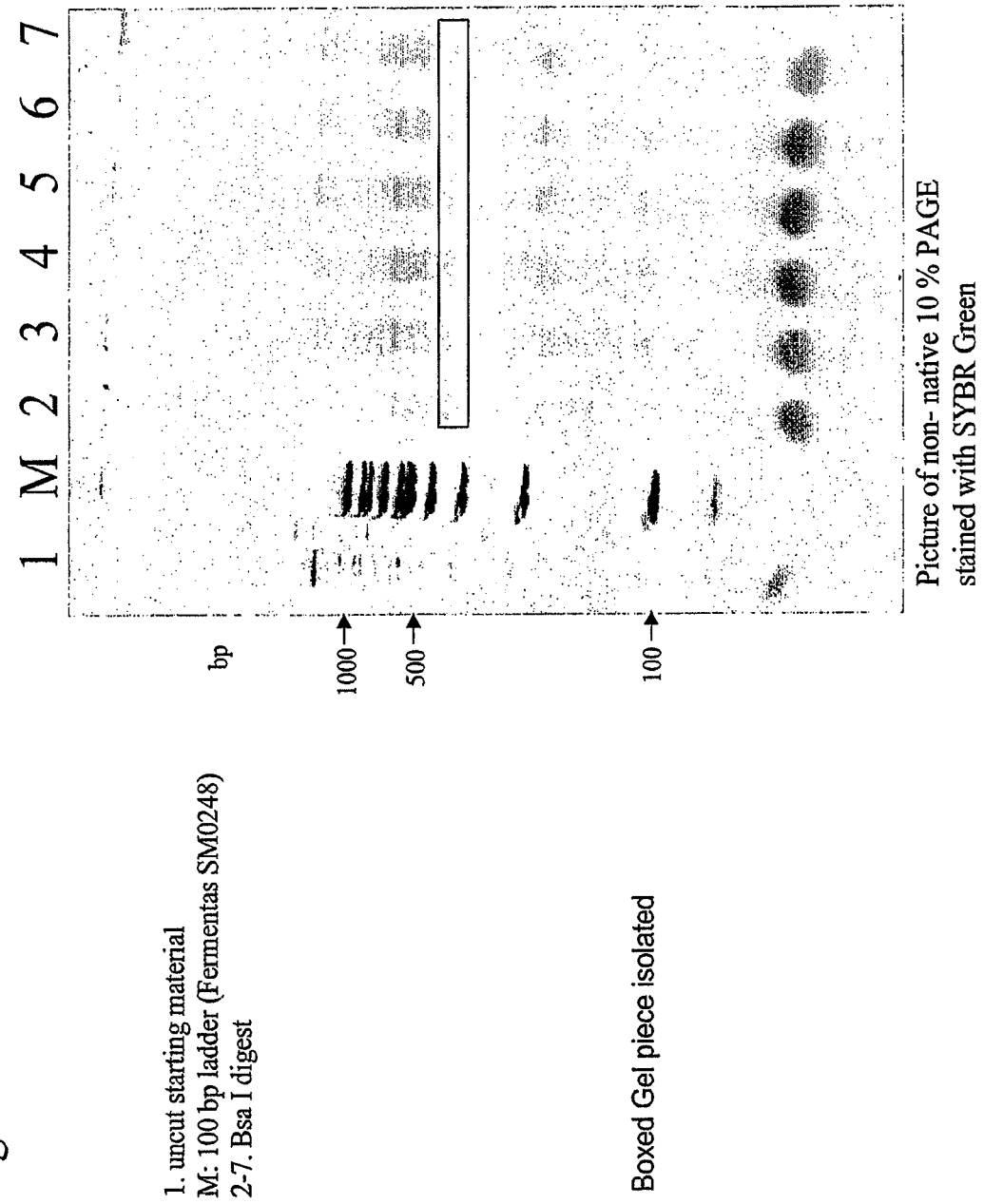
FIG. 35 shows the result of the experiments reported in example 22.

In FIG. 35 is shown a picture of the gel after SYBR green staining. Uncut DNA was loaded in lane 1 as a reference. A prominent band migrating with an apparent size in the excess of 1000 bp is observed (Note the "spil over" from the marker loaded in lane M). Multible bands were observed in lanes 2-7 where the Bsa I digest was loaded, thus indicating that the BsaI digest was not complete. However, the band of interest was excised from the gel (boxed on the figure), and the DNA was extracted from the gel piece by the "crush and soak" method, ethanol precipitated and redissolved in 40 μl H$_2$O as described previously.

Ligation of Fresh Position 1 Module Directed by Codon/Anticodon Interaction.

Fresh position 1 module, vip271, was ligated onto the Bsa I digested and purified DNA Star Structure. Vip066 was included in the ligation reaction as a ligation aid, and to introduce a biotin molecule into the ligation product, thus facilitation downstream purification. Annealing of vip271 and vip066 will generate a product with a 4 nucleotide 5' overhang (vip271) which in this context is called the anticodon. The sequence was therefore chosen in such a way that it was reverse complement to the codon on position 1 in the DNA Star Structure. Consequently codon/anticodon hybridization is capable of guiding the ligation of the two incoming oligoes with the DNA Star Structure. Vip271 and vip066 were mixed in 1× Ligase buffer (NEB B0202S), 50 mM NaCl, with 50 pmoles of each oligonucleotide in a volume of 10 µl. The annealing was performed on a PCR machine using the annealing program described above.

Then, the annealed vip271/vip066 were mixed with the Bsa I digested and purified DNA Star Structure (30 µl), and the 5' ends were phosphorylated by Polynucleotide Kinase; 12.5 units Polynucleotide Kinase (NEB M0201) were included in a 50 µl reaction volume in 1× Ligase Buffer, 50 mM NaCl. The reaction was incubated for 30 minutes at 37° C.

Then, the cognate ends of the molecules were joined by a DNA ligase, which formed a phosphordiesther bond between the juxtaposed 3' end of vip066 and 5' end of the Bsa digested DNA, and between the juxtaposed 3' end of the BsaI digested DNA 5' end of vip271. T4 DNA ligase (NEB M0202L) was added in 1× Ligase Buffer, 50 mM NaCl, and 20 units/µl enzyme were added, giving a final reaction volume of 60 µl. The ligation was incubated overnight at 16° C.

Substitution

The next step was to eliminate the original position 1 module from the Star Structure. The molecule was re-folded allowing the fresh position 1 module to be part of the three-way junction and a covalent bond between the original position 1 and the DNA Star Structure was eliminated. Furthermore, a helper oligo (vip194) was introduced, which did anneal to the Pvu. II site in the original loop in the distal end of the $2^{nd}$ stem (see FIG. 36) thus forming a double stranded substrate for Pvu II. Consequently, both the covalent bond and the base pairing were destroyed between the original position 1 module and the Star Structure. Furthermore the fresh position 1 module was introduced as a part of the three-way junction.

43 µl of the ligation reaction was mixed with 200 moles of vip194 in 10 mM Tris-HCl pH 8, 1 mM EDTA, 100 mM NaCl, 0.1% Triton X-100 in a total volume of 60 µl. The denaturation and annealing was performed in the PCR machine for 5 minutes at 95° C. and for 30 seconds steps at the following temperatures: 80° C., 65° C., 50° C., 45° C., 30° C., 20° C.

The DNA was then captured on Streptavidin-coated magnetic beads (Dynal). 30 µl beads were washed 2× in 2×BWT (2 M NaCl, 10 mM Tris-HCl, pH 8, 1 mM EDTA, 0.1% Triton X-100). After the final wash, the beads were suspended in 60 µl 2×BWT, and 60 vip194/Star Structure annealing reaction was added. Incubation was done for 15 minutes at room temperature with gentle shaking. The beads now with the DNA attached to them, were captured on a magnet and subsequently suspended in Pvu II digest Buffer: 22 µl $H_2O$ and 3 µl 10× Pvu II digest Buffer was added to the beads, and 5 µl Pvu II (10 units/µl; Fermentas ER0637) were added. The digest was incubated for 6 h at 37° C. After the digest, the beads were separated from the supernatant on the magnet.

Throughout the procedure aliquots was saved for analysis by 10% TBE-urea gel (Invitrogen) stained with SYBR green (Molecular Probes) according to the manufactures protocol. A picture of the gel is shown in FIG. 36.

The purified Bsa I digested Star Structure was loaded in lane 1; a prominent band of the expected apparent size of around 600 nt was observed. The ligation product of the Bsa I digested Star Structure with fresh module for position 1/helper oligo (vip066) was loaded in lane 2. A prominent band with an apparent size in the excess of 1000 nt was observed, thus indicating a successful ligation. The beads after the Pvu II digest were loaded in lane 4. A band with an apparent size in the excess of 1000 nt was observed. This band corresponds to undigested DNA which is seen by comparison to lane 2. However, in the supernatant from the Pvu II digest (lane 5) a band with an apparent size of around 600 nt was observed. This band corresponds to the expected apparent size of around 600 nt of a successful substitution product. The fact that it was found in the supernatant show that the fresh module on position 1 has substituted the original module on position 1 in the star structure.

Consequently, successful translation, i.e. codon/anticodon directed module substitution has been demonstrated.

List of oligonuclotides oligonucleotides used in the examples

| Name | SEQ ID NO: | Sequence | Modification |
| --- | --- | --- | --- |
| vip006 | SEQ ID NO: 14 | CTCGTTTTCGAGACCGACTCTGGAAGTGTCACCGGATCTGG | 5'P |
| vip007 | SEQ ID NO: 15 | TTGGAAAAACCAACCAGATCCGGTGACTGTCAAGGCTGAGGT | 5'P |
| vip008 | SEQ ID NO: 16 | GAGGGAGAGCCTCACCTCAGCCTTGACTCTTCCAGAGTCGGT | 5'P |
| vip009 | SEQ ID NO: 17 | GAGGGAGAGCCTCACCTCAGCCTTGACTGGAGAACGCATTCT | 5'P |
| vip010 | SEQ ID NO: 18 | ACACAAGAAGTGTAGAATGCGTTCTCCTCTTCCAGAGTCGGT | 5'P |
| vip016 | SEQ ID NO: 19 | CTCGTTTTCGAGACCGACTCTGGAAGXGTCACCGGATCTGG | X = amine-C6-dT |
| vip017 | SEQ ID NO: 20 | TTGGAAAAACCAACCAGATCCGGTGACXGTCAAGGCTGAGGT | X = amine-C6-dT |
| vip018 | SEQ ID NO: 21 | GAGGGAGAGCCTCACCTCAGCCTTGACXCTTCCAGAGTCGGT | X = amine-C6-dT |
| vip019 | SEQ ID NO: 22 | GAGGGAGAGCCTCACCTCAGCCTTGACXGGAGAACGCATTCT | X = amine-C6-dT |
| vip020 | SEQ ID NO: 23 | ACACAAGAAGTGTAGAATGCGTTCTCCXCTTCCAGAGTCGGT | X = amine-C6-dT |

-continued

| Name | SEQ ID NO: | Sequence | Modification |
|---|---|---|---|
| vip027 | SEQ ID NO: 24 | ACTATGAGGGCTGTCTGTGG | None |
| vip028 | SEQ ID NO: 25 | TAGCAAGCCCAATAGGAACC | None |
| vip029 | SEQ ID NO: 26 | ACTATGAGGGCTGTCTGTGGCAGTCACGAG | None |
| vip030 | SEQ ID NO: 27 | AAAACTCGTGACTGGGTTCCTATTGGGCTTGCTA | 5'P |
| vip031 | SEQ ID NO: 28 | TTTTCGAGACCGACTCTGGAAGTGTCACCGGATCTGG | 5'P |
| vip034 | SEQ ID NO: 29 | ACTATGAGGGCTGTCTGTGG | 5' biotin |
| vip038 | SEQ ID NO: 30 | TAGCAAGCCCAATAGGAACC | 5' biotin |
| vip046 | SEQ ID NO: 31 | ACTCTGGAAGXGTCACCGGAT | X = amine-C6-dT |
| vip048 | SEQ ID NO: 32 | GAGGGAGAGCCTCACCTCAGCCTTGACACACACXCTTCCAGAGTCGGT | 5'P, X = amine-C6-dT |
| vip056 | SEQ ID NO: 33 | CTCGTTTTCGAGACCGACTCTGGAAGAGTGTGTTGTCACCGGATCTGG | |
| vip068 | SEQ ID NO: 34 | CAGCCTTGACXCTTCCAGAGT | X = amine-C6-dT |
| vip070 | SEQ ID NO: 35 | CTCTCTCGTGACTGGGTTCCTATTGGGCTTGCTA | |
| vip076 | SEQ ID NO: 36 | ACTCTGGAAGXGTCACCGGATCTGG | X = amine-C6-dT |
| vip078 | SEQ ID NO: 37 | GAGGGAGAGCCTCACCTCAGCCTTGACTCTTCCAGAGTGGTTCCTATTGGGCTTGCTA | |
| vip132 | SEQ ID NO: 38 | TTGGAAAAACCAACCAGATCCGGTGACTGTGTGTGTCAAGGCTGAGGT | |
| vip133 | SEQ ID NO: 39 | GAGGGAGAGCCTCACCTCAGCCTTGACACACACTCTTCCAGAGTCGGTCTCG | |
| vip161 | SEQ ID NO: 40 | AGAGCGAGACCGACTCTGGAAGTGTCACCGGATCT | |
| vip162 | SEQ ID NO: 41 | GGTTGGCAGGGCCCACTAGCTCAGGATCCACCCAACCAGATCCGGTGACTGTGTGTGTCAAGGCTGAG | |
| vip163 | SEQ ID NO: 42 | GTGAGGCTGAATTCTCTGTACCTGGTACCTCCCTCACCTCAGCCTTGACACACACTCTTCCAGAGTCGGTCTCG | |
| vip164 | SEQ ID NO: 43 | GTGGGCCCTG | |
| vip165 | SEQ ID NO: 44 | GTGGATCCTG | |
| vip192 | SEQ ID NO: 45 | GGTTGGCACAGCTGACTAGCTCAGAGCTCACCCAACCAGATCCGGTGACTGTGTGTGTCAAGGCTGAG | |
| vip193 | SEQ ID NO: 46 | GTGAGGCTCCCGGGTCTGTACCTATTAATTCCCTCACCTCAGCCTTGACACACACTCTTCCAGAGTCGGTCTCG | |
| vip194 | SEQ ID NO: 47 | GTCAGCTGTG | |
| vip195 | SEQ ID NO: 48 | GTGAGCTCTG | |
| vip066 | SEQ ID NO: 49 | XCTTCCAGAGTCGGTCTCG | X = 5' bio |
| vip088 | SEQ ID NO: 97 | XCAGCCTTGACTCTTCCAGAGT | X = 5' bio |
| vip202 | SEQ ID NO: 98 | CAGGTCGCTGAGAGGTTGAC | |
| vip203 | SEQ ID NO: 99 | ACGTCCGAGTCAGAAGTGTG | |
| vip206 | SEQ ID NO: 100 | CAGGTCGCTGAGAGGTTGACCAGTCACGAG | |
| vip207 | SEQ ID NO: 101 | CTCTcTCGTGACTGCACACTTCTGACTCGGACGT | |
| vip224 | SEQ ID NO: 102 | XACGTCCGAGTCAGAAGTGTG | X = 5' bio |
| vip231 | SEQ ID NO; 103 | AGAGCGAGACCGACTCTGGAAGXGTCACCGGATCT | X = NH2-C6-dT |
| vip238 | SEQ ID NO: 104 | TTTTCGAGACCGACTCTGGAAGXGTCACCGGATCT | X = NH2-C6-dT |

| Name | SEQ ID NO: | Sequence | Modification |
|---|---|---|---|
| vip262 | SEQ ID NO: 105 | GGTTGGCACAGCTGACTAGCTCAGAGCTCACCCAACCAGAT CCGGTGACTGTGTGXGTCAAGGCTGAG | X = NH2-C6-dT |
| vip263 | SEQ ID NO: 106 | GTGAGGCTCCCGGGTCTGTACCTATTAATTCCCTCACCTCAG CCTTGACACACACXCTTCCAGAGTCGGTCTCG | X = NH2-C6-dT |
| vip269 | SEQ ID NO: 107 | GGTTGGCACAGCTGACAAAAACAGAGCTCACCCAACCAGAT CCGGTGACTGTGTGXGTCAAGGCTGAG | X = NH2-C6-dT |
| vip270 | SEQ ID NO: 108 | GTGAGGCTCCCGGGTCGAGAGCTATTAATTCCCTCACCTCAGC CTTGACACACACXCTTCCAGAGTCGGTCTCG | X = NH2-C6-dT |
| vip271 | SEQ ID NO: 109 | CTCTCGAGACCGACTCTGGAAGXGTCACCGGATCTGGTTGGGT- GAGCTCTG | X = NH2-C6-dT |

The invention claimed is:

1. A method for creating one or more chemical compounds comprising the steps of:
   - (i) providing N (N=3-100) carrier modules comprising:
     - (1) a first position carrier module having
       - a) a nucleic acid segment capable of hybridizing to a nucleic acid segment of the N position carrier module, and
       - b) a nucleic acid segment capable of hybridizing to a segment of a second position carrier module,
     - (2) n position carrier module(s) (occupying positions 2 to N−1) having a nucleic acid segment capable of hybridizing to a nucleic acid segment of a n−1 carrier module, and a nucleic acid segment capable of hybridizing to a segment of a n+1 carrier module, and
     - (3) a N position carrier module having a nucleic acid segment capable of hybridizing to a nucleic acid segment of the N−1 carrier module, and a nucleic acid segment capable of hybridizing to a segment of said first carrier module, wherein
   at least three of said carrier modules comprise an associated chemical group (CG) situated in the mid section between the hybridization segments and optionally a codon segment situated external to one of the hybridization segments; wherein said mid section comprises 1 to 20 nucleotides, and each hybridization segment consists of 12 or more nucleotides;
   - (ii) contacting said carrier modules under conditions allowing hybridization of said hybridization segments so as to form a structure resembling a star, wherein said star structure comprises a reaction center and a plurality of stems, and each stem is formed by two hybridizing segments complementing each other, and at least one of the stems extends radially from the reaction center so that the mid section between the two hybridization segments on each carrier module is pointing towards the center,
   thus bringing said chemical groups into reactive proximity; and
   - (iii) providing conditions allowing chemical reaction(s) of the chemical groups resulting in the formation of a chemical compound, where the chemical compound is covalently associated with at least one of said carrier modules.

2. A method according to claim 1 further comprising the step of providing conditions allowing ligation of the termini of module n−1 to module n and module N−1 to module N, thereby forming a continuous nucleic acid molecule with stem-loop structures and a chemical compound associated therewith.

3. The method according to claim 2, wherein said ligations are performed enzymatically or chemically; and sequentially, or simultaneously.

4. The method of claim 1, wherein the chemical compound is covalently associated with at least one of said carrier molecules or a continuous nucleic acid molecule resulting from ligation of said carrier modules.

5. The method according to claim 1, wherein the contacting of the carrier modules is performed sequentially or simultaneously.

6. The method according to claim 1, wherein the chemical reaction(s) are performed sequentially or simultaneously.

7. The method according to claim 1, further comprising a priming site for a DNA polymerase, RNA polymerase or reverse transcriptase site in at least the first carrier module and/or at least in the N carrier module.

8. The method according to claim 1, comprising the further step of performing an enzymatic extension reaction to display the chemical compound.

9. The method according to claim 1, wherein N is 3, 4, 5, 6 or 7 and wherein each of the carrier modules comprise an associated chemical group (CG) situated in the mid section and a codon segment situated external to one of the hybridization segments.

10. The method according to claim 1, wherein a library of more than one compound is synthesized by having a repertoire of carrier modules on one or more positions.

11. The method according to claim 10, wherein the repertoire on at least one position comprises at least 10 different carrier modules.

12. The method according to claim 10, wherein the repertoire on at least two positions comprises at least 10 different carrier modules.

13. The method according to claim 1, wherein the chemical group is associated with a nucleobase of the mid section.

14. The method according to claim 1, wherein the chemical group is associated with a phosphodiester linkage of the mid-section.

15. The method according to claim 1, wherein the chemical group is associated to the midsection through one or more covalent bonds.

16. A method for screening a library of more than one chemical compound prepared as disclosed in claim 8, comprising the steps of:
probing the library for library members having a chemical compound of desired property; partitioning the library members having desired property from library members not having desired property; and
thereby obtaining an enriched pool of library members having desired property.

17. The method according to claim 16, wherein the method further comprises amplifying the nucleic acid of the members of the enriched pool, said nucleic acid being indicative of the history of the chemical reaction(s).

* * * * *

SEQUENCE LISTING

```
<160> NUMBER OF SEQ ID NOS: 109

<210> SEQ ID NO 1
<211> LENGTH: 13
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(9)
<223> OTHER INFORMATION: n is a, c, g, or t

<400> SEQUENCE: 1
ggccnnnnng gcc                                                          13

<210> SEQ ID NO 2
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(12)
<223> OTHER INFORMATION: n is a, c, g, or t

<400> SEQUENCE: 2
gaagacnnnn nn                                                           12

<210> SEQ ID NO 3
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(12)
<223> OTHER INFORMATION: n is a, c, g, or t

<400> SEQUENCE: 3
cttctgnnnn nn                                                           12

<210> SEQ ID NO 4
<211> LENGTH: 10
<212> TYPE: DNA
<213> ORGANISM: Artificial Sequence
<220> FEATURE:
```

```
<223> OTHER INFORMATION: Synthetic sequence
<220> FEATURE:
<221> NAME/KEY: misc_feature
<222> LOCATION: (8)..(10)
<223> OTHER INFORMATION: n is a, c, g, or t

<400> SEQUENCE: 4 cctcagcnnn                                                                  10

<210> SEQ ID NO 5
<211> LENGTH: 10
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(10)
<223> OTHER INFORMATION: n is a, c, g, or t

<400> SEQUENCE: 5 ggagtcgnnn                                                                  10

<210> SEQ ID NO 6
<211> LENGTH: 18
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(13)
<223> OTHER INFORMATION: n is a, c, g, or t

<400> SEQUENCE: 6
ggagtcgnnn nnncgact                                                         18

<210> SEQ ID NO 7
<211> LENGTH: 15
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(15)
<223> OTHER INFORMATION: n is a, c, g, or t

<400> SEQUENCE: 7
cctcagcnnn nnnnn                                                            15

<210> SEQ ID NO 8
<211> LENGTH: 15
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(15)
<223> OTHER INFORMATION: n is a, c, g, or t

<400> SEQUENCE: 8
ggagtcgnnn nnnnn                                                            15

<210> SEQ ID NO 9
<211> LENGTH: 13
<212> TYPE: DNA
<213> ORGANISM: Artificial Sequence
```

```
<220> FEATURE:
<223> OTHER INFORMATION: Synthetic sequence
<220> FEATURE:
<221> NAME/KEY: misc_feature
<222> LOCATION: (6)..(13)
<223> OTHER INFORMATION: n is a, c, g, or t

<400> SEQUENCE: 9
tcagcnnnnn nnn                                                          13

<210> SEQ ID NO 10
<211> LENGTH: 21
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(15)
<223> OTHER INFORMATION: n is a, c, g, or t

<400> SEQUENCE: 10
cctcagcnnn nnnnngaatt c                                                 21

<210> SEQ ID NO 11
<211> LENGTH: 21
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(15)
<223> OTHER INFORMATION: n is a, c, g, or t

<400> SEQUENCE: 11
ggagtcgnnn nnnnncttaa g                                                 21

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(15)
<223> OTHER INFORMATION: n is a, c, g, or t

<400> SEQUENCE: 12
ggagtcgnnn nnnnncttaa                                                   20

<210> SEQ ID NO 13
<211> LENGTH: 14
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(13)
<223> OTHER INFORMATION: n is a, c, g, or t

<400> SEQUENCE: 13
tcagcnnnnn nnng                                                         14

<210> SEQ ID NO 14
<211> LENGTH: 41
<212> TYPE: DNA
```

<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P

<400> SEQUENCE: 14
ctcgttttcg agaccgactc tggaagtgtc accggatctg g                41

<210> SEQ ID NO 15
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P

<400> SEQUENCE: 15
ttggaaaaac caaccagatc cggtgactgt caaggctgag gt               42

<210> SEQ ID NO 16
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P

<400> SEQUENCE: 16
gagggagagc ctcacctcag ccttgactct tccagagtcg gt               42

<210> SEQ ID NO 17
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P

<400> SEQUENCE: 17
gagggagagc ctcacctcag ccttgactgg agaacgcatt ct               42

<210> SEQ ID NO 18
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P

<400> SEQUENCE: 18
acacaagaag tgtagaatgc gttctcctct tccagagtcg gt               42

<210> SEQ ID NO 19
<211> LENGTH: 41
<212> TYPE: DNA
<213> ORGANISM: Artificial Sequence
<220> FEATURE:
<223> OTHER INFORMATION: oligonucleotide primer
<220> FEATURE:

<221> NAME/KEY: misc_feature
<222> LOCATION: (27)..(27)
<223> OTHER INFORMATION: n=amine-C6-dT

<400> SEQUENCE: 19
ctcgttttcg agaccgactc tggaagngtc accggatctg g    41

<210> SEQ ID NO 20
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (28)..(28)
<223> OTHER INFORMATION: n=amine-C6-dT

<400> SEQUENCE: 20
ttggaaaaac caaccagatc cggtgacngt caaggctgag gt    42

<210> SEQ ID NO 21
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (28)..(28)
<223> OTHER INFORMATION: n=amine-C6-dT

<400> SEQUENCE: 21
gagggagagc ctcacctcag ccttgacnct tccagagtcg gt    42

<210> SEQ ID NO 22
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (28)..(28)
<223> OTHER INFORMATION: n=amine-C6-dT

<400> SEQUENCE: 22
gagggagagc ctcacctcag ccttgacngg agaacgcatt ct    42

<210> SEQ ID NO 23
<211> LENGTH: 42
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (28)..(28)
<223> OTHER INFORMATION: n=amine-C6-dT

<400> SEQUENCE: 23
acacaagaag tgtagaatgc gttctccnct tccagagtcg gt    42

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer -continued

<400> SEQUENCE: 24
actatgaggg ctgtctgtgg                                          20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 25
tagcaagccc aataggaacc                                          20

<210> SEQ ID NO 26
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 26
actatgaggg ctgtctgtgg cagtcacgag                               30

<210> SEQ ID NO 27
<211> LENGTH: 34
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5' P

<400> SEQUENCE: 27
aaaactcgtg actgggttcc tattgggctt gcta                          34

<210> SEQ ID NO 28
<211> LENGTH: 37
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P

<400> SEQUENCE: 28
ttttcgagac cgactctgga agtgtcaccg gatctgg                       37

<210> SEQ ID NO 29
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5' biotinylated

<400> SEQUENCE: 29
actatgaggg ctgtctgtgg                                          20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5' biotinylated

<400> SEQUENCE: 30
tagcaagccc aataggaacc                                                    20

<210> SEQ ID NO 31
<211> LENGTH: 21
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (11)..(11)
<223> OTHER INFORMATION: n=amine-C6-dT

<400> SEQUENCE: 31
actctggaag ngtcaccgga t                                                  21

<210> SEQ ID NO 32
<211> LENGTH: 48
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<223> OTHER INFORMATION: 5'P
<220> FEATURE:
<221> NAME/KEY: misc_feature
<222> LOCATION: (34)..(34)
<223> OTHER INFORMATION: n=amine-C6-dT

<400> SEQUENCE: 32
gagggagagc ctcacctcag ccttgacaca cacncttcca gagtcggt                     48

<210> SEQ ID NO 33
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 33
ctcgttttcg agaccgactc tggaagagtg tgttgtcacc ggatctgg                     48

<210> SEQ ID NO 34
<211> LENGTH: 21
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (11)..(11)
<223> OTHER INFORMATION: n=amine-C6-dT

<400> SEQUENCE: 34
cagccttgac ncttccagag t                                                  21

<210> SEQ ID NO 35
<211> LENGTH: 34
<212> TYPE: DNA
<213> ORGANISM: Artificial Sequence
<220> FEATURE:

<223> OTHER INFORMATION: oligonucleotide primer

<400> SEQUENCE: 35
ctctctcgtg actgggttcc tattgggctt gcta                                34

<210> SEQ ID NO 36
<211> LENGTH: 25
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (11)..(11)
<223> OTHER INFORMATION: n=amine-C6-dT

<400> SEQUENCE: 36
actctggaag ngtcaccgga tctgg                                          25

<210> SEQ ID NO 37
<211> LENGTH: 58
<212> TYPE: DNA
<213> ORGANISM: Artificial Sequence
<220> FEATURE:
<223> OTHER INFORMATION: oligonucleotide primer

<400> SEQUENCE: 37
gagggagagc ctcacctcag ccttgactct tccagagtgg ttcctattgg gcttgcta     58

<210> SEQ ID NO 38
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 38
ttggaaaaac caaccagatc cggtgactgt gtgtgtcaag gctgaggt                48

<210> SEQ ID NO 39
<211> LENGTH: 52
<212> TYPE: DNA
<213> ORGANISM: Artificial Sequence
<220> FEATURE:
<223> OTHER INFORMATION: oligonucleotide primer

<400> SEQUENCE: 39
gagggagagc ctcacctcag ccttgacaca cactcttcca gagtcggtct cg           52

<210> SEQ ID NO 40
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 40
agagcgagac cgactctgga agtgtcaccg gatct                              35

<210> SEQ ID NO 41
<211> LENGTH: 68
<212> TYPE: DNA
<213> ORGANISM: Artificial Sequence
<220> FEATURE:
<223> OTHER INFORMATION: oligonucleotide primer

<400> SEQUENCE: 41

```
ggttggcagg gcccactagc tcaggatcca cccaaccaga tccggtgact gtgtgtgtca    60
aggctgag                                                            68

<210> SEQ ID NO 42
<211> LENGTH: 74
<212> TYPE: DNA
<213> ORGANISM: Artificial Sequence
<220> FEATURE:
<223> OTHER INFORMATION: oligonucleotide primer

<400> SEQUENCE: 42
gtgaggctga attctctgta cctggtacct ccctcacctc agccttgaca cacactcttc    60
cagagtcggt ctcg                                                     74

<210> SEQ ID NO 43
<211> LENGTH: 10
<212> TYPE: DNA
<213> ORGANISM: Artificial Sequence
<220> FEATURE:
<223> OTHER INFORMATION: oligonucleotide primer

<400> SEQUENCE: 43
gtgggccctg                                                          10

<210> SEQ ID NO 44
<211> LENGTH: 10
<212> TYPE: DNA
<213> ORGANISM: Artificial Sequence
<220> FEATURE:
<223> OTHER INFORMATION: oligonucleotide primer

<400> SEQUENCE: 44
gtggatcctg                                                          10

<210> SEQ ID NO 45
<211> LENGTH: 68
<212> TYPE: DNA
<213> ORGANISM: Artificial Sequence
<220> FEATURE:
<223> OTHER INFORMATION: oligonucleotide primer

<400> SEQUENCE: 45
ggttggcaca gctgactagc tcagagctca cccaaccaga tccggtgact gtgtgtgtca    60
aggctgag                                                            68

<210> SEQ ID NO 46
<211> LENGTH: 74
<212> TYPE: DNA
<213> ORGANISM: Artificial Sequence
<220> FEATURE:
<223> OTHER INFORMATION: oligonucleotide primer

<400> SEQUENCE: 46
gtgaggctcc cgggtctgta cctattaatt ccctcacctc agccttgaca cacactcttc    60
cagagtcggt ctcg                                                     74

<210> SEQ ID NO 47
<211> LENGTH: 10
<212> TYPE: DNA
<213> ORGANISM: Artificial Sequence
<220> FEATURE:
<223> OTHER INFORMATION: oligonucleotide primer
```

```
<400> SEQUENCE: 47
gtcagctgtg                                                                  10

<210> SEQ ID NO 48
<211> LENGTH: 10
<212> TYPE: DNA
<213> ORGANISM: Artificial Sequence
<220> FEATURE:
<223> OTHER INFORMATION: oligonucleotide primer

<400> SEQUENCE: 48
gtgagctctg                                                                  10

<210> SEQ ID NO 49
<211> LENGTH: 19
<212> TYPE: DNA
<213> ORGANISM: Artificial Sequence
<220> FEATURE:
<223> OTHER INFORMATION: Chemically synthesized optionally derivatised
      oligonuclotides
<220> FEATURE:
<221> NAME/KEY: modified_base
<222> LOCATION: (1)..(1)
<223> OTHER INFORMATION: 5' biotin
<220> FEATURE:
<221> NAME/KEY: misc_feature
<222> LOCATION: (1)..(1)
<223> OTHER INFORMATION: n is a, c, g, or t

<400> SEQUENCE: 49
ncttccagag tcggtctcg                                                        19

<210> SEQ ID NO 50
<211> LENGTH: 28
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(4)
<223> OTHER INFORMATION: n is a, c, g, t or u
<220> FEATURE:
<221> NAME/KEY: misc_feature
<222> LOCATION: (17)..(17)
<223> OTHER INFORMATION: Reactive group R

<400> SEQUENCE: 50
nnnntggtct tcgaagucac cggatctg                                              28

<210> SEQ ID NO 51
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(9)
<223> OTHER INFORMATION: n is a, c, g, t or u
<220> FEATURE:
<221> NAME/KEY: misc_feature
<222> LOCATION: (25)..(25)
<223> OTHER INFORMATION: Reactive group R

<400> SEQUENCE: 51
ggtannnnnt acccagatcc ggtgutccaa ggctga                                     36

<210> SEQ ID NO 52
```

```
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(9)
<223> OTHER INFORMATION: n is a, c, g, t or u
<220> FEATURE:
<221> NAME/KEY: misc_feature
<222> LOCATION: (25)..(25)
<223> OTHER INFORMATION: Reactive group R

<400> SEQUENCE: 52
ggtgnnnnnc acctcagcct tggauggaac ctcagc                                  36

<210> SEQ ID NO 53
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(9)
<223> OTHER INFORMATION: n is a, c, g, t or u
<220> FEATURE:
<221> NAME/KEY: misc_feature
<222> LOCATION: (25)..(25)
<223> OTHER INFORMATION: Reactive group R

<400> SEQUENCE: 53
taggnnnnnc ctagctgagg ttccucttcg aagacca                                 37

<210> SEQ ID NO 54
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: n is a, c, g, t or u
<220> FEATURE:
<221> NAME/KEY: misc_feature
<222> LOCATION: (25)..(25)
<223> OTHER INFORMATION: Reactive group R
<220> FEATURE:
<221> NAME/KEY: misc_feature
<222> LOCATION: (33)..(37)
<223> OTHER INFORMATION: n is a, c, g, t or u
<220> FEATURE:
<221> NAME/KEY: misc_feature
<222> LOCATION: (53)..(53)
<223> OTHER INFORMATION: Reactive group R
<220> FEATURE:
<221> NAME/KEY: misc_feature
<222> LOCATION: (69)..(73)
<223> OTHER INFORMATION: n is a, c, g, t or u
<220> FEATURE:
<221> NAME/KEY: misc_feature
<222> LOCATION: (89)..(89)
<223> OTHER INFORMATION: Reactive group R
<220> FEATURE:
<221> NAME/KEY: misc_feature
<222> LOCATION: (105)..(109)
<223> OTHER INFORMATION: n is a, c, g, t or u
<220> FEATURE:
<221> NAME/KEY: misc_feature
<222> LOCATION: (125)..(125)
<223> OTHER INFORMATION: Reactive group R

<400> SEQUENCE: 54
```

```
nnnntggtct tcgaagucac cggatctggg tannnnntac ccagatccgg tgutccaagg    60
ctgaggtgnn nnncacctca gccttggaug gaacctcagc taggnnnnnc ctagctgagg   120
ttccucttcg aagacca                                                  137
```

<210> SEQ ID NO 55
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<223> OTHER INFORMATION: n is a, c, g, t or u
<220> FEATURE:
<221> NAME/KEY: misc_feature
<222> LOCATION: (25)..(25)
<223> OTHER INFORMATION: Chemical compound resulting from chemical
      groups R
<220> FEATURE:
<221> NAME/KEY: misc_feature
<222> LOCATION: (33)..(37)
<223> OTHER INFORMATION: n is a, c, g, t or u
<220> FEATURE:
<221> NAME/KEY: misc_feature
<222> LOCATION: (69)..(73)
<223> OTHER INFORMATION: n is a, c, g, t or u
<220> FEATURE:
<221> NAME/KEY: misc_feature
<222> LOCATION: (105)..(109)
<223> OTHER INFORMATION: n is a, c, g, t or u

<400> SEQUENCE: 55

```
nnnntggtct tcgaagucac cggatctggg tannnnntac ccagatccgg tgutccaagg    60
ctgaggtgnn nnncacctca gccttggaug gaacctcagc taggnnnnnc ctagctgagg   120
ttccucttcg aagacca                                                  137
```

<210> SEQ ID NO 56
<211> LENGTH: 195
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical compound resulting from chemical
      groups R
<220> FEATURE:
<221> NAME/KEY: misc_feature
<222> LOCATION: (28)..(31)
<223> OTHER INFORMATION: n is a, c, g, t or u
<220> FEATURE:
<221> NAME/KEY: misc_feature
<222> LOCATION: (60)..(64)
<223> OTHER INFORMATION: n is a, c, g, t or u
<220> FEATURE:
<221> NAME/KEY: misc_feature
<222> LOCATION: (96)..(100)
<223> OTHER INFORMATION: n is a, c, g, t or u
<220> FEATURE:
<221> NAME/KEY: misc_feature
<222> LOCATION: (132)..(136)
<223> OTHER INFORMATION: n is a, c, g, t or u
<220> FEATURE:
<221> NAME/KEY: misc_feature
<222> LOCATION: (165)..(168)
<223> OTHER INFORMATION: n is a, c, g, t or u

<400> SEQUENCE: 56
gtaaaacgac ggccagtcag tcacgacnnn ntggtcttcg aagucaccgg atctgggtan    60
nnnntaccca gatccggtgu tccaaggctg aggtgnnnnn caccteagcc ttggauggaa   120 cctcagctag gnnnnnccta gctgaggttc cucttcgaag accannnngt cgtgactgcg   180
aaagggtcag tgctg                                                    195

<210> SEQ ID NO 57
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R

<400> SEQUENCE: 57
tttttggtct tcgaagucac cggatctg                                       28

<210> SEQ ID NO 58
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R

<400> SEQUENCE: 58
aaggtggtct tcgaagucac cggatctg                                       28

<210> SEQ ID NO 59
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R

<400> SEQUENCE: 59
gtgttggtct tcgaagucac cggatctg                                       28

<210> SEQ ID NO 60
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R

<400> SEQUENCE: 60
cccctggtct tcgaagucac cggatctg                                       28

<210> SEQ ID NO 61
<211> LENGTH: 36
<212> TYPE: DNA
<213> ORGANISM: Artificial Sequence
<220> FEATURE:
<223> OTHER INFORMATION: Synthetic polynucleotide

```
<220> FEATURE:
<221> NAME/KEY: misc_feature
<222> LOCATION: (25)..(25)
<223> OTHER INFORMATION: Chemical group R

<400> SEQUENCE: 61 ggtaggggt acccagatcc ggtgutccaa ggctga                              36

<210> SEQ ID NO 62
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 62
ggtaccccct acccagatcc ggtgutccaa ggctga                             36

<210> SEQ ID NO 63
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 63
ggtaaaaaat acccagatcc ggtgutccaa ggctga                             36

<210> SEQ ID NO 64
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 64
ggtatttttt acccagatcc ggtgutccaa ggctga                             36

<210> SEQ ID NO 65
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 65
ggtggagagc acctcagcct tggauggaac ctcagc                             36

<210> SEQ ID NO 66
<211> LENGTH: 36
<212> TYPE: DNA
<213> ORGANISM: Artificial Sequence
<220> FEATURE:
```

<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 66
ggtggggttc acctcagcct tggauggaac ctcagc                              36

<210> SEQ ID NO 67
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 67
ggtgccccac acctcagcct tggauggaac ctcagc                              36

<210> SEQ ID NO 68
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 68 ggtggtttte acctcagcct tggauggaac ctcagc                              36

<210> SEQ ID NO 69
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 69
taggaagaac ctagctgagg ttccucttcg aagacca                             37

<210> SEQ ID NO 70
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 70
taggtttccc ctagctgagg ttccucttcg aagacca                             37

<210> SEQ ID NO 71
<211> LENGTH: 37
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 71
taggccgttc ctagctgagg ttccucttcg aagacca                                37

<210> SEQ ID NO 72
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R

<400> SEQUENCE: 72
taggcgctac ctagctgagg ttccucttcg aagacca                                37

<210> SEQ ID NO 73
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R
<220> FEATURE:
<221> NAME/KEY: misc_feature
<222> LOCATION: (53)..(53)
<223> OTHER INFORMATION: Chemical group R
<220> FEATURE:
<221> NAME/KEY: misc_feature
<222> LOCATION: (89)..(89)
<223> OTHER INFORMATION: Chemical group R
<220> FEATURE:
<221> NAME/KEY: misc_feature
<222> LOCATION: (125)..(125)
<223> OTHER INFORMATION: Chemical group R

<400> SEQUENCE: 73
cccctggtct tcgaagucac cggatctggg taggggtac ccagatccgg tgutccaagg         60
ctgaggtggg gttcacctca gccttggaug gaacctcagc taggaagaac ctagctgagg       120
ttccucttcg aagacca                                                     137

<210> SEQ ID NO 74
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R
<220> FEATURE:
<221> NAME/KEY: misc_feature
<222> LOCATION: (53)..(53)
<223> OTHER INFORMATION: Chemical group R
<220> FEATURE:
<221> NAME/KEY: misc_feature
<222> LOCATION: (89)..(89)
<223> OTHER INFORMATION: Chemical group R
<220> FEATURE:
```

<221> NAME/KEY: misc_feature
<222> LOCATION: (125)..(125)
<223> OTHER INFORMATION: Chemical group R

<400> SEQUENCE: 74
tttttggtct tcgaagucac cggatctggg taaaaaatac ccagatccgg tgutccaagg    60
ctgaggtgga gagcacctca gccttggaug gaacctcagc taggtttccc ctagctgagg   120
ttccucttcg aagacca                                                  137

<210> SEQ ID NO 75
<211> LENGTH: 141
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical group R
<220> FEATURE:
<221> NAME/KEY: misc_feature
<222> LOCATION: (53)..(53)
<223> OTHER INFORMATION: Chemical group R
<220> FEATURE:
<221> NAME/KEY: misc_feature
<222> LOCATION: (89)..(89)
<223> OTHER INFORMATION: Chemical group R
<220> FEATURE:
<221> NAME/KEY: misc_feature
<222> LOCATION: (125)..(125)
<223> OTHER INFORMATION: Chemical group R

<400> SEQUENCE: 75 tttttttaccc agatccggtg utccaaggct gaggtaaaaa atacccagat ccggtgutcc    60
aaggctgagg tggagagcac ctcagccttg gauggaacct cagctaggaa gaacctagct   120
gaggttccuc ttcgaagacc a                                             141

<210> SEQ ID NO 76
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical compound resulting from chemical
      groups R

<400> SEQUENCE: 76
cccctggtct tcgaagucac cggatctggg taggggtac ccagatccgg tgutccaagg     60
ctgaggtggg gttcacctca gccttggaug gaacctcagc taggaagaac ctagctgagg   120
ttccucttcg aagacca                                                  137

<210> SEQ ID NO 77
<211> LENGTH: 137
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical compound resulting from chemical
      groups R

<400> SEQUENCE: 77

```
tttttggtct tcgaagucac cggatctggg taaaaaatac ccagatccgg tgutccaagg    60
ctgaggtgga gagcacctca gccttggaug gaacctcagc taggtttccc ctagctgagg   120
ttccucttcg aagacca                                                  137
```

```
<210> SEQ ID NO 78
<211> LENGTH: 141
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (17)..(17)
<223> OTHER INFORMATION: Chemical compound resulting from chemical
      groups R

<400> SEQUENCE: 78
```

```
tttttaccc agatccggtg utccaaggct gaggtaaaaa atacccagat ccggtgutcc     60
aaggctgagg tggagagcac ctcagccttg gauggaacct cagctaggaa gaacctagct   120
gaggttccuc ttcgaagacc a                                             141
```

```
<210> SEQ ID NO 79
<211> LENGTH: 195
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: Chemical compound resulting from chemical
      groups R

<400> SEQUENCE: 79
```

```
gtaaaacgac ggccagtcag tcacgacccc ctggtcttcg aagucaccgg atctgggtag    60
ggggtaccca gatccggtgu tccaaggctg aggtgggggtt cacctcagcc ttggauggaa  120
cctcagctag gaagaaccta gctgaggttc cucttcgaag accaggggggt cgtgactgca  180 aaagggtcag tgctg                                                    195
```

```
<210> SEQ ID NO 80
<211> LENGTH: 195
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: Chemical compound resulting from chemical
      groups R

<400> SEQUENCE: 80
```

```
gtaaaacgac ggccagtcag tcacgacttt ttggtcttcg aagucaccgg atctgggtaa    60 aaataccca gatccggtgu tccaaggctg aggtggagag cacctcagcc ttggauggaa    120
cctcagctag gtttcccta gctgaggttc cucttcgaag accaaaaagt cgtgactgca   180
aaagggtcag tgctg                                                    195
```

```
<210> SEQ ID NO 81
<211> LENGTH: 199
<212> TYPE: DNA
<213> ORGANISM: Artificial Sequence
```

<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: Chemical compound resulting from chemical
      groups R

<400> SEQUENCE: 81
gtaaaacgac ggccagtcag tcacgacttt tttacccaga tccggtgutc caaggctgag    60
gtaaaaaata cccagatccg gtgutccaag gctgaggtgg agagcacctc agccttggau   120
ggaacctcag ctaggaagaa cctagctgag gttccucttc gaagaccaaa aagtcgtgac   180
tgcaaaaggg tcagtgctg                                                199

<210> SEQ ID NO 82
<211> LENGTH: 229
<212> TYPE: DNA
<213> ORGANISM: Artificial Sequence
<220> FEATURE:
<223> OTHER INFORMATION: Synthetic polynucleotide

<400> SEQUENCE: 82
actatgaggg ctgtctgtgg cagtcacgag ttttcgagac cgactctgga gtgtcaccgg    60
atctggttgg aaaaaccaac cagatccggt gactgtcaag gctgaggtga gggagagcct   120
cacctcagcc ttgactggag aacgcattct acacaagaag tgtagaatgc gttctcctct   180
tccagagtcg gtctcgaaaa ctcgtgactg ggttcctatt gggcttgct              229

<210> SEQ ID NO 83
<211> LENGTH: 166
<212> TYPE: DNA
<213> ORGANISM: Artificial Sequence
<220> FEATURE:
<223> OTHER INFORMATION: Synthetic polynucleotide

<400> SEQUENCE: 83
ttttcgagac cgactctgga gtgtcaccgg atctggttgg aaaaaccaac cagatccggt    60
gactgtcaag gctgaggtga gggagagcct cacctcagcc ttgactggag aacgcattct   120
acacaagaag tgtagaatgc gttctcctct tccagagtcg gtctcg                  166

<210> SEQ ID NO 84
<211> LENGTH: 210
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (192)..(192)
<223> OTHER INFORMATION: Chemical group R

<400> SEQUENCE: 84
ttttcgagac cgactctgga gtgtcaccgg atctggttgg aaaaaccaac cagatccggt    60
gactgtcaag gctgaggtga gggagagcct cacctcagcc ttgactggag aacgcattct   120
acacaagaag tgtagaatgc gttctcctct tccagagtcg gtctcgaaaa cgagaccgac   180
gactctggaa gugtcaccgg atctggttgg                                    210

<210> SEQ ID NO 85
<211> LENGTH: 37
<212> TYPE: DNA
<213> ORGANISM: Artificial Sequence

```
<220> FEATURE:
<223> OTHER INFORMATION: Synthetic polynucleotide

<400> SEQUENCE: 85
ttttcgagac cgactctgga gtgtcaccgg atctggt                                    37

<210> SEQ ID NO 86
<211> LENGTH: 173
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (155)..(155)
<223> OTHER INFORMATION: Chemical group R

<400> SEQUENCE: 86
tggaaaaacc aaccagatcc ggtgactgtc aaggctgagg tgagggagag cctcacctca           60
gccttgactg gagaacgcat tctacacaag aagtgtagaa tgcgttctcc tcttccagag          120
tcggtctcga aaacgagacc gacgactctg gaagugtcac cggatctggt tgg                 173

<210> SEQ ID NO 87
<211> LENGTH: 217
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (155)..(155)
<223> OTHER INFORMATION: Chemical group R
<220> FEATURE:
<221> NAME/KEY: misc_feature
<222> LOCATION: (199)..(199)
<223> OTHER INFORMATION: Chemical group R

<400> SEQUENCE: 87
tggaaaaacc aaccagatcc ggtgactgtc aaggctgagg tgagggagag cctcacctca           60
gccttgactg gagaacgcat tctacacaag aagtgtagaa tgcgttctcc tcttccagag          120
tcggtctcga aaacgagacc gacgactctg gaagugtcac cggatctggt tggttttttcc         180 aaccagagat ccggtgactg tcaaggctga ggtgagg                                   217

<210> SEQ ID NO 88
<211> LENGTH: 182
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (120)..(120)
<223> OTHER INFORMATION: Chemical group R
<220> FEATURE:
<221> NAME/KEY: misc_feature
<222> LOCATION: (164)..(164)
<223> OTHER INFORMATION: Chemical group R

<400> SEQUENCE: 88
tgaggtgagg gagagcctca cctcagcctt gactggagaa cgcattctac acaagaagtg           60
tagaatgcgt tctcctcttc cagagtcggt ctcgaaaacg agaccgacga ctctggaagu          120
gtcaccggat ctggttggtt tttccaacca gagatccggt gactgtcaag gctgaggtga          180
gg                                                                         182
```

```
<210> SEQ ID NO 89
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 89
tggaaaaacc aaccagatcc ggtgactgtc aaggc                                 35

<210> SEQ ID NO 90
<211> LENGTH: 224
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (117)..(117)
<223> OTHER INFORMATION: Chemical group R
<220> FEATURE:
<221> NAME/KEY: misc_feature
<222> LOCATION: (159)..(159)
<223> OTHER INFORMATION: Chemical group R
<220> FEATURE:
<221> NAME/KEY: misc_feature
<222> LOCATION: (205)..(205)
<223> OTHER INFORMATION: Chemical group R

<400> SEQUENCE: 90
tgaggtgagg gagagcctca cctcagcctt gactggagaa cgcattctac acaagaagtg     60
tagaatgcgt tctcctcttc cagagtcggt ctcgaaaacg agaccgacga ctctggaagu    120
gtcaccggat ctggttggtt tttccaacca gagatccggt gactgtcaag gctgaggtga    180
ggctctccct cacctcagcc ttgacuggag aacgcattct acac                      224

<210> SEQ ID NO 91
<211> LENGTH: 182
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (75)..(75)
<223> OTHER INFORMATION: Chemical group R
<220> FEATURE:
<221> NAME/KEY: misc_feature
<222> LOCATION: (117)..(117)
<223> OTHER INFORMATION: Chemical group R
<220> FEATURE:
<221> NAME/KEY: misc_feature
<222> LOCATION: (164)..(164)
<223> OTHER INFORMATION: Chemical group R

<400> SEQUENCE: 91
cattctacac aagaagtgta gaatgcgttc tcctcttcca gagtcggtct cgaaaacgag     60
accgacgact ctggaagugt caccggatct ggttggtttt tccaaccaga gatccggtga    120
ctgtcaaggc tgaggtgagg ctctcccctca cctcagcctt gacuggagaa cgcattctac    180
ac                                                                    182

<210> SEQ ID NO 92
<211> LENGTH: 42
<212> TYPE: DNA
<213> ORGANISM: Artificial Sequence
<220> FEATURE:
<223> OTHER INFORMATION: Synthetic polynucleotide
```

<400> SEQUENCE: 92
tgaggtgagg gagagcctca cctcagcctt gactggagaa cg	42

<210> SEQ ID NO 93
<211> LENGTH: 224
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (75)..(75)
<223> OTHER INFORMATION: Chemical group R
<220> FEATURE:
<221> NAME/KEY: misc_feature
<222> LOCATION: (117)..(117)
<223> OTHER INFORMATION: Chemical group R
<220> FEATURE:
<221> NAME/KEY: misc_feature
<222> LOCATION: (164)..(164)
<223> OTHER INFORMATION: Chemical group R
<220> FEATURE:
<221> NAME/KEY: misc_feature
<222> LOCATION: (206)..(206)
<223> OTHER INFORMATION: Chemical group R

<400> SEQUENCE: 93
cattctacac aagaagtgta gaatgcgttc tcctcttcca gagtcggtct cgaaaacgag	60 accgacgact ctggaagugt caccggatct ggttggtttt tccaaccaga gatccggtga	120 ctgtcaaggc tgaggtgagg ctctccctca cctcagcctt gacuggagaa cgcattctac	180 acttcttgtg tagaatgcgt tctccucttc cagagtcggt ctcg	224

<210> SEQ ID NO 94
<211> LENGTH: 175
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(25)
<223> OTHER INFORMATION: Chemical group R
<220> FEATURE:
<221> NAME/KEY: misc_feature
<222> LOCATION: (68)..(68)
<223> OTHER INFORMATION: Chemical group R
<220> FEATURE:
<221> NAME/KEY: misc_feature
<222> LOCATION: (100)..(100)
<223> OTHER INFORMATION: Chemical group R
<220> FEATURE:
<221> NAME/KEY: misc_feature
<222> LOCATION: (157)..(157)
<223> OTHER INFORMATION: Chemical group R

<400> SEQUENCE: 94
tcgaaaacga gaccgacgac tctggaagug tcaccggatc tggttggttt ttccaaccag	60 agatccggtg actgtcaagg ctgaggtgag gctctccctc acctcagcct tgacuggaga	120 acgcattcta cacttcttgt gtagaatgcg ttctccuctt ccagagtcgg tctcg	175

<210> SEQ ID NO 95
<211> LENGTH: 49
<212> TYPE: DNA
<213> ORGANISM: Artificial Sequence
<220> FEATURE:
<223> OTHER INFORMATION: Synthetic polynucleotide

```
<400> SEQUENCE: 95
cattctacac aagaagtgta gaatgcgttc tcctcttcca gagtcggtc                49

<210> SEQ ID NO 96
<211> LENGTH: 235
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (53)..(53)
<223> OTHER INFORMATION: Chemical group R
<220> FEATURE:
<221> NAME/KEY: misc_feature
<222> LOCATION: (95)..(95)
<223> OTHER INFORMATION: Chemical group R
<220> FEATURE:
<221> NAME/KEY: misc_feature
<222> LOCATION: (137)..(137)
<223> OTHER INFORMATION: Chemical group R
<220> FEATURE:
<221> NAME/KEY: misc_feature
<222> LOCATION: (179)..(179)
<223> OTHER INFORMATION: Chemical group R

<400> SEQUENCE: 96
actatgaggg ctgtctgtgg cagtcactcg aaaacgagac cgacgactct ggaagugtca    60
ccggatctgg ttggtttttc caaccagaga tccggtgact gtcaaggctg aggtgaggct   120
ctccctcacc tcagccttga cuggagaacg cattctacac ttcttgtgta gaatgcgttc   180
tccucttcca gagtcggtct cgttttcgag tgactgggtt cctattgggc ttgct        235

<210> SEQ ID NO 97
<211> LENGTH: 22
<212> TYPE: DNA
<213> ORGANISM: Artificial Sequence
<220> FEATURE:
<223> OTHER INFORMATION: Chemically synthesized optionally derivatised
      oligonuclotides
<220> FEATURE:
<221> NAME/KEY: modified_base
<222> LOCATION: (1)..(1)
<223> OTHER INFORMATION: 5' biotin
<220> FEATURE:
<221> NAME/KEY: misc_feature
<222> LOCATION: (1)..(1)
<223> OTHER INFORMATION: n is a, c, g, or t

<400> SEQUENCE: 97
ncagccttga ctcttccaga gt                                             22

<210> SEQ ID NO 98
<211> LENGTH: 20
<212> TYPE: DNA
<213> ORGANISM: Artificial Sequence
<220> FEATURE:
<223> OTHER INFORMATION: Chemically synthesized optionally derivatised
      oligonuclotides

<400> SEQUENCE: 98
caggtcgctg agaggttgac                                                20

<210> SEQ ID NO 99
<211> LENGTH: 20
<212> TYPE: DNA
<213> ORGANISM: Artificial Sequence
<220> FEATURE:
<223> OTHER INFORMATION: Chemically synthesized optionally derivatised
``` oligonuclotides

<400> SEQUENCE: 99
acgtccgagt cagaagtgtg                                                   20

<210> SEQ ID NO 100
<211> LENGTH: 30
<212> TYPE: DNA
<213> ORGANISM: Artificial Sequence
<220> FEATURE:
<223> OTHER INFORMATION: Chemically synthesized optionally derivatised
      oligonuclotides

<400> SEQUENCE: 100
caggtcgctg agaggttgac cagtcacgag                                        30

<210> SEQ ID NO 101
<211> LENGTH: 34
<212> TYPE: DNA
<213> ORGANISM: Artificial Sequence
<220> FEATURE:
<223> OTHER INFORMATION: Chemically synthesized optionally derivatised
      oligonuclotides

<400> SEQUENCE: 101
ctctctcgtg actgcacact tctgactcgg acgt                                   34

<210> SEQ ID NO 102
<211> LENGTH: 21
<212> TYPE: DNA
<213> ORGANISM: Artificial Sequence
<220> FEATURE:
<223> OTHER INFORMATION: Chemically synthesized optionally derivatised
      oligonuclotides
<220> FEATURE:
<221> NAME/KEY: modified_base
<222> LOCATION: (1)..(1)
<223> OTHER INFORMATION: 5' biotin
<220> FEATURE:
<221> NAME/KEY: misc_feature
<222> LOCATION: (1)..(1)
<223> OTHER INFORMATION: n is a, c, g, or t

<400> SEQUENCE: 102
nacgtccgag tcagaagtgt g                                                 21

<210> SEQ ID NO 103
<211> LENGTH: 35
<212> TYPE: DNA
<213> ORGANISM: Artificial Sequence
<220> FEATURE:
<223> OTHER INFORMATION: Chemically synthesized optionally derivatised
      oligonuclotides
<220> FEATURE:
<221> NAME/KEY: misc_feature
<222> LOCATION: (23)..(23)
<223> OTHER INFORMATION: n=NH2-C6-dT

<400> SEQUENCE: 103
agagcgagac cgactctgga agngtcaccg gatct                                  35

<210> SEQ ID NO 104
<211> LENGTH: 35
<212> TYPE: DNA
<213> ORGANISM: Artificial Sequence
<220> FEATURE:
<223> OTHER INFORMATION: chemically synthesized optionally derivatised
      oligonucleotides
<220> FEATURE:

```
<221> NAME/KEY: misc_feature
<222> LOCATION: (23)..(23)
<223> OTHER INFORMATION: n=NH2-C6-dT

<400> SEQUENCE: 104
ttttcgagac cgactctgga agngtcaccg gatct                                  35

<210> SEQ ID NO 105
<211> LENGTH: 68
<212> TYPE: DNA
<213> ORGANISM: Artificial Sequence
<220> FEATURE:
<223> OTHER INFORMATION: chemically synthesized optionally derivatised
      oligonucleotides
<220> FEATURE:
<221> NAME/KEY: misc_feature
<222> LOCATION: (56)..(56)
<223> OTHER INFORMATION: n=NH2-C6-dT

<400> SEQUENCE: 105
ggttggcaca gctgactagc tcagagctca cccaaccaga tccggtgact gtgtgngtca       60
aggctgag                                                                68

<210> SEQ ID NO 106
<211> LENGTH: 74
<212> TYPE: DNA
<213> ORGANISM: Artificial Sequence
<220> FEATURE:
<223> OTHER INFORMATION: chemically synthesized optionally derivatised
      oligonucleotides
<220> FEATURE:
<221> NAME/KEY: misc_feature
<222> LOCATION: (56)..(56)
<223> OTHER INFORMATION: n=NH2-C6-dT

<400> SEQUENCE: 106
gtgaggctcc cgggtctgta cctattaatt ccctcacctc agccttgaca cacacncttc       60
cagagtcggt ctcg                                                         74

<210> SEQ ID NO 107
<211> LENGTH: 68
<212> TYPE: DNA
<213> ORGANISM: Artificial Sequence
<220> FEATURE:
<223> OTHER INFORMATION: chemically synthesized optionally derivatised
      oligonucleotides
<220> FEATURE:
<221> NAME/KEY: misc_feature
<222> LOCATION: (56)..(56)
<223> OTHER INFORMATION: n=NH2-C6-dT

<400> SEQUENCE: 107
ggttggcaca gctgacaaaa acagagctca cccaaccaga tccggtgact gtgtgngtca       60
aggctgag                                                                68

<210> SEQ ID NO 108
<211> LENGTH: 74
<212> TYPE: DNA
<213> ORGANISM: Artificial Sequence
<220> FEATURE:
<223> OTHER INFORMATION: chemically synthesized optionally derivatised
      oligonucleotides
<220> FEATURE:
<221> NAME/KEY: misc_feature
<222> LOCATION: (56)..(56)
<223> OTHER INFORMATION: n=NH2-C6-dT

<400> SEQUENCE: 108
```

```
gtgaggctcc cgggtcgaga gctattaatt ccctcacctc agccttgaca cacacncttc    60
cagagtcggt ctcg                                                      74

<210> SEQ ID NO 109
<211> LENGTH: 51
<212> TYPE: DNA
<213> ORGANISM: Artificial Sequence
<220> FEATURE:
<223> OTHER INFORMATION: chemically synthesized optionally derivatised
      oligonucleotides
<220> FEATURE:
<221> NAME/KEY: misc_feature
<222> LOCATION: (23)..(23)
<223> OTHER INFORMATION: n=NH2-C6-dT

<400> SEQUENCE: 109
ctctcgagac cgactctgga agngtcaccg gatctggttg ggtgagctct g             51
```